United States Patent
Ofer

(10) Patent No.: US 9,405,885 B2
(45) Date of Patent: Aug. 2, 2016

(54) DRUG DISCOVERY METHOD

(75) Inventor: Dror Ofer, Omer (IL)

(73) Assignee: Keddem Bioscience Ltd., Yavne (IL)

( * ) Notice: Subject to any disclaimer, the term of this patent is extended or adjusted under 35 U.S.C. 154(b) by 0 days.

(21) Appl. No.: 13/153,487

(22) Filed: Jun. 6, 2011

(65) Prior Publication Data

US 2011/0237458 A1   Sep. 29, 2011

Related U.S. Application Data

(63) Continuation of application No. 10/523,131, filed as application No. PCT/IL02/00614 on Jul. 24, 2002, now Pat. No. 8,019,550.

(51) Int. Cl.
| | |
|---|---|
| G06F 19/16 | (2011.01) |
| C40B 40/00 | (2006.01) |
| C40B 30/04 | (2006.01) |
| G01N 33/53 | (2006.01) |
| G06F 19/00 | (2011.01) |
| C12Q 1/68 | (2006.01) |
| C07H 21/00 | (2006.01) |

(52) U.S. Cl.
CPC ............... *G06F 19/16* (2013.01); *C40B 30/04* (2013.01); *C40B 40/00* (2013.01); *G01N 33/53* (2013.01); *G06F 19/706* (2013.01); *C07H 21/00* (2013.01); *C12Q 1/68* (2013.01); *G01N 2500/00* (2013.01); *G06F 19/707* (2013.01)

(58) Field of Classification Search
CPC .... G01N 33/53; G01N 2500/00; C40B 40/00; C40B 30/04; C07H 21/00; C12Q 1/68
See application file for complete search history.

(56) References Cited

U.S. PATENT DOCUMENTS

| | | | |
|---|---|---|---|
| 5,846,722 | A | 12/1998 | Kauvar et al. |
| 6,143,776 | A | 11/2000 | Erlanson |
| 6,297,021 | B1 * | 10/2001 | Nienaber et al. ............... 435/7.1 |
| 6,335,155 | B1 | 1/2002 | Wells et al. |
| 6,813,615 | B1 | 11/2004 | Colasanti et al. |
| 8,019,550 | B2 | 9/2011 | Ofer |
| 2002/0012943 | A1 | 1/2002 | Fowlkes et al. |
| 2004/0052131 | A1 | 3/2004 | Komuro et al. |
| 2005/0277117 | A1 | 12/2005 | Ofer |

FOREIGN PATENT DOCUMENTS

| | | |
|---|---|---|
| EP | 1252141 | 2/2001 |
| JP | 2001-208728 | 8/2001 |
| JP | 2002-530727 | 9/2002 |

(Continued)

OTHER PUBLICATIONS

Wermuth et al. (Pure & Appl. Chem., 1998, 70:1129-1143).*

(Continued)

*Primary Examiner* — Jeremy C Flinders

(57) ABSTRACT

A method of obtaining information about a chemically active area of a target molecule, for example for drug discovery, comprising:
  providing a set of substantially rigid chemical gauges;
  reacting said target with a plurality of gauges of said set of gauges;
  assaying a binding of said gauges with said target to obtain a plurality of assay results; and
  analyzing said assay results to obtain information about said chemically active area.

28 Claims, 5 Drawing Sheets

(56) References Cited

FOREIGN PATENT DOCUMENTS

| WO | WO 98/16835 | 4/1998 |
|---|---|---|
| WO | WO 99/31267 | 6/1999 |
| WO | WO 99/49314 | 9/1999 |
| WO | WO 00/00823 | 1/2000 |
| WO | WO 00/25106 | 5/2000 |
| WO | WO 00/39585 | 7/2000 |
| WO | WO 00/60507 | 10/2000 |
| WO | WO 01/56987 | 8/2001 |
| WO | WO 01/98245 | 12/2001 |
| WO | WO 02/21336 | 3/2002 |
| WO | WO 02/42773 | 5/2002 |
| WO | WO 02/44128 | 6/2002 |
| WO | WO 2004/010136 | 1/2004 |

OTHER PUBLICATIONS

Nienaber et al. (Nature Biotech., 2000, 18:1105-1108).*
Villar et al. (Molecular Diversity, 2000, 5:13-24).*
Rockway et al. (Structure, 2000, 8:553-563).*
Henkin et al. (J. Biol. Chem., 2000, 275:7239-7248).*
Powers et al. (J. Med. Chem., 2002, 45:3222-3234).*
Examination Report Dated May 30, 2011 From the Instituto Mexicano de la Propriedad Industrial Re. Application No. PA/a/2005/001038 and Its Summary in English.
Requisition by the Examiner Dated Jun. 10, 2011 From the Canadian Intellectual Property Office Re.: Application No. 2,493,461.
Response Dated Jul. 20, 2011 Examination Report of May 30, 2011 From the Instituto Mexicano de la Propriedad Industrial Re. Application No. PA/a/2005/001038.
Reexamination Decision Dated Aug. 11, 2011 From the Patent Office of the People's Republic of China Re.: Application No. 028296621 and Its Summary Into Englilsh.
Notice of Reason for Rejection Dated Oct. 9, 2012 From the Japanese Patent Office Re. Application No. 2004-522657 and Its Translation Into English.
Office Action Dated Nov. 21, 2012 From the Israeli Patent Office Re.: Application No. 166450 and Its Translation Into English.
Translation of Notification of Reasons for Rejection Dated Mar. 7, 2012 From the Japanese Patent Office Re.: Application No. 2004-522657.
"Chem-X Offers Innovative Software Solutions for Compound Discovery", 30 P., 1998. www.oxmol.com/chemdesign/products.html.
"The LDS Advantage: Biology, Efficient High Throughput Screening", 1 P., 2000. www.pcop.com/discovery/disc-ids/ids_effhts.html.
"The LDS Advantage: Biology, SAR From Primary Screening", 1 P., 2000. www.pcop.com/discovery/disc-ids/ids_screening4sar.html.
"The LDS Advantage: Chemistry, Benefits of Early Library Design", 1 P., 2000. www.pcop.com/discovery/disc-ids/ids_benefits-design.html.
"The LDS Advantage: Chemistry, Benefits of Large, Diverse Libraries", 1 P., 2000. www.pcop.com/discovery/disc-ids/ids_big_libs.html.
"The LDS Advantage: Chemistry, The LDS Collection", 1 P., 2000. www.pcop.com/discovery/disc-ids/ids_collection.html.
Communication Pursuant to Article 94(3) EPC Dated Sep. 15, 2010 From the European Patent Office Re. Application No. 02755589.5.
Examination Report Dated Mar. 14, 2006 From the Government of India, Patent Office Re.: Application No. 254/CHENP/2005.
Examination Report Dated Dec. 23, 2010 From the Government of India, Patent Office Re. Application No. 1078/CHENP/2007.
Examination Report Dated Sep. 23, 2010 From the Instituto Mexicano de la Propriedad Industrial Re. Application No. PA/a/2005/001038.
Examiner's Report Dated Feb. 26, 2008 From the Australian Government, IP Australia Re.: Application No. 2002321793.
International Preliminary Examination Report Dated Jan. 12, 2006 From the International Preliminary Examining Authority Re.: Application No. PCT/IL02/00614.
International Search Report Dated Aug. 19, 2003 From the International Searching Authority Re.: Application No. PCT/IL02/00614.
Notice of Allowance Dated Mar. 23, 2011 From the US Patent and Trademark Office Re.: U.S. Appl. No. 10/523,131.
Notice of Decision for Final Rejection Dated May 11, 2009 From the Korean Intellectual Property Office Re.: Application No. 10-2005-7001234 and Its Translation Into English.
Notice Requesting Submission of Opinion Dated Nov. 10, 2008 From the Korean Intellectual Property Office Re.: Application No. 10-2005-7001234 and Its Translation Into English.
Notification of Reasons of Rejection Dated Nov. 17, 2009 From the Japanese Patent Office Re.: Application No. 2004-522657 and Its Translation Into English.
Notification of Reasons of Rejection Dated Dec. 24, 2008 From the Japanese Patent Office Re.: Application No. 2004-522657 and Its Translation Into English.
Office Action Dated Feb. 1, 2009 From the Israeli Patent Office Re.: Application No. 166450 and Its Translation Into English.
Office Action Dated Feb. 1, 2009 From the Israeli Patent Office Re.: Application No. 166450.
Official Action Dated Sep. 2, 2010 From the US Patent and Trademark Office Re.: U.S. Appl. No. 10/523,131.
Official Action Dated Jun. 3, 2008 From the US Patent and Trademark Office Re.: U.S. Appl. No. 10/523,131.
Official Action Dated Mar. 3, 2009 From the US Patent and Trademark Office Re.: U.S. Appl. No. 10/523,131.
Official Action Dated Jul. 21, 2009 From the US Patent and Trademark Office Re.: U.S. Appl. No. 10/523,131.
Requisition by the Examiner Dated Sep. 7, 2010 From the Canadian Intellectual Property Office Re.: Application No. 2,493,461.
Requisition by the Examiner Dated Sep. 18, 2009 From the Canadian Intellectual Property Office Re.: Application No. 2,493,461.
Response Dated Jan. 3, 2011 to Official Action of Sep. 2, 2010 From the US Patent and Trademark Office Re.: U.S. Appl. No. 10/523,131.
Response Dated Mar. 3, 2011 to Decision of Rejection of Nov. 10, 2010 From the Japanese Patent Office Re. Application No. 2004-522657.
Response Dated Mar. 6, 2011 to Requisition by the Examiner of Sep. 7, 2010 From the Canadian Intellectual Property Office Re.: Application No. 2,493,461.
Response Dated Mar. 15, 2011 to Communication Pursuant to Article 94(3) EPC of Sep. 15, 2010 From the European Patent Office Re. Application No. 02755589.5.
Response Dated Mar. 16, 2010 to Requisiton by the Examiner of Sep. 18, 2009 From the Canadian Intellectual Property Office Re.: Application No. 2,493,461.
Response Dated Apr. 21, 2009 to Official Action of Mar. 3, 2009 From the US Patent and Trademark Office Re.: U.S. Appl. No. 10/523,131.
Response Dated Dec. 22, 2009 to Official Action of Jul. 21, 2009 From the US Patent and Trademark Office Re.: U.S. Appl. No. 10/523,131.
Response Dated Mar. 23, 2010 to Notification of Reasons of Rejection of Nov. 17, 2009 From the Japanese Patent Office Re.: Application No. 2004-522657.
Response Dated Nov. 25, 2010 to Examination Report of Sep. 23, 2010 From the Instituto Mexicano de la Propriedad Industrial Re. Application No. PA/a/2005/001038.
Search Report Dated Nov. 22, 2005 From the Intellectual Property Office of Singapore Issued by the Australian Patent Office Re.: Application No. SG 200501106-9.
Supplementary European Search Report Dated Jun. 2, 2009 From the European Patent Office Re.: Application No. 02755589.5.
The Decision of Final Rejection of the Application Dated Feb. 20, 2009 From the Patent Office of the People's Republic of China Re.: Application No. 028296621 and Its Translation Into English.
Translation of Decision of Rejection Dated Nov. 10, 2010 From the Japanese Patent Office Re. Application No. 2004-522657.
Translation of Notification of Reasons of Rejection Dated Dec. 21, 2007 From the Japanese Patent Office Re.: Application No. 2004-522657.

(56) References Cited

OTHER PUBLICATIONS

Translation of the Office Action Dated Sep. 5, 2008 From the Patent Office of the People's Republic of China Re.: Application No. 028296621.
Translation of the Office Action Dated Apr. 6, 2007 From the Patent Office of the People's Republic of China Re.: Application No. 028296621.
Written Opinion Dated Aug. 2, 2006 From the Intellectual Property Office of Singapore Issued by the Australian Patent Office Re.: Application No. SG 200501106-9.
Written Opinion Dated Nov. 22, 2005 From the Intellectual Property Office of Singapore Issued by the Australian Patent Office Re.: Application No. SG 200501106-9.
Abagyan et al. "High-Througput Docking for Lead Generation", Current Opinion in Chemical Biology, XP002525846, 5(4): 375-382, Aug. 2001.
Borman "Redefining the Scientific Method", Combinatorial Chemistry, Special Report, 78(20): 53-65, 2000, www.cen.acs.org/isubscribe/journals/cen/78/i20/print/7820combi1.html.
Bunin et al. "The Combinatorial Synthesis and Chemical and Biological Evaluation of A 1,4-Benzodiazepine Library", Proc. Natl. Acad. Sci. USA, 91: 4708-4712, 1994.
Carell et al. "New Promise in Combinatorial Chemistry: Synthesis, Characterization, and Screening of Small-Molecule Libraries in Solution", Chemistry & Biology, 2(3): 171-183, 1995.
Coffen et al. "Molecular Diversity, Biological Activity and Common Ground Shared by Both", Medical Chemistry Research, 8: 206-218, 1998.
Darvas et al. "A Photoactivatable Library Approach for Target Identification and Validation", Journal of the American Chemical Society, Abstract # MEDI-245, 2002.
Davies "Using Pharmacophore Diversity to Select Molecules to Test From Commercial Catalogues", American Chemical Society, Chap. 27: 309-316, 1995.
Davies et al. "Combinatorial Chemistry Library Design Using Pharmacophore Diversity", Network Science, 6 P., 2000. www.netsci.org/Science/Combichem/feature05.html.
Ellman et al. "Combinatorial Thinking in Chemistry and Biology", Proc. Natl. Acad. Sci. USA, 94: 2779-2782, 1997.
Erlanson et al. "Site Directed Ligand Discovery", PNAS, 6(10): 755-769, 1999.
Fejzo et al. "The SHAPES Strategy: An NMR-Based Approach for Lead Generation in Drug Discovery", Chemistry & Biology, 6(10): 755-769, 1999. Abstract.
Ferguson et al. "Designing Chemical Libraries for Lead Discovery", Journal of Biomolecular Screening, 1(2): 16 P., 1996.
Iiajduk et al. "Design of Adenosine Kinase Inhibitors From the NMR-Based Screening of Fragments", Journal of Medical Chemistry, 43(25): 4781-4786, 2000.
Maly et al. "Combinatorial Target-Guided Ligand Assembly: Identification of Potent Subtype-Selective C-Src Inhibitors", PNAS, 97(6): 2419-2424, 2000.
Mason et al. "Library Design and Virtual Screening Using Multiple 4-Point Pharmacophore Fingerprints", Pacific Symposium on Biocomputing, 5: 573-584, 2000.
Mason et al. "Partition-Based Selection", Perspectives in Drug Discovery and Designs, 7/8: 85-114, 1997.
McGregor "A Pharmacophore Map of Small Molecule Protein Kinase Inhibitors", Journal of Chemical Information and Modeling, 47(6): 2374-2382, Nov.-Dec. 2007.
Pattarawarapan et al. "A Rigid Linker-Scaffold for Solid-Phase Synthesis of Dimeric Pharmacophores", Journal of Combinatorial Chemistry, 3(1): 102-116, 2001.
Pickett et al. "Diversity Profiling and Design Using 3D Pharmacophores: Pharmacophores-Derived Queries (PDQ)", Journal of Chemical Informations in Computer Science, 36: 1214-1223, 1996.
Pickett et al. "DIVSEL and COMPLIB—Strategies for the Design and Comparison of Combinatorial Libraries Using Pharmacophoric Descriptors", Journal of Chemical Informations in Computer Science, 38: 144-150, 1998.
Roberts "NMR Spectroscopy in Structure-Based Drug Design", Current Opinion in Biotechnology, XP002525847, 10(1): 42-47, Feb. 1999.
Sanners-Lowery et al. "High-Performance Mass Spectrometry as a Drug Discovery Tool: A High-Throughput Screening Assay to Identify RNA-Binding Ligands", Proceedings of SPIE—The International Society for Optical Engineering, 4264: 27-36, 2001.
Sofia et al. "The Generation of Carbohydrate-Based Combinatorial Libraries for Drug Discovery", Medical Chemistry Research, 8:7/8: 362-378, 1998.
Translation of Questioning Dated Jul. 6, 2011 From the Japanese Patent Office Re. Application No. 2004-522657.
Response Dated Dec. 6, 2011 to Requisition by the Examiner of Jun. 10, 2011 From the Canadian Intellectual Property Office Re.: Application No. 2,493,461.
Response Dated Jun. 30, 2011 to the Office Action of Mar. 21, 2011 From the Patent Office of the People's Republic of China Re.: Application No. 028296621.
Translation of the Office Action Dated Mar. 21, 2011 From the Patent Office of the People's Republic of China Re.: Application No. 028296621.
Translation of Notification of Reasons for Rejection Dated Mar. 29, 2013 From the Japanese Patent Office Re. Application No. 2011-052633.
European Search Report and the European Search Opinion Dated Mar. 19, 2013 From the European Patent Office Re. Application No. 12185888.0.
Notification of European Publication Number and Information on the Application of Article 67(3) EPC Dated Mar. 20, 2013 From the European Patent Office Re. Application No. 12185888.0.
Anzini et al. "Mapping and Fitting the Peripheral Benzodiazepine Receptor Binding Site by Carboxamide Derivatives. Comparison of Different Approaches to Quantitative Ligand-Receptor Interaction Modeling", Journal of Medicianl Chemistry, XP002430074, 44(8): 1134-1150, Jan. 1, 2001. Abstract, p. 1135, 1-h col., Line 1—r-h col., Line 24, p. 1137, r-h col., Line 62-p. 1146, r-h col., Line 17, p. 1149, r-h col., Lines 26-59, Figs.2, 5.
Beno et al. "The Design of Combinatorial Libraries Using Properties and 3D Pharmacophore Fingerprints", Drug Discovery Today, DDT, XP055054944, 6(5): 251-258, Mar. 1, 2001. Abstract, Fig.2.
Liang et al. "Anatomy of Protein Pockets and Cavities: Measurement of Binding Site Geometry and Implications for Ligand Design", Protein Science, XP000915965, 7(9): 1884-1897, Jan. 1, 1998. Abstract, p. 1885, 1-h col., Lines 1-22, Fig.1.
Sotriffer et al. "Identification and Mapping of Small-Molecule Binding Sites in Proteins: Computational Tools for Structure-Based Drug Design", Il Farmaco, XP002577118, 57(3): 243-251, Mar. 1, 2002. Abstract, p. 244, 1-h col., Lines 21-31, p. 246, r-h col., Line 52-p. 249, 1-h col., Line 27.
Formal Opinion Dated Aug. 22, 2014 From the Servico Publico Federal, Ministerio do Desenvolvimento, Industria e Comercio Exterior, Instituto Nacional da Propriedade Industrial do Brazil Re. Application No. PI0215858-2 and Its Translation Into English.
Office Action Dated May 4, 2014 From the Patent Office of the People's Republic of China Re. Application No. 201110355854.8 and Its Translation Into English.
Office Action Dated Aug. 24, 2015 From the State Intellectual Property Office of the People's Republic of China Re. Application No. 201110355854.8 and Its Translation Into English.
Office Action Dated Feb. 13, 2015 From The State Intellectual Property Office of the People's Republic of China Re. Application No. 201110355854.8 and Its Translation Into English.
Office Action and Search Report Dated Apr. 29, 2016 From the State Intellectual Property Office of the People's Republic of China Re. Application No. 201110355854.8 and Its Translation Into English.

* cited by examiner

DRUG DISCOVERY METHOD

RELATED APPLICATIONS

This application is a continuation of U.S. patent application Ser. No. 10/523,131, filed Jan. 21, 2005, which is National Phase Application of PCT Patent Application No. PCT/IL02/00614 having International Filing Date of Jul. 24, 2002. The contents of all of the above applications are incorporated by reference as if fully set forth herein.

FIELD OF THE INVENTION

The present invention relates to methods of molecule affinity determination, for example, for use in discovering new drugs.

BACKGROUND OF THE INVENTION

The development of a new pharmaceutical, from conception to readiness for marketing, typically costs hundreds of millions of dollars and takes many years. The development process starts with a step of matching a molecule (a potential pharmaceutical) to a target, e.g., a protein in a human body or in a microorganism. The matching of a molecule to a pharmaceutical is known as a drug lead, as it may lead to the development of a drug. The molecule is then modified to be more active, more selective and more pharmaceutically acceptable (e.g., less toxic and more easily administered). The failure rates at these stages are very high.

With the development of combinatorial chemistry and automated screening techniques, a new method of drug discovery has been developed. In this new method, a large library of molecules is chemically tested against a target, with the molecule having a best match being used as a starting point for finding a lead and/or as a lead. Some of these libraries are constructed empirically, for example, based on available molecules and/or molecules known to act as pharmaceuticals. Other libraries are constructed to have a wide a range as possible of different molecules. Other libraries are constructed so that individual molecules will have as great a chance as possible in matching a target. In general, molecules are selected to be as diverse as possible and to be drug like (e.g., size, chemical behavior) so that if a match is found it can serve as a lead.

Some references to such libraries and/or other discovery methods include, Pickett S.D. at al., J. Chem. Inf. Comput. Sci. 36(6), p. 1214-23 (1996) and Ferguson A. M. et al., J. Biomol. Scr. 1(2), p. 65 (1996), Bunin A. B. et. al., Proc. Natl. Acad. Sci. USA 91, p. 4708-12 (1994), Ellman J. et. al., Proc. Natl. Acad. Sci. USA 94, p. 2779-82 (1997) and Maly D. J. et. al., Proc. Natl. Acad. Sci. USA 97(6), p. 2419-24 (2000), the disclosures of which are incorporated herein by reference.

Another, virtual, structure based, type of screening is known. In the virtual method, a model of the target is generated (e.g., x-ray crystallography, estimated tertiary layout, analogy). Then, the affinity of a large number of molecules is determined by calculating docking behavior of a model of the molecule in the model of the target. Due to the relatively primitive state of molecular modeling and the resulting lack of availability of models, this method is not currently very successful.

Sunesis, inc., in D J Maly et al PNAS 97(6), p 2419-24 (2000), the disclosure of which is incorporated herein by reference, suggest using large fragments of molecules as leads and then linking together such matching leads that are found into larger leads that are tested again for matching. The fragments are provided with pre-defined linkers, for the linking together.

PCT application PCT/US99/06734 (WO 99/49314), the disclosure of which is incorporated herein by reference, also describes a scheme of using fragments, and then linking the fragments to provide leads.

SUMMARY OF THE INVENTION

An aspect of some embodiments of the invention relates to a target characterization method, in which a plurality of small, measurement molecules interact with a target and the target is characterized based on an analysis of the interactions of the measurement molecules with the target. In an exemplary embodiment of the invention, none of the measurement molecules is used as a lead or as a fragment of a lead, nor are the molecules selected for interaction based on their drug-type diversity. Rather, the measurement molecules are selected based on their expected ability to measure various chemical and/or physical dimensions of the target. In an exemplary embodiment of the invention, while the number of measurement molecules is relatively small (e.g., $<10^6$), this number spans the space of characterization of the target molecule and can suffice to provide a relatively complete characterization of the target. In other embodiments, only a partial characterization is needed and/or obtained. Alternatively or additionally, while the measurement molecules are selected for span reasons, they are also used as leads or as fragments of a lead.

In an exemplary embodiment of the invention, a complete process of drug discovery comprises:

(a) selecting a target;

(b) optionally selecting a set of measurement molecules useful for the target, or using a universal library;

(c) characterizing the target using the set of measurement molecules;

(d) reconstructing a pharmaceutical model of the target, based on the characterization; and (e) using the model to forward a discovery process, for example, select, reject, filter and/or design a drug lead.

In some embodiments of the invention, a typical measurement molecule can make one of several measurements, and a processing method, for example clustering, is optionally used to extract the particular measurements made by the molecules.

In an exemplary embodiment of the invention, the measurement molecules are a set of chemical gauges, of which some, typically a small number, bind to the target, typically at one or more active sites of the target. The binding of a gauge to the target can be determined using various assay methods, including substantially any of those known in the art, for example, by detecting a change in the chemical or biological behavior of the target or by detecting a reduction in the number of free gauge molecules in a sample. In a particular example, a functional assay for a protease (e.g., of an HIV protein) comprises linking a fluorescent molecule onto a protein (or other peptide). The protease is allowed to interact with a gauge, and this interaction is expected to reduce or counteract (or enhance) its affinity for the protein, which change in affinity may be determined by measuring the fluorescent properties (e.g., polarization) of the mixture of protein and protease. In an exemplary embodiment of the invention, each gauge is selected to have an affinity to one or more particular geometric layouts. In an exemplary embodiment of the invention, the total geometry of a target area is reconstructed from the determination of affinity (and/or lack of affinity) of a plurality of gauges.

In an exemplary embodiment of the invention, each of the gauges is constructed from a scaffold to which a plurality of particular chemical moieties are attached. Three such moieties define a triangle of moieties which includes both a definition of the moieties at the vertexes and the distance between the vertexes. In an exemplary embodiment of the invention, the scaffolds and moieties are selected so that the triangles are relatively rigid, however, some degree of play in the length of the triangle sides (inter-moiety distances) may be desirable.

Each such moiety triangle matches a particular spatial layout of three binding sites that match the moieties. Optionally, the distance between the moieties is varied for different gauges, so that a range of triangles with various desired combinations of moieties and distances between the moieties is provided. As will be shown below, a gauge library that includes a spanning set of such triangles, both with regards to distance and with regards to moiety is not prohibitively large.

In an exemplary embodiment of the invention, the scaffold and/or the moieties are selected to have a minimum flexibility, so that they more specifically define the geometric features that they match.

Optionally, the scaffolds and/or the moieties are selected to have a low molecular weight, so as to improve linking of low affinity gauges and/or targets and possibly provide information for such cases.

In an exemplary embodiment of the invention, when selecting gauges for a measurement library, some degree of overlap of moiety triangle is provided. For example, an repetition overlap factor of 2 or 3 maybe provided (e.g., each triangle appears in at least 2 or 3 gauges). This is expected to increase the probability of finding a triangle that binds, especially in view of problems which may occur such as steric clashes, chemical mismatch and/or solubility. Typically, an exact repetition of the moiety triangle is not available, so a nearly similar triangle is used for providing the overlap. In some cases, the triangles are selected so that for at least some pairs of moieties on the target, a triangle with a smaller distance between the same moieties and a triangle with a larger distance between the same moieties are both available for binding. This provides a non-repetition overlap factor. Alternatively to 2 or 3, a lower or higher overlap factor, for example 4 or 6, and/or possibly a fractional factor (e.g., an average overlap), may be used. The overlap may be uniform on the library, or a greater overlap may be provided for some triangles and/or molecules, for example for molecules where there is a greater probability of steric clashing due to the scaffold and/or other moieties, or based on experimental results which indicate that certain gauges and/or triangles are difficult to bind.

It should be noted that if a molecule is required to distort in order to bind, its likelihood of binding is typically lower. Thus, the actual overlap between two dissimilar triangles of two gauges may be non-uniform and dependent on the total binding probability. In general, if a probability of discovery of biding in an assay is negligible, it is assumed that the gauge does not bind. This helps define the range of distortion that can be used to define coverage and overlap. In some embodiments of the invention, the molecules are substantially rigid, so the cut-off of degree of distortion is more clearly defined and limited.

A particular exemplary drug discovery process in accordance with an exemplary embodiment of the invention, is as follows:

(a) Synthesize a library of small molecules designed to span all possible 3-point pharmacophores (all combinations of 3 elementary chemical moieties and distances between them). This is a finite library which may include, for example ~100,000 compounds. This is termed a USL (Universal Screening Library), due to its generalized nature of ability (e.g., in some embodiments of the invention) to be used for mapping a wide range of targets for which small molecule drugs are designed.

(b) For any target, screen the USL against that target, looking for weakly active compounds (affinity of ~100 microM). Theoretical considerations and experimental data indicate that 100-1000 hits should be expected for any target.

(c) Computationally analyze the active molecules, seeking:
  1. 3-Point-Pharmacophores (3PP's) involved in binding of the hits.
  2. Reconstruction of the binding-site topography in terms of chemical moieties involved in binding. Generate the complete pharmacophore (~10-20 points) of the binding-site.

(d) Computationally identify molecules that may compliment a large enough (e.g., 6-8 points for nanoMolar binding) subset of the full pharmacophore. Optionally, by knowing which parts of these molecules are not directly involved in binding, design them to meet predefined drug-like qualities (e.g. using Lipinski's rules of 5).

(e) Using well known chemical knowledge, chose those molecules most amenable to synthesis and other considerations (e.g., toxicity) and synthesize those as possible drug candidates.

(f) Testing and iterations.

An aspect of some embodiments of the invention relates to estimating a spatial layout of binding locations in a target molecule. In an exemplary embodiment of the invention, the binding of a plurality of small molecules to the target is determined, for example using assay methods. In an exemplary embodiment of the invention, the small molecules are selected to have or are each modeled as a set of geometrical sub-structures which may, on its own, bind to the target. In one example, the geometrical sub-structure may be three moieties arranged in a triangle. In an exemplary embodiment of the invention, the assay results are analyzed to determine which of the many geometrical sub-structures in the small molecules, actually bind to the target molecule. In an exemplary embodiment of the invention, a clustering method is used to determine which geometrical sub-structures bind, by clustering together molecules that bind and that have similar geometrical sub-structures. The output of the clustering method may be a list of all the probably binding sub-structures. Optionally, the sub-structures used for analysis and for design of the gauges is triangular.

In an exemplary embodiment of the invention, a score based method is used to convert a list of geometric sub-structures (e.g., triangles) into a complete geometric structure, by:

(a) generating possible structures from the list of sub-structures;

(b) associating a "correctness" score with each structure; and (c) selecting between structures based on their score.

In an exemplary embodiment of the invention, the score represents the probability of two sub-structures sharing a portion in the structure and, optionally, a higher score is provided for a structure in which a portion is shared, as that represents a more cohesive structure. Alternatively or additionally, the score represents the probability of two different moieties binding to a same binding location, and, optionally, a higher score provided if more moieties share a same binding site, as this represents a minimization of pharmacophore points to the minimum required. Other heuristic rules may be used as well.

In an exemplary embodiment of the invention, the set of all potential models is not actually built. Instead a search is made of the space of models and the models are built (and/or rejected) ad-hoc based on the determined sub-structures.

In an alternative embodiment of the invention, a clustering method is used, comprising for example:

(a) generating (all) possible structures from the found triangles, optionally using particular construction rules;

(b) finding the most common large sub-structures that are shared by multiple structures; and (c) selecting a particular common sub-structure, optionally using a scoring method, such as cluster size, edge size and thresholding of cluster size, possibly selecting a most common substructure from all those that pass a certain threshold. In some cases, more than one final resulting sub-structure will be provided.

It should be noted that an actual pharmacophore may not be a limited size and strictly defined entity, for example, a point that is technically outside the active area, can act as a pharmacophore if a small molecule drug binding to that point includes a tail that blocks the active area from interacting with the substrate. Often however, the "relevance" of a binding area will decrease as the area is further away from an active area, a control area and/or a conformance changing area. In addition, the binding affinity of a protein is often significantly smaller away from such areas.

In an exemplary embodiment of the invention, the structures for clustering are generated in the following manner:

(a) a triangle is selected as a base sub-structure;

(b) a point is added to the base sub-structure, if there are two triangles that, together with a triangle on the sub-structure, define a tetrahedral; and (c) (b) is repeated until there are no unused triangles left to add.

An aspect of some embodiments of the invention relates to finding one or more molecules (e.g., a drug lead) that is expected to match a target, from a plurality of geometric and/or chemical measurements of the target area. The measurements are optionally used to generate a reconstruction model of the target, against which model various processing methods may be applied, for example using suitable computer hardware or software. In an exemplary embodiment of the invention, the measurements are provided by interacting the target with a plurality of gauge molecules and determining the degree of binding of the gauge molecules to the target. For example, a set of triangular geometries is determined by gauge matches and is correlated to recreate a three-dimensional model of the target area.

Optionally, the target area is compared to structures of known pharmaceuticals or pharmaceutical like materials, for example a drug lead library. Alternatively or additionally, the target area geometry is used to select a most likely candidate from a relatively small plurality of materials. Alternatively or additionally, the matching is used during the process of drug development, to select or reject modifications of drug leads, which do or do not match the target area geometry.

In a particular example, if one wants to satisfy Lipinski's rules by adding or subtracting H-bond donors/acceptors, knowing which ones are important for binding would indicate which ones not to remove, and knowing which parts of the molecule are not important would indicate where additions can be made without hurting the binding.

An aspect of some embodiments of the invention relates to a library of gauges for measuring a biochemical target. In an exemplary embodiment of the invention, the library comprises a large number of molecules constructed by attaching moieties on a relatively small number of scaffolds. In an exemplary embodiment of the invention, the moieties are selected to have as low a molecular weight as possible. Alternatively or additionally, the library is designed to cover, in a desired manner, a set of parametrically defined geometric sub-structures. Possibly, the geometric sub-structures are triangles, with different moieties at their vertexes. In one example, the range of different triangle dimensions is evenly covered.

In an exemplary embodiment of the invention, the library is selected to provide same (overlapping) geometric sub-structures based on several scaffolds and/or in several molecules, for example, each sub-structure being provided twice or thrice. Optionally, the overlapping is designed to take into account steric clashes and/or different chemistries of different scaffolds and/or gauges.

In an exemplary embodiment of the invention, the scaffolds used include at least two, at least five, at least seven, at least 10 or any greater or intermediate number, such as at least all of the following scaffolds: mono-carbone; pyrrole; quinoline pyrazinoquinazoline; isoindoloindole; isoindoloindole with an oxygen moiety attached; indolo[2,3-b]quinoline; pyrolizine; 2,2'-bipyrrolone; indolizine; Thiophene; 1H-Pyrrole; Furan; Benzene; Pyridine; Pyrimidine; Pyrazine; 6H-Thieno[2,3-b]pyrrole; 1,6-Dihydro-pyrrolo[2,3-b]pyrrole; 1H-Indole; Thieno[2,3-d]pyrimidine; 6,7-Dihydropyrazolo[1,5-a]pyrimidine; Quinoline; Isoquinoline; Quinoxaline; 3,4-Dihydro-benzo[e][1,4]diazepin-5-one; 3,8-Dihydro-4H-pyrrolo[2,3-e][1,4]diazepin-5-one; 3,4-Dihydro-thieno[2,3-e][1,4]diazepin-5-one; 3,6-Dihydro-4H-pyrrolo[3,2-e][1,4]diazepin-5-one; 5H,11H-Dibenzo[b,f][1,5]diazocine-6,12-dione; 1,4-Dihydro-10H-1,4,10-1,4,10-triaza-benzo[a]cyclopenta[e]cyclooctene-5,11-dione; 4H,10H-1-Thia-4,10-diaza-benzo[a]cyclopenta[e]cyclooctene-5,11-dione; Dipyrrolo[1,2-c;2',1'-e]imidazol-5-one; 1,4,7,9-Tetrahydro-1,4,6,9-tetraaza-dicyclopenta[a,e]cyclooctene-5,10-dione; 4,7,9-Trihydro-1-thia-4,6,9-triaza-dicyclopenta[a,e]cyclooctene-5,10-dione; 2,4,9,Trihydro-1lambda*4*,6-dithia-4,9-diaza-dicyclopenta[a,e]cyclooctene-5,10-dione; 6,9-Dihydro-5H-1-thia-5,8,9,triaza-cyclopenta[a]azulen-4-one; 3,10,Dihydro-4H-[1,4]diazepino[5,6-b]indol-5-one; 3,6-Dihydro-4H-[1,4]diazepino[6,5-b]indol-5-one; 7,8-Dihydro-1H-1,7,10-triaza-cyclohepta[e]inden-6-one; 8,9-Dihydro-3H-3,6,9-triaza-cyclohepta[e]inden-10-one; 7,8-Dihydro-1H-1,5,8-triaza-cyclohepta[f]inden-9-one; 8,9-Dihydro-5,6,9,11-tetraaza-cyclohept[b]naphthalene-10-one; 3,4-Dihydro-[1,4]diazepino[5,6-b]quinolin-5-one; 8,9-Dihydro-4,8,11-triaza-cyclohepta[a]naphthalene-7-one; 11H-10,11-Diaza-benzo[b]fluorine; α-hydroxyacids; α-aminoacids; cohels; Bicyclo[2.2.2]octane; 2-Methylene-2,3-dihydrobenzo[1,4]dioxine; 6,7-Dihydro-2H-pyrazino[1,2-a]pyramidine; 9H-Fluorene; 1,4-Diaza-bictclo[2.2.2]octane; 1-Aza-bicyclo[2.2.2]octane; Pyrido[2,3-d]pyrimidine; 5-Methylene-1,5-dihydro-pyrrol-2-one; Bezno[4,5]imidazo[1,2-a]pyrimidine; 1,4-Dihydrobenzo[4,5]imidazo[1,2-a]pyrimidine; 4,10-Dihydro-1,4a,10-triaza-phenanthren-9-one; 1,5-Dihydro-imidazo[1,2-a]pyrimidin-2-one; 1,2,3,5-Tetrahydro-imidazo[1,2-a]pyrimidine; Thiazolo[3,2-a]thieno[2,3-d]pyrimidin-5-one; 1,9-Dithia-4a,10-diaza-cyclopenta[b]fluoren-4-one; 5,6-Dihydro-1-thia-5,7,8,9a-tetraaza-cyclopenta[e]azulen-4-one; 6,10-Dihydro-5H-1-thia-5,7,10a-triaza-benzo[e]azulen-4-one; 4,5-Dihydro-3-thia-4,5a,10-triaza-cyclopenta[a]fluorine; 8H-1-Thia-cyclopenta[a]indene; 3-Thia-4,5a,10-triaza-cyclopenta[a]fluorine; 6,7,9,11-Tetrahydro-10-thia-6,9- diaza-indeno[1,2-a]azulene-5,8-dione; 2,3,6,7,12a-Hexahydropyrazino[1',2':1,6]pyrido[3,4-b]indole-1,4-dione; 5,10-Dihydro-4H-2,3a,10-triaza-cyclopenta[a]fluorine; 5H-Pyrido[4,3-b]indole; 11H-Indolizino[1,2-b]quinolin-9-one; 1,2-Dihydro-2,4a,9,-triaza-anthracene-3,10-dione; 6H-Isoindolo[2,1-a]indole; 1,5-Dihydro-benzo[b][1,4]diazepin-2-one; 5,10-Dihydro-dibenzo[b,e][1,4]diazepin-11-one; 5,11-Dihydro-benzo[e]pyrido[3,2-b][1,4]diazepin-6-one; 4,9-Dihydro-3-thia-4,9-diaza-benzo[f]azulen-10-one; Benzo[g]quinoxaline; Pyrazino[2,3-b]quinoxaline; Pyrido[2,1-b]quinazolin-11-one; 1-Thia-4a,9-diaza-cyclopenta[b]naphthalene-4-one; 2-Methylene-4H-benzo[1,4]thiazin-3-one.

In general, the greater the number of scaffolds, the easier it is to find right sizes of gauges and also deal with a wider range of steric clash conditions and/or different chemistries. On the other hand, smaller number of scaffolds, promotes uniformity of chemical behavior and synthesis methods.

In an exemplary embodiment of the invention, the moieties used include, at least 2, at least 4, at least 6, or any greater number, such as all of the following moieties: Me, Et, Pr, Ph, $CO_2H$, OH, $NH_2$, ketone, halides, such as Cl or Br, other acids such as $SO_3H$, $PO_3H_2$, and NH—C=NH(—$NH_2$) (Guanidine).

In general, using more moieties may provide greater accuracy in characterizing binding, at a possible expense of library size. Using fewer moieties may also simplify synthesis methods.

An aspect of some embodiments of the invention relates to selecting a gauge library for use in characterizing a target. In an exemplary embodiment of the invention, a range of dimensions of target geometries is estimated, as well as bond types of binding locations. A set of molecules that spans the range of possible sizes and bond types is selected from a larger available set of molecules. The selection may be, for example, electronic with selected molecules being synthesized in response to selection or the selection is physical, with the gauge molecules already available. Optionally, the estimation uses various information known about the target. Alternatively or additionally, the estimation is made using a first screening library, that is, for example, more flexible in the affinity of its bond types and/or uses molecules that are more flexible.

Optionally, the gauges are selected so that the library will have considerable repetition, for example to overcome steric clashes and/or other properties of the molecules, that might prevent binding. Optionally, the library includes at least one, or possibly more than one multi-point binding geometries, for at least some of the physical geometries, for example, triangles and pentagons.

In accordance with exemplary embodiments of the invention, such a library can be used on its own or as part of a different library for various uses. In an exemplary embodiment of the invention, such a spanning library is used to increase the probability of binding of any of the gauges in the library to the target, desirably, a considerable number of gauges. It is noted that a standard lead library often provides no bindings at all. Optionally, the bindings results are used to gather information about the target, especially statistical information. Optionally, the statistical information is used to provide structural information about the target. Optionally, the structural information comprises a chemical and/or geometrical structure of a significant part of the target, for example, an active area thereof. It should be noted that in an exemplary embodiment of the invention, once even a single binding is found, useful information about the target is available and any library that assists in guaranteeing this binding has a use.

An aspect of some embodiments of the invention relates to designing and/or creating a gauge library for use in characterizing target molecules by geometrical and/or chemical measurements.

In an exemplary embodiment of the invention, library construction comprises:

(a) identifying molecules that may be suitable as gauges;

(b) determining if the identified molecules provide required gauges; and (c) verifying that the molecules are realistic, for example being readily synthesizable and/or having desirable chemical behavior. It should be noted that this order is flexible, for example as shown below.

In one example, this method is used when basing at least part of a gauge library on existing libraries. In some libraries, (c) is already performed when the library is originally composed. Further, in some case, rather than select molecules, known existing binding results of certain molecules are used as input, instead of selecting a gauge and physically testing the binding affinity.

Alternatively, candidate gauges may be provided as a group, for example, when a new scaffold is added to a library. A large number of candidates then arise, as attachments of different moieties to the scaffold. In this case, however, an opposite step may be taken—a scaffold may be rejected because it does not add any (or enough) gauges that do not overlap with existing gauges. For some parts of the spanned space, scaffolds that generate few gauges may be suitable.

In an alternative method, chemical design methodology is applied to design gauges and/or scaffolds that have desired properties and/or geometries, for example, to fill in missing parts of a measurement space.

In an exemplary embodiment of the invention, one or more of the following are considered to be desirable properties of gauges, however, a gauge need not have all or even any of the following properties, in order to be useful for some embodiments of the invention:

(a) High rigidity. This may allow measurements to be more exact, however, a small degree of flexibility may be desirable, to allow complete coverage of all the space. Rigid means that the length and/or relative angles of the bonds do not change a significant amount.

(b) Low mass. This may increase the chance of bonding even if affinity is low and only three points on the gauge bind.

(c) Small size. This may allow targets to be more easily measured and steric clashes more easily avoided.

(d) Non-toxic. This may allow the use of the gauge in living cells. However, due to the differing sensitivity of different cells, this often cannot be ensured.

(e) Good chemical behavior. This means that the gauge is soluble and binds under conditions that do not distort the gauge, or distort it by a known amount.

(f) Strong binding. This means in one embodiment of the invention, for example, 1-100 micromolar, which is useful for example if solubility is low or toxicity is high.

In an exemplary embodiment of the invention, one or more of the following are considered to be good properties of scaffolds, however, a scaffold need not have all or even any of the following properties, in order to be useful for some embodiments of the invention:

(a) Easy to attach moieties (e.g., synthesize gauges) and obtain pure solutions of particular gauges.

(b) Provide a wide range of sizes.

(c) Have many (e.g., ≥3, better >4, >5) attachment points.

While every hydrogen atom in a molecule is potentially an attachment point, in an exemplary embodiment of the invention, a useful attachment point is accessible for chemical manipulation.

(d) What (relatively rare in other gauges) chemistries possibilities and/or gauge sizes are added to the library, by inclusion of the scaffold.

(e) Allow attachment of various combinations of moieties, as not all combinations will work with all scaffolds.

In an exemplary embodiment of the invention, one or more of the following are considered to be desirable properties of a gauge library:

(a) Spanning of a range of distances between bonds.

(b) Chemical spanning. At points on opposite ends of bonds, a wide range of moieties are provided.

(c) Sub-structure spanning. For the sub-structure selected, e.g., a triangle, all possible triangle configurations in a target can bind to at least one gauge in the library.

(d) Small. The smaller the library the better. For practical reasons, the library cannot be too small, however, very large libraries are generally not necessary.

(e) Variations of gauge properties within library to match the density of gauge coverage, for example, less rigid bond lengths to cover missing or spaced apart bonds.

(f) Uniform coverage. Various types of uniformity may be provided, for example, uniformity in absolute sizes or uniformity corrected for chemical dependencies. For example, the density of distances for short bond lengths will be higher than for long bond lengths, to provide a same normalized density for different lengths.

(g) Degree and type of overlap. While more overlap is generally better for reconstruction and chemical generalization, it often comes at a cost of library size and cost. An overlap of three (e.g., each triangle is provided in three gauges) is an exemplary compromise.

In general, however, the desirable properties may depend on the target, environment and/or type of discovery method being applied. In particular, it is noted that in some cases, the generated library is only partial, for example spanning only a part of the space, being suitable for only part of a target, being in a lower resolution, having less (or no) overlap and/or being prone to fail for some types of targets.

A broad aspect of some embodiments of the invention relates to molecules, such as gauges and scaffolds and methods of synthesis thereof, which may find use for libraries in accordance with exemplary embodiments of the invention.

There is thus provided in accordance with an exemplary embodiment of the invention, a method of obtaining information about a chemically active area of a target molecule, comprising:

providing a set of substantially rigid chemical gauges;

reacting said target with a plurality of gauges of said set of gauges;

assaying a binding of said gauges with said target to obtain a plurality of assay results; and analyzing said assay results to obtain information about said chemically active area. Optionally, said gauges allow rotation of moieties of said gauges. Alternatively or additionally, said gauges are constructed using a rigid scaffold.

In an exemplary embodiment of the invention, constituent atoms of said gauges do not move more than 1 Å unless at least 20 Kcal/Mol are applied to the gauge.

In an exemplary embodiment of the invention, analyzing comprises identifying a plurality of spatial and chemically specific bindings configurations in said target active area. Optionally, said configurations comprise triangular configurations. Alternatively or additionally, identifying comprises identifying a configuration that matches a configuration of a bound gauge. Alternatively or additionally, identifying comprises identifying a configuration that does not match a configuration of a bound gauge. Optionally, identifying comprises identifying by statistical analysis of said assay results. Optionally, identifying comprises identifying by clustering.

In an exemplary embodiment of the invention, identifying comprises assuming each gauge indicates a single configuration. Alternatively or additionally, identifying comprises assuming at least some of the gauges indicate a plurality of configurations. Alternatively or additionally, identifying comprises classifying gauges by chemical moieties at vertexes of said configurations.

In an exemplary embodiment of the invention, the method comprises reconstructing a spatial map of at least part of said chemically active area, from at least two of said assay results, said part including at least four chemical binding areas. Optionally, said part includes at least six chemical binding areas.

In an exemplary embodiment of the invention, the method comprises reconstructing a spatial map of at least part of said chemically active area, from at least two of configurations, said part including at least four chemical binding points. Optionally, said part includes at least six chemical binding areas.

In an exemplary embodiment of the invention, reconstructing comprises:

test-reconstructing a plurality of spatial maps from said configurations;

scoring said maps; and selected a spatial map based on its score. Alternatively or additionally, reconstructing comprises:

test-reconstructing a plurality of spatial maps from said configurations;

clustering said maps according to common substructures; and selected a spatial map based on a relative property of a cluster it belongs to. Optionally, said relative property comprises size.

In an exemplary embodiment of the invention, said spatial map includes enough binding points to ensure binding of a small molecule drug having a chemical profile matching the binding points. Optionally, said spatial map includes at least 6 binding points. Optionally, said spatial map includes at least 8 binding points.

In an exemplary embodiment of the invention, said set of gauges comprises a set of gauges with at least 10,000 gauges. Optionally, said set of gauges comprises a set of gauges with at least 50,000 gauges.

In an exemplary embodiment of the invention, said gauges comprise moieties arranged in spatial configurations and wherein said gauges are selected to span a virtual space of spatial chemical configurations.

In an exemplary embodiment of the invention, substantially each point of virtual space that is spanned by said gauges is covered by at least two gauges. Optionally, substantially each point of virtual space that is spanned by said gauges is covered by at least three gauges.

In an exemplary embodiment of the invention, at least 0.5% of said gauges bind with said target. Optionally, at least 1% of said gauges bind with said target. Optionally, at least 3% of said gauges bind with said target.

In an exemplary embodiment of the invention, at least 50% of said gauges are defined by adding moieties to a set of fewer than 100 scaffolds. Optionally, at least 50% of said gauges are defined by adding moieties to a set of fewer than 50 scaffolds.

In an exemplary embodiment of the invention, at least said set of gauges uses fewer than 15 different chemical moieties to define the chemical behavior of said gauges.

In an exemplary embodiment of the invention, at least said set of gauges uses fewer than 10 different chemical moieties to define the chemical behavior of said gauges.

In an exemplary embodiment of the invention, said assay is a functional assay. Alternatively or additionally, said assay is a binding assay. Alternatively or additionally, said assay is a cellular assay. Alternatively or additionally, said assay is a flow-through assay.

In an exemplary embodiment of the invention, said functional assay is performed in the presence of a natural substrate of said target.

In an exemplary embodiment of the invention, said target comprises a protein including a biochemically active area adapted to engage a substrate. Optionally, said chemically active area comprises an area including said biochemically active area. Alternatively or additionally, said chemically active area comprises a control area of said protein.

In an exemplary embodiment of the invention, analyzing comprises analyzing successful binding of at least 60 gauges. Alternatively or additionally, analyzing comprises analyzing successful binding of at least 10 gauges. Alternatively or additionally, analyzing comprises analyzing successful binding of at least 100 gauges.

In an exemplary embodiment of the invention, identifying comprises identifying at least 40 different configurations. Alternatively or additionally, identifying comprises identifying at least 10 different configurations. Alternatively or additionally, identifying comprises identifying at least 100 different configurations.

In an exemplary embodiment of the invention, the method comprises:

comparing said map to a lead data base; and selecting a lead from said data base for further use responsive to a semblance or lack of semblance between said lead and said map.

Alternatively or additionally, the method comprises:

comparing said map to a lead data base; and rejecting a lead from said data base for further use responsive to a semblance between said lead and said map.

Alternatively or additionally, the method comprises:

constructing a lead to have a semblance to said map. Optionally, constructing comprises constructing using said gauges or scaffolds used to define said gauges.

In an exemplary embodiment of the invention, the method comprises:

comparing said configurations to a lead data base; and selecting a lead from said data base for further use responsive to a matching of said configurations to said lead.

In an exemplary embodiment of the invention, the method comprises constructing a lead based on said configurations.

In an exemplary embodiment of the invention, the method comprises selecting at least one of said gauges as a lead for drug discovery.

In an exemplary embodiment of the invention, the method comprises comparing the binding of gauges with similar binding geometries to obtain steric clashing data; and analyzing said steric clashing data to provide geometrical information about said target.

There is also provided in accordance with an exemplary embodiment of the invention, a method of identifying the existence of a plurality of chemical-spatial configurations in a target, comprising:

assaying the target with a plurality of gauges having know chemical-spatial configurations at vertexes thereof, to provide a plurality of assay results;

defining an array of spaces, one space for each set of chemical behaviors of the vertexes of each configuration;

indicating said results according to said spaces, to generate clusters; and identifying the existence of a configuration in said target from said clusters. Optionally, indicating comprises spreading an indication responsive to a spreading function. Optionally, said spreading function is dependent on an estimated energy of binding of a gauge to said target.

There is also provided in accordance with an exemplary embodiment of the invention, a method of reconstructing a spatial shape of a chemical binding configuration of a target from a set of sub-shapes, each of which indicates a part of said binding configuration, comprising:

selecting a base from said sub-shapes;

selecting at least two sub-shapes having the property that they match each other at least along one side thereof and match said base along another side thereof;

accumulating said sub-shapes to said base; and repeating said selecting and said accumulating until all of said sub-shapes are used or cannot be used, thereby providing a shape of a binding configuration of said target. Optionally, the method comprises variationally repeating said selecting, accumulating and repeating using a different order of selection of sub-shapes. Optionally, the method comprises repeating said selecting a base and said variationally repeating for a plurality of different base selections. Optionally, the method comprises clustering a plurality of such shapes according to shared sub-component shapes. Optionally, the method comprises selecting a sub-component shape as a resulting shape based on said clustering.

In an exemplary embodiment of the invention, said sub-shapes comprise triangles. Alternatively or additionally, said sub-shapes define chemical behavior at their vertexes and wherein two sides are said to match if the chemical behavior at their vertexes match.

In an exemplary embodiment of the invention, two sides are said to match if their length is similar.

There is also provided in accordance with an exemplary embodiment of the invention, a method of selecting a scaffold for use in generating a part of a screening library, comprising:

providing a potential scaffold molecule including a plurality of possible attachment points for moieties;

determining a rigidity of the molecule; and rejecting said potential scaffold molecule responsive to a lack of rigidity of said scaffold. Optionally, said lack of rigidity is absolute. Alternatively, said lack of rigidity is relative to other potential scaffolds.

In an exemplary embodiment of the invention, the method comprises selecting a scaffold based on a number of rings thereof.

In an exemplary embodiment of the invention, the method comprises:

determining a plurality of gauge molecules that can be generated by adding moieties to said potential scaffold molecule;

determining for an existing library portion what spatial chemical configurations are added by said molecules; and selecting said potential scaffold molecule if one or more significant spatial chemical configurations can be added by it to said library portion. Optionally, the method comprises selecting a scaffold based on a number of configurations added by said scaffold. Alternatively or additionally, said significant spatial configurations are configurations not previously provided or overlapped with.

There is also provided in accordance with an exemplary embodiment of the invention, a method of selecting a gauge molecule to be added to a screening library, comprising:

providing a set of chemical molecules and at least a part of a screening library;

selecting a potential gauge molecule from said set of chemical molecules;

determining a rigidity of said potential gauge molecule; and rejecting said potential gauge molecule responsive to a lack of rigidity of said gauge molecule. Optionally, said lack of rigidity is absolute. Alternatively, said lack of rigidity is relative to other potential scaffolds.

In an exemplary embodiment of the invention, the method comprises:

determining a spanning, in chemical configuration space, of said part of a screening library;

determining at least one spatial chemical configuration of said potential molecule; and selecting said potential gauge molecule if it adds at least one significant spatial chemical configuration to said screening library.

Optionally, providing a set of molecules comprises generating said molecules using a single scaffold to which moieties are selectively attached. Alternatively or additionally, providing a set of molecules comprises providing a chemical library.

In an exemplary embodiment of the invention, said gauge is selected if it adds at least one spatial chemical configuration not previously provided or overlapping a provided configuration.

There is also provided in accordance with an exemplary embodiment of the invention, a method of creating at least a portion of a screening library, comprising:

selecting a scaffold molecule to which moieties can be added;

determining a plurality of potential gauges which can be created by attaching moieties to said scaffold; and selecting a subset of said gauges that do not substantially overlap in chemical configurations. Optionally, the method comprises rejecting potential gauges that add over six spatial chemical configurations.

There is also provided in accordance with an exemplary embodiment of the invention, a method of reducing a screening library, comprising:

for each molecule in at least part of said library, determining substantially all the spatial chemical configurations of a certain order of binding points provided by the molecule; and removing a plurality of molecules which add redundant spatial chemical configurations. Optionally, said certain order is three.

There is also provided in accordance with an exemplary embodiment of the invention, a method of reducing a screening library, comprising:

for each molecule in at least part of said library, calculating a binding probability of said molecules based on energetic considerations; and removing at least some molecules whose binding probability is below a threshold value. Optionally, said binding probability is calculated using a formula which is inversely dependent on a flexibility of the molecule. Alternatively or additionally, said binding probability is at least estimated based on a solubility of the molecule.

There is also provided in accordance with an exemplary embodiment of the invention, a method of designing a screening library for a projected target molecule task, comprising:

determining a desired range of distances between binding points to be directly identified by said library;

determining a desired overlap between measures provided by gauge molecules of said library;

determining a set of desired binding types to be discriminated between; and generating a plurality of gauges, said gauges each defining a plurality of binding types and distances between them, such that said gauges cover a spatial chemical configuration space that includes said distances and said binding types with said desired overlap. Optionally, generating a plurality of moieties comprises generating by attaching moieties to scaffolds. Alternatively or additionally, said gauges cover a spatial chemical configuration space of triplets of binding points. Alternatively or additionally, said projected target molecule task comprises proteins.

In an exemplary embodiment of the invention, said overlap is at least two. Alternatively said overlap is at least four. Alternatively, said overlap is at least six.

In an exemplary embodiment of the invention, said gauges are substantially rigid. Alternatively or additionally, said coverage takes into account an inherent flexibility of binding.

In an exemplary embodiment of the invention, generating comprises generating substantially same configurations by different gauges, thereby providing at least part of said overlap. Optionally, generating comprises providing a repetition factor of at least two.

In an exemplary embodiment of the invention, generating comprises generating substantially different configurations by different gauges, which different configurations overlap due to a degree of flexibility thereof, thereby providing at least part of said overlap.

In an exemplary embodiment of the invention, the method comprises generating a set of drug leads for said target based on said information. Optionally, the method comprises removing known drug leads for said target from said set.

There is also provided for in accordance with an exemplary embodiment of the invention, a lead set produced by one of the methods described above.

There is also provided in accordance with an exemplary embodiment of the invention, a drug lead comprising:

a plurality of substantially rigid scaffolds molecule sections;

at least one link interconnecting said scaffold molecule sections; and a plurality of moieties attached to said scaffolds.

There is also provided in accordance with an exemplary embodiment of the invention, a screening library comprising:

at least 10,000 molecules generated by attaching moieties to a set of fewer than 50 scaffold molecules. Optionally, fewer than 20 scaffold molecules are used to generate said at least 10,000 molecules. Alternatively or additionally, said scaffolds include at least one of the following scaffold molecules: Thiophene; 1H-Pyrrole; Furan; Benzene; Pyridine; Pyrimidine; Pyrazine; 6H-Thieno[2,3-b]pyrrole; 1,6-Dihydro-pyrrolo[2,3-b]pyrrole; 1H-Indole; Thieno[2,3-d]pyrimidine; 6,7-Dihydro-pyrazolo[1,5-a]pyrimidine; Quinoline; Isoquinoline; Quinoxaline; 3,4-Dihydro-benzo[e][1,4]diazepin-5-one; 3,8-Dihydro-4H-pyrrolo[2,3-e][1,4]diazepin-5-one; 3,4-Dihydro-thieno[2,3-e][1,4]diazepin-5-one; 3,6-Dihydro-4H-pyrrolo[3,2-e][1,4]diazepin-5-one; 5H,11H-Dibenzo[b,f][1,5]diazocine-6,12-dione; 1,4-Dihydro-10H-1,4,10-1,4,10-triaza-benzo[a]cyclopenta[e]cyclooctene-5,11-dione; 4H,10H-1-Thia-4,10-diaza-benzo[a]cyclopenta[e]cyclooctene-5,11-dione; Dipyrrolo[1,2-c;2',1'-e]imidazol-5-one; 1,4,7,9-Tetrahydro-1,4,6,9-tetraaza-dicyclopenta[a,e]cyclooctene-5,10-dione; 4,7,9-Trihydro-1-thia-4,6,9-triazadicyclopenta[a,e]cyclooctene-5,10-dione; 2,4,9,Trihydro-1lambda*4*,6-dithia-4,9-diaza-dicyclopenta[a,e]cyclooctene-5,10-dione; 6,9-Dihydro-5H-1-thia-5,8,9,triaza-cyclopenta[a]azulen-4-one; 3,10,Dihydro-4H-[1,4]diazepino[5,6-b]indol-5-one; 3,6-Dihydro-4H-[1,4]diazepino[6,5-b]indol-5-one; 7,8-Dihydro-1H-1,7,10-triaza-cyclohepta[e]inden-6-one; 8,9-Dihydro-3H-3,6,9-triaza-cyclohepta[e]inden-10-one; 7,8-Dihydro-1H-1,5,8-triaza-cyclohepta[f]inden-9-one; 8,9-Dihydro-5,6,9,11-tetraaza-cyclohept[b]naphthalene-10-one; 3,4-Dihydro-[1,4]diazepino[5,6-b]quinolin-5-one; 8,9-Dihydro-4,8,11-triaza-cyclohepta[a]naphthalene-7-one; 11H-10,11-Diaza-benzo[b]fluorine; α-hydroxyacids; α-aminoacids; cohels; Bicyclo[2.2.2]octane; 2-Methylene-2,3-dihydrobenzo[1,4]dioxine; 6,7-Dihydro-2H-pyrazino[1,2-a]pyramidine; 9H-Fluorene; 1,4-Diaza-bictclo[2.2.2]octane; 1-Aza-bicyclo[2.2.2]octane; Pyrido[2,3-d]pyrimidine; 5-Methylene-1,5-dihydro-pyrrol-2-one; Bezno[4,5]imidazo[1,2-a]pyrimidine; 1,4-Dihydro-benzo[4,5]imidazo[1,2-a]pyrimidine; 4,10-Dihydro-1,4a,10-triaza-phenanthren-9-one; 1,5-Dihydro-imidazo[1,2-a]pyrimidin-2-one; 1,2,3,5-Tetrahydro-imidazo[1,2-a]pyrimidine; Thiazolo[3,2-a]thieno[2,3-d]pyrimidin-5-one; 1,9-Dithia-4a,10-diaza-cyclopenta[b]fluoren-4-one; 5,6-Dihydro-1-thia-5,7,8,9a-tetraaza-cyclopenta[e]azulen-4-one; 6,10-Dihydro-5H-1-thia-5,7,10a-triaza-benzo[e]azulen-4-one; 4,5-Dihydro-3-thia-4,5a,10-triaza-cyclopenta[a]fluorine; 8H-1-Thia-cyclopenta[a]indene; 3-Thia-4,5a,10-triaza-cyclopenta[a]fluorine; 6,7,9,11-Tetrahydro-10-thia-6,9-diaza-indeno[1,2-a]azulene-5,8-dione; 2,3,6,7,12a-Hexahydropyrazino[1',2':1,6]pyrido[3,4-b]indole-1,4-dione; 5,10-Dihydro-4H-2,3a,10-triaza-cyclopenta[a]fluorine; 5H-Pyrido[4,3-b]indole; 11H-Indolizino[1,2-b]quinolin-9-one; 1,2-Dihydro-2,4a,9,-triaza-anthracene-3,10-dione; 6H-Isoindolo[2,1-a]indole; 1,5-Dihydro-benzo[b][1,4]diazepin-2-one; 5,10-Dihydro-dibenzo[b,e][1,4]diazepin-11-one; 5,11-Dihydro-benzo[e]pyrido[3,2-b][1,4]diazepin-6-one; 4,9-Dihydro-3-thia-4,9-diaza-benzo[f]azulen-10-one; Benzo[g]quinoxaline; Pyrazino[2,3-b]quinoxaline; Pyrido[2,1-b]quinazolin-11-one; 1-Thia-4a,9-diaza-cyclopenta[b]naphthalene-4-one; 2-Methylene-4H-benzo[1,4]thiazin-3-one.

In an exemplary embodiment of the invention, at least 4 of said scaffolds have exactly a single ring. Alternatively or additionally, at least 4 of said scaffolds have exactly two rings. Alternatively or additionally, at least 4 of said scaffolds have exactly three rings. Alternatively or additionally, at least 4 of said scaffolds have exactly four rings. Alternatively or additionally, said library includes at least 50,000 thus generated molecules. Alternatively or additionally, said library includes at least 100,000 thus generated molecules.

In an exemplary embodiment of the invention, said scaffolds include at least three of said following scaffold molecules. Alternatively or additionally, said scaffolds include at least ten of said following scaffold molecules.

In an exemplary embodiment of the invention, said generated molecules are substantially rigid. Alternatively or additionally, said molecules span a configuration space of spatial geometrical patterns of binding point types, including at least 25% of the patterns that exist in protein targets. Optionally, said molecules span at least 50% of the patterns.

In an exemplary embodiment of the invention, said molecules span a space defining at least 4 distinct binding point chemistry types.

In an exemplary embodiment of the invention, said molecules span a space defining at least 5 distinct binding point chemistry types.

There is also provided in accordance with an exemplary embodiment of the invention, a screening library, comprising:

at least 100 gauge molecules generated by attaching moieties to at least one of the following scaffolds: Thiophene; 1H-Pyrrole; Furan; Benzene; Pyridine; Pyrimidine; Pyrazine; 6H-Thieno[2,3-b]pyrrole; 1,6-Dihydro-pyrrolo[2,3-b]pyrrole; 1H-Indole; Thieno[2,3-d]pyrimidine; 6,7-Dihydro-pyrazolo[1,5-a]pyrimidine; Quinoline; Isoquinoline; Quinoxaline; 3,4-Dihydro-benzo[e][1,4]diazepin-5-one; 3,8-Dihydro-4H-pyrrolo[2,3-e][1,4]diazepin-5-one; 3,4-Dihydro-thieno[2,3-e][1,4]diazepin-5-one; 3,6-Dihydro-4H-pyrrolo[3,2-e][1,4]diazepin-5-one; 5H,11H-Dibenzo[b,f][1,5]diazocine-6,12-dione; 1,4-Dihydro-10H-1,4,10-1,4,10-triaza-benzo[a]cyclopenta[e]cyclooctene-5,11-dione; 4H,10H-1-Thia-4,10-diaza-benzo[a]cyclopenta[e]cyclooctene-5,11-dione; Dipyrrolo[1,2-c;2',1'-e]imidazol-5-one; 1,4,7,9-Tetrahydro-1,4,6,9-tetraaza-dicyclopenta[a,e]cyclooctene-5,10-dione; 4,7,9-Trihydro-1-thia-4,6,9-triaza-dicyclopenta[a,e]cyclooctene-5,10-dione; 2,4,9,Trihydro-1lambda*4*,6-dithia-4,9-diaza-dicyclopenta[a,e]cyclooctene-5,10-dione; 6,9-Dihydro-5H-1-thia-5,8,9,triaza-cyclopenta[a]azulen-4-one; 3,10,Dihydro-4H-[1,4]diazepino[5,6-b]indol-5-one; 3,6-Dihydro-4H-[1,4]diazepino[6,5-b]indol-5-one; 7,8-Dihydro-1H-1,7,10-triaza-cyclohepta[e]inden-6-one; 8,9-Dihydro-3H-3,6,9-triaza-cyclohepta[e]inden-10-one; 7,8-Dihydro-1H-1,5,8-triaza-cyclohepta[f]inden-9-one; 8,9-Dihydro-5,6,9,11-tetraaza-cyclohept[b]naphthalene-10-one; 3,4-Dihydro-[1,4]diazepino[5,6-b]quinolin-5-one; 8,9-Dihydro-4,8,11-triaza-cyclohepta[a]naphthalene-7-one; 11H-10,11-Diaza-benzo[b]fluorine; α-hydroxyacids; α-aminoacids; cohels; Bicyclo[2.2.2]octane; 2-Methylene-2,3-dihydrobenzo[1,4]dioxine; 6,7-Dihydro-2H-pyrazino[1,2-a]pyramidine; 9H-Fluorene; 1,4-Diaza-bictclo[2.2.2]octane; 1-Aza-bicyclo[2.2.2]octane; Pyrido[2,3-d]pyrimidine; 5-Methylene-1,5-dihydro-pyrrol-2-one; Bezno[4,5]imidazo[1,2-a]pyrimidine; 1,4-Dihydro-benzo[4,5]imidazo[1,2-a]pyrimidine; 4,10-Dihydro-1,4a,10-triaza-phenanthren-9-one; 1,5-Dihydro-imidazo[1,2-a]pyrimidin-2-one; 1,2,3,5-Tetrahydro-imidazo[1,2-a]pyrimidine; Thiazolo[3,2-a]thieno[2,3-d]pyrimidin-5-one; 1,9-Dithia-4a,10-diaza-cyclopenta[b]fluoren-4-one; 5,6-Dihydro-1-thia-5,7,8,9a-tetraaza-cyclopenta[e]azulen-4-one; 6,10-Dihydro-5H-1-thia-5,7,10a-triaza-benzo[e]azulen-4-one; 4,5-Dihydro-3-thia-4,5a,10-triaza-cyclopenta[a]fluorine; 8H-1-Thia-cyclopenta[a]indene; 3-Thia-4,5a,10-triaza-cyclopenta[a]fluorine; 6,7,9,11-Tetrahydro-10-thia-6,9-diaza-indeno[1,2-a]azulene-5,8-dione; 2,3,6,7,12a-Hexahydropyrazino[1',2':1,6]pyrido[3,4-b]indole-1,4-dione; 5,10-Dihydro-4H-2,3a,10-triaza-cyclopenta[a]fluorine; 5H-Pyrido[4,3-b]indole; 11H-Indolizino[1,2-b]quinolin-9-one; 1,2-Dihydro-2,4a,9,-triaza-anthracene-3,10-dione; 6H-Isoindolo[2,1-a]indole; 1,5-Dihydro-benzo[b][1,4]diazepin-2-one; 5,10-Dihydro-dibenzo[b,e][1,4]diazepin-11-one; 5,11-Dihydro-benzo[e]pyrido[3,2-b][1,4]diazepin-6-one; 4,9-Dihydro-3-thia-4,9-diaza-benzo[f]azulen-10-one; Benzo[g]quinoxaline; Pyrazino[2,3-b]quinoxaline; Pyrido[2,1-b]quinazolin-11-one; 1-Thia-4a,9-diaza-cyclopenta[b]naphthalene-4-one; 2-Methylene-4H-benzo[1,4]thiazin-3-one.

Optionally, said molecules are generated using at least one of the following scaffolds: Thiophene; 1H-Pyrrole; Furan; Benzene; Pyridine; Pyrimidine; Pyrazine; 6H-Thieno[2,3-b]pyrrole; 1,6-Dihydro-pyrrolo[2,3-b]pyrrole; 1H-Indole; Thieno[2,3-d]pyrimidine; 6,7-Dihydro-pyrazolo[1,5-a]pyrimidine; Quinoline; Isoquinoline; Quinoxaline; 3,4-Dihydro-benzo[e][1,4]diazepin-5-one; 3,8-Dihydro-4H-pyrrolo[2,3-e][1,4]diazepin-5-one; 3,4-Dihydro-thieno[2,3-e][1,4]

diazepin-5-one; 3,6-Dihydro-4H-pyrrolo[3,2-e][1,4]diazepin-5-one; 5H,11H-Dibenzo[b,f][1,5]diazocine-6,12-dione; 1,4-Dihydro-10H-1,4,10-1,4,10-triaza-benzo[a]cyclopenta[e]cyclooctene-5,11-dione; 4H,10H-1-Thia-4,10-diaza-benzo[a]cyclopenta[e]cyclooctene-5,11-dione; Dipyrrolo[1,2-c;2',1'-e]imidazol-5-one.

In an exemplary embodiment of the invention, said at least 100 molecules comprise at least 300 molecules. Alternatively or additionally, said at least 100 molecules of said library are generated using a single one of said scaffolds.

There is also provided in accordance with an exemplary embodiment of the invention, a screening library comprising a set of at least 10,000 substantially rigid molecules. Optionally, said set comprises at least 50,000 substantially rigid molecules. Alternatively or additionally, said set comprises at least 100,000 substantially rigid molecules.

In an exemplary embodiment of the invention, said set is selected to have a an expected binding rate of at least 0.1% of the library for protein targets in general. Optionally, said expected binding rate is at least 0.5%.

In an exemplary embodiment of the invention, said set is designed to provide molecules with a uniformity of hit probability for a generalized target of within a ratio of 1:100 for the whole set. Optionally, said ratio is within 1:10.

In an exemplary embodiment of the invention, said set spans a space of spatial chemical configurations, each such configuration defining a certain plurality of binding points having distances between them, the set covering substantially all possible configurations in the space in a given range of distances.

There is also provided in accordance with an exemplary embodiment of the invention, a screening library, comprising:

a plurality of at least 5,000 gauge molecules, each such molecule defining at least one spatial configuration of binding type points, wherein substantially each point in a space of such configurations is covered by at least two different gauge molecules. Optionally, each point is covered by at least two substantially identical spatial configurations. Alternatively or additionally, each point is covered by at least two substantially different spatial configurations. Alternatively or additionally, said space is a space of triangles defined by binding type at vertexes and distances between vertexes. Optionally, said space includes distances of between 4 Å and 8 Å (angstrom=$10^{-10}$ meters). Alternatively or additionally, said space includes distances of between 2 Å and 10 Å. Alternatively or additionally, said space includes at least 5 different binding types. Optionally, said space includes at least 7 different binding types.

In an exemplary embodiment of the invention, said space includes omni-directional binding types. Alternatively or additionally, said space includes directional binding types.

In an exemplary embodiment of the invention, said substantially each point in said space is covered by at least three gauges.

In an exemplary embodiment of the invention, substantially all the gauges include a plurality of configurations of said space.

There is also provided in accordance with an exemplary embodiment of the invention, a method of obtaining information about a binding behavior of a target molecule, comprising:

providing a set of substantially rigid chemical gauges, a significant number of said gauges being expected to bind with said target;

reacting said target with a plurality of gauges of said set of gauges; and physically analyzing a structure of said target bound to a gauge. Optionally, physically analyzing comprises analyzing using NMR. Alternatively or additionally, physically analyzing comprises analyzing using X-ray crystallography. Alternatively or additionally, physically analyzing comprises analyzing using binding with a set of gauges. Alternatively or additionally, the method comprises virtually super-imposing a plurality of structures obtained by said physically analyzing.

There is also provided in accordance with an exemplary embodiment of the invention, a method of constructing a lead, comprising:

providing a set of substantially rigid chemical gauges;

reacting said target with a plurality of gauges of said set of gauges;

assaying a binding of said gauges with said target to obtain a plurality of assay results; and constructing a lead based on said assay results. Optionally, constructing a lead comprises linking together a plurality of gauges found to bind in said assaying. Alternatively or additionally, constructing a lead comprises modifying an existing molecule to have moieties that correspond to binding locations found by said assaying.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

Figure 1:
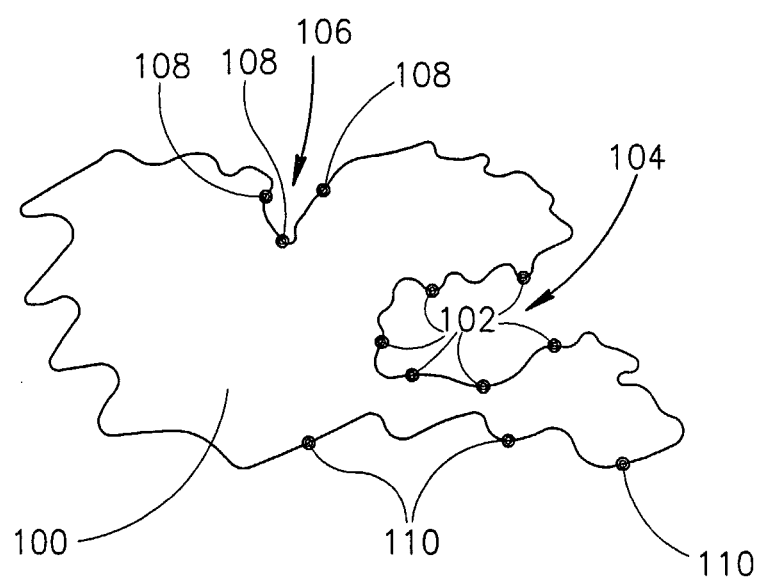
FIG. 1 is a schematic diagram of a target protein including a plurality of binding points.

1. OVERVIEW
2. EXEMPLARY PROCESS OF DRUG DISCOVERY
3. DETAILS OF PROCESS
   3.1 TARGET MEASUREMENT

4. EXEMPLARY ASSAYS
  4.1 FUNCTIONAL ASSAY
  4.2 BINDING ASSAY
5. GAUGES, GENERAL
  5.1 EXEMPLARY GAUGE
  5.2 NUMBER OF MOIETIES IN A MEASURE
  5.3 NUMBER OF MOIETIES IN A GAUGE
  5.4 MOIETY TYPES
  5.5 OVERLAP OF MEASURES IN A SET
6. RECONSTRUCTION
  6.1 TRIANGLE EXTRACTION
  6.2 LAYOUT CONFIGURATION RECONSTRUCTION
  6.3 RECONSTRUCTION VARIATIONS
  6.4 ALTERNATIVE RECONSTRUCTION METHOD
7. ANALYSIS
  7.1 OVERVIEW
  7.2 RECONSTRUCTION VERIFICATION
  7.3 BINDING STRENGTH
  7.4 INTER-BOND INTERACTIONS
  7.5 GEOMETRIC ANALYSIS
  7.6 DETERMINATION OF STERIC CLASHES
  7.7 IDENTIFICATION OF CONTROL AREAS
  7.8 OTHER MAP ANALYSIS
8. USE IN DRUG DISCOVERY PROCESSES
  8.1 OVERVIEW
  8.2 DRUG GENERATION
  8.3 LEAD GENERATION
  8.4 LEAD DESCRIPTION
  8.5 LEAD SEARCH
  8.6 LEAD REJECTION
  8.7 TARGETED MAPPING
  8.8 TARGET SUITABILITY TESTING
  8.9 TARGET PARTITIONING
  8.10 DRUG AND LEAD ANALYSIS AND ENHANCEMENT
  8.11 DRUG SELECTION
  8.12 DRUG ENHANCEMENT
  8.13 DRUG FAILURE ANALYSIS AND REENGINEERING
  8.14 ADDITIONAL DRUG DISCOVERY RELATED ANALYSIS
  8.15 STREAMLINE DISCOVERY PROCESS
  8.16 UTILITY GENERATION
9. EXEMPLARY DISCOVERY APPLICATIONS
  9.1 OVERVIEW
  9.2 SCREENING BASED DRUG DESIGN
  9.3 ALTERNATIVE SCREENING BASED DRUG DESIGN
  9.4 STRUCTURE-BASED DRUG DESIGN
  9.5 MODULAR ASSEMBLY OF LIGANDS
10. EXEMPLARY NON-DISCOVERY USES
11. USING PRIOR INFORMATION
12. ITERATIVE MEASUREMENT
13. GAUGES, PHYSICAL PROPERTIES
  13.1 OVERVIEW
  13.3 VOLUMETRIC GEOMETRY OF GAUGES
  13.4 FLEXIBILITY
  13.5 GAUGE LENGTHS
  13.6 ENVIRONMENTAL STABILITY
  13.7 UNIQUENESS OF GAUGES AND OVERLAP OF SIDES AND TRIANGLES
  13.8 GAUGE MASS AND SIZE
14. PARTICULAR AND GENERAL GAUGE SET DESIGN
  14.1 EXAMPLE SPANNING LIBRARY SIZE
  14.2 GAUGE SUBSET SELECTION
  14.3 GAUGE LIBRARY DESIGN
  14.4 LIBRARY BUILDING METHOD
  14.5 SCAFFOLD SELECTION METHOD
  14.6 GAUGE SELECTION METHOD
  14.7 GAUGE SYNTHESIS
  14.8 MIXED LIBRARY DESIGN
  14.9 ENSURING LIBRARY RELIABILITY
  14.10 HUMAN INTERACTION DURING LIBRARY DESIGN
15. EXPERIMENTS AND EXAMPLES
  15.1 EXPERIMENT 1
  15.2 EXPERIMENT 2
16. SYNTHESIS BOOK
  16.1 Benzenes, Pyrimidines 6-membered ring scaffold
  16.2 Indolo[2,3-b]quinoline 6,6,5,6 cyclic scaffold
  16.3 isoindoloindoles and isoindoloindolones 6,5,5,6 tetra cyclic scaffolds
    16.3.1 Isoindoloindolones
  16.4 The single atom scaffold
  16.5 Benzodiazepines 6,7 bicyclic scaffold
  16.6 Pyrazinoquinazolinone -6,6,6 tricyclic scaffold
  16.7 Pyrrole -5 membered ring scaffold
  16.8 Thiophenes and related scaffolds
    16.8.1 5,5 bicyclic scaffolds
    16.8.2 5,6-bicyclic scaffolds
    16.8.3 5,8,5 5,8,6 tricyclic and 5,5,8,6 5,5,8,5 tetracyclic scaffolds
    16.8.4 5,7 bicyclic scaffold
    16.8.5 5,6,5,6 Tetracyclic and 5,6,5 tricyclic scaffolds
    16.8.6 5-6-5-6 tetracyclic scaffold
    16.8.7 5-6-5 tricyclic scaffold 1. Overview The high specificity of many biological molecules, such as enzymes, is created by the existence, in such a molecule, of a particular spatial arrangement of binding locations. It is believed that for a substrate molecule to succeed in usefully interacting with the enzyme, it must match (at least part of) the particular spatial arrangement. In the pharmaceutical industry, this specificity can be utilized by finding small molecules that mimic the shape and chemical affinities of the substrate molecule. In a typical drug discovery method, such a small molecule is found by trying out millions of small molecules and, once finding a molecule which appears to have some affinity, chemically fine tuning that "lead" until a better binding is found. In an exemplary embodiment of the invention, the particular spatial arrangement is mapped and this map is used to assist in the drug discovery process and, ultimately, in finding new and useful small molecule drugs. It should be noted that, in general, the spatial geometry of the binding locations is three dimensional.

In the following description, the molecule is called a target and the spatial arrangement is called a target area or a pharmacophore. However, as will be clear, a mapping method in accordance with an exemplary embodiment of the invention and/or its derivatives have uses beyond drug discovery, for example, developing herbicides and targeted anti-bodies. Thus, the terms used are used for convenience and not for limiting the desired coverage, except where noted otherwise.

FIG. 1 is a schematic diagram of a target protein 100 including a plurality of binding locations 102 (and 108). As shown, binding locations 102 are arranged in a target area 104, which is designed to accept the substrate of the protein. In some proteins, a target area of interest is a control area 106 of the protein (with binding locations 108), which, when bound, changes the behavior of the protein (e.g., changing the configuration of the substrate receiving area of the protein). Possibly, a plurality of non-functional binding locations 110 are found on the outside of the protein.

Although the following description focuses on finding small molecules for affecting enzymatic proteins, target 100 may be any bio-molecule whose biological behavior may be desirably affected by the binding of a molecule to it. For example, target 100 may be one or more of DNA, RNA, signaling proteins such as hormones, structural hormones, growth factors, other proteins, anti-bodies, cell receptors, ion channels, cytokines, complexes, membranes, toxins (biological and synthetic), small and large molecule drugs and carbohydrates. Non-biological application are also envisioned, for example for assessing enzymes used for washing and industrial uses. In addition, the searched-for molecule need not be a small molecule, for some applications, for example, it may be a peptide, protein, antibody or metal complex.

In accordance with some exemplary embodiments of the invention, the mapping of target area 104 (or 106) is provided by making multiple geometrical and/or chemical affinity measurements of the target area and then correlating the measurements to provide a three dimensional model of target area 104. In an exemplary embodiment of the invention, the measurements are made using a set of selective gauge molecules. In an exemplary embodiment of the invention, the gauges are selective to certain bond geometries and/or certain chemical affinities, with an optional small range of flexibility. In a set of gauges a large range of geometries, sizes and/or affinities is optionally provided using a larger number of specific gauges.

In an exemplary embodiment of the invention, each gauge molecule makes multiple measurements simultaneously and there is an overlap between the measurements made by different gauge molecules. A processing step is optionally provided in which the composite measurement from gauges are inter-related to yield an indication of individual measurements which are then used for reconstructing a three-dimensional map. Additional side information is optionally used for the processing and/or or for analyzing and/or using the results of the processing. Various examples of such side information are described below.

2. Exemplary Process of Drug Discovery

Figure 2:
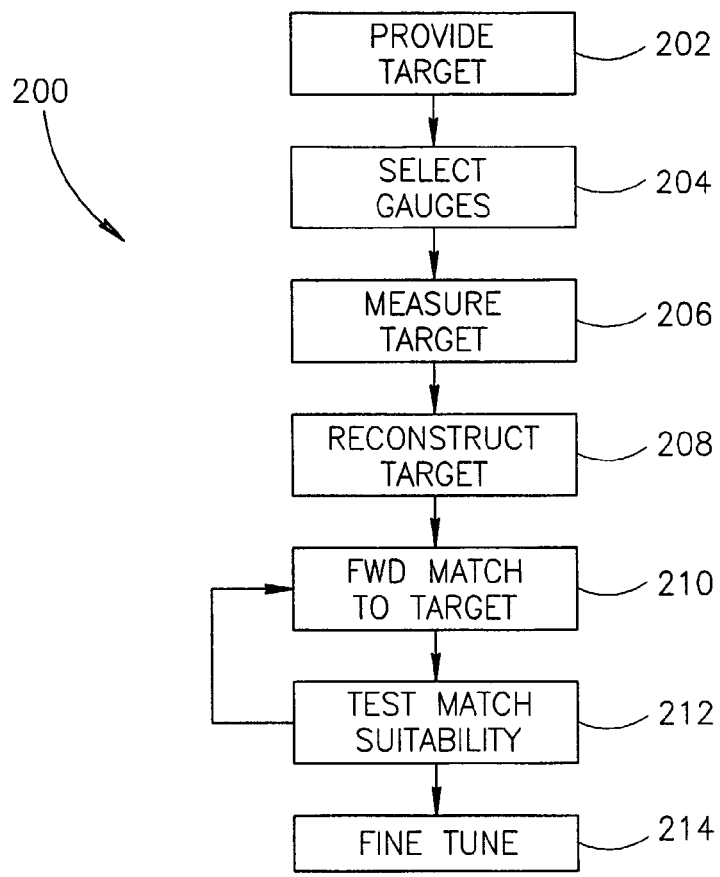
FIG. 2 is a flowchart of a method of drug discovery, in accordance with an exemplary embodiment of the invention.

FIG. 2 is a flowchart of a method of drug discovery 200, in accordance with an exemplary embodiment of the invention. At 202, a target 100 for which a drug is to be developed, is provided. Optionally, at 204, a subset of gauges is selected for the measurement of target 100. Alternatively, a single set of gauges is used for all targets.

At 206, the gauges are used to measure the spatial layout of interaction locations 102 and/or 108.

At 208, a model of at least part of the active and/or control areas of target 100 is reconstructed from the measurements. At 210 and 212 one or more molecules that match the measurements are determined. At 214, the matching molecules are further processed to provide drugs.

Further details of this method are described below. Alternative methods are also described below.

3. Details of Process 3.1 Target Measurement

Figure 3:
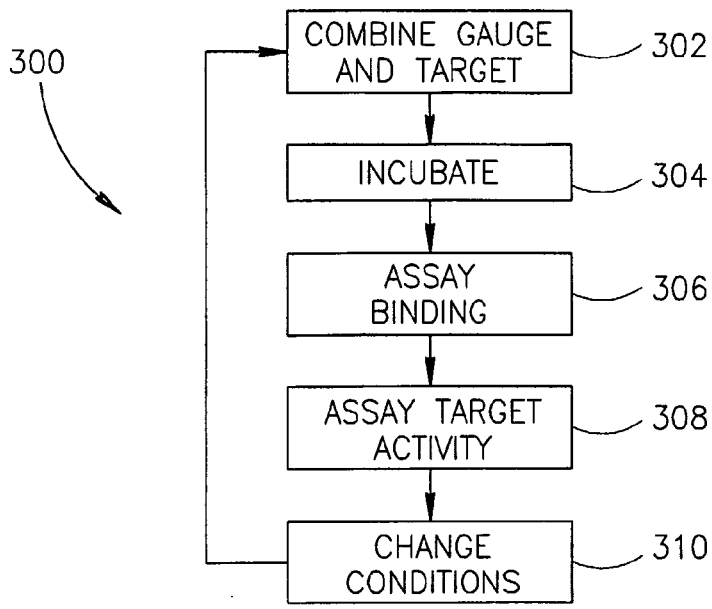
FIG. 3 is a flowchart of a method of target measurement, in accordance with an exemplary embodiment of the invention.

FIG. 3 is a flowchart of a method of target measurement 300, in accordance with an exemplary embodiment of the invention. At 302, an amount of target 100 and one or more gauges are combined in a container, and possibly allowed to incubate (304) so that gauges can bind to interaction locations in target 100. In some embodiments of the invention, the target is also incubated with a substrate or another molecule. Such incubation may be provided for various reasons, for example, to force a conformal change on the target to assist in dissolving, to keep the target alive and/or as part of a functional assay. The target may be in a relatively pure state, for example a purified replicated DNA segment. Alternatively, the target may be provided in a more natural environment, for example in a living cell or with associated molecules (e.g., whose interactive effects may be unknown). Optionally, a plurality of overlapping gauges (i.e., overlapping in them being able to measure same or similar spatial geometries) are incubated together in a same assay.

At 306, the degree of binding of the gauge to target 100 is optionally determined. The method used may depend on the type of assay used, various examples of which are provided below. Alternatively or additionally, at 308, an effect on the function of target 100 is determined, various examples are provided below.

It should be noted that assays suitable for detecting binding of a test molecule to a target molecule are well known for drug discovery and many are suitable for the present invention, possibly with no modification.

The assaying process may then be repeated with a different gauge and/or different conditions (310), such as solvent, temperature and pH. Varying the conditions may be used, for example, to determine the strength of the binding and/or to compensate for unavailable gauges, for example by forcing conformal changes on target 100. The repetition may depend on preliminary binding results for one or more gauges and/or may depend on preliminary measurements or measurement failures.

In an exemplary embodiment of the invention, the assays are at a 1-100 micro Molar concentration of the gauge. However, other concentrations may be used. The concentration may depend, for example, on the solubility of the gauge and/or various toxic or other effects associated with the gauge. In many cases, the concentrations used will depend on the sensitivity of the assay.

The purity of the target may or may not be important, for example, depending on the affinity of the gauge to the impurities and/or on the sensitivity of the assay to the impurities.

4. Exemplary Assays 4.1 Functional Assay

Many types of functional assaying methods are known in the art. In general, the treated target is provided with its normal substrate (for proteins) and a measurement of enzymatic activity is used to determine the functional effect of the gauge, relative to a baseline or a control portion of material. Automated parallel assay devices, such as manufactured by Tecan (Switzerland), Zymark (USA) or Cybio (DE) can perform multiple functional assays in parallel, for example, for different gauges and/or for better statistics on a single gauge-target match.

Functional assays may be on various levels, for example, on a molecular, cellular or organism level. In general, any known functional assay may be used to assay the functionality of a gauge.

In an exemplary embodiment of the invention, the gauge acts like a ligand of the target and compete or otherwise affects the functionality of the target. These effects may be of various types, for example, the gauge may bind where the normal substrate is supposed to bind, the gauge may bind near where the substrate binds, but still block the substrate from binding, the gauge may bind in a way that does not block the substrate but would, if the gauge were larger (suitable for a binding assay) and/or the gauge may be agnostic rather than antagonistic in its behavior, enhancing the affinity of the target for the substrate.

DNA targets can be assayed, for example, using replication methods (e.g., to see if replication is inhibited or enhanced). Alternatively, DNA targets are assayed by determining their interaction with DNA chips after the test binding. Such DNA chips typically include a substrate on which a plurality of short DNA segments are mounted in a known pattern, with the segments selected to bind (e.g. be specific and complementary) to portions of a searched for DNA sequence and/or match sections of a non-linear DNA segment. It is expected that the type and/or relative frequencies of bindings to various short DNA segments on a DNA chip depend on the degree and/or location of binding of a gauge to a DNA molecule. For example, a gauge may block a certain part of a DNA molecule from matching up with a DNA chip segment. In another example, a gauge may force a conformal change in a DNA molecule, which change will interfere with binding with one DNA chip segment but which may allow binding with a previously unsuitable DNA chip segment.

4.2 Binding Assay

In a binding assay, the binding of a gauge to a target is directly measured. It should be noted, however, that a binding assay may be less indicative than a functional assay, as a gauge can bind at a location outside of the target area and provide no useful information about the target area. In addition, the sensitivity of a binding assay may be lower, since the detection sensitivity of binding is usually lower and typical binding rates are also quite low. However, in some cases, a functional assay cannot be performed, for example if the gauge interacts with the substrate, or if a target function is not known, or may be difficult or time consuming to perform, for example if the assay requires a living cell. Also, a gauge may bind in an active area without this binding affecting the functionality, as measured by a particular functional assay.

Various types of binding assays are known in the art and may be used, for example as described in the Handbook of Drug Screening, edited by Ramakrishna Seethala and Prabhavathi B. Fernandes, in Drugs and the Pharmaceutical Sciences, Volume 114, New York, N.Y., Marcel Dekker, 2001, the disclosure of which is incorporated herein by reference.

Both functional assays and binding assays may be performed in many ways, the current technology being robotic performance of tests and the emerging technology being flow-through analysis (e.g., using DNA chips). It should be noted that 100,000 test systems are becoming available, which means that in some embodiments of the invention, screening using a gauge library can be completed in one step (day). Optionally, this is used to prevent the need to clean out gauge delivery systems between screening targets.

In some embodiments of the invention, the binding assay (of a functional assay) includes modifying a gauge, for example, attaching a fluorescent material to the gauge. Depending on the attachment point, this may cause conformal changes in some of the gauges and/or cause steric clashes. It is expected that the overlap between gauges will overcome this problem, at least in a significant number of cases.

In other embodiments of the invention, the gauges are not changed, or are changed in non-material ways. For example, for an NMR binding assay or an x-ray crystallography binding assay no change is required. In a radioactivity based assay, radioactive isotopes can be used in the gauges. In an exemplary embodiment of the invention, non-radioactive isotopes (half spin isotopes) are used in producing the gauges, to provide binding detection and/or better analysis of NMR data. In these assays, unbound gauges may be separated from the targets, for example, using methods known in the art, for example, if the target is bound to a surface, washing will remove unbound gauges.

In some embodiments of the invention, the binding of the gauge has a non-functional effect on the target, which may be detected or measured, for example, affecting a vibration frequency of a fluorescent tail attached to the gauge or the target.

In an exemplary embodiment of the invention, the gauge binds with the target in a manner similar to that of a ligand of the target. Various techniques, for example as known in the art (e.g., NMR, IR) may be used to analyze the combined target/gauge structure. Optionally, once a binding gauge or other substrate is found, a gauge set is used to measure the combined target/ligand structure.

In some binding assays, a plurality of differently marked gauges may be assayed simultaneously and possibly differentially, for example, by a attaching a different florescent marker to different gauge used together and/or using different radioactive isotopes for different gauges.

Optionally, the binding assay (and/or a functional assay) may include changing various environmental parameters, such as temperature, pH and/or other environmental variables, for example to determine a strength of binding.

In an exemplary embodiment of the invention, a binding assay is used to determine a baseline level of binding of the gauge outside active areas of the target. In one example, the degree of binding of a particular gauge to alpha helixes in a protein may be known from an analog of the target. The total binding to the target, however, includes bindings to non-helix parts of the protein and/or target areas of the target.

In an exemplary embodiment of the invention, it is noted that a large number of hits are expected and/or an overlap between gauges is provided. As a result, lower quality and/or faster assays are used, since noise caused by low binding rates may be less of a problem. In one example, borderline results form two assays are combined, based on a repetition of triangular measures between the gauges used in the assays.

5. Gauges, General 5.1 Exemplary Gauge

Figure 4A:
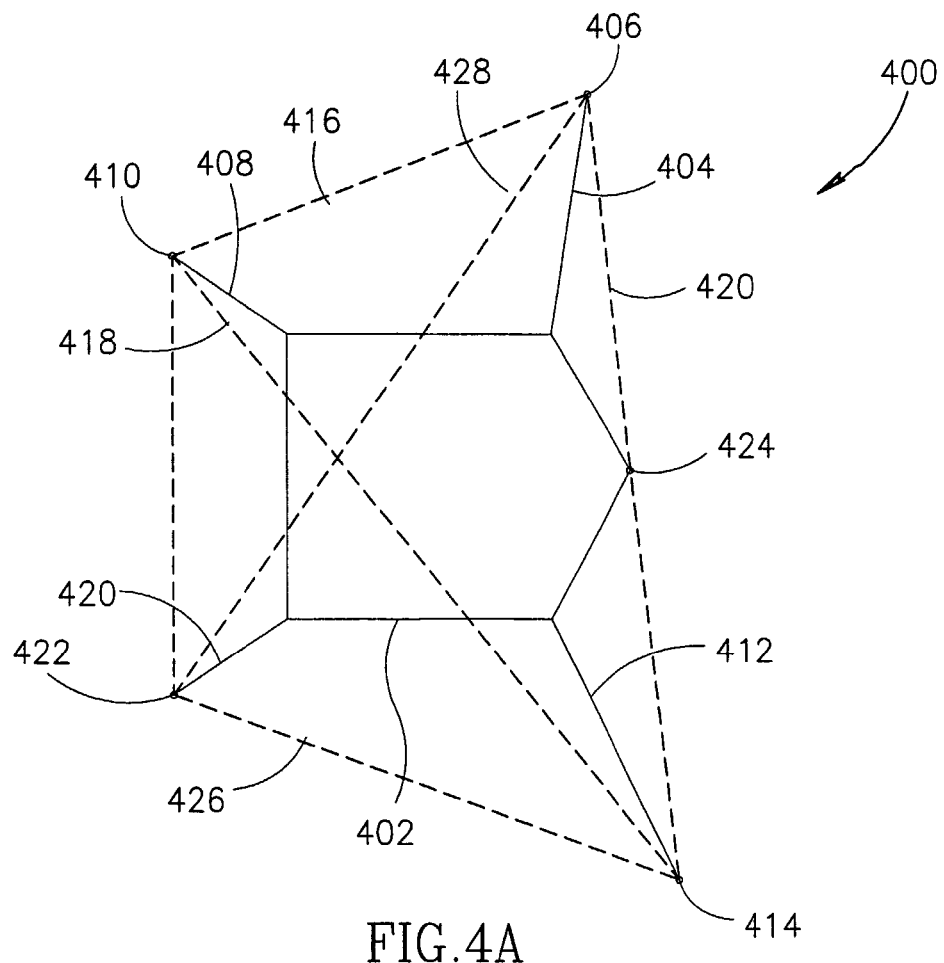
FIG. 4A is a schematic illustration of an exemplary gauge, in accordance with an exemplary embodiment of the invention.

FIG. 4A is a schematic illustration of an exemplary gauge 400, in accordance with an embodiment of the invention.

Gauge 400 comprises a scaffold 402 and four chemical moieties 406, 410, 414 and 422attached to scaffold 402 via bonds 404, 408, 412 and 420, respectively. This is only an exemplary gauge, as the properties of all of these elements may vary, for example as described below. In particular, one or more of the type of moiety, number of moieties, type of bond, distance between moiety and scaffold, type of scaffold and location of connection to the scaffold may be varied for different gauges, sets of gauges and/or embodiments of the invention.

In an exemplary embodiment of the invention, a plurality of moieties cooperate to define a measure. In an exemplary embodiment of the invention, the gauge purpose is to detect interaction locations that bind to those moieties that define a measure at the distances between the moieties. The matching of a measure to the target molecule may be indicated by the binding of the gauge. In an exemplary embodiment of the invention, a basic unit of measure is a triangle (or other geometric shape) defined by a subset of all the moieties. As will be described below, the shape of a triangle has particular properties which make it suitable for some embodiments. In general, if a gauge includes more than the number of moieties in a measure (e.g., more than two moieties for a linear measure, more than three for a triangle), more than one measure may be provided by a single gauge. Thus, in the exemplary embodiment of the invention shown, a plurality of different triangle measures are defined in a single gauge. In some embodiments and in some cases, a gauge will include only one measure, for example, gauge 400 includes only a single four-point measure, but four triangle measures. Exemplary methods of determining which of various possible measures actually bound, are described below.

Figure 4B:
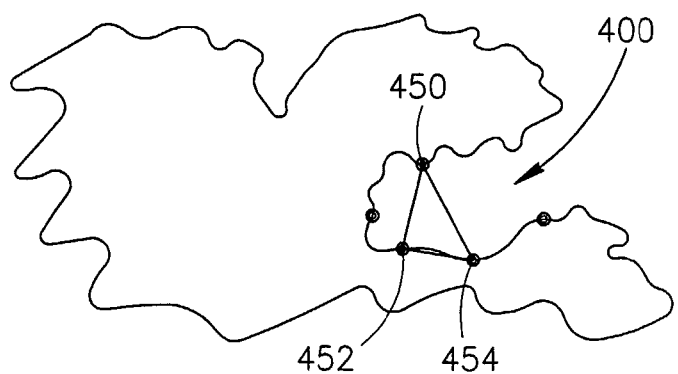
FIG. 4B shows the gauge of FIG. 4A, interacting with the target protein of FIG. 1.

One triangle geometry is shown by dashed lines 416, 418 and 420 that define the distances between pairs of moieties of gauge 400. As noted above, in an exemplary embodiment of the invention, the gauge purpose is to detect interaction locations that bind to those moieties (406, 410, 414) at the distances defined by dashed lines 416, 418 and 420 (e.g., triangle sides). Assuming gauge 400 included only moieties 406, 410 and 414, then a binding of gauge 400 to target 100 can be is used as an indication that three interaction sites, of a type suitable to bind to moieties 406, 410 and 414 are approximately at the respective distances defined by gauge 400. Since gauge 400 defines multiple triangles, a binding of gauge 400indicates that at least one of the triangles defined by the moieties, binds. FIG. 4B shows gauge 400, interacting with target 100, at three interaction locations 450, 452 and 454. Non-interacting moieties and the rest of the gauge are not shown.

5.2 Number of Moieties in a Measure

As noted, each plurality of moieties defines a measures. While the present invention accommodates, in some embodiments thereof measures, with two, three, four and/or other numbers of moieties and/or gauge sets including a mixture of different measures, in an exemplary embodiment of the invention, the basic measure used is a triangle, with three moieties. Using a triangle may provide one or more of the following potential benefits:

(a) A triangle defines a stable spatial relationship, which may be useful as a unit component when "constructing" a model in three dimensions of the target area, from the binding results.

(b) There are fewer possible triangles than four-sided measures (for example). Thus, generating a library that includes measures that cover an entire space is less time consuming. Further, as it is desirable in some embodiments of the invention to provide overlap between measures, such overlapping measures are more easily provided if there are fewer measures. It is possible that chemical limitations may prevent the construction of high-order measure gauge libraries.

(c) A triangle always lies in a plane (e.g., three points define a plane), which may be mathematically useful for some reconstruction methods.

(d) For some applications, a triangle represents the lowest number of binding points that will result in a measurable binding to a target active area. A typical drug includes six or more binding points, often as many as ten or more. Conversely, a higher-order measure may bind too strongly. In other applications, the optimal number of moieties in a measure may be higher or lower, of course.

Alternatively, a measure including two moieties are used, for example, defining lines. Alternatively or additionally, four- or higher valance measures are used, for example, to define more uniquely an interaction location configuration. In some embodiments of the invention, a mix of different valance measures may be used, in the gauge set and/or in the reconstruction, for example, 2-point, 3-point, 4-point and 5-point measures, which may or may not be planar.

5.3 Number of Moieties in a Gauge

In an exemplary embodiment of the invention, the number of moieties in a gauge is between four and ten, however, a smaller (e.g., three) or greater number may be provided. Some scaffolds may be limited in the number of different moieties, moiety positions and/or moieties combinations possible. Larger numbers of moieties are generally desirable if the moieties define different triangle measures. Conversely, gauges with multiple attachment points and/or gauges with many moieties may be more prone to steric clashes and/or other adverse interactions between the moieties, which inhibit binding.

While the scaffold itself has chemical properties and may be considered as having moieties, in some embodiments of the invention, these properties are ignored, for example during library design and/or during binding results analysis. Alternatively, the properties of the scaffold may be considered, for example only during analysis and/or during library design.

5.4 Moiety Types

In an exemplary embodiment of the invention, the moieties are selected to reflect the types of bonds that the drug is expected to make with the target. In an exemplary embodiment of the invention, the moieties are selected based on their chemical behavior. If a particular behavior is exhibited by several moieties, in an exemplary embodiment of the invention, only a smallest one of the moieties is selected. In some embodiments of the invention, multi-purpose moieties, which can bind to several different binding sites, are used instead of moieties which can only bind to one type of target site. The specificity of the moieties selected may depend, for example, on the total number of moieties, their size and their amenability for chemical processing. It should be noted that some of the moieties are directional, while others are non-directional. Where available, non-directional bonds may be preferred over directional bonds. In some exemplary embodiments of the invention, two levels of measurement are performed, a coarse resolution level and a fine resolution level. More specific moieties may be used during the fine resolution level of measurement. Additional details and methods for optionally reducing the number of moieties used in some embodiments of the invention, are described below.

Following is a list of moieties of which one or more may be attached to gauges:

a. Hydrogen bond donor. Directional bond.
b. Hydrogen bond acceptor. Directional bond
c. Positive charge. Non-directional bond.
d. Negative charge. Non-directional bond.
e. Aromatic ring. Directional bond.
f. Hydrophobic group. Non-directional in general, however, some, e.g., rings, may be directional with a preferred direction perpendicular to the ring plane. Different moieties may be used in other embodiments of the invention, for example, also providing one or more of Halogen, Carbonyl, Phosphate and Sulfate bonds. It should be noted that the different moieties may differ greatly in the their chemical affinities or they may differ less or even slightly. In some exemplary gauge sets, the slight difference between moiety affinities is used to fine tune a measurement distinction between bond types.

With respect to the directional bonds, in some embodiments of the invention, it is assumed that the bond has sufficient spatial flexibility so that a small number, e.g., seven, different directional bonds will suffice to cover all the possible bond directions. Alternatively, smaller or greater numbers of bond directions may be used. Optionally, different directional bonds have different numbers of directions represented in a gauge library. The angular distribution of the directions may be, for example uniform, or it may be non-uniform, for example depending on the bond type.

Several different sizes of hydrophobic bonds may exist. In an exemplary embodiment of the invention, two sizes are selected and represented by different moieties. An aromatic ring may also serve, as an oversized hydrophobic moiety.

Alternatively or additionally, an aromatic ring is used to match aromatic bonds with other rings and/or some types of hydrogen bonds.

The above selection of moieties and directions results in 25 unique moieties, which can be attached to scaffolds. An exemplary set of moieties is described below.

In an exemplary embodiment of the invention, a subset of the above moieties is used. Use is made of the rotational flexibility of hydrogen bond donors and/or receivers. Although such flexibility will generally reduce chemical bonding probability, the mass of a hydrogen atom used in a hydrogen bond moiety is sufficiently low that the reduction in probability may not materially affect the results of the measurement method, at least for some gauges and assays.

Alternatively or additionally, rotational flexibility is allowed for aromatic rings. Although aromatic rings have a high mass, the large bond area of the ring compensates for the reduction in bond strength caused by allowing rotational flexibility of the ring.

Alternatively or additionally, some polar bonds may be represented by a single moiety, such as OH, which can act as both a hydrogen bond donor and as an acceptor.

Optionally, for example if chemical information can be done without, more general moieties are used and a smaller number of triangles in a library is spanning.

5.5 Overlap of Measures in a Set

In an exemplary embodiment of the invention, the triangle space as a whole is spanned by providing a plurality of triangles, each with sufficient freedom in its parameters (e.g., bond length, chemical affinity), so that each triangular arrangement of binding points can be expected to bind to one of the triangles to a measurable degree. Optionally, the coverage of each triangle in the triangle space overlaps with the coverage of other triangles, to ensure that no parts of the space are left uncovered.

As will be explained in greater detail below, in an exemplary embodiment of the invention, a gauge library is designed such that each possible triangular arrangement of binding points appears in (or fits within the parameters of) more than one gauge. In some cases, exactly congruent triangles cannot be provided, instead, triangles that are roughly congruent are provided (e.g., similar moieties, side lengths). These congruent triangles may have the same coverage in triangle space or not. For example, assuming same moieties, two triangles with the following side lengths are provided: (3, 4, 5) and (3.1, 3.9, 5.2) (measurements in angstrom. These triangles may, for example, cover the part of triangle space from (2, 3, 4) to (4, 5, 6).

In some embodiments of the invention, at least some of the triangle space is spanned by a set of triangles with overlapping coverage. For example, for the same part of triangle space, the provided triangles are (2, 3, 4.5) and (2.5, 3.5, 5.3), which have overlapping, but different coverage.

While overlapping is useful for various reasons, for example, as described below, it does increase the size of the library. When overlapping is provided, the reconstruction method used optionally takes the overlapping into account.

6. Reconstruction

After process 300 (FIG. 3) is repeated for as many gauges as desired, the measured affinities of gauges 400 to target 100 are optionally used to reconstruct a model of the spatial distribution of interaction areas 102. An exemplary method is described below.

In an exemplary (theoretical) mapping process for a particular target molecule, which uses a 75,000 gauge library, it is expected that about 400 of the gauges will bind to the target. Due to repetition of triangles in the library and/or due to the overlap in coverage of non-congruent triangles in the exemplary library, the number of real triangles defined by the target area and bound to by gauges is expected to be smaller. In one (theoretical) example, the number of "real" triangles that are defined by the target area and bound to by gauges is 100 different triangles.

Taking for example a 10-point pharmacophore, such a pharmacophore may include, for example, 10*9*8/6 triangles, which is 120 triangles. In some embodiments of the invention, not all of these triangles are identified, for example, due to high similarity between triangles (below distinguishing ability) or due to lack of binding (e.g., due to steric clashes). The 10 point structure can, of course be reconstructed with fewer than 100% of the triangles, especially of the missing triangles are missing randomly. For example, 50% of the triangles may be sufficient.

However, the actual situation is more forgiving. A typical pharmacophore may include 20 points, of which, typically only between 8 and 10 need to be identified in order to provide good binding. Thus, any substructure of the pharmacophore that includes 8-10 correct points can serve as a good starting point for drug generation. Fewer identified points can also be useful, for example as described below.

Although various methods may be used to reconstruct the layout, in an exemplary embodiment of the invention a two step method is used. First, the "real" triangles are estimated from the results of the assay, optionally using a clustering algorithm. Then, a suitable layout using the triangles is found, optionally using a scoring based search algorithm or a clustering algorithm. In other implementations, a single step or multiple step method may be used.

6.1 Triangle Extraction

In an exemplary embodiment of the invention, this step of the process has two parts, however, in other implementations, this step has a single part or more than two parts. One part is determining which triangle measures matched. This part may be less than trivial, for example, due to the fact that each gauge includes multiple triangles. However, the repetition of triangles between gauges may assist in differentiation. Another, optional, part of the process is determining the real distances involved, rather than those defined by a measure. For example, a real distance between two moieties may be 4.3 angstrom, while binding triangle measures have distances of 4 and 5 angstrom. In some embodiments of the invention, it is desirable to estimate the real distance, 4.3 angstrom, from the binding results. Optionally, this is provided by the overlap in coverage of the different triangle measures.

In an exemplary embodiment of the invention, the two parts of the process are provided in a single compound process, for example using clustering. Alternatively a two step method may be used. Optionally, an iterative method is used with an estimate of which measures bound being used to estimate real distances and the real distances being used to improve the earlier estimate of which measures bound.

Figure 5:
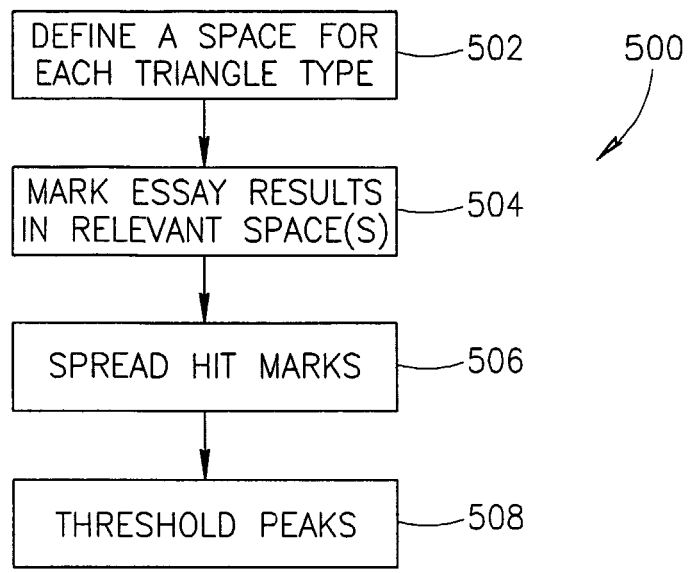
FIG. 5 is a flowchart of a method of determining which triangles did bind to a target, in accordance with an exemplary embodiment of the invention.

FIG. 5 is a flowchart of a method 500 of determining which triangles did bind to a target, in accordance with an exemplary embodiment of the invention.

At 502, a space is defined for each type of triangle (defined by the moieties of the triangle). Each such space has three dimensions, each one representing a length of a side of the triangle.

At 504, a notation is made in a space at a location $\{x,y,z\}$ if a gauge including that type of triangle with sides of lengths $\{x,y,z\}$ was shown to bind to the target. It should be noted that for two different scaffolds, exactly matching triangles may be difficult to generate. Instead, the triangles may be nearly matching, for example having slightly different lengths of sides.

In an exemplary embodiment of the invention, the assay results are used as a binary input, there is either a bond or not. Alternatively, for example if conformal changes are observed or there is a measure of activity and/or bonding, the bond strength may be represented by a continuous or multi-step amplitude, using a hit notation.

In an exemplary embodiment of the invention, if a single gauge includes multiple triangles, a hit is marked in each one of the relevant spaces. Alternatively or additionally, if a single triangle can match two different type triangles, for example due to overlap between moiety affinity, it is also marked in multiple spaces. Optionally, the amplitude of the marking is normalized to the number of spaces that are marked by the gauge. Alternatively or additionally, a different amplitude is provided in each space, responsive to an a priori probability of bonding.

At 506, the hits notations are replaced by a spatial spread function. In an exemplary embodiment of the invention, the spread function represents the probability of that triangle forming a bond at different distances represented by the spread. Alternatively or additionally, the spreading is between spaces, for example, if two moieties overlap in their affinities.

Alternatively, the hit indication is provided originally as a spreading function.

In an exemplary embodiment of the invention, the spreading is a defined as $$f = e^{-\frac{\Delta x^2}{\sigma x^2}}$$

where $\Delta x$ is the difference between the lengths of the sides and $\sigma x$ is a value representing the difficulty in bending the molecule so that it can perform the bond. In an exemplary embodiment of the invention, $\sigma x$ is a function of x, for example $\sigma x = a\sqrt{x}$. In an exemplary application, parameter "a" is 1.414. Possibly, the spread function is non-uniform in space, for example, to reflect non-uniform characteristics of the bond. Optionally, at least some of the spreading functions are derived empirically, by binding gauges having controlled distances between bonds, with targets having known models. Alternatively or additionally, such empirical testing is used for other purposes, for example, to determine flexibility in bond length, multiple chemical affinity of moieties and/or symmetry of the spreading function. Optionally, targets are classified according to their flexibility as well. Optionally, in an iterative process, once a model is estimated, a flexibility of the target is estimated and/or decided, for example form a table, and used to correct the spreading function used.

The spread hits are then combined, for example by addition, and peaks are found in the result (508). In an exemplary embodiment of the invention, peaks are selected based on their shape. Alternatively or additionally, peaks are selected based on their amplitude passing a threshold. This threshold can represent, for example, the number of triangles that need to bind, to indicate a possible match. The threshold may be the same for all spaces or it may be different. Optionally, the threshold and/or decision making method is selected based on the clustering statistics, for example from a table of previous empirical results. Alternatively or additionally, the threshold is selected so that a minimum number of matches be found. Optionally, if there is a large number of sub-threshold matches, a different gauge set is used for the binding process.

It is noted that in some embodiments of the invention, for any given triplet of binding points there are generally about 12 triangles, or more, that can be expected to bind. For example, both a shorter side and a longer side are expected to bond to a pair of binding locations having an intermediate distance between them. In addition, each triangle type can appear multiple times, for example, three times in the set. In some sets, each (or some) triangle point in the triangle space is covered by 24 triangles—8 triangle designs that have longer and shorter sides in various combinations, times 3, if each triangle is provided three times. Additional overlap may be provided by ambiguous moieties.

Optionally, by analyzing correlation between spaces and gauges, some four-point geometrical matching (or higher) may be found as well.

6.2 Layout Configuration Reconstruction

Figure 6A:
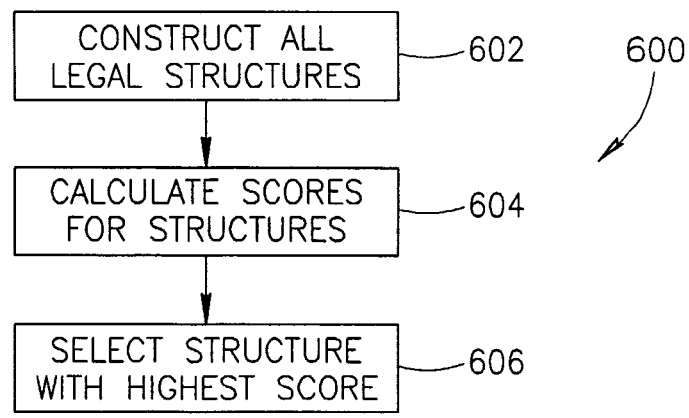
FIG. 6A is a flowchart of a method of determining a spatial layout of binding locations from the results of the method of FIG. 5, in accordance with an exemplary embodiment of the invention.

FIG. 6A is a flowchart of a method 600 of determining a spatial layout of binding locations from the results of the method of FIG. 5, in accordance with an exemplary embodiment of the invention. In an exemplary embodiment of the invention, the method comprises constructing all the configurations (e.g., three dimensional shapes) that can be constructed from the identified triangles and ranking the configurations using a scoring method, ultimately selecting the configuration with a highest score.

At 602, all the possible configurations that can be constructed from the triangles found in FIG. 5, are constructed. Alternatively to building computer models of all the possible configurations, in an exemplary embodiment of the invention, the configurations are generated ad hoc. For example, in conjunction with the scoring method described below, a configuration may be constructed, or its construction advanced, only if it is likely to have a useful score. For example, once a configuration solution has a score below the highest found so far, that lower solution is ignored.

In an exemplary embodiment of the invention, the construction method is by building up a structure piece by piece. For example, a triangle is added to an existing configuration only if has a side length and/or moieties that match a side length with a pair of moieties on the structure. A threshold of size difference may be defined for allowing the matching of two sides. Alternatively or additionally, a threshold of matching between moieties may be defined. Optionally, the moieties are required to match at the ends of the matching side, or to have an overlapping chemical behavior. Such thresholds may depend on the length and/or types of moieties and/or other properties of the gauges and/or the target. It is noted that a first gauge may bind to a particular binding location using a different binding method from a second gauge, as long as the binding location supports both binding methods.

In an exemplary embodiment of the invention, the construction of a configuration is by sequentially selecting a triangle from the list of available (bond) triangles, until all the triangles are used at least once. Used triangles may remain in the list for repeated use. Alternatively, the configuration may be built up using modules, each of which is constructed from sub-modules, and, ultimately, triangles.

At 604, a score is calculated for each configuration. Such a score is optionally a heuristic value indicating the reasonableness of the assay results being derived from the target having the configuration. Various scoring methods may be used. In an exemplary embodiment of the invention, the scoring method is based on the particular linking together of triangles in the configuration and/or on the probability of the triangles themselves being correct in the first place.

In an exemplary embodiment of the invention, the score is a product of scores for each shared triangle side. In an exemplary embodiment of the invention, the score for a triangle side that is shared between two triangles is an estimated probability of the two sides of the two triangles binding to a same pair of binding locations. In an exemplary embodiment of the invention, the score is the product of the above spreading function, for the x, y and z axes. Alternatively or additionally, other, simpler scores, may be used, for example, based only on the difference in sizes of the sides.

In an exemplary embodiment of the invention, the score does not depend on the lack of a triangle. For example, if a generated configuration includes a three point configuration for which no suitable gauge matched, it is not assumed that the configuration is incorrect, nor is the score reduced. Alternatively, the score may be reduced responsive to the existence of triangles that are found in a configuration and not found on any matching gauge, for example, based on their count.

Alternatively or additionally, some configurations may be ruled out based on heuristics, for example rules that describe what the layout typically looks like. Alternatively or additionally, prior information is used to rule out some configurations, for example, a partial model or knowledge of a molecule that binds well to the target.

At 606, the structure with the highest score is selected as the map layout of the binding locations for the target. As noted above, 602-606 may be carried out as an iterative search and construction method, for example with structures being built ad hoc as the search progresses and indicates a certain structure has a score above a threshold (and so will its dependents). Many suitable search methods are known in the art, for example, in the art of graph search and in the art of searching game trees (e.g., for chess playing programs).

6.3 Reconstruction Variations

In an exemplary embodiment of the invention, a target may have several active areas. In an exemplary embodiment of the invention, the reconstruction is allowed to recreate a disjoint configuration structure, with each disjoint part representing a map of one target area. Optionally, such a reconstruction may be required even for a single active area, if enough triangles (e.g. gauge moieties) that interconnect the disjoint parts failed to bind (for various reasons) and/or were not available in the gauge set used, so that a continuous structure cannot be reconstructed from the triangles that did match.

Optionally, the above reconstruction allows a triangle to appear only once in a reconstructed configuration. Even if a triangle actually appears twice (or more) in the real configuration, the redundancy of similar triangles will generally still enable the structure to be reconstructed. Alternatively or additionally, a triangle is allowed to appear more than once, however, this may affect the score, for example, reducing it. Alternatively, an iterative experimental approach, as described below, is used, to block part of the target (e.g., with a suitable antibody or small molecule drug) and see if the triangle still matches.

Optionally, user intervention is allowed, for example, for viewing the final structure or several candidate structures. For example, if a determination cannot be made, a human may be requested to select among options, force certain matches and/or configuration parts and/or to remove certain possibilities from consideration, based on, for example human experience and judgment and/or additional information about the target of various types.

It should be noted that one possibly output of the clustering and/or shape reconstruction methods is an input to an interactive process and/or to further drug development. For example, the application of the above methods can show where more exact data is lacking for forming a complete result and/or where there are ambiguities between possible solutions.

It should be noted that the resulting structure may have a mirror (e.g., symmetry) ambiguity, due to the sole use of triangles. Optionally, this ambiguity is solved by using at least one 4- or higher-point measure, optionally constructed or selected to bind in only one of the possibilities. Alternatively or additionally, the effect of steric clashes is used to distinguish between the two possibilities. Alternatively or additionally, prior information is used to distinguish between them.

6.4 Alternative Reconstruction Method

Figure 6B:
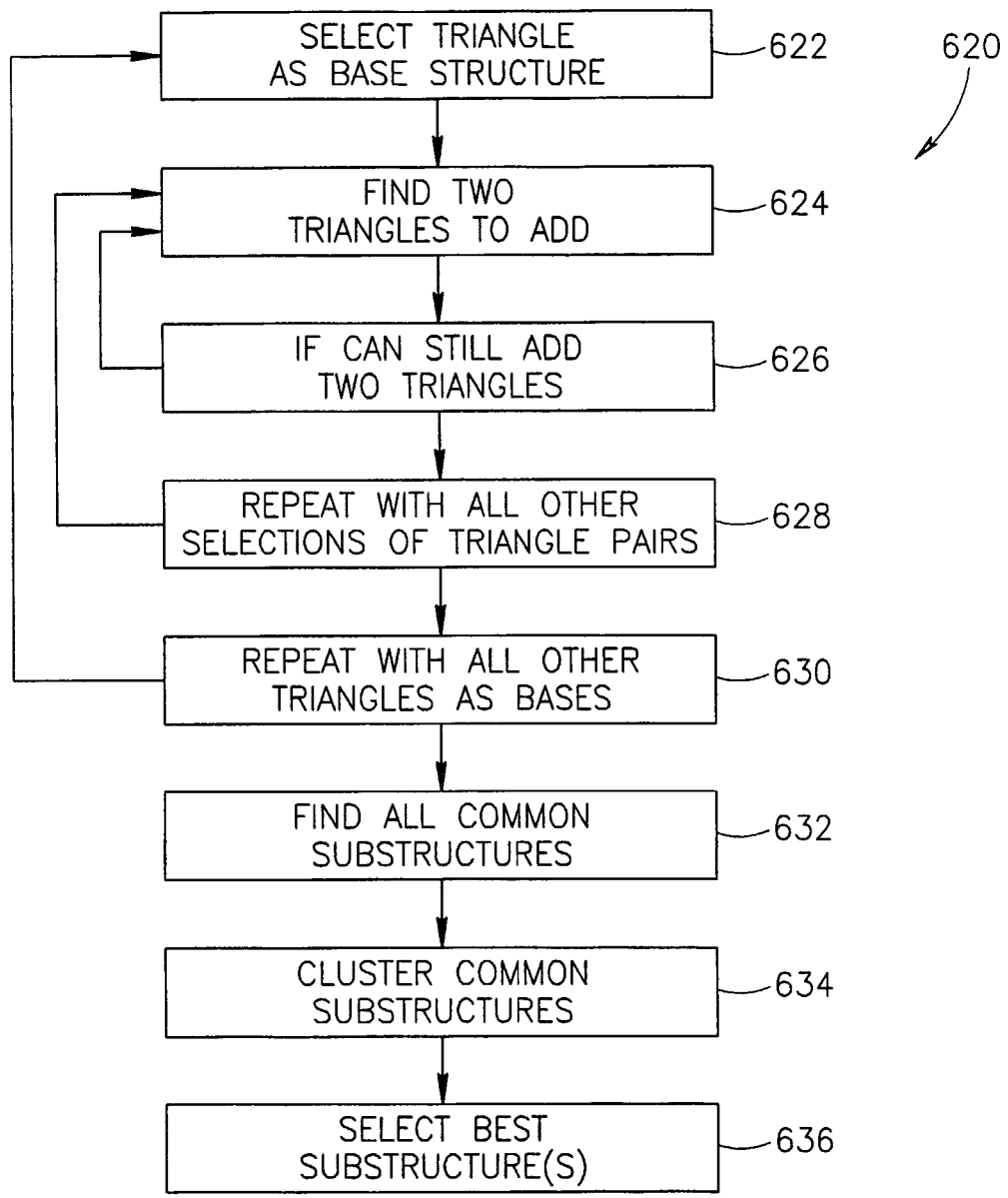
FIG. 6B is a flowchart of an alternative method of determining a spatial layout of binding locations from the results of the method of FIG. 5, in accordance with an exemplary embodiment of the invention.

FIG. 6B is a flowchart 620 of an alternative reconstruction method, using clustering for shape reconstruction, in accordance with an exemplary embodiment of the invention.

At 622, a triangle is selected from the set of found triangles, that were found to bind in the assay and clustering of FIG. 5. This triangle is used as a base for constructing a structure.

At 624, a pair of triangles is selected from the remaining found triangles, such that the two triangles share a side with each other and each triangle also shares a side with a part of the structure (e.g., which two sides of the structure may or may not be sides of a same triangle, depending, for example on the implementation). When the triangle pair is added to the structure the structure grows by one point in space.

624 is repeated (626) until no triangle pairs can be added. This completes one potential structure.

Often, there are several possible choices to make at 624, for example, for selecting the triangle pair and/or for deciding where to add them. At 628, a tree of possible structures is performed, by repeating 624 and 626 for each possible choice of triangle pairs and their location. This process may be done, a priori, for example, by spawning multiple threads each time multiple triangle pairs are available for selection and/or each time such pairs may be attached at different locations.

At 630, 622-628 are repeated by selecting all possible triangles as bases, in turn (or in parallel). Alternatively, other methods of generating all the possible structures from the triangles may be used. Optionally, a pruning method is used, for example, if a structure is clearly unsuitable or unable to utilize a significant percentage of the triangles (e.g., 30%, 50%, 70% or any smaller, intermediate or greater value), the structure is dropped. Generally, the greater the number of triangles allowed to be ignored, the easier it will be to provide a structure (e.g., even under noisy conditions). However, the structure will be less constrained by the assay results and may be less dependable.

At 632, all substructures found in the generated potential structures. Optionally, only some of the substructures are found, for example, only the largest or only those above a certain size. In an exemplary embodiment of the invention, the method applied is a maximum likelihood algorithm for finding a most likely structure.

At 634, these substructures are clustered, with each point representing a structure in which the substructure is found. In an exemplary embodiment of the invention, the clustering space is defined per triangle type (e.g., type of moieties on the triangle) and the space is spanned by the sides of the triangles. Thus, for example, a 10 point sub-structure of a 20 point structure is marked in a space that includes the same number of moiety types as the sub-structure, with a location in that space determined by the three Cartesian locations of each of the points (e.g., 30 dimensions for a 10 point sub-structure). Various orientations are optionally dealt with by selecting a certain triangle to be a base triangle having an orientation. Alternatively or additionally, the space is marked with structures in a rotationally symmetric manner (or thus analyzed) so that the results from different orientations may be compared. An exemplary algorithm is described in R. Nussinov, H. J. Wolfson, "Efficient Detection of Three Dimensional Structural Motifs in Biological Macromolecules by Computer Vision Techniques", PNAS, volume 88, pp. 10495-10499, December 1991, the disclosure of which is incorporated herein by reference.

At 636, a best substructure is selected. It is assumed that if a substructure is common enough and large enough it is both correct and useful. In an exemplary embodiment of the invention, a thresholding is applied to select only those substructures with structures and clusters over a minimum size. Other selection methods may be used as well, for example scoring, for example based on accumulated score of matching up pairs of triangles (this matching up may be thresholded during constructions, for example using a preset threshold).

Alternatively, other methods of finding a large common substructure are used.

It should be noted that while the clustering method may generate a structure that does not use all the triangles and is not complete, a complete map of the pharmacophore is not essential for many embodiments of the invention, for example for lead generation and finding.

7. Analysis 7.1 Overview

The above process of measuring and reconstructing a target area can be used to provide a wide range of information. The quality of the information and its type can be of varying kinds. Following are exemplary types of parameters which may be used to classify such information:

(a) Completeness. The information may be complete or partial, for example, a complete target area model or a model of only part of an area.

(b) Factual or statistical. An example of factual information is an exact model. An example of statistical information is a set of relative probabilities for a set of possible models.

(c) Independence. Information may be independent of other information, for example, being an exact model or it may be dependent, for example a parameteric model whose exact value depends on additional information. In addition, information derived using the above methods may be used as partial information for a different process.

(d) Substantiation. The information may be supported by other information or it may stand on its own or even be in conflict with other information.

(e) Positiveness. The information may be positive, in that it indicates what exists if is desirable, or negative, in that it can be used primarily to knock out certain possibilities.

While the information garnered may be about the binding locations, in some case, the information is regarding the geometry of the target at non binding locations as well. As will be described below, for example, a geometrical structure can also affect the usefulness of a drug lead.

In some embodiments of the invention the analysis is used to acquire information about the gauges themselves, for example, their relative binding affinity, and/or their chemical behavior (e.g., pH dependencies). Such information may be general or it may be for groups of targets, for example, different for different families of proteins and the same within a family.

As can be appreciated, such a widely varying range of information is amenable to many methods of analysis, some of which are described below and to many applications, some of which are also described below. In particular, some exemplary analysis methods are directed to garnering further information about the target area and for error detection and analysis and some exemplary applications are integrated as part of a drug discovery process.

In some case, the results of the analysis are integrated into the reconstruction as geometrical and/or chemical information. Alternatively or additionally, the information is associated with the reconstruction and/or the target, for example, in a manner similar to that used for drug leads. This manner generally depends on the type of database used for storing information.

7.2 Reconstruction Verification

In an exemplary embodiment of the invention, the error size and/or type of the layout is determined. In one example, the reconstructed layout is analyzed to generate theoretical binding values for the gauge set used. Differences between these theoretical binding values and actual binding values may be used to indicate parts of the layout which are not exact and/or to indicate a degree of inaccuracy of the layout and/or the reconstruction process as a whole.

Alternatively or additionally, physical verification is applied, for example, by applying an additional testing method and/or assay library to select between alternatives or for verification.

7.3 Binding Strength

In an exemplary embodiment of the invention, the generated layout is analyzed to estimate the relative binding strength of binding points in the target area. In an exemplary embodiment of the invention, the reconstructed layout is modeled and theoretical binding values for the gauge set are calculated. Variation in the actual binding values may be partly caused by a reduced or increased affinity of target area. Such estimation is generally statistical in nature since there are many variables that affect binding probability. However, it is expected that if a bond length and type are known and the exact positioning of the gauge in the target area can be determined (e.g., and its energetic consequences), than at least a statistical analysis of binding strength may be provided. Optionally, a baseline is provided by analyzing molecules with known behaviors, or by comparing the binding of different, but similar gauge-triangles.

7.4 Inter-Bond Interactions

In an exemplary embodiment of the invention, the analysis is used to determine an interaction between the binding of different binding points. For example, such an analysis can compare the contribution of a binding point to the binding of a certain gauge, as compared to what is expected (e.g., based on energy and other calculations) and/or as compared to the apparent contribution of that binding point to the binding of a different gauge. This may indicate, for example, the effect of the bonding to one interaction location on the affinity of a neighboring interaction location. Optionally such interactions are estimated and/or modeled using a model of electronic charge distribution in the target.

7.5 Geometric Analysis

For some purposes, and to some degree of accuracy, the determined layout can be considered to be a cast of the target area. In an exemplary embodiment of the invention, the geometry of the target area is analyzed. Additional information may be provided by determining which gauges did not bind or bound with a lower affinity (which, if the binding geometry was similar is assumed, in some embodiments of the invention, to be due to steric clashes). This may assist in further defining the geometry of the target area. It should be noted that some steric clashes can be predicted from the geometry of the layout. Any failed binding which has no other apparent reason and should have matched the determined geometry, may be assumed to result from a projection of matter that does not define a noticeable binding point. This is described in more detail below.

In an exemplary embodiment of the invention, the geometric analysis is used to determine a size of entry hole into area 104 (e.g., where arrow 400 is shown in FIG. 4B). A small hole and/or certain moieties at the hole entrance may rule out the possibility of certain drug sizes and/or types. Alternatively or additionally, the geometrical analysis is used for classifying the target, for example, based on the size of substrate that it might work on. In an exemplary embodiment of the invention, geometrical analysis (e.g., for substrate determination) is supported by chemical analysis of the moieties in target area 104. Determination of the geometry may also be useful in deciding what marking methods of small molecules and/or gauges may work (e.g., not to use large florescent markers, if the entry hole is small).

It should be appreciated that in some cases it may be easier to reconstruct the geometry of a target area, rather than its chemical binding pattern or vice versa.

7.6 Determination of Steric Clashes

In an exemplary embodiment of the invention, steric clashes are detected in the analysis process and/or used to provide additional geometric and/or chemical information about the target. In an exemplary embodiment of the invention, steric clashes during the binding process are determined by comparing the affinities of different gauges with same triangles. This comparison optionally takes into account one or more of entry hole size, chemical behavior of the gauge, degree of matching to the binding geometry and/or other binding locations. Steric clashes are, for example, caused when the proximity or potential overlap of the gauge and the target molecule reduce the binding affinity.

As the shape of the gauges is known and, in some embodiments of the invention relatively rigid, steric clashes may be expected to result from the non-participating moieties of the gauge and/or the scaffold itself.

In an exemplary embodiment of the invention, the steric clashes are used to generate a map of locations near the target that interfere with gauge atoms, thus possibly indicating occupied (e.g., by atoms, electric fields) parts of the target, which do not, apparently cause a binding interaction with any gauge, to a noticeable degree.

In an exemplary embodiment of the invention, the map is used to provide further information about the shape of the active area in target 100. Alternatively or additionally, the map is used for assisting in drug development, for example, by filtering out potential drugs that would have the same steric clashes. Optionally, some level of filtering can be achieved simply by matching the drug geometry to the geometry of gauges that should have, but did not, bind well.

Geometrical and/or chemical affinity analysis may also be used to determine a shape of the natural substrate of the target, for example, if it is not clearly known and/or to determine which part of the substrate is engaged by area 104.

7.7 Identification of Control Areas

In an exemplary embodiment of the invention, the binding results and/or reconstruction are analyzed to detect one or more control area of the target. Generally, control areas do not bind to the "main" substrate of the target, instead binding to a separate hormone or other modifier molecule. This secondary binding typically affects the binding behavior of the target area.

In an exemplary embodiment of the invention, control areas are identified by their size and by their being disjoint from a main target area layout reconstruction. Alternatively or additionally, control areas are identified by testing bindings with pairs of gauges (or in the presence of various molecules, optionally selected a-priori or after the detection of the presence of control areas) to detect intra-gauge binding dependence. Alternatively or additionally, control areas are identified from the shape of the reconstructed layout. Alternatively or additionally, the presence of control areas is detected by there being left-over gauge bindings that are not needed and/or do not fit in the reconstruction.

In an exemplary embodiment of the invention, depending on whether binding to a control area is desirable or undesirable, the differential identification of control areas may be used for screening potential drug leads.

7.8 Other Map Analysis

The map or model of the target may be analyzed to yield other information, in accordance with exemplary embodiments of the invention. For example, as noted above, the distance of a binding point from a control area or active area can affect the type of drug developed. For example, a drug that binds in the control area may have an enhancing effect on the target, for example that of an agonist. A molecule that binds near the control area or active area, or inside the active area, may cause the target to be less sensitive to signals and/or incapable of acting, e.g., an antagonistic effect. Thus, in an exemplary embodiment of the invention, the location of the binding area on the target is used to assist in determining what sort of therapeutic effect to expect from a developed drug. For example, a binding area near a target area may indicate a drug whose tail blocks access to the target area.

In another example, binding areas that are outside the target area, can be used to enhance a drug design. A drug may be constructed (or discovered) to include parts that bind in the target area and parts that bind outside the target area. The combination of binding areas provides a binding strength greater than that provided individually by each area, while the part of the molecule bound in the target area can provide the desired therapeutic effect. Alternatively or additionally, a molecule that binds to two separate areas may cause a conformal change or prevent such a change in the target molecule.

8. Use In Drug Discovery Processes

8.1 Overview

Drug discovery is a very long and expensive process whereby drugs for curing diseases are found. The process starts with identifying a target to be affected by the drug, finding potential drugs that affect the target and then determining which, if any of the potential drugs is safe and dependable. Often, no suitable drug is found and one of the drug candidates is modified in various ways in an attempt to make it more suitable. One cause of difficulty of the drug discovery process is the difficulty in knowing what molecule will affect the target. As will be described below, in some embodiments of the invention, the methods of the invention are used to at least partly reduce this difficulty. Another cause for difficulty is the many unexpected side effects of potential drugs which render them unsuitable and/or unpredictable. Again, as described below, some methods of the invention may be used to at least partly reduce this difficulty.

Typically, drug discovery methods try to answer two questions. One, is there/what is a drug molecule that binds strongly and affects a target molecule. Two, how to ensure that these drug molecules have the proper ADMET profile (ADMET stands for Absorption Distribution Metabolism Excretion Toxicity) which translates into success in clinical trials. In an exemplary embodiment of the invention, the method, materials and/or apparatus described herein are used to select, design and/or aim towards potential drug molecules that have chemical characteristics that are known or believed to improve the ADMET profile. Lipinski rules are an example. It should be appreciated that by knowing which parts of the molecule are relevant to binding and which are not (as provided, for example by comparing a molecule to a model of the target), one can more easily modify (or plan in advance) potential drug lead compounds to bind tightly and/or meet any well defined qualities.

In general, the above methods and especially the various models of the target can be useful in selecting molecules or research methods that conform to the map and rejecting those that do not. Other uses of the above measurement process are also described below, for example using an additional step of mapping to check a theory. As can be expected, different methods (existing and new) of drug discovery may be affected differently by the use of exemplary embodiments of the invention.

It should be appreciated that various embodiments of the invention may be implemented in an automatic manner. However, due to the great cost considerations, in some embodiments of the invention, the application is semi-automatic, for example, using the methods to change the discovery process, for example, by adding a filtering step or a candidate generation step, while still allowing for the use of human judgment, for example, deciding if certain generalized and vague criteria are met. In some case, the entire process is controlled using a human intelligence, with various ones of the steps, for example, mapping and/or rejecting leads are performed manually. Changing thresholds and redoing a step is an example of a decision which may be reserved for a human, for example.

8.2 Drug Generation

One relatively new type of drug discovery is actually drug generation, a new molecule is designed to have a desired function. In an exemplary embodiment of the invention, the above chemical and/or geometrical map of the target are used to assist this process. For example synthesis may be assisted by showing what shape an active part of the drug must have (or limit the range of possible shapes).

In an exemplary embodiment of the invention, drug synthesis comprises taking gauges from the library and modifying them, for example replacing moieties, so that they better match the target. In some cases, the replacement moieties have the same affinity but a different binding strength, for example, selecting NH2 or OH for a Hydrogen bond donor, and choosing an optimal size for a for hydrophobic moiety. It should be appreciated that an strength based classification of moieties may also used in the library construction, for example, providing multiple strengths of Hydrogen donors or multiple sizes or hydrophobic moieties. One possible use is to achieve a better uniformity of binding strength between moieties. Another is to provide a library with higher accuracy.

In an exemplary embodiment of the invention, scaffolds and/or molecule parts for use in drug synthesis are constructed as a result of target mapping processes. For example, by analyzing target geometries, a set of scaffolds that spans (with attached moieties) most of the target spaces may be found. The specific scaffolds may be, for example, constructed from sub-scaffolds or be selected from libraries of chemicals, for example using a process similar to that described below for finding gauges in libraries. Sets of moieties or moiety clusters may be selected, for example based on a statistical analysis of how moieties are clustered together in a family of targets or in a general list of targets. Optionally, the statistics are collected over the mapping of many targets. Optionally, the targets are selected to be exemplary for expected future targets. It is expected of course, that in some cases a perfect drug will not be generated using such synthesis methods, but the synthesized drug may be a good starting point for drug enhancement.

8.3 Lead Generation

Often simpler than drug synthesis is lead generation, in which a lead, which is not expected to be a suitable drug, is generated and then enhanced and modified using processes known in the art. In an exemplary embodiment of the invention, the map is used to describe a potential molecule, for synthesis as a drug lead. In an exemplary embodiment of the invention, the map is used as a set of constraints and a search is made to find a molecule meeting the constraints. Additional constraints can be, for example, known synthesis methods, a base molecule form being used as a starting point. An exemplary software which may be used is LUDI sold by MSI (USA). The LUDI system operates by attaching basic chemical components together in order to obtain a required pharmacophore-match or other molecule.

The potential molecule may then be synthesized and developed into a drug, as is well known in the art.

In an alternative method, a potential drug molecule may be constructed by linking together molecules of the gauge library or other molecules having suitable moieties or structure, so that the resulting molecule has a higher affinity than a single gauge. This molecule may then be optimized, for example by removing unnecessary moieties and/or adding moieties to provide various desired properties. Optionally, the gauges are attached using a scaffold, rather than directly to each other. Optionally, by analyzing what gauges link (e.g., using clustering), it is possible to achieve a better estimate of a desired size and/or chemical properties of the fragments to be linked. For example, the selection of two gauges to be linked together may be based on actual binding of additional (or other gauges), for example, 2, 4, 5, 6 or more gauges. For each such set of gauges that bind, a best gauge or other molecule is selected for the linking. Alternatively or additionally, higher specificity gauges are used to determine which of the several possible triangle measures of a gauge actually bound. Such higher specificity gauges may be generated, for example, by removing moieties from existing gauges (or generating such gauges using any method known in the art). Such higher specificity gauges may also be used for other embodiments of the invention, for example, to improve clustering statistics. Generally, however, due to the relative large number of possible such gauges, they are used when there is a way to limit the range of possible triangles. Alternatively, the large number of more specific gauges, for example, gauges with 1, 2, 3 or 4 triangles are created for use as a library or as part of a library of gauges.

In an exemplary embodiment of the invention, knowledge of the structure of the target is used to correctly locate the linker and/or chose a suitable linker that does not suffer steric clashes with the target.

In an exemplary embodiment of the invention, the gauges are selected for linking without actually constructing a model. Instead, the actually binding gauges are selected and linked together. Alternatively, the model is used to decide which gauges to link and how to link them. Such a model may also be used in other lead-linking schemes, for example, as described in the background, to guide the choice of which fragments to link, what length of link to provide, where to attach and/or at what orientation to attach. Optionally, the lead is constructed in steps from the gauges, and each step is tested to see if it meets its expected behavior.

Alternatively or additionally, instead of using a model as provided herein, a different type of model is used, for example a model of the target bound to a gauge, for example generated using X-ray Crystallography and/or NMR. This model, for example, generated once for each of a plurality of gauges may be used to decide what linking distance and type to provide when creating a lead from gauges. Alternatively or additionally, a new molecule may be designed and constructed to have binding points at some or all of the locations shown by the crystallography model to bind, for example, for two, three or more gauges. In general, this type of method assumes that once the configuration of the bound target-gauge pair is known, an exact model may be unnecessary, since actual conformance information is available. Alternatively or additional, as noted herein, a measurement may be made of the bond target.

8.4 Lead Description

In an exemplary embodiment of the invention, the map is used to describe one or more profiles of molecules which would be expected to have an effect on the target. In an exemplary embodiment of the invention, the profiles generated take into account one or more of:

(a) geometry of interaction location layout;
(b) affinity of interaction locations;
(c) size of entrance into the active area(s);
(d) identification of potential control area(s);
(e) synthesizability; and
(f) expandability, e.g., that additional moieties can be attached.

Typically, a molecule requires at least five or six bonds to form a strong enough docking in the target, so as to affect the a target at nano-Molar concentrations. The exact number may depend, for example, on the affinity of the interaction locations. A single target will generally provide a large number of possible profiles. These profiles may be matched against libraries, for example, using methods known in the art.

In an exemplary embodiment of the invention, the profiles are generated using a format that is matched for a particular search software and/or library data structure. In an exemplary embodiment of the invention, searching by pharmacophore is provided, for example as known in ISIS base from MDL (when searching 3D databases).

8.5 Lead Search

In an exemplary embodiment of the invention, the map is used to search through a library of known molecules, for a possible match. Possibly, the map is used in place of analytical models of the target, in known virtual scanning techniques. In an exemplary embodiment of the invention, the library is pre-processed so that molecules in the library are described in terms of the moieties and geometries of the layout model and/or the gauges used in measuring the target. Alternatively or additionally, an existing library is pre-processed to yield a gauge-compatible description of its contents, for example, each molecule being defined as a parametric model based on measurement gauges. It should be noted that this description may not be a one-to-one mapping, for example, a same molecule may be described using two different sets of moieties, as there is some overlap between moieties chemical behavior.

In an exemplary embodiment of the invention, potential leads are identified based on them including or being able to include a large number of moieties at the required positions, as indicated by the map. In one example, a search is made for 3 point or higher (e.g., 4, 5, 6, 7 or more) matches. In another example, each molecule in a library is tested for the number of moieties it includes in the required positions and for the availability of attachment points to attach missing moieties. In an exemplary embodiment of the invention, the missing moieties are added one by one until a suitable drug lead (e.g., strong enough binding) is created.

An exemplary search is performed by ISIS base, by MDL.

One possible type of search comprises going over all available 3D structures in which to search, breaking them down into sets and/or subsets of pharmacophore points and looking for a fit within a tolerance range defined in a query.

8.6 Lead Rejection

In an exemplary embodiment of the invention, the results of the above methods are used in rejecting leads that otherwise appear suitable. In one example, a lead (or family of leads) is rejected if the above models imply a lack of binding and/or steric clashes. In another example, an assumption is made that if a lead is suitable, a gauge corresponding to a triangle (or other number) of moieties on the lead is expected to bind to the target. If no such gauge is found or an analysis of the data implies that the probability of a triangular binding of the three moieties in a gauge is unlikely to have happened, the lead is rejected, or subjected to additional scrutiny. Alternatively or additionally, a matching of a certain gauge may also indicate the lead is unsuitable.

In one example, workers in the field can use the information provided to determine if a certain lead is likely to be capable of being optimized (reasonably). For example, one expects that by directly adding or removing specific moieties (e.g., what is often considered to be a main type of small changes in a molecule) affinity can be significantly improved (often at least 3-4 orders of magnitude are required). By knowing what the changes should be or could be (e.g., where additional points need to be added, which information may be provided by some embodiments of the invention) one can see if one specific lead can undergo the required changes, e.g. has putative attachment points in the right positions. Specific gauges (e.g., that bound) will indicate what the required changes could be.

These methods may also be used to reject certain lead modifications provided during lead enhancement processes.

It should be noted that some lead rejection methods do not require all possible gauges and/or triangle measures to be available. Rather, even a partial library is useful, for example for rejecting certain leads. In one example, a partially-spanning library is used generating a partial map (e.g., part of space, disjoint and/or not all binding points), which can be used to reject some leads and/or indicate potential suitability of others and for search. Further, even the binding or failure of binding of a single gauge may indicate suitability or lack of suitability of a lead. Generally, due to the uncertainty involved in all chemical processes at this time, decisions are not made on the basis of a single binding assay.

8.7 Targeted Mapping

In some embodiments of the invention, gauge binding is assayed during the discovery process. In one example, the binding is used to test a theory or an assumption regarding the leads. For example, if a certain lead is expected to be suitable, at least one of several particular gauges may be expected to bind. Leads may be ranked, for example, based on how well such targeted binding is. Alternatively or additionally, a part of the layout may be remapped as a result of the discovery process. For example, the discovery process may indicate conflicting evidence of the layout structure. In another example, a higher resolution mapping of part of the layout may be required, for example, to more exactly determine the distance between two moieties. In some cases, instead of assaying with a full set of gauges, gauges are selected based on them being most likely to bind (or not) to the particular desired parts of the layout. For example, if the distance between two points on the layout needs to be determined, gauges that are less likely to bind at other points of the layout are selected. In another example, the moieties used are more specific, for example, having a more limited repertoire of chemical behavior and/or have a greater directionality. This may require using a different scaffold. Possibly the gauges used for such remapping have fewer triangles per gauges, for example between one and three, to reduce unexpected binding probability. Alternatively or additionally, gauges are selected so that steric clashes prevent binding in undesired locations. In some cases, these gauges are not in the basic mapping library used for initially determining the layout. In some cases, the required gauges are synthesized ad hoc, rather than selected from an existing library.

8.8 Target Suitability Testing

In an exemplary embodiment of the invention, the map is used to determine the suitability of a target to be a target for a drug. A suitability value may be, for example binary or it may be graded (discrete or continuous). In some embodiments of the invention, a suitability value is not a scalar, for example, being a vector, with each element of the vector indicating a different aspect of suitability. A similar structure may be used to indicate suitability of leads and potential drugs.

One example of the use of target suitability testing is where there are multiple potential targets. For example, in some diseases, there is a possibility of selecting between a plurality of target proteins, or selecting different parts in the chain of protein synthesis (e.g., DNA transcription, protein-chain creation, protein folding, protein post-processing and protein deployment). Some of these potential targets may be unsuitable.

In an exemplary embodiment of the invention, the map can be analyzed to detect such suitability, for example, by rejecting targets with an active area that is too large (for some types of treatment). The size of the target area can be detected from the layout geometry. Alternatively or additionally, a target may be deemed unsuitable due to its having a too generally active (non-specific) target area, which can be determined, for example, by analyzing the specificity of the determined target layout. Alternatively or additionally, a target may be deemed unsuitable, because its active area that has very weak affinities (e.g., a large drug molecule with many binding points may be required). Alternatively or additionally, a target may be deemed unsuitable due to its similarity to a housekeeping protein. This similarity may be determined by comparing the layouts of the target with those of known housekeeping proteins. Similarity to any human protein may assist in determining potential side effects ahead of time. In lead grading, a lead may be evaluated based on a probability of its interfering with a housekeeping protein, which is optionally determined by checking the binding of a lead to model layouts of housekeeping proteins.

In an exemplary embodiment of the invention, a database of layouts of housekeeping proteins is provided. such a database may be provided using methods known in the art. Alternatively or additionally, at least part of the database is provided by systematically mapping housekeeping proteins. Alternatively or additionally, at least part of the database is provided by generating "worst case" target area geometries or a range of possible geometries for the active areas, based a knowledge of the structure of substrates that are acted on by the protein. Such a worst case target area may also be used as prior information to assist in deciding which of several reconstructions is correct.

8.9 Target Partitioning

In an exemplary embodiment of the invention, the map is used to identify parts of the target as being potential "exact" targets, and on which the drug discovery method can be focused. Although the target, as a whole, is what is being affected by the drug, it can be affected in many ways, for example, different drugs may block different parts of an active area. Alternatively or additionally, some drugs may cause conformal changes. Alternatively or additionally, some drugs may interact with control areas on the target. Alternatively or additionally, some drugs may be agonistic, while some antagonistic. Alternatively or additionally, some binding areas may be useful for staging (e.g., as a base for attaching molecules closer to a target area), rather than direct activity. Binding areas may be classified based on the type of effect that may be expected from a molecule binding to those areas. This classification may be, for example, manual. Alternatively or additionally, automatic classification may be provided, for example, based on target template structures (e.g., which indicated for a certain class of protein what each area of the protein might do).

Optionally, potential control areas that can change the target, are identified. Possibly, such control areas are identified based on a binding in a binding assay. Optionally, a model of the target is used to assess whether binding at the potential control location can cause conformal changes, for example, based on the proximity of interaction locations on different, adjacent parts of the protein.

In an exemplary embodiment of the invention, the active areas are segmented into different "exact targets" based on the sub-areas that have a potential for drug interaction, for example, based on their geometry. Alternatively or additionally, segmentation is based on selecting such sub-areas that are not common to similar sub-areas of housekeeping proteins (e.g., segmentation into special and common binding areas).

8.10 Drug and Lead Analysis and Enhancement

In an exemplary embodiment of the invention, the above layout is used for analyzing existing drugs or drug leads, for example, to assist in improving or reengineering the drug or in screening.

In an exemplary embodiment of the invention, the layout is used to determine which of a plurality of target areas on a target are interacting with the drug or which target from a plurality of possible targets are interacting with a given drug. This methodology may be used, for example, to analyze the effect of drugs whose operation method is not clear.

In another example, the drug is analyzed to determine which part of the drug binds to the target. This can serve as a basis of a process for modifying the drug, in which the binding parts of a drug are retained and other parts of the drug are modified. Alternatively or additionally, when modifying the drug, care is taken not to distort the active part of the drug so that it does not bind, or distort the drug as a whole so that steric clashes are caused.

It should be noted that a single drug may interact with two different targets in a desirable manner, each target interacting with different, possibly overlapping, parts of the drug. Such activity of a drug is optionally determined by comparing the drug structure to that of the targets.

In some cases, the exact spatial and chemical properties of the drug (or a protein substrate) are not known. However, by determining the layout of targets which bind to the drug, the spatial and chemical layout of the active part of the drug (or substrate) may be estimated.

In another example, the layout is used to determine the pharmaceutical activity of synthesis byproducts. When a drug is produced using a particular process, various byproducts are produced as well, some with a beneficial activity and some with a non-beneficial activity. In an exemplary embodiment of the invention, the structure of such byproducts is compared to target areas of the target and of housekeeping proteins in an attempt to estimate what side effects they might cause. A process for drug manufacture is optionally selected or rejected based on a thus-estimated activity of the byproducts, given that the type and amount of byproducts produced by a particular process can be determined. Alternatively or additionally, such comparison may be used to assist in improving a production method and/or in deciding which synthesis parameters to use. This testing may also be used for regulatory purposes, for example to approve or disapprove generic drugs.

8.11 Drug Selection

In many cases, there may be multiple drugs which can treat an illness. Knowledge of which target (and housekeeping proteins and/or other human proteins) is affected by a drug and how it interacts can be useful in selecting between alternative treatments, in preventing side effects, preventing or controlling drug-interactions and/or in selecting treatments for diseases that no exact drug has been selected for, for example exotic tropical diseases and some viral diseases.

In an exemplary embodiment of the invention, the layout of a target is used to select which of a plurality of available drugs or drug leads appears to be most suitable for interacting with a the target. In the case of drugs, this may allow selecting alternative treatment protocols. Also, in some cases, knowledge of the interaction method will assist in selecting those times and/or associated protocols and/or drug combinations at which the drug is most effective and/or has minimal side effects.

Alternatively or additionally, drugs may be designed to interact with multiple targets. For example, a lead that interacts with multiple targets (e.g., of a same or different disease or syndrome) or target area portions may be awarded a higher scoring for further processing that other leads.

A possibly related use is the finding of a new use for an old drug and/or assisting in determining how to modify an old drug for a new use. For example, when searching for leads that match a template, a search may also be made through databases of drugs, to see which drug has a structure that is prophesied by the modeling process to provide good binding. Existing drugs, in general, have the other properties (AD-MET).

8.12 Drug Enhancement

As noted above, knowledge of the interaction method and/or problems of interaction with a target area, can assist in modifying a lead to become a drug. Alternatively or additionally, such knowledge may be put to use in enhancing an existing drug and/or modifying a drug to interact with a target related to an existing target. By comparing the layouts of the two targets, for example, possibly useful changes in a drug may be determined. Alternatively or additionally, the layout of the target area may be used to assess problems with the binding of the drug to the target (e.g., too strongly or too weakly) and/or determine the effect of modification of the drug on such binding behavior. In an exemplary embodiment of the invention, the potential drug when bound is assessed against the model, to determine if a moiety exists that can be theoretically added, which will bind to another point in a binding area.

Alternatively or additionally, drug enhancement comprises enhancing a drug to match more than one target, or a variety of target mutations, for example including one moiety to bind for one mutation and one moiety to bind for another mutation, for example, in HIV some proteins have two main varieties and countless sub-varieties. This enhancement may interfere with other properties of the drug, but the tradeoff may be considered useful.

Alternatively or additionally, a drug may be designed to bind to a subset of binding points that is common to a plurality of targets or mutations, for example, models of the plurality of targets are analyzed to determine shared binding points. The various drug discovery methods are then optionally applied assuming that only these binding points exist. Real assaying of a potential drug may be carried out on the multiple targets to ensure that the various modifications of the drug did not make it fail to bind to one of the targets. Alternatively or additionally, when a modification is made, it is determined whether the modified drug will bind to the common binding locations and/or have steric clashes. It should be noted that there might be other reasons to discover a drug that binds only to a subset of the possible binding points, for example, if a mutation is expected in one of the binding points and/or to allow the drug to work even if an interfering molecule is bound to one of the binding points.

8.13 Drug Failure Analysis and Reengineering

Often, a drug will come out to market and then fail. The method described herein may be useful in determining a reason for the failure and then possibly assisting in rescuing the drug. In an exemplary embodiment of the invention, the layout of the target of the drug and/or other proteins that the drug is believed to have interacted with (e.g., based on the type of side effects), are generated. The drug is then compared to the targets to determine failures in binding to the correct target and/or undesirable binding to non-targets. It should be appreciated that while such comparison may be theoretically possible using other means, it is believed that prior to the availability of target mapping, such large scale molding of active areas of targets was not practical, due to time and cost limitations.

In an alternative embodiment of the invention, it is noted that a drug may be suitable for only part of the public, for example, due to individual differences. In an exemplary embodiment of the invention, the genes that express inadvertent targets and/or targets are used to reconstruct models or samples of the targets and then map the active areas of the models. The results may show that an individual has a sensitivity to the drug and/or that a different individual is resistant to the effects of the drug. Alternatively or additionally, the testing may be done against pathogen strains, to determine differential sensitivity to drugs. In some cases, the genetic differences are linked to already known markers, for example sensitivity to sulfates is linked to a G6PD deficiency for sulfates, so that the classification of people as being compatible with the drug may be simple. Alternatively, a genetic test may be applied prior to selecting which drug to use on a person.

8.14 Additional Drug Discovery Related Analysis

Additional analysis methods may also enhance a drug discovery process. For example, many drugs have side effects due to their interaction with housekeeping proteins or proteins that cause feeling of malaise if interfered with. Examples include GI proteins and liver proteins. Some drug targets are known to be similar to such proteins. In an exemplary embodiment of the invention, models are generated for such potential side-effect generators. Any potential drug lead is rejected (or scores lower) if it is shown to bind to one of these prohibited models. Alternatively or additionally, drugs that have a known side effect are analyzed to determine which protein they bind to and this protein and/or the particular binding locations are used for defining a prohibition of binding of a potential drug.

In another example of an analysis, potential drug molecules are analyzed to see if they bind as a substrate to certain enzymes. Such binding may indicate a speed of incapacitation of a drug or its excretion. Alternatively or additionally, such binding may be useful for identifying pro-drugs, that are activated by their interaction with certain enzymes, such as liver enzymes. In this case, a drug may include two sets of active areas, one for activation of the drug and one for binding of the drug to its target. Optionally, biding to a protease (or other manipulating protein) is ensured by adding binding moieties or gauges to a drug molecule at suitable locations.

In another example, a set of target molecules that are all known to be affected by a same protein or molecule are analyzed to determine of they have common binding geometries to which the molecule bonds. This may help, for example, in fine tuning the molecule to bind more selectively, for example, by adding a moiety which will interfere with other target molecules and/or assist in binding to a particular target molecule.

8.15 Streamline Discovery Process

As can be appreciated a discovery process typically includes going through various dead ends. In an exemplary embodiment of the invention, mapping of the targets is used to select parts of the discovery process that are likely to fail and prevent them from being attempted. Some examples (some of which are described elsewhere in this application) include, dropping targets that do not seem suitable for improvement, identifying targets likely to have side effects and weeding out libraries. In an exemplary embodiment of the invention, weeding out existing libraries is performed by removing from a library leads that have an expected low probability of binding and/or appear redundant to other molecules. For example, a molecule that is very flexible is less likely to bind. The probability of binding may be estimated, for example using energetic considerations based on the molecule's degrees of freedom.

8.16 Utility Generation

While many proteins and molecules are catalogued, many of them do not have a known utility. Determining an exact utility for a protein or a molecule may require a very large expenditure. In an exemplary embodiment of the invention, potential utilities for molecules and for proteins may be generated on a large scale in the following manner. A molecule may have a utility as a gauge or it may have a utility as a lead or drug. In an exemplary embodiment of the invention, existing target area layouts, for example, 10, 50, 100, 1000 or any smaller, greater or intermediate number are matched to the molecule to see if binding is likely. It is expected that many molecules will turn out to have a potential utility. In general, more matching is more work, but increases probability of success.

In a similar manner, mapping proteins provides an indication of its active area shape, potential substrates and/or potential drugs which might affect it. In an exemplary embodiment of the invention, a utility is found for a protein by determining its substrate. Optionally, the protein active area layout is compared to structures of known substrates and proteins.

In this manner, a library and individual drugs and proteins may be said to have an expected utility. For example, the protein may be for one of the following protein families GPCR's, Proteases, Kinases, Ion Channels messenger proteins or any type of peptide or other macro-molecule found in a living organism.

9. Exemplary Discovery Applications

9.1 Overview

In this section existing discovery methods will be described, as well as possible modifications that take into account the methods described herein.

While many approaches to drug discovery are known, the following two main approaches generally encompass the existing methods.

9.2 Screening Based Drug Design

This discovery method works by screening a target against a large number of molecules and then attempting to enhance any matches to produce a drug. The process is as follows:

(a) Provide a general library of compounds for screening, equally relevant to all target proteins. Typical sizes of such libraries grow constantly at roughly one order-of-magnitude (factor of 10) per decade. Current typical sizes are 1-10 million. The libraries are often proprietary and maintained by each corporation independently.

(b) Screen the corporate library against the chosen target. Look for compounds exhibiting at least weak activity (significant activity at concentrations typically 1-100 $\mu M$) of the type required with relation to the target.

(c) If no hit is found, the process ends here. Apparently, this is often the case, possibly in above 70% of the cases. If hits are found, an optimization stage is initiated, in which the final outcome is expected to be a compound with strong activity (at concentrations typically nM) against the target. This is done in one or a combination of the following two methods:

1. In case there is only one hit or all hits are variations of one molecular theme, a large number of analogues of the hit are synthesized. This group of compounds is sometimes known as a "focused library". These are also screened against the target protein. The purpose here is to define a direction for increasing the activity of the original hit by identifying chemical moieties and positions on the original hit that increase activity. This process is known as developing a QSAR (Quantitative Structure Activity Relationship).

2. If a number of chemical groups have been identified as hits, a computational process of identifying possible pharmacophores (molecular substructures directly involved in binding of the hits to the target) is executed. These may indicate not only possible directions for optimization, but also their feasibility for a given molecular starting point (both from a physical point of view and from a synthesis point of view).

(d). Drug like qualities are generally a byproduct of this process. Molecules in the initial screening library are often chosen to possess drug-like qualities. During the optimization process, only partial information is available so that simultaneously satisfying drug-like requirements and increased activity are seldom under direct control. Final drug-candidates that may result from this process closely resemble hit compounds in the initial screening library.

(e) Testing. The drug-candidates are tested, for example in live animal models and then in humans, to determine there efficacy. Many drug candidates fail at this point and lacking any basis for modification, fail completely.

In an exemplary embodiment of the invention, the above described inventive methods may be used to improve the above drug discovery process, for example one or more of:

(a) Hit rate. As stated above, in most cases, no hits are found for a new target. By generating a mapping of the target, the leads used for screening can be better selected. Even leads with very weak affinity may be selected for further improvement, due to the combined indication of very weak activity and matching a map. Alternatively or additionally, the method of designing a gauge library is applied to a molecule library, to reduce duplication and to assist in ensuring coverage of binding space. This may be done, for example, by analyzing the library to identify gauges in triangle space and/or uneven distribution leads in this space. In addition, excessive overlapping may be determined. Alternatively or additionally, the library may be analyzed to determine molecules that are unlikely to ever bind, for example, due to them having excess flexibility and no known binding partners. Alternatively or additionally, if the screening is in stages, molecules may be selected for each stage based on them having less overlap with each other.

Alternatively or additionally, some binding results may be ignored, for example, molecule with high flexibility may add too much noise (binding to many molecules in many ways) and therefore be ignored, at least in a first stage of processing.

Alternatively or additionally, the gauges that bind can themselves be used as leads (and many of such bindings are expected). Often the gauge library is small compared to the corporate library and can be added to it with a relatively small penalty. In an exemplary embodiment of the invention, results from the "old" library will serve as initial starting points for optimization (as before) but optimization will be directed by information gained from screening using gauges. Possibly, a gauge library binding assay is performed on a target with an interacting lead. This type of assay can be used to determine if the lead (or molecule from a library) is interacting with the active area or not (e.g., based on whether and the extent that it affects the binding of the gauge library). This assay may be compared to an assay performed with other binding leads and/or with no bound leads at all. The effect of lead chemistry may be determined by checking the assay in the presence of one or more chemically similar but non-interacting leads.

(b) Process directing. If the target is mapped and a lead starting point is known, there are still many ways of enhancing the lead to produce a drug. In an exemplary embodiment of the invention, knowledge of the target geometry and/or chemical behavior is used to assist in directing the modification process, replacing physical experiments with virtual ones and/or assisting in culling out (probably) useless leads. In addition, it is noted that various combinatorial generation of lead modifications can be simplified by selecting only those lead modifications that are meaningful (or are most meaningful) in view of the target layout and/or based on the three-dimensional structure of the leads (e.g., by checking which triangles are exhibited by which lead and by which lead modification). Optionally, a mismatch between the results predicted by the determined layout and actual binding activity of the leads may be useful in correcting the layout, better understanding the chemistry of the lead and/or predicting other leads that might show promise.

(c) Drug recovery. Even if a drug fails the final testing stages, in an exemplary embodiment of the invention, the above methods may be used to determine the reasons for the failure and/or provide guidance in reengineering the drug.

9.3 Alternative Screening Based Drug Design

Chemical genomics or chemogenomics have lately become very popular. They are based on the idea that instead of first finding a target first and then finding a compound for it, the opposite process is applied: first screen compounds against whole cell assays looking for the phenotypic result (e.g., selective death of cancer cells). Then, once an active compound is found, the target is sought. One possible advantage of this approach is working in parallel on multiple targets, many of which may not even be known. However, existing screening libraries cannot guarantee finding hits. In an exemplary embodiment of the invention, a gauge library as described herein is used and is expected to have a plurality of gauges that interact with the cells. While the interactions may be weak, a non-trivial number of such interactions may be expected.

9.4 Structure-Based Drug Design

This method assumes that accurate modeling software for simulating molecular processes is used. The process is as follows:

(a) Obtain an accurate and detailed three-dimensional structure of the target protein. Usually done via X-ray crystallography or NMR analysis (both experimental). Computational approaches also exist, but are generally not accurate.

(b) Identify the active site in the protein structure (not always straightforward for new, unfamiliar targets).

(c) Identify relevant binding points in the active site, also known as pharmacophore points. These are points where weak (non-covalent) binding can occur. A potential Ligand must satisfy a number (usually 6 or more) of these points simultaneously in order to achieve nM affinity.

(d) Design molecules that "fit" the active site, both geometrically and in terms of satisfying enough pharmacophore points. Both this stage and the previous are done using "docking" or molecular-mechanics type simulation software.

In an exemplary embodiment of the invention, the herein described inventive methods may be used to improve the above drug discovery process, for example one or more of:

(a) Linked structure. 3D structures of proteins are apparently, in many cases, of little use in and of themselves. Much experience has shown that it is difficult to design strong binders based on this (e.g., geometrical) information alone. In an exemplary embodiment of the invention, it is noted that useful information is present in 3D structures of the target with bound ligands. While such ligands are not known initially, in an exemplary embodiment of the invention, gauges that bind to the target are used in place of such ligands, with the expectation that a significant number of such binding gauges will be found. In an exemplary embodiment of the invention, the gauge binding process is applied and then the target is modeled (e.g., using NMR or X-ray crystallography), possibly several times, with different gauges linked. The shape of the target area with the linked gauges is expected to be useful for designing strong binders using methods known in the art. Possibly, the known methods may be modified, for example, to combine the results of different configurations caused by different binding locations of different gauges. Optionally, the provision of multiple binding gauges (e.g., 5, 10, 25, 50, 100 or any smaller, intermediate or larger number) will assist in determining the binding mode(s) of the target, possibly enhancing the understanding by providing partial binding modes as well. In general, the provision of more gauges, means more work, but may enhance the accuracy of the analysis.

In an exemplary embodiment of the invention, the linked structure results from a plurality of gauges are combined, for example by super position with the target as a reference. This superposition may yield a total model of the binding area of a target and/or fully bound configuration, rather than a partial one might be provided by each gauge.

(b) Comparison. In an exemplary embodiment of the invention, the shape of the active area determined by the simulation model is compared to the shape of the area as determined by the mapping process. Differences between the two may assist in correcting the mapping/reconstruction method or it correcting the simulation model. Optionally, the simulation model is used to select between alternative reconstruction and/or to assist in fine-tuning a reconstruction, for example, by assisting in calculating more exact distances and/or indicating which possible moieties could be taking part in the binding.

(c) Identification of binding points. In general, modeling software is not accurate enough to predict binding points in a protein target. Also active areas may be difficult to identify. This is especially the case for novel targets. In an exemplary embodiment of the invention, the above methods circumvent one or both of these problems by identifying potential binding points/modes experimentally, e.g., using a standard assay library of gauges. Then these active areas are analyzed in greater depth using docking software, for example to predict the affinity of new compounds to a specific target.

9.5 Modular Assembly of Ligands

This method, which is apparently used by Sunesis inc., works by constructing leads from parts that show affinity. The process is as follows:

(a) Synthesize a finite library of elementary molecular fragments that include a "linker port" (i.e. a site on the molecule at which linking can be easily implemented). These are typically small molecules previously identified as pharmacologically "interesting", and which are amenable to including the standard "linker port".

(b) Screen the elementary fragments against the target protein, looking for extremely (~1 mM) low affinity. This step is typically problematic.

(c) Link groups of two or more fragments via their "linker port" components in order to achieve increased affinity. The distance between two fragments, i.e. the length of the linking chain, may be varied and optimized.

In an exemplary embodiment of the invention, the herein described inventive methods may be used to improve the above drug discovery process, for example one or more of:

(a) The elementary fragments are currently not designed in the art using any logic that may be viewed as exhaustive, i.e. typical diversity metrics are used (as in standard screening libraries) but these do not yield a finite list. Consequently, hits are seldom found (for general targets), even less than for general screening libraries, probably due to very low affinity expected, which poses many technical problems (e.g. solubility). In an exemplary embodiment of the invention, the set of fragments is selected based on spanning the space. For example, fragments may be pairs (or triplets) of moieties, having distances and moiety types selected to span the possibility space.

(b) Geometry, i.e. the proper distance and orientation between two weakly binding moieties, is totally absent from the initial screening results in the art. In the linking stage, only very limited geometry variation may be tried (i.e. the length of the linker). In an exemplary embodiment of the invention, the binding of a gauge library is used to provide geometrical hints (or a complete model) which assist in deciding how to put together fragments, which fragments to put together and what distances to set between the fragments. This may also assist in determining what type of linker to use when linking fragments. This may also be used for synthesizing a new molecule that includes the binding parts of the binding gauges, spaced apart by a suitable structure (e.g., a variation on a known drug).

10. Exemplary Non-Discovery Uses

The above measurement methods may also be applied to uses other than drug discovery. A different gauge set may be required for some uses.

In one exemplary embodiment of the invention, the measurement methods are used to assess toxicity, for example, to identify housekeeping proteins that may have adverse interactions with a certain drug or potential toxin. This may be useful in determining toxicity of industrial or household chemicals.

In another exemplary embodiment of the invention, the measurement methods are used to predict antibody affinity to a material and/or cell, for example by identifying binding sites on an antibody and/or a material.

In another exemplary embodiment of the invention, the measurement methods are used to map the outside of an organism, for example, a virus, *rickettsia* bodies, worm, protozoa, fungus, ameba or a bacteria. This may be useful in the development of vaccines. For example, a vaccine is often more effective if it is made from a protein whose shape does not change. By determining which parts of the binding areas on the outside of a pathogen do not change, such determination may assist in selecting a particular protein from the pathogen for vaccination use and/or to assist in assessing the chances of creating a useful vaccine. In order to prevent auto-immune responses, the active areas of existing vaccine material may be mapped, to see if the pattern resembles that of bodily proteins to too great an extent. It should be noted that this matching may be dependent on an individual's genetic material.

Alternatively to absolute measurements, in some embodiments of the invention, the above methods are used for determining relative measurements, for example, for measuring conformal changes in a protein, under different conditions. A same (or different—e.g., to match new expected measurements) binding assay may be applied to the protein under different conditions. Possibly, more flexible gauges and/or less stable gauges are used for this application.

In another exemplary embodiment of the invention, the above measurement method is used to find new agricultural chemicals, such as insecticides and herbicides that are target-specific by affecting proteins known to be crucial only for some types of pests or weeds. Alternatively or additionally, artificial hormones are developed to match targets in plant cells.

11. Using Prior Information

The above process has been described, in some examples, as a blind process, which assumes a neutral starting point of substantially no knowledge about the target. In some cases, there exists prior knowledge about the target, gleaned from various sources and/or by previous measurements of the target. Such prior information may be used in many ways. Following are some examples.

In an exemplary embodiment of the invention, the prior information is sufficient to propose several alternatives. A binding assay with the gauge library, with or without reconstruction may provide enough information for selecting between the alternatives, for example between alternative models of which part of a lead interacts with a target or selecting between two target area layout reconstructions. Optionally, to this end, the gauge set can be reduced to only those gauges that will distinguish and/or that are needed by either one of the models.

In another example, crystallography, NMR, IR spectrum and/or chemical properties of the target are used in the above reconstruction process, for example, to resolve ambiguities and/or to overcome lack of data. In one example, these methods show how one or more gauges actually bind in the target. In another example, these methods or other prior knowledge are used to force a certain structure to be reconstructed, rather than following the above described score based reconstruction. For example, forcing the structure to include a certain sub-shape (e.g., a tetrahedral portion) that would not otherwise be reconstructed from the assay data.

In another example, if part of the target is known, it can be reacted with a substrate that blocks out that known part, so that the measurement will only apply to the unknown portion.

Alternatively, the statistics of interaction in the known portion may be used to assist in associating binding statistics with structure in the unknown portion. For example, a computer model or an analogue target may be used to provide an estimate of which gauges bind and at what strength, to the known portion. In the assay results analysis, gauges that bind to the known area are ignored, not used in the assay and/or their binding strength reduced during the analysis. Optionally, a gauge is not removed from consideration if removing it will leave no triangles of a certain size and/or moieties for binding to the unknown area. Alternatively, the library as a whole is used, for example, as noted above that simultaneous screening using 100,000 assays at a time, is a current technology.

In another example, when an iterative measurement method is used, prior information may provide insight into desirable starting points.

Optionally, the prior information is used as an input for modifying the binding process, for example by varying the binding environment.

In another example, the prior information is used to set the environmental conditions used during measurements, for example, using information from previous assay attempts with a similar protein to indicate what environmental conditions are likely to provide bindings and/or at least not interfere.

In an exemplary embodiment of the invention, prior information is used for the design of specific scaffolds, moieties and/or gauges to better measure a particular target. The molecules may be, for example, designed ad hoc, and/or a sub-library constructed by selecting previously known molecules. In an exemplary embodiment of the invention, a scaffold is selected for such a sub-library due to a small (e.g., 0.5 A) difference in a side of a triangle due to the change in scaffold. In a regular mapping process, such a difference may not be important, but in high-resolution mapping, for some targets (e.g., where binding is weak) it may be important. Similarly, a set of gauges may be provided to cover a certain range of sizes and/or chemical behaviors at a finer resolution.

12. Iterative Measurement

In some ways similar to the use of prior information, iterative measurement allows information form a previous measurement step to be used, for example, to better tune a current step or to reject certain possibilities.

In some embodiments of the invention, instead of a one step measurement process, for example as described in some of the embodiments above, an iterative measurement method is used. In one example of this method, a lower resolution reconstruction is generated. Then additional assaying is performed, using a same or different gauge library and a higher resolution reconstruction is provided. The earlier reconstruction may be used, for example, as a starting point for the reconstruction process and/or to assist in selecting which gauges to use in the additional assaying. In an exemplary embodiment of the invention, such an iterative method is used, for example, when the cost and/or time to perform a single complete assay are large.

In an exemplary embodiment of the invention, an iterative measurement uses more flexible gauges (explained below) in a first set of measurement than in a second set of measurements. Alternatively or additionally, a different subset of gauges is used for the different sets of measurement.

The difference between the stages may be in correctness of the reconstruction, for example, which interaction locations lie where. Alternatively or additionally, the difference may be in accuracy, for example, in the distance between two binding locations or the bond angle of an interaction location. In an exemplary embodiment of the invention, the above assumptions of range coverage, for example, for hydrophobic bond sizes and for directional bonds are made stricter in later reconstruction iterations, for example, providing 15 directional bonds. However, not all the measurements may need to be redone. Instead, only those gauges that bond to interaction locations that are expected to change in the model, are used. Various search methods known in the art may be used to assist in providing and/or determining convergence of the assay and reconstruction process, for example, hill-climbing.

13. Gauges, Physical Properties 13.1 Overview

Various uses of gauges are described above, some of which may use a complete gauge library (e.g., completely spanning and having sufficient resolution) and some which may, alternatively or additionally, use a partial library. One or more of several issues are optionally considered in the design of such libraries. Exemplary such issues and considerations that may optionally be used when designing and/or selecting gauges, gauge designs and/or gauges sets are described below. It is noted that some of the issues relate to the properties of the individual gauges and some to the properties of the gauges as a set. The design (and/or selection) of a complete set of gauges may address multiple issues and various tradeoffs, for example as shown in the exemplary gauge set described below. These issues are explored below. In general, it should be noted that even some of the gauges in a gauge set are not useful, this does not generally detract from the usefulness of the gauge set as a whole.

FIG. 4A showed an exemplary gauge 400. A typical gauge set includes a large plurality of gauges. Possibly, all the gauges share a basic common design, as will be described below, however this is not essential. In addition, there can be many gauges, gauge designs and gauge sets that are useful for measurement.

In an exemplary embodiment of the invention, a significant portion of a gauge set is based on permutations of a small number of basic molecules, called scaffolds. In this design method, a scaffold includes a plurality of attachment points and each gauge is created by selecting a scaffold and mounting various moieties at the attachment points. One potential benefit of this approach is that fewer different chemical processes are required for synthesizing a library. Another potential benefit is that the generated library has more predictable chemical behavior, reflected, for example in the environments used for assaying. Another potential benefit is that a more predictable and/or controlled set of distances between moieties may be achieved. Another potential benefit is simplicity is designing a spanning library. Another potential benefit is that it is easier to ensure spanning in a library or library portion. Another potential benefit is using this type of permutations (possibly with scaffolds novel to the library) supports generation of missing or desired measures, ad-hoc. In one case, for example, new gauges with particular distances are generated by modifying an existing scaffold. It should be noted that not all these potential advantages are expected in every embodiment of the invention.

It should be appreciated that for a given library, parts may be based on scaffolds, while other parts are generated using other means, for example, selection form an existing molecular library and/or constructed using various molecular construction, design and synthesis methods known in the art for attempting to custom create molecules with certain properties. Further, the entire library can be non-scaffold based. It should also be appreciated that not all scaffold-based libraries provide all, some or even any of the above potential benefits.

13.2 Scaffold

In FIG. 4A, gauge 400 is shown to include a scaffold 402, to which four moieties are attached, at four of possibly more potential attachment points. In an exemplary embodiment of the invention, gauges 400 are selected to span a range of distances between moieties. In an exemplary embodiment of the invention, by varying the locations of connection of moieties among available attachment points, different inter-moiety distances are fixed for a single scaffold. A greater range of possible values is optionally achieved by providing a range of possible scaffolds. It should be noted however, that no scaffold is required, per se. Rather, it is expected that at least for some embodiments of the invention, it may be more cost effective to create a library combinatoricly using scaffolds. This is exemplified in FIG. 4B, where the gauge is shown as a triangle defined by its moieties and the distance between them, without any reference to the scaffolding.

However, in an exemplary embodiment of the invention, a scaffold is provided on which multiple different gauges are constructed. A plurality of different or same moieties may be selectively attached to different locations on the scaffold, using relatively standardized methods of combinatorial-chemistry, thus creating a range of gauges, possibly having generally known chemical properties (e.g., solvency, vapor pressure, stability).

In some embodiments of the invention, the scaffold(s) is selected so that it does not extend to or out of the triangle shape(s) defined by the moieties. Alternatively or in some cases, the scaffold and/or some of the moieties do interfere with the binding, and may cause steric clashes. By providing a range of scaffolds, steric clashes may be avoided for some gauges and/or the causes of the steric clashes may be determined.

In some embodiments of the invention, the scaffold geometry and/or chemistry is meaningful.

Optionally, the participation of the scaffold in the provision of binding triangles is ignored in the design of the gauge set. Alternatively, the scaffold chemical activity is noted during the design of the set, for example, for providing one or more moieties. Optionally, the effect of the scaffold on providing binding, repelling and/or interfering bonds, is considered during reconstruction or analysis. Alternatively or additionally, the geometry of the scaffold is taken into account during analysis, e.g., to determine causes for steric clashes.

Alternatively or additionally, triangle binding analysis ignores any binding triangles that are probably not exposed to the target (e.g., based on gauge geometry).

13.3 Volumetric Geometry of Gauges

Triangles, as a rule, define a plane, which may or may not be the plane of the scaffold (if any). In an exemplary embodiment of the invention, when gauges are selected for inclusion in a library they are selected so that their attached moieties lie in a plane or in some other desirable conformity. A planar arrangement has a potential advantage of preventing multistable (e.g., conformal changing) molecules from being included, which is not desirable in some embodiments of the invention, as they may confuse the analysis and/or reduce the binding probabilities. Possibly, a set of gauges is provided, to cover a range of possible non-planar orientations. In some embodiments this is more desirable than selecting a molecule that exhibits conformal changes. Molecules with conformal changes may be excluded using other methods as well, for example, by analyzing each potential gauge. Alternatively or additionally, the gauges are selected so that the dimensions of the gauge or of particular triangles in it do not change, even if other parts of the gauge exhibit conformal changes. Optionally, a certain triangle in a gauge may be neutralized by making it energetically unlikely to bind, for example, by ensuring that that triangle exhibits conformal changes or adding flexibility to the bonds of one or more of its moieties. It should be noted however, that such exact modification of a gauge may not be possible, for example, due to the small size of a gauge or its possible effect on other parts of the gauges and/or other triangles.

13.4 Flexibility

The flexibility of a gauge can adversely affect one or both of the amount of information provided by the gauges matching and the affinity of the gauge to the target. While it is true that flexible molecules are more likely to find an arrangement of points to bind to, increased flexibility may, at least in some cases, reduce the overall probability of binding of a molecule, for entropic reasons. In addition, the binding of a flexible molecule provides less precise information than the binding of a rigid molecule.

Thus, although a greater number of interaction location layouts can be matched using a flexible gauge, in an exemplary embodiment of the invention, at least some relatively rigid gauges are selected for the gauge library, so that the measurements using these gauges are more precise. Optionally, substantially all gauges in a gauge set are substantially rigid. In an exemplary embodiment of the invention, the gauges are translationally rigid, in that the distance between moieties does not change much. Alternatively or additionally, the gauges are rotationally rigid, in that the relative orientation of the moieties does not change. Optionally, flexibility extends to chemical specificity of the moieties, for example, by selecting moieties that are either more or less specific. For example, one can chose moieties that have only one function (i.e., for hydrophobic chose tert-butil or a non-aromatic ring (e.g. cyclohexane) or for hydrogen bonds avoid using a hydroxyl (OH) (which is both a donor and acceptor), or vice versa.

In an exemplary embodiment of the invention, however, a small degree of flexibility is provided, for example to ensure overlap between gauges. In one example, the degree of flexibility is sufficient so that a pair of moieties in the target can be matched by multiple pairs of moieties in the gauges, with different distances between them. In an exemplary embodiment of the invention, the gauges are designed such that each distance between moieties in the target can be matched both by a gauge that has a slightly longer distance and by a gauge that has a slightly shorter distance. The degree of flexibility may be defined so that a relatively low amount of energy is required to bend or stretch the gauge so that it can match the moiety layout in the target. The relevant energy levels may depend, for example, on the assay sensitivity, on the gauge concentration and/or the assaying environment.

Optionally, at least a small number of the gauges are flexible, for example to compensate for gauges that are not available. For example, as noted herein, rotational flexibility may be allowed for hydrogen bond participants and/or aromatic rings. Alternatively or additionally, flexible gauges are used to assist in providing coarse level information which may be later fine-tuned using rigid gauges. Optionally, the reduced amount of information (e.g., by lack of binding and/or less precision) is compensated for by the redundancy of the gauges and triangle measures in the gauges.

It should be noted that particular method of determining which triangle bound, described above, provides a significantly greater weight to rigid triangles. It should be noted that in a single gauge, triangles may have different rigidities.

In an exemplary embodiment of the invention, the Catalyst software from Accelrys (formerly MSI) is used to assess the rigidity of a gauge.

In an exemplary embodiment of the invention, at least 20%, 40%, 60%, 80% or any smaller, intermediate or larger percentage of the gauges are rigid. In general, if more rigid gauges are used, they are easier to analyze using the methods described herein. However, such gauges may not be available and/or it may be desirable for various reasons to use non-rigid molecules, for example, if such molecules are similar to drugs or have other properties believed to make them suitable for screening.

In an exemplary embodiment of the invention, a substantially rigid molecule (or bond) is defined as a molecule which has a single entropic configuration and, in which, except for hydrogen atoms, no bond changes by more than 1 Å using less than 20 kCal/Mole. Alternative embodiments of the invention may allow less rigidity, for example allow greater movement, such as 0.8 Å, 1.5 Å, 2 Å or any greater, smaller or intermediate value, at 10 kCal/Mole, 15 kCal/Mole, 30 kCal/Mole, 40 kCal/Mole or any smaller, intermediate or greater application of energy. It should be appreciated that absolutely rigid molecules are generally not possible. Instead, the term "substantially rigid" is used in the claims. As the molecules become less rigid, they may bind with more difficulty and be less specific in the meaning of their binding. However, less rigid molecules may be easier to obtain and/or use to ensure coverage, for example.

Typically, rigid molecules are those for which all single bonds are either part of a ring or attach "end" atoms i.e. at one of their ends (e.g., single atoms or simple moieties such as $NH_2$, for which rotation is uninteresting in some cases). Once the ring grows too much, for example beyond 5 or 6 atoms in some cases, the ring becomes flexible. Larger rings may also be rigid, for example, if there are never more than 2 adjacent single bonds whose atoms participate only in single bonds (i.e. if any of the atoms in the ring are themselves attached by a double bond to an atom that is not a member of the ring, this also may rigidify that segment of the ring). A single covalent bond is rotationally free, unless it is part of a ring.

13.5 Gauge Lengths

In an exemplary embodiment of the invention, the gauge sides lengths (i.e., the distances between the center of mass of the moieties) are selected to cover a range of expected distances between interaction locations and/or dimensions of small molecule drugs. Alternatively, for example, for non-small molecule drugs, a different range may be selected than for small molecule drugs. In an exemplary embodiment of the invention, the selected range is between 2 Å and 12 Å. In another example, the range is to under 10 Å, or under 8 Å. Alternatively or additionally, the range is from above 3 Å or above 4 Å. In some cases, an "outer length" or an "inner length" may be useful, which are defined from the outside or inside of the moieties taking part in a triangle.

In an exemplary embodiment of the invention, the sampling is selected to uniformly sample an energy cost required for a molecule to accommodate the sampling resolution. For example, if a first triangle side is x Å and a second triangle side is y Å, the range of distances covered by the first side should require a same amount of energy to modify the molecule to fit the range, as the range of distances covered by the second side. Generally, this means that as the molecule is larger, the binding range, for a same amount of energy, increases. Optionally, the allowed amount of energy is a parameter of the assaying process, the target and/or the gauges used, for example, to allow a detectable binding by the gauges.

In an exemplary embodiment of the invention, the range is covered by intermediate sizes, so that at least one gauge will match each intra-moiety distance, for each pair of moieties.

Alternatively or additionally, at least two gauges or gauge sides are similar in moiety geometry. Alternatively, only two gauge sides match. Different environments may dictate a different number of gauges, for example, some bonds may exhibit more flexibility at one temperature, but not at another.

The sampling of distances by the gauges may be even along the range or it may vary, for example being exponential and/or stepped, due to the effect of the changing scaffolds between triangles, to achieve different triangle side lengths.

It should be noted that some sets of side lengths cannot be combined in a single triangle, due to the required relationship in a triangle, namely, that the sum of lengths of any two sides be greater than the length of the third side.

13.6 Environmental Stability

In an exemplary embodiment of the invention, the gauges are applied to the target under normal physiologic conditions, including controlled pH, temperature and ionic content. They may thus be selected to perform correctly only in the standard environment.

However, in some embodiments, the testing range may not match the physiological conditions normally present. In a particular example, a desired property of a drug may be activity at hyperthermia temperatures or for patients with a fever and not at normal physiological temperatures.

A special set of gauges may be used for non-physiological conditions, for example replacing some gauges with others. Alternatively or additionally, a relatively stable set of gauges may be provided, which exhibit a same behavior over a wide range of environments. Alternatively or additionally, even if the gauge properties change, if the change is known and spanning is retained, the reconstruction method may be adjusted (e.g., the locations and/or amplitudes in triangle space) to account for environmental effects.

Another possible environmental variable is the type of solvent used, as some gauges may not be very soluble in water, so assaying may use non-standard solvents.

In another example, the target may exhibit conformal changes, which are desired to be measured, under small changes in the environment, such as the concentration of calcium ions. It may be desirable that the gauges do not exhibit the same sensitivity as the target protein to the changes.

Alternatively or additionally, the gauges may be designed or selected to change in different environments, thus, for example, allowing a single gauge to make multiple measurements, each at different environments.

13.7 Uniqueness of Gauges and Overlap of Sides and Triangles

As alluded to above, two different gauge-sides lengths may match a particular interaction location configuration, for example, by an interaction location being capable of binding to two different moieties and/or due to flexibility in the gauges (and/or the target), which cannot be completely eliminated.

In an exemplary embodiment of the invention, the overlap between gauge measurements is controlled to be substantially constant over the gauge space. Alternatively or additionally, the overlap is minimized. Alternatively, at least a minimum amount of overlap is encouraged, for example to compensate for various eventualities where a gauges does not bind or an assay fails or to provide additional linking information.

It should be noted that even if substantially rigid gauges are used, there is a level of tolerance inherent in the interaction, so that some freedom is always available, albeit, possibly at the expense of binding strength.

If the degree of overlap is known, its effects can be compensated for in the above reconstruction method, for example during clustering. Alternatively or additionally, if an expected degree of overlap does not exhibit expected effects, the measurement is suspect.

In an exemplary embodiment of the invention, however, a large degree of overlap is provided, for example a factor of two, three or more repetition of triangles. Fractional overlap may be provided, for example, by using moieties that have non-orthogonal affinities (in the detectable range) and/or as a result of partial overlapping between triangles. Generally however, an exactly same triangle will not be repeated, for example, due to differences between scaffoldings and/or effect of other moieties within a scaffolding.

Thus, alternatively or additionally, to accidental overlap, some or all triangles are repeated between gauges. In an exemplary embodiment of the invention, this repetition is used to compensate for the effect of steric clashes and/or other unexpected chemical behavior exhibited by some of the gauges. Alternatively or additionally, the repetition is provided to assist in determining which triangle bound, based on the binding of gauges. To this effect, the gauges may be selected so that there is a lesser overlap between gauges with respect to the other triangles the two gauges include. It appears, however, that if the scaffolds are sufficiently different, the probability of most of the triangles in one scaffold overlapping with most of the triangles in another scaffold is small. This may assist in distributing the overlapping between different scaffolds and gauges. Alternatively, similar scaffolds may be used, so that a greater degree of overlapping of triangles of same gauges may be provided. It should be noted that part of the overlap is provided by the fact that the gauges may have some degree of flexibility, so a same triangular array of binding points can be matched by triangles of different sizes. In one exemplary embodiment of the invention, the library is designed so each triangular array of points can be matched by at least one larger triangle and at least one smaller triangle. This overlap may be in addition or instead of repetitive type overlap where a substantially same triangle is provided at least twice.

Optionally, the order of moieties in a particular scaffold is controlled to account for expected steric clashes, for example, to assure that at least some triangles will not have the same steric clash problems as other triangles.

Alternatively or additionally, a mixture of gauges, having same triangles, but different expected steric clashes may be mixed in a single assay, to help avoid the steric clash problem.

In an exemplary embodiment of the invention, while triangle overlap in general and are not exactly the same, the gauge triangles of at least some of the library, for example, 20%, 40% 60% or any smaller intermediate or larger percentage, are selected so that distribution of triangles in triangle space forms a relatively discrete grid, with clusters of triangles near grid points. Alternatively, at least some of the library, for example, 20%, 40%, 60% or any smaller, intermediate or larger percentage, is selected so that the coverage of the triangle space is relatively uniform, with less clustering. As noted above, overlap may be useful to overcome various causes of non-binding. However, greater overlap may mean a larger library.

It should be noted that overlap degree need not be uniform. For example, certain triangle sizes may be more prone to steric clashes (e.g., if they all use large scaffolds), in which case a greater overlap may be provided. Optionally, the clustering methods take the degree of overlap into account, for example to determine a threshold for deciding if a triangle was bound.

13.8 Gauge Mass and Size

In an exemplary embodiment of the invention, the gauges are selected to have a minimal mass. It is expected that as mass increases, a gauge is more energetic and less likely to bind. Alternatively or additionally, greater mass often means greater size and more chance for steric clashes. In an exemplary embodiment of the invention, the scaffolds are selected to have a mass under 200, not including moieties. Possibly, the increases mass of benzene ring moieties is offset, at least in part by their enhanced affinity. Alternatively or additionally, gauges are selected by size, for example to be no larger than 4 fusen rings in size (e.g., about 10 Å). Alternatively or additionally, when selecting a molecule for inclusion as a gauge, the selection is failed if the molecule is too large or too massive. It should be noted that in some case, the size considerations are relative. For example, it is desirable in some embodiments of the invention that a triangle have sides on the order of a size of a scaffold. Small triangles on a large scaffold may be ignored when considering the triangles contributed by a particular gauge, and possibly forced to be provided by a smaller scaffold.

It should be appreciated that these examples are not limiting and a gauge may be larger and/or have a greater mass or be limited to be smaller and/or have a smaller mass, depending on the application or implementation, for example.

14. Particular and General Gauge Set Design 14.1 Example Spanning Library Size

Under certain assumptions, the following is an estimation of the number of gauges and triangles in a complete spanning library for small molecules on protein targets.

Assuming the range of lengths to be covered is 9 A°, at steps of 1 A°, the number of possible triangles is $10*10*10/(2*3)$ (factor of 2 for triangle in equality and factor of 3 for rotational degeneracy. Assuming 10 moieties and moiety directions, gives about 166,000 triangles. Assuming an overlap factor of 3 and 5 triangles per gauge, gives about 100,000 gauges. These numbers are of course only exemplary, but may serve to clarify the following description of library design.

It can be seen that the size of the library depends on the triangle space to be spanned, the degree of accuracy, complexity of gauges and the degree of overlap. Any of these may be varied in accordance with exemplary embodiments of the invention, for example, yielding libraries with between 10,000 or fewer gauges and 1,000,000 or more gauges. Exemplary intermediate library sizes include 30,000, 60,000, 80,000, 200,000 and 550,000 gauges. In addition a library may include non-gauge elements or may form part of a much larger screening library, for example as described above. In general, the more gauges in a library the more work it is to apply as a whole. However, greater accuracy, specificity and coverage may be available as the library size increases.

An example of smaller gauge libraries, are those that have only 7 moieties, reduce the sampling distance to 8 and/or reduce the overlap factor to 2. Smaller and larger libraries and/or other modifications of library parameters, can also be provided in some embodiments of the invention, as well as various partial libraries.

In another example, all gauges are designed to include a single triangle (or a small number), in which case about 166,000 gauges are needed (if there is no overlap). In such a specific-gauge library, the initial clustering step is optionally omitted. However, it is noted that gauges will generally include, at least inadvertently, more than one measure, so that clustering may still be useful. In some cases, a moiety is provided on a gauge to prevent the scaffold part of the gauge from participating as part of a measure and/or to reduce the number of different triangles provided by a particular gauge.

14.2 Gauge Subset Selection

A particular type of gauge library is a subset library, which may be smaller than a standard library (but it may be larger, for example, if it has a higher resolution of lengths and/or moiety types).

In an exemplary embodiment of the invention, only a subset of all the gauges are used for a particular measurement. In some cases this is because of the use of an iterative approach, which does not use all the available gauges at every step. Alternatively or additionally, it may be desired to reduce the number of assays performed. Alternatively or additionally, this may be the result of a large overlap between different gauges. In an exemplary embodiment of the invention, gauges are selected to better operate in an environment (e.g., temperature, pH, solvent used) and/or exhibit fewer adverse interactions with the target and/or the assay, for example, in a cellular assay. Alternatively or additionally, this may be the result of a failure to create a complete spanning library, for example as shown in the example above which may be nearly universally useful for all protein targets of small drugs.

It should be noted that one potential advantage of rigid gauges is that the geometry of many rigid molecules is minimally affected by environmental changes, even if their chemical behavior is affected. This may allow the gauge set to be more universal.

In an exemplary embodiment of the invention, gauges for the subset are selected based on the target type, for example, the expected range of distances between the interaction locations.

Alternatively or additionally, the gauges are selected responsive to a measurement need. For example, if a certain interaction location has an unknown size but is known to have a weak affinity, a denser sampling of the moiety size range may be used for that interaction location (e.g., for gauges that are expected to bind to that location).

Alternatively or additionally, the gauges are selected responsive to knowledge of the available drug types, for example, the types of possible hydrogen bond directions in the drug. Alternatively or additionally, the gauges are selected to better distinguish between two potential drugs, by providing better resolution for the differences between the drugs.

In some embodiments of the invention, the gauges are selected so that an approximately correct model can be reconstructed, even for those parts of the target for which lower resolution gauges are used. Alternatively, the gauges are selected to determine if a certain drug should bind to the target, so only gauges required for measuring a smaller range of possible configurations are necessary.

Optionally, the gauges are selected responsive to a desired type of bond matching, for example, if the target and/or potential drug is known to include sulfate bonds, gauges including sulfate moieties are used.

In an exemplary embodiment of the invention, a method of selecting a gauge subset comprises:

(a) determining a use of the gauge subset;

(b) determining a rule or rules for selection of gauges to meet said use (e.g., sizes, moieties, densities, etc., e.g., as above);

(c) selecting from the library a plurality of gauges that meet said rule(s); and (d) optionally, determining if the resulting library is likely to provide the desired information for said use. For example, a simulation may be made to see if the assay results are likely to result in a reconstruction (e.g., based on assay binding rate, density of coverage, properties or target and/or degree of overlap required to distinguish between triangles on a gauge).

In another example, the information is partial information and a simulation is run to see if the information can be distinguished.

14.3 Gauge Library Design

The following table shows an exemplary set of scaffolds for a gauge library design:

TABLE I

AutoNom Name:
Thiophene

AutoNom Name:
1H-Pyrrole

AutoNom Name:
Furan

AutoNom Name:
Benzene

AutoNom Name:
Pyridine

AutoNom Name:
Pyrimidine

AutoNom Name:
Pyrazine

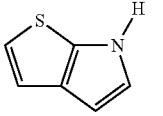

AutoNom Name:
6H-Thieno[2,3-b]pyrrole

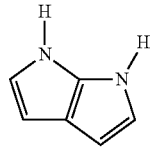

AutoNom Name:
1,6-Dihydro-pyrrolo[2,3-b]pyrrole

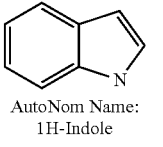

AutoNom Name:
1H-Indole

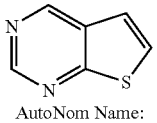

AutoNom Name:
Thieno[2,3-d]pyrimidine

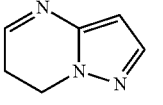

AutoNom Name:
6,7-Dihydro-pyrazolo[1,5-a]pyrimidine

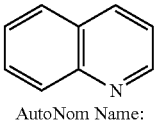

AutoNom Name:
Quinoline

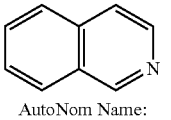

AutoNom Name:
Isoquinoline

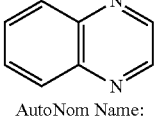

AutoNom Name:
Quinoxaline

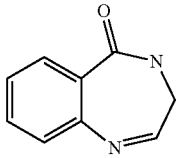 [SMILES: O=C1NCC=Nc2ccccc21]

AutoNom Name:
3,4-Dihydro-benzo[e][1,4]diazepin-5-one

TABLE I-continued

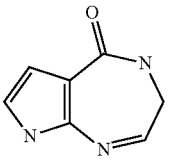

AutoNom Name:
3,8-Dihydro-4H-pyrrolo
[2,3-e][1,4]diazepin-5-one

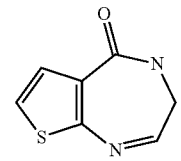 [SMILES: O=C1NCC=Nc2[nH]ccc21]

AutoNom Name:
3,4-Dihydro-thieno
[2,3-e][1,4]diazepin-5-one

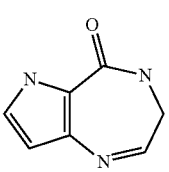 [SMILES: O=C1NCC=Nc2cc[nH]c21]

AutoNom Name:
3,6-Dihydro-4H-[1,4]diazepino
[6,5-b]indol-5-one

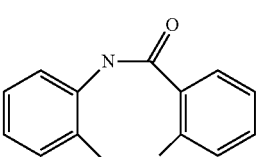

AutoNom Name:
7,8-Dihydro-1H-1,7,10-triaza-
cyclohepta[e]inden-6-one

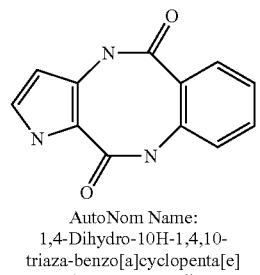

AutoNom Name:
3,6-Dihydro-4H-pyrrolo
[3,2-e][1,4]diazepin-5-one

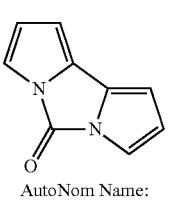

AutoNom Name:
5H,11H-Dibenzo[b,f][1,5]
diazocine-6,12-dione

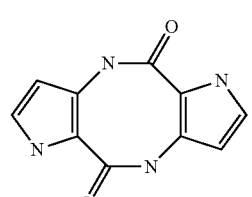

AutoNom Name:
8,9-Dihydro-3H-3,6,9-triaza-
cyclohepta[e]inden-10-one

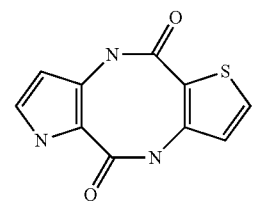 [SMILES: O=C1Nc2ccsc2C(=O)Nc2cc[nH]c21]

AutoNom Name:
7,8-Dihydro-1H-1,5,8-triaza-
cyclohepta[f]inden-9-one

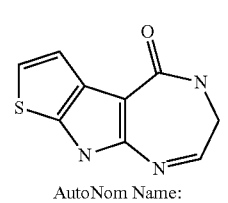

AutoNom Name:
1,4-Dihydro-10H-1,4,10-
triaza-benzo[a]cyclopenta[e]
cyclooctene-5,11-dione

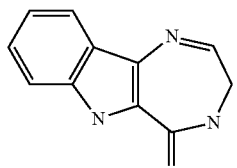

AutoNom Name:
4H,10H-1-Thia-4,10-diaza-
benzo[a]cyclopenta[e]
cyclooctene-5,11-dione

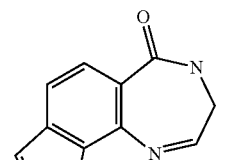

AutoNom Name:
8,9-Dihydro-5,6,9,11-tetraaza-
cyclohepta[b]naphthalen-10-one

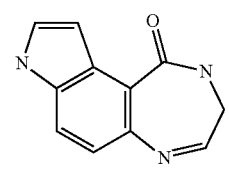 [SMILES: O=C1NCC=Nc2ccc3[nH]ccc3c21]

AutoNom Name:
3,4-Dihydro-[1,4]diazepino[5,6-
b]quinolin-5-one

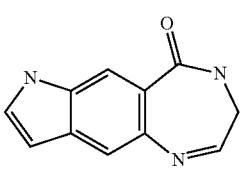 [SMILES: O=C1NCC=Nc2cc3cc[nH]c3cc21]

AutoNom Name:
Dipyrrolo[1,2-c;2',1'-e]
imidazol-5-one

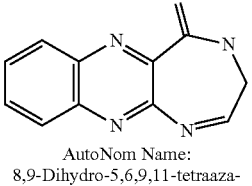

AutoNom Name:
1,4,7,9-Tetrahydro-1,4,6,9-
tetraaza-dicyclopenta[a,e]
cyclooctene-5,10-dione

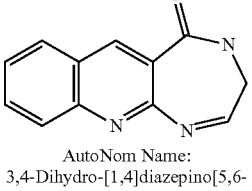

AutoNom Name:
8,9-Dihydro-4,8,11-triaza-
cyclohepta[a]naphthalen-7-one

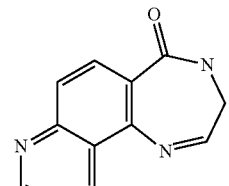

AutoNom Name:
11H-10,11-Diaza-benzo[b]fluorene

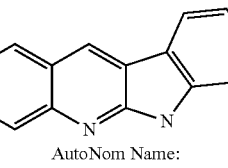

AutoNom Name:
4,7,9-Trihydro-1-thia-4,6,9-
triaza-dicyclopenta[a,e]
cyclooctene-5,10-dione

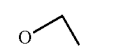

AutoNom Name:
2,4,9-Trihydro-1lambda*4*,6-
dithia-4,9-diaza-dicyclopenta[a,e]
cyclooctene-5,10-dione

AutoNom Name:
α-hydroxyacids

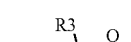

AutoNom Name:
α-aminoacids

AutoNom Name:
cohels

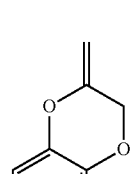

AutoNom Name:
Bicyclo[2.2.2]octane

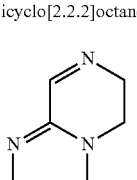

AutoNom Name:
6,9-Dihydro-5H-1-thia-5,8,9-
triaza-cyclopenta[a]azulen-4-one

AutoNom Name:
3,10-Dihydro-4H-[1,4]
diazepino[5,6-b]indol-5-one

AutoNom Name:
2-Methylene-2,3-dihydro-
benzo[1,4]dioxine

AutoNom Name:
6,7-Dihydro-2H-pyrazino
[1,2-a]pyrimidine

TABLE I-continued

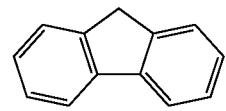 [SMILES: c1ccc2c(c1)Cc1ccccc1-2]
AutoNom Name:
9H-Fluorene

AutoNom Name:
1,4-Diazza-bicyclo[2.2.2]octane

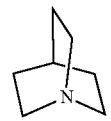
AutoNom Name:
1-Aza-bicyclo[2.2.2]octane

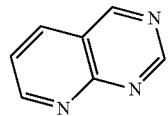
AutoNom Name:
Pyrido[2,3-d]pyrimidine

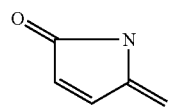
AutoNom Name:
5-Methylene-1,5-dihydro-pyrrol-2-one

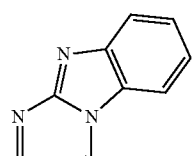
AutoNom Name:
Benzo[4,5]imidazo[1,2-a]pyrimidine

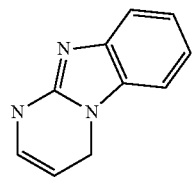 [SMILES: C1=CNc2nc3ccccc3n2C1]
AutoNom Name:
1,4-Dihydro-benzo[4,5]imidazo[1,2-a]pyrimidine

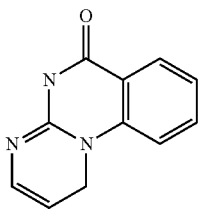 [SMILES: O=C1NC2=NC=CCN2c2ccccc21]
AutoNom Name:
4,10-Dihydro-1,4a,10-triaza-phenanthren-9-one

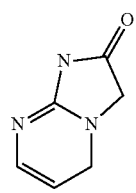
AutoNom Name:
1,5-Dihydro-imidazo[1,2-a]pyrimidin-2-one

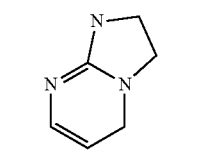
AutoNom Name:
1,2,3,5-Tetrahydro-imidazo[1,2-a]pyrimidine

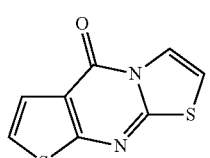
AutoNom Name:
Thiazolo[3,2-a]thieno[2,3-d]pyrimidin-5-one

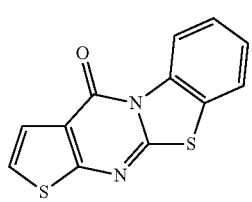 [SMILES: O=c1c2ccsc2nc2sc3ccccc3n12]
AutoNom Name:
1,9-Dithia-4a,10-diaza-cyclopenta[b]fluoren-4-one

TABLE I-continued

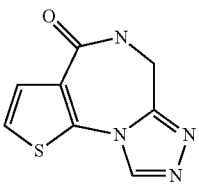 [SMILES: O=C1NCc2nncn2-c2sccc21]
AutoNom Name:
5,6-Dihydro-1-thia-5,7,8,9a-tetraaza-cyclopenta[e]azulen-4-one

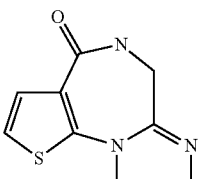
AutoNom Name:
6,10-Dihydro-5H-1-thia-5,7,10a-triaza-benzo[e]azulen-4-one

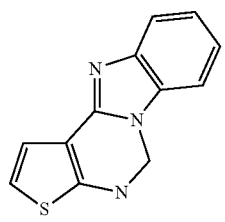 [SMILES: c1ccc2c(c1)nc1n2CNc2sccc2-1]
AutoNom Name:
4,5-Dihydro-3-thia-4,5a,10-triaza-cyclopenta[a]fluorene

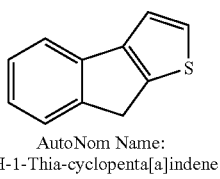
AutoNom Name:
8H-1-Thia-cyclopenta[a]indene

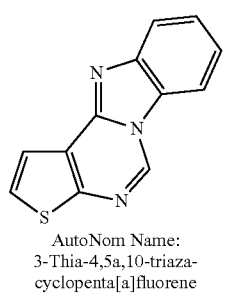
AutoNom Name:
3-Thia-4,5a,10-triaza-cyclopenta[a]fluorene

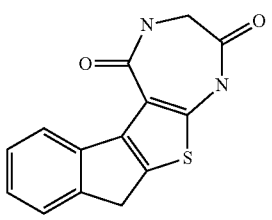 [SMILES: O=C1CNC(=O)c2c(sc3c2-c2ccccc2C3)N1]
AutoNom Name:
6,7,9,11-Tetrahydro-10-thia-6,9-diaza-indeno[1,2-a]azulene-5,8-dione

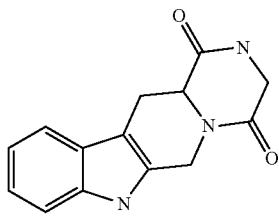 [SMILES: O=C1NCC(=O)N2Cc3[nH]c4ccccc4c3CC12]
AutoNom Name:
2,3,6,7,12,12a-Hexahydro-pyrazino[1',2':1,6]pyrido[3,4-b]indole-1,4-dione

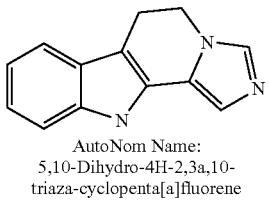
AutoNom Name:
5,10-Dihydro-4H-2,3a,10-triaza-cyclopenta[a]fluorene

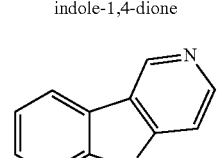
AutoNom Name:
5H-Pyrido[4,3-b]indole

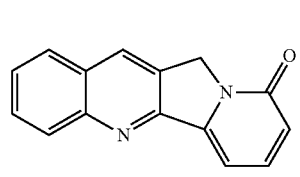 [SMILES: O=c1cccc2n1Cc1cc3ccccc3nc1-2]
AutoNom Name:
11H-Indolizino[1,2-b]quinolin-9-one

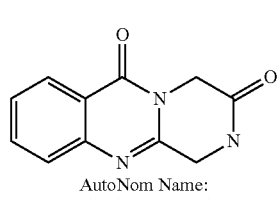
AutoNom Name:
1,2-Dihydro-2,4a,9-triaza-anthracene-3,10-dione

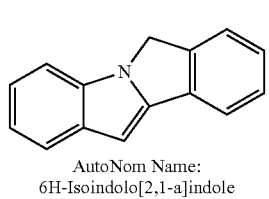
AutoNom Name:
6H-Isoindolo[2,1-a]indole

TABLE I-continued

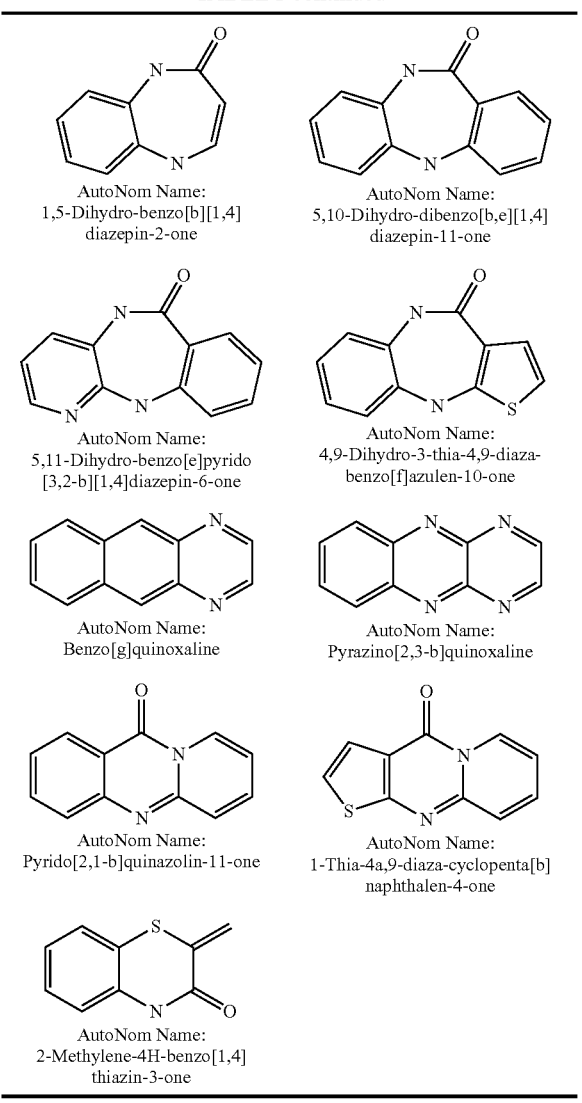

In an exemplary embodiment of the invention, the moieties are Me (methyl), Et (eteyl), Pr (propyl), Ph(phenol), $CO_2H$, OH and $NH_2$. Although the moieties may be connected at any of the R locations, not all the possible gauges are needed, as explained above. The indolizine scaffold can have, at R1, either COOH or $NH_2$, both of which are shown in the table. In particular, applicants have found that in general, a scaffold with four or five attachment points can span its entire range of triangles with M moieties, using only about $M^3$ different gauges. This is believed to be generally true (e.g., the exponent is not much higher than 3) for scaffolds with a larger number of attachment points.

It should be noted that even if a library does not cover all the possible triangles, a viable reconstruction is still possible for many drug targets and/or considerable utility attached to the library. Also, as noted above, partial reconstruction is useful in some cases. Also, as noted above, gauge matching can be used as leads and/or to reject leads, even if no reconstruction is possible, in some cases. In some embodiments of the invention, a failure of the method is typically self-evident and does not create an unproductive search after non-existent leads.

Alternatively to constructing a library of gauges from scratch, at least part of the library can be generated by scanning existing libraries for molecules that include triangles having desired sizes and/or moieties. Optionally, molecules that are small and rigid are selected, as described above. This type of library, for example, may not be based on a set of scaffolds.

14.4 Library Building Method

From the above description, it should be clear that there are many methods that may be used to construct a library. The following exemplary method is described, at least partly to illustrate various applications of the above rules:

(a) determine library parameters: e.g., spanning range and accuracy desired for library;
(b) select moieties for library;
(c) select a scaffold;
(d) generate gauges from the scaffold;
(e) add generated gauges if they are suitable;
(f) repeat (c)-(e) until the library spans the range with a desired accuracy and/or coverage; and
(g) optionally, check library.

In accordance with example embodiments of the invention, a resource allocation algorithm is used, for example the greedy method or the first fit method. These names refer to methods of selecting from a set of possible resources, which resource to allocate at a particular time, for example, which gauge to choose for a library from available gauges on a scaffold or which scaffold to add to the library. Many such methods are known in the art and may be used, noting that the method is not required, in some embodiments of the invention, to provide an optimal solution, just a working or reasonable solution.

An alternative method is a selection-based library construction method. In this method, existing molecule libraries are scanned for molecules that have gauge-like properties (e.g., as described herein). The resulting potential gauges may be filtered out to remove redundancies. It is expected however, that in the current state of public libraries, scanning such libraries will not yield a complete gauge library. Optionally, such a selected gauge library will be completed using other techniques, such as scaffold based gauge generation.

It should be appreciated that given a large number of possible gauges and a smaller actual required number, there are many optimization techniques for selecting a suitable and/or optimal set of gauges that meet the required number. As noted above, the selection may be based on the use to which the library is put and/or be based on considerations such as diversity, chemical behavior and ability to synthesize. In addition, a part of a library may be replaced, for example with a set of gauges constructed from other scaffolds or using molecules selected from a library of potential leads. In an exemplary embodiment of the invention, at (g) a constructed library is optimized, for example, removing redundancies and ensuring that desired distributions (e.g., of triangles, chemical properties) and overlaps (e.g., of lengths and/or moieties) meet certain guidelines and/or are optimal.

14.5 Scaffold Selection Method

In an exemplary embodiment of the invention, scaffolds in general are selected to have certain desirable properties, for example, one or more of:

(a) small size;
(b) rigidity;
(c) suitability for combinatorial chemistry;
(d) including a plurality of attachment points, for example, 3, 4, 6, 10, 12 or any smaller intermediate or larger number, for attaching moieties and/or chemical markers (e.g., for binding assays, chemical manipulation);
(e) a geometric arrangement of the attachment points so that a range of triangle sides can be provided;

(f) 3D structure, for example planar or volumetric may be preferred for different situations;

(g) number of excess protrusions (in some cases may be desirable to be small), to which moieties may or may not be attached, so that excess is relative to a perfect scaffold where the useful (e.g., for the library or for a particular triangle) moieties define the shape of the scaffold; and/or (h) solubility (may be determined, for example, based on the number of polar atoms in the scaffold).

In general, as more attachment points for moieties are provided, the scaffold is more able to provide triangles of various sizes, however, this may adversely affect the scaffold (and gauge size) and many of the triangles may be useless. In a scaffold in general, it may be useful to designate only some of the potential attachment points as attachment points to be used. This may reduce the number of different synthesis methods used and/or promote uniformity thereof.

Not all or even any of these properties are essential in some embodiments of the invention. As a practical matter, small rings and ring chains appear to meet these criteria. Thus, in an exemplary embodiment of the invention, a set of scaffolds may be generated by reviewing existing known rings and small chains for molecules that meet the desired criteria. In an exemplary embodiment of the invention, during this type of selection an effort is made to select scaffolds having a range of sizes (e.g., distances between attachment points), so that a range of triangles may be generated using the scaffolds.

In addition to scaffold criteria in general, a selection of scaffolds for a library may impose other criteria, for example that the scaffolds generate a spanning library of gauges and/or a range of chemistries and/or require a relatively small number of relatively low complexity process to generate the gauges.

In an exemplary embodiment of the invention, the scaffold selection process is as follows. Given an existing library portion, a new scaffold is selected from a list of available potential scaffolds if it answers at least one of the following criteria:

(a) the scaffold generates a large number of triangles that are missing from the libraries, for example, 10, 50, 100 or any smaller intermediate or larger number, such as a user set number;

(b) the scaffold generates at least one (or a small number of triangles, such as less than 20, less than 10 or less than 5, or any other user set value) triangles that have evaded generation using other scaffolds and form missing portions of the library;

(c) the scaffold has a significant amount of known chemistry (e.g., methods for manipulation and/or adding moieties); and (d) the scaffold adds the potential for a desired amount of overlap.

In general, if a larger the number of gauges is produced, it may be easier to complete a library. However, not all scaffolds can generate large numbers useful triangles.

It should be noted that in some divergence based methods of library design, each library element is selected to be as different as possible, so that this type of selection methods and/or at least some of the criteria used cannot be applied and run against conventional ideas.

It should be noted that as the library fills up, consideration (b) may be given more weight, with the possibility of searching or constructing a scaffold that has the desired properties (e.g., to form required triangles). Further, the search may lead to selection of less rigid scaffolds, for example, to ensure coverage or due to lack of suitable more rigid scaffolds.

In an exemplary embodiment of the invention, during an optional optimization stage of the library, scaffolds are assessed as to their quality (e.g., meeting scaffold criteria), number of triangles generated and/or uniqueness of triangles generated. A scaffold may be removed from the library if it is determined to be less useful or unneeded based on one or more of these considerations.

One difference between scaffolds is the number of rings in a scaffold. In general, as the number of rings increases, so does the scaffold size and weight. For some applications, the number of rings in a scaffold may be used as a heuristic to determine what approximate triangle sizes the scaffold can provide. For some applications, multi-ring scaffolds may be necessary. Alternatively or additionally, single or bi-ring scaffolds may be useful for small triangle sand/or for reducing steric clashes.

14.6 Gauge Selection Method

In an exemplary embodiment of the invention, gauges in general are selected to have certain desirable properties, for example, one or more of:

(a) small size;

(b) large numbers of triangles;

(c) high or otherwise desirable binding affinity, for example in the range of 1-100 micro Molar;

(d) rigidity;

(e) the attached moieties defining the volume of the molecule;

(f) relatively uniform binding probability for all moieties, for example a factor of ten between moieties and a factor of 100 between molecules in a library, however, in other embodiments other, smaller or greater factors (e.g., ~1, 5, 20, 50, 130, 250, 1000 or any smaller, intermediate or greater factor) may be provided for one or both criteria; and/or (g) chemical behavior, such as (i) solubility, for example in a natural solute of the target (or an approximation thereof), for example water at a given pH, with some detergent such as DMSO to aid solubility, (ii) lack of reactivity with expected contaminants, (iii) lack of chemical reactivity (creation of covalent bonds) with a target protein i.e., with amino acids or known typical combinations of them and/or with a substrate, (iv) desired behavior over a range of properties.

In general, a higher uniformity of binding means that the assays have a same meaning. However, it is generally not practical to provide such narrowly defined materials, and a certain latitude is useful if a realistic set of chemical is to be provided.

When generating a library (or part thereof) by selection of gauges from existing molecule screening libraries, each molecule is, for example screened against the desired criteria. A molecule may be selected or rejected. Alternatively or additionally, a molecule may have a score of suitability associated with it. Similarly, a set of potential gauges may be generated from scaffolds.

In an exemplary embodiment of the invention, gauges are selected from the generated/selected set, based on one or both of suitability (e.g., relative or absolute) and meeting of group criteria. In an exemplary embodiment of the invention, one or more of the following group criteria are applied, for example as binary criteria or as part of a score:

(a) That uniqueness of the triangles provided and/or them matching missing triangles.

(b) Matching of flexibility of the gauges and/or individual triangles, to desired flexibility.

(c) Shape of gauge as a whole, for example, being elongate or being round. The shape may be a consideration, for example when building a library in which shapes are varied so that steric-clashes will not reject all of a certain triangle. To this end, the shape of the gauge may interact with the location of specific triangle son the gauge, e.g., if a same triangle is found on two elongate gauges, it may be desirable that on one of the gauges the triangle is in an axial direction and in the other, in a trans-axial direction. Alternatively or additionally, shape considerations relates to the three-dimensional shape of the gauge and/or relative layout of triangles in the gauge.

(d) That certain non-triangle measures are found, for example specific non-triangle measures or that a uniform (or other) distribution of such 4-5—or other multi-point measures are provided.

It should be noted that for gauges and/or scaffolds, the determination of suitability may include, for example one or more of using simulation and molecular analysis software, chemical laboratory testing and/or searching literature for the same or similar chemicals.

The above selection method may be useful when designing a single universal library (or a set of such libraries for broad uses). It should be noted however, that some, similar or other selection methods may be used when generating personal and/or ad-hoc libraries, searching for gauges or measures with particular properties and/or when defining a gauge and/or scaffold to be generated.

14.7 Gauge Synthesis

The generation of a gauge library from scaffolds, in some embodiments of the invention, may assist in the serial synthesis of the gauges. In libraries that are not (or are partially not) scaffold based, standard synthesis methods may be used.

In an exemplary embodiment of the invention, the gauges are synthesized, for example using liquid phase methods as described below, and impurities are removed using standard methods, for example using HPLC.

In an exemplary embodiment of the invention, a parallel synthesis method is used, in which a plurality of gauges are synthesized at once and then separated. It should be noted that in some embodiments of the invention, only a small number of the gauges that can be created by a scaffold are actually needed. Alternatively or additionally, even if many of the particular gauges cannot be created, a sufficient number of alternative gauges may be available, to provide spanning and/or overlap of a desired triangle space. For example, on a five point scaffold with 10 moieties, 100,00 combinations are possible, of which 1000 are sufficient cover all the triangles. Thus the choosing can be, for example, ad hoc, such as based on the actual yield (e.g., relative yield) or based on the prior design of the library.

In an exemplary embodiment of the invention, combinatorial chemistry methods are used to attach moieties, each at a different attachment point of a scaffold, optionally so that all combination of moieties are created. Each final compound is made attached to a polymer bead (for example) for ease of separation. The beads may be color coded for assistance in separation and/or identification of the created gauge.

Alternatively, other solid phase methods, for example as described below or as known in the art, are used.

14.8 Mixed Library Design

As noted above, in order to be useful, a complete universal library is not required. Further, a gauge library may be included into a "regular" screening library. In an exemplary embodiment of the invention, at least 0.05%, 0.1%, 0.5%, 1%, 5%, 10%, 20%, 40% or any smaller, intermediate or larger percentage of the molecules in a library used for screening, measuring and/or other uses comprise gauge-like molecules. Of such gauges, for example, less than 50%, or greater than 30%, 60%, 80%, 90%, or any smaller, intermediate or larger percentage of the gauges are scaffold-based gauges, where a scaffold is used to generate at least 5 gauges with less than 20% overlap in triangles defined by attached moieties. As noted above, while a library may include standard screening parts, providing significant numbers of gauge-like molecules may assist in applying the methods described herein.

In an exemplary embodiment of the invention, the library comprises at least 5,000, 10,000, 20,000, 50,000, 80,000 ,100,000 or any intermediate or greater number of gauges. These gauges may be, for example, scaffold based gauges, plain gauges and/or rigid gauges. These gauges may span, for example, 5%, 20%, 40%, 80%, 100% or any smaller, intermediate or greater percentage of the triangle space, for example, with an overlap of 1.1, 1.5, 2, 3 or any smaller, intermediate or greater degree. As noted above, when spanning is better, the degree of success may be higher, albeit at a cost of using a larger library. Smaller libraries may be easier to apply and still yield useful results, in many cases.

One significant difference between gauges and other lead libraries (e.g., diversity based libraries), in accordance with some exemplary embodiments of the invention, is that a relatively large number of matches is expected using gauge based libraries. For example, at least 0.01%, 0.05%, 0.1%,0.2%, 0.5%, 1%, 3%, 5%, 10% or any smaller, intermediate or greater percentage of numbers is expected to bind. The percentage of binding may depend, for example on the ratio between gauges and non-gauge leads in a library.

It should be appreciated that these percentages are not mere numbers. Rather, they represent a qualitative difference from libraries where more often than not, no leads bind. The greater the probability of finding one or more leads and the greater the number of leads, the more likely it is that a drug will be found. However, of binding is too likely, the quality of information provided by the binding may be reduced.

A library may also include a mix of three-point measures and higher valance measures. While any gauge that includes more than three moieties includes a high valance measure, in an exemplary embodiment of the invention, the library is designed to span the higher valance space. For example, the library spans at least 0.1%, 0.3%, 0.5% or at least 1% or any smaller intermediate or larger percentage of the space of the higher valance measures. The spanning may be, for example, continuous (e.g., the whole library at a low resolution or part of the library at a high resolution) or it may be discrete (e.g., isolated parts of the library). In general, higher valance measures may require a very large number, for example, 20,000,000 for a spanning equivalent to the 100,000 library of the triangles, so commercial implementation may depend on the availability of even more parallel assays than available today. Optionally, the higher valance measures are provided to be more flexible, so that a lower resolution is required to span the space.

14.9 Ensuring Library Reliability

In an exemplary embodiment of the invention, once a library is constructed and/or during its construction, various quality assurance processes may be employed. In one example, the library is analyzed to ensure that it meets the spanning, overlap and/or accuracy criteria set for the library. Any missing triangle and/or gauge may be provided at this point or noted as missing. Alternatively or additionally, molecules with low solubility or high toxicity are removed and/or replaced with molecules exhibiting similar spatial chemical configurations.

In an exemplary embodiment of the invention, feedback from use of the library is used to calibrate the library, reconstruction process and/or to assist in library design.

In an exemplary embodiment of the invention, the theoretical modeling of the library is compared to its actual behavior, for example, by running test assays against randomly selected targets having a known and/or an unknown structure. Two examples of molecules with known structures are thoroughly mapped proteins and structures constructed from DNA or RNA, with optional attached elements. Optionally, the targets are not random and are selected to test certain assumption in the theoretical model of the library. Alternatively or additionally, the calibration is provided by analysis the results of real uses of the library over time.

In an exemplary embodiment of the invention, one or more of the following data is provided by such analysis:

(a) assay binding rates for gauges and families (e.g. similar) gauges;

(b) dependency between environmental conditions and binding rates and/or conformal changes for one or more gauges;

(c) Baysian probability of steric clashes between gauges (and triangles thereof) with overlapping triangles;

(d) actual degree of overlap between triangles;

(e) dependency between target type and gauge binding; and/or (f) parameter values (e.g., thresholds) for the various algorithms.

Other properties of the library, for example general rigidity of the gauges and correctness of values in the data bank may also be provided by such or other analysis.

In an exemplary embodiment of the invention, as a result of the above findings, the library is amended, for example, by removing redundant gauges and/or searching for gauges to generate the missing triangles.

Alternatively or additionally, as a result of the above findings, later generation of libraries and sub-set libraries is modified to take the calibration information into account, for example in a specific manner as relating to specific gauges and/or in a general manner as it relates to statistical deviation of the behavior of scaffolds and/or families of gauges from their appropriate theoretical models and/or as parameters for such models.

Alternatively or additionally, the reconstruction process is calibrated, for example to better distinguish which triangle matched, the actual coverage of each triangle, the spatial shape (in triangle space) of a match and/or the relative binding strength of various triangle measures and/or gauges.

14.10 Human Interaction during Library Design

The process of designing a library may be automatic, semi-automatic or manual. In general, when more potential gauges and/or scaffolds are available and suitable modeling software is available as well, automated designing may be provided. one example of this is once a complete library is available, selecting a sub-set may be completely automatic, once the desired parameters are provided. Some of the library may be generated automatically in any case, for example selection of gauges from existing libraries and/or selection of scaffolds from existing libraries. The determination of ease of synthesis may be required to be manual if no earlier information is available. It is noted, however, that in an exemplary embodiment of the invention, the scaffolds are chosen to have known chemical behavior and synthesis paths, so that attachment of moieties should require little or no research work. In some cases, however, a human may be required to not only select between alternatives but actually to find a particular missing gauge or suggest a scaffold design. It is noted, however, that the mathematical description of the library in accordance with some embodiments of the invention, assists and may allow complete or nearly complete automatic generation of a library using constructive synthesis and/or analysis of existing molecules. Possibly, such a library may then be optimized, for example as described above, possibly manually, especially to assist in providing an easy to synthesize library.

As noted above, the reconstruction process may be completely automatic or it may include a manual aspect. In general, however, it is expected that the high hit rate of binding of gauges will reduce or eliminate any need for human intervention, at least in some of the steps of drug discovery. Of course, once mapping is completed, a human user may desired to test the effect of various assumptions, for example, how the reconstructed layout depends on various assumptions made on the target conformity. Also, in some case a human expert (or an expert system) may be used to select among alternative or select likely leads, since in many cases the method will generate a small number of possibilities from which one or two should be selected, failing that costs may be very high.

In an exemplary embodiment of the invention, one point for human intervention in the drug discovery process is in designing drug candidates that match a final pharmacophore (e.g., model). It is noted, that various software exists to assist or automate this step. Typically however (at this point in time), human judgment is better at assessing synthetic feasibility for complex molecules. If the suggested drugs are created by linking together gauges or simple fragments, however, automatic assessment and possibly generation methods, may be reasonable.

15. Experiments and Examples 15.1 Experiment 1

Some of the above measurement method was testing using the following experiment.

In this experiment, known inhibitors of HIV-1 Protease were analyzed to detect a set of triangle measures that should exhibit binding to HIV-1 Protease. A set of molecules including the triangle measures were selected and physically assayed and shown to have the expected binding to HIV-1 Protease. The results indicate that triangles are a viable geometrical sub-structure that can be used to measure a target by binding.

The following entries in the PDB (Protein Data Base) were extracted as structures of HIV-1 Protease with known, bound, inhibitors: 1ajv 1ajx 1dif 1gno 1hbv 1hih 1hos 1hps 1hpv 1hpx 1hsg 1hte 1htf 1htg 1hvi 1hvj 1hvk 1hvl 1ohr 1sbg 1upj 2bpv 2bpw 2bpx 2bpy 2bpz 2upj 3tlh 5hvp 7upj.

The structures were super-imposed using the protein as a reference frame, so that the spatial position and orientation of the inhibitors was superimposed. The inhibitor molecules were then decomposed into moieties and those were clustered in space. Strong bonding locations were identified based on the same moiety in different molecules binding to a substantially same binding location in the protease. Confidence in these locations was increased by verifying that the protein moieties at those locations were compatible with the inhibitor molecule moieties.

Triplets of the inhibitor moieties at the strong binding locations were selected as "triangles". Gauges, for example, of a gauge set as described above, that have those triangles, are expected to bind, or at least some of them should bind.

The triplets were used as a query input for a search in MDL's ACD-SC (available chemical directory for screening). Molecules that matched the queries (moieties and size) and the rigidity requirements were selected, as shown in the following table.

TABLE II
| No. | Compound | MW | Density (g/ml) | Cat. No. | mg for 1 mM in 10 ml |
|---|---|---|---|---|---|
| 1 | 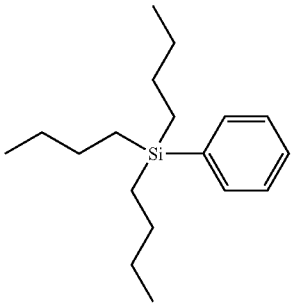 [SMILES: CCCC[Si](CCCC)(CCCC)c1ccccc1] | 276.35 | | S-83425-4 | 2.8 |
| 2 | 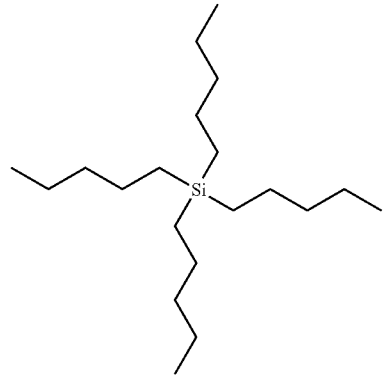 [SMILES: CCCCC[Si](CCCCC)(CCCCC)CCCCC] | 403.26 | 1.008 | 36,667-6 | 4.00 µl |
| 3 | 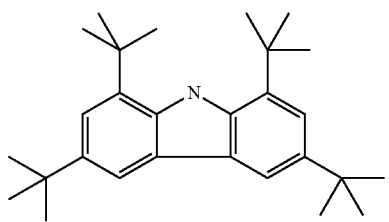 [SMILES: CC(C)(C)c1cc(C(C)(C)C)c2[nH]c3c(C(C)(C)C)cc(C(C)(C)C)cc3c2c1] | 391.35 | | S-63995-8 | 3.9 |
| 4 | 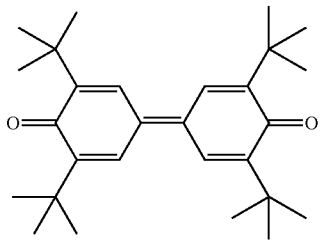 [SMILES: CC(C)(C)C1=CC(=C2C=C(C(C)(C)C)C(=O)C(C(C)(C)C)=C2)C=C(C(C)(C)C)C1=O] | 408.32 | | S-84651-1 | 4.1 |
| 5 | 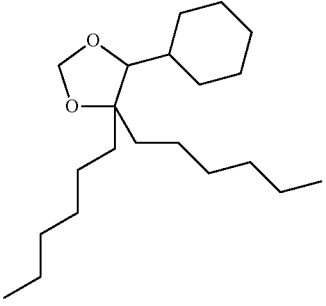 [SMILES: CCCCCCC1(CCCCCC)OCOC1C1CCCCC1] | 324.55 | | S-2210-2 | 3.2 |

TABLE II-continued

| No. | Compound | MW | Density (g/ml) | Cat. No. | mg for 1 mM in 10 ml |
|---|---|---|---|---|---|
| 6 | | 464.56 | | R-15419-9 | 4.6 |
| 7 | | 445.57 | | S-22759-5 | 1.9 |
| 8 | | 445.57 | | S-22675-0 | 1.9 |
| 9 | | 446.17 | | S-95285-0 | 4.5 |
| 10 | | 412.53 | | S-9757-9 | 4.1 |

TABLE II-continued
| No. | Compound | MW | Density (g/ml) | Cat. No. | mg for 1 mM in 10 ml |
|---|---|---|---|---|---|
| 11 | 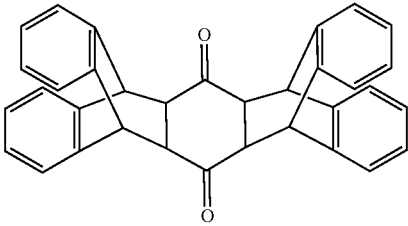 [SMILES: O=C1C2C3c4ccccc4C(c4ccccc43)C2C(=O)C2C3c4ccccc4C(c4ccccc43)C12] | 464.56 | | R-15449-0 | 4.6 |
| 12 | 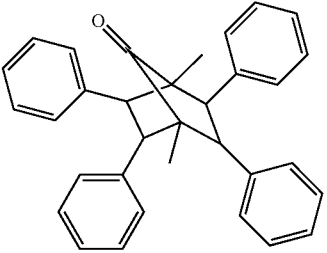 [SMILES: CC12C(=O)C(C)(C(c3ccccc3)C1c1ccccc1)C(c1ccccc1)C2c1ccccc1] | 438.57 | | R-15358-3 | 4.4 |
| 13 | 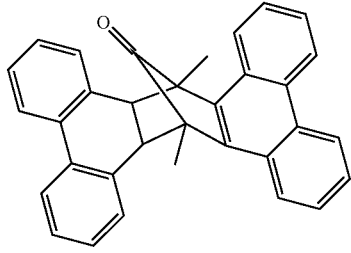 [SMILES: CC12C(=O)C(C)(c3c1c1ccccc1c1ccccc31)C1c3ccccc3-c3ccccc3C12] | 436.55 | | R-15353.2 | 4.4 |
| 14 | 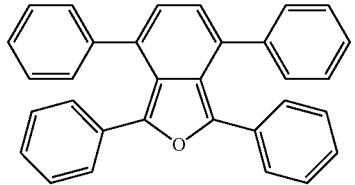 [SMILES: c1ccc(-c2ccc(-c3ccccc3)c3c(-c4ccccc4)oc(-c4ccccc4)c23)cc1] | 422.53 | | R-33994-6 | 4.2 |
| 15 | 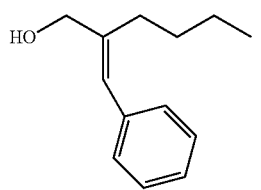 | 204.16 | | S-52812-9 | 2.0 |
| 16 | 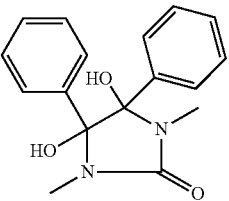 [SMILES: CN1C(=O)N(C)C(O)(c2ccccc2)C1(O)c1ccccc1] | 298.34 | | S-6426-3 | 3.0 |

TABLE II-continued

| No. | Compound | MW | Density (g/ml) | Cat. No. | mg for 1 mM in 10 ml |
|---|---|---|---|---|---|
| 17 | | 200.32 | 0.887 | 46443-0 | 2.26 μl |
| 18 | | 234.34 | | 27302-3 | 2.3 |
| 19 | | 280.37 | | R-22433-2 | 2.8 |
| 20 | | 236.36 | | 44642-4 | 2.4 |
| 21 | | 268.33 | | S-4228-6 | 2.7 |
| 22 | | 344.38 | | NRB-01407 | 3.4 |

TABLE II-continued

| No. | Compound | MW | Density (g/ml) | Cat. No. | mg for 1 mM in 10 ml |
|-----|----------|-----|----------------|----------|----------------------|
| 23 | [structure: 4-hydroxy-3-pentyl-1-methyl-2,6-diphenylpiperidine] | 377.51 | | RJC-03605 | 3.8 |
| 24 | [structure: 4-hydroxy-2-phenyl-1-azaspiro piperidine-cyclohexane] | 245.37 | | JFD-03358 | 2.5 |
| 25 | [structure: 4-hydroxyimino-3-pentyl-1-methyl-2,6-diphenylpiperidine] | 350.31 | | RJC-03637 | 3.5 |
| 26 | [structure: 3,3',5,5'-tetra-tert-butyl-4,4'-diphenoquinone] | 408.63 | | RJC-03257 | 4.1 |
| 27 | [structure: pyrido-pyrimidine trione with phenyl, methyl substituents] | 435.49 | | JFD-01334 | 4.4 |
| 28 | [structure: dichloro pyrido-pyrimidine dione with diphenyl substituents] | 460.32 | | RJC-02058 | 4.6 |

TABLE II-continued

| No. | Compound | MW | Density (g/ml) | Cat. No. | mg for 1 mM in 10 ml |
|---|---|---|---|---|---|
| 29 | | 456.59 | | RJC-02951 | 4.6 |
| 30 | | 477.41 | | BTB-14801 | 4.8 |
| 31 | | 280.29 | | BTB-11623 | 2.8 |
| 32 | | 295.43 | | RJC-03631 | 3.0 |
| 33 | | 212.25 | | RJF-00720 | 2.1 |

TABLE II-continued

| No. | Compound | MW | Density (g/ml) | Cat. No. | mg for 1 mM in 10 ml |
|---|---|---|---|---|---|
| 34 | methyl 7-methoxy-1,4a-dimethyl-1,2,3,4,4a,9,10,10a-octahydrophenanthrene-1-carboxylate | 302.41 | | 25,612-6 | |
| 35 | 9,10-dioxo-9,10-dihydroanthracene-2-carboxylic acid | 252.23 | | 25,272-7 | |
| 36 | 2,2,2-trichloro-1-phenylethyl acetate | 267.54 | | 29,126-9 | |
| 37 | 2,5-bis(trifluoromethyl)benzoic acid | 258.12 | | 23,319-6 | |
| 38 | 2,6-dibromo-4-methylphenol | 265.94 | | 30,118-3 | |
| 39 | N-(methoxycarbonyl)arginine | 308.34 | | 16,263-9 | |

The molecules numbering up to 33 were expected to exhibit binding behavior, due to them including at least one triplet. The molecules numbered 34 and up are superficially similar but do not include the required triangles.

All of molecules were actually assayed and appeared to show activity (effect on HIV-1 Protease) at various concentrations (between 10 and 1000 micro-molar). Of these molecules 1-33 about 60% were found to be active, in particular molecules 7, 9, 23 and 27. Also molecules 34-39 were assayed, with no activity shown, as expected.

As noted above, these results appear to indicate that gauges, in general, that have a triangle measure that matches the target layout, should, often enough, bind in a detectable manner.

15.2 Experiment 2

In this experiment, assay results performed by others were used to reconstruct the spatial layout of binding locations, for known molecules and then compared to the current state of the art.

The NCI maintains a database of molecules that have tested positive for activity against HIV. 43,000 results (in the October 1999 release) are available at "dtp.nci.nih.gov", under "public data", then "results from AIDS antiviral screen". From these molecules were selected a subset that showed at least a moderate level of activity and were rigid enough to allow determination of the spatial position of all their moieties. This resulted in fewer than 200 molecules. The moiety triangles in these selected molecules were clustered.

The clustering results showed a good match to the results of experiment I and the triangles of the molecules were found in the PDB structures.

These results appear to indicate that a set of gauges (e.g., the molecules that were tested for HIV) can be used to measure and then reconstruct an active area.

In addition, these results appear to indicate that at least part of a suitable library may be generated by selecting suitable gauges from available libraries, rather than by construction using scaffolds. It should be appreciated that it may not be required to determine the spatial positions of all the moieties, for example only of the moieties with a high binding affinity. Moieties with low affinities may be removed, in some cases.

16. Synthesis Book

Following is a synthesis book, arranged in chapters, for some of the scaffolds (and gauges derived from them), shown in table I. A most important aspect of this synthesis is that it illustrates that suitable scaffolds and gauges are available and can be generated using known chemical processes applied to standard or modified sources and/or by changing their parameters in an expected manner. The references described in this book are incorporated herein by reference. In any case, the partial library described in the appendix has at least the property that is can serve in many cases to provide a partial reconstruction and/or a significant increase in lead matching.

It should be appreciated that the novel materials described in the book, the manipulation methods thereof, synthesis methods thereof and groups of molecules from this book are also considered to be within the scope of at least some aspects of the invention, for example, a library including one, two, four, six, eight or any intermediate number of scaffolds as described therein. Alternatively or additionally, a library in accordance with an exemplary embodiment of the invention, includes at least 100, 300, 500, 1000, 2000, 4000, 10,000, 20,000 or any smaller, intermediate or larger number of gauges from this book. While it is useful to select gauges from the book, for example by using the scaffolds described therein to span part of the library, this is not required.

16.1 Benzenes, Pyrimidines 6-Membered Ring Scaffold

The Biginelli dihydropyrimidine synthesis (pathway below) is a promising multi component condensation, which involves the one-pot cyclocondensation of β-ketoesters 2, aldehydes 3, and ureas 4 providing the heterocycle 1, which can be oxidized to the corresponding pyrimidine moiety.

Biginelli-general multicomponent approach.

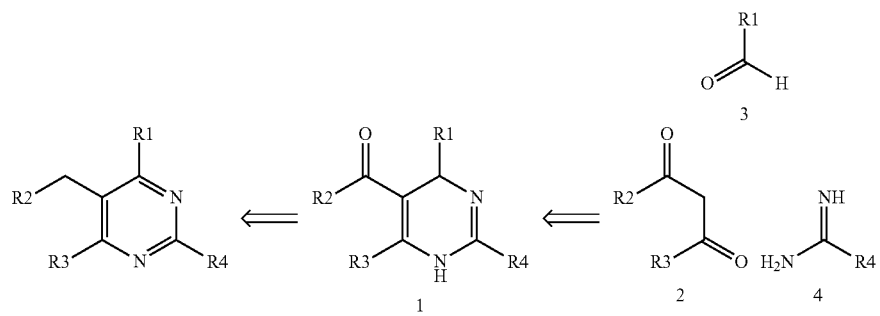

Several protocols have been developed for solution phase Biginelli reactions[1] In order to drive the reactions to completion, however generally, an excess of two of the three components 2-4 has often to be employed, and purification steps are required. The solid phase synthesis provides the desired dihydropyrimidines in good yield and superior purity directly after cleavage from the resin[2] (pathway below):

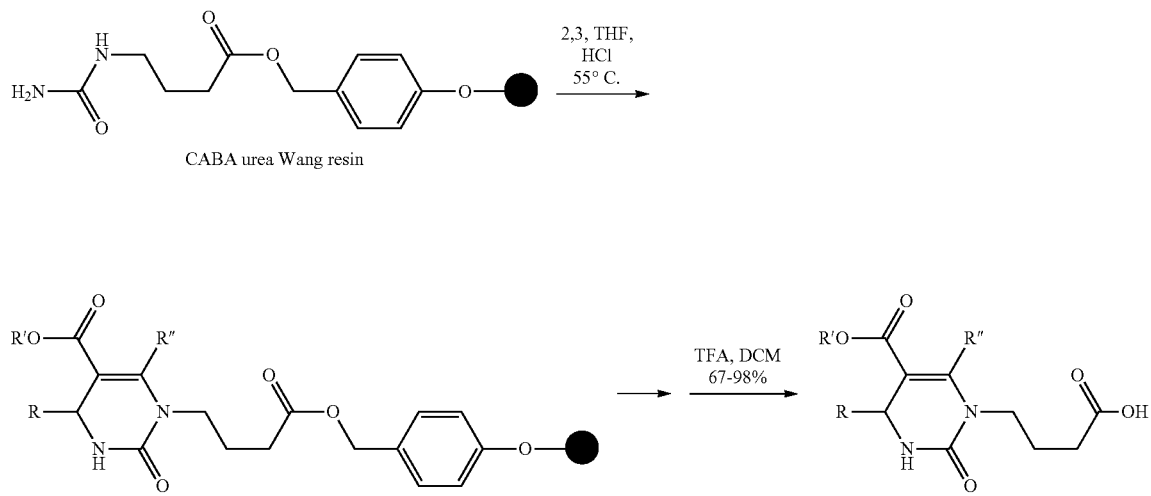

Another approach for the SP synthesis of highly substituted pyrimidines was recently published[3]. In this work the synthesis starts from polymer-bonded thiouronium salt 5, which undergoes cyclocondensation with acetylenic ketones 6 to form carboxy pyrimidines 7 (pathway below).

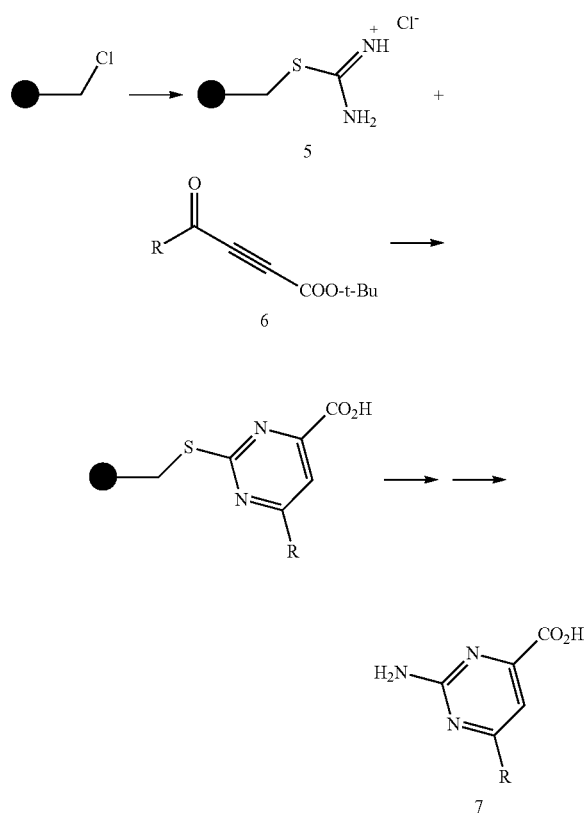

Tetra substituted pyrimidines a can be prepared via a modified Bigenelli's synthesis as described in the pathway below:

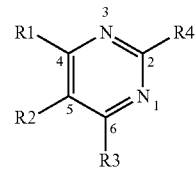

First the imidine functionalities are formed on the acid labile resin to produce the resin immobilized amidines 23[4], urea 24 and guanidine 25[2]. Actually, these amidines served as the first Biginelli building block. Next, the addition of the two other Biginelli building blocks, namely 2 and 3, to 23-25 leads to generation of dihydropyrimidine scaffolds 20, 21 and 22[5], respectively. The consequent reduction of ketone moieties ($NaBH_4$, $BF_3OEt_2$) leads to 14, 15 and 16, which after cleavage (TFA, DCM, 1:1) followed by mild oxidation (CAN, $CH_3CN$) affords the desired pyrimidines 8, 9[5] and 10 respectively. The CAN could be removed, after the completion of the oxidation, by Solid Phase Extraction (SPE) or by simple 96 well SePack. Other oxidation reagents such as $MnO_2$[6], O-chloranil[7], $KMnO_4$[8], and $CrO_3$, AcOH, $H_2SO_4$[9] can also be used. In case R3=OMe (when the building block 2 is β-ketoester) dihydropyrimidines 20, 21 and 22 undergo hydrolysis of ester (LiOH, THF or 5% alcoholic KOH[10], producing the 4-carboxy-dihydropyrimidines 17, 18 and 19 respectively. Following by the same mode as for 8, 9 and 10 (1. TFA, DCM, 1:1; 2. CAN, $CH_3CN$) 17, 18 and 19 react to give the sub-library of 4-carboxy-pyrimidines 11, 12 and 13 respectively. It should be noted that in case of unsymmetrical 1,3 diketones 2 a mixture of 2 isomers are obtained.

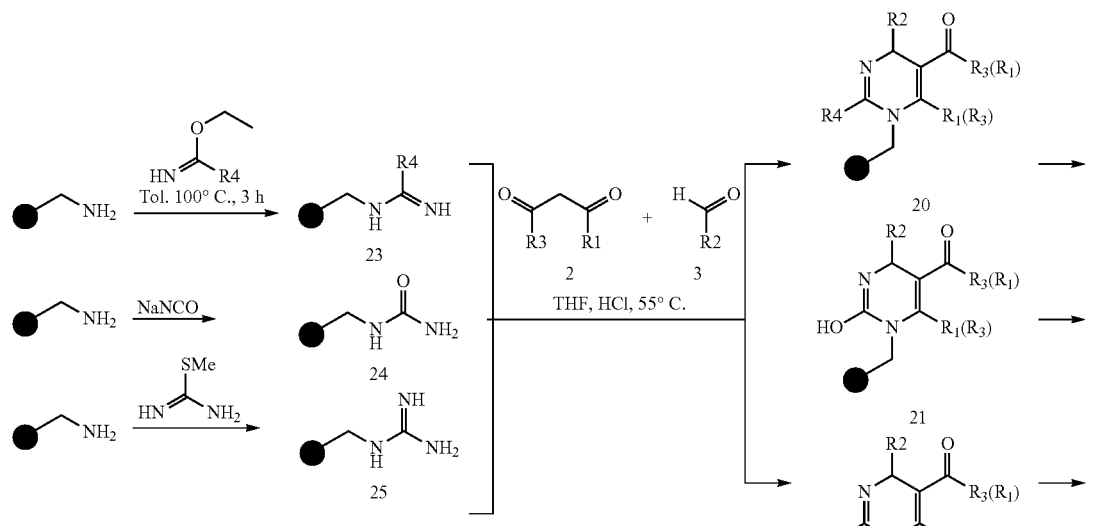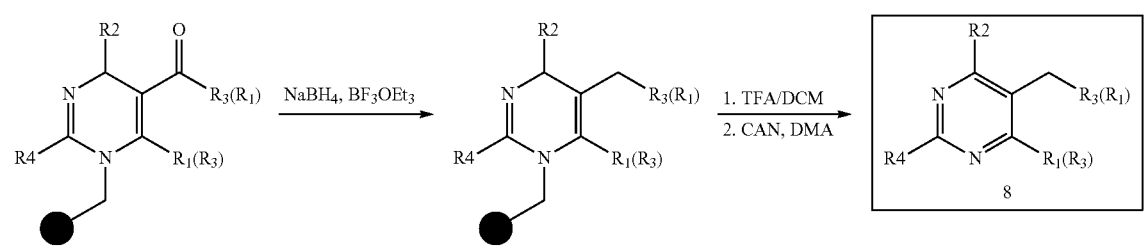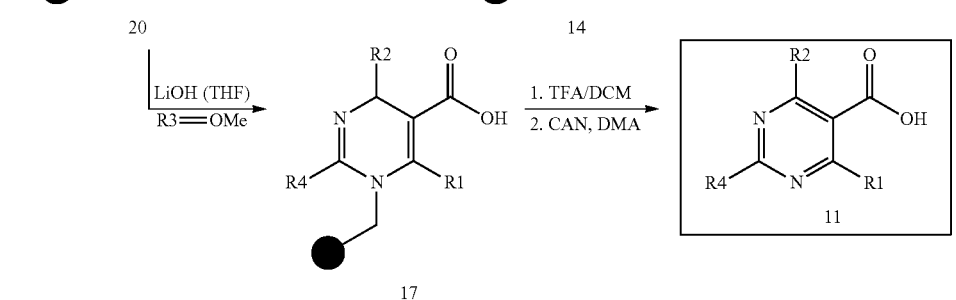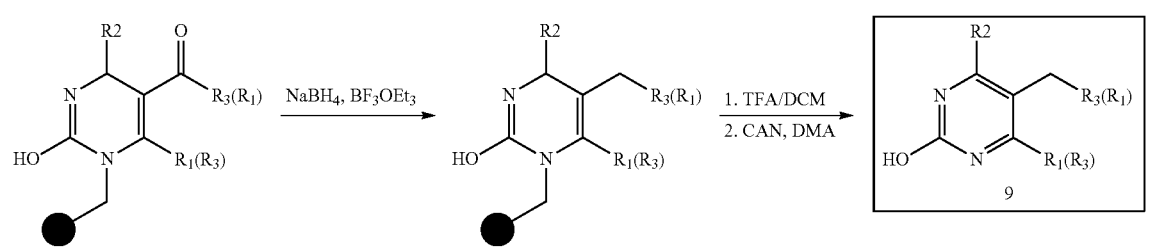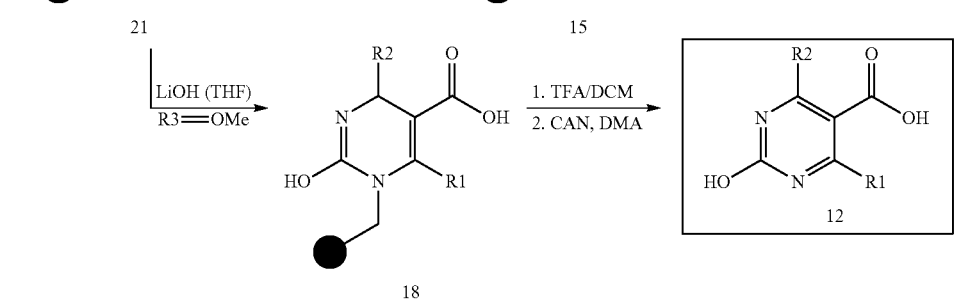

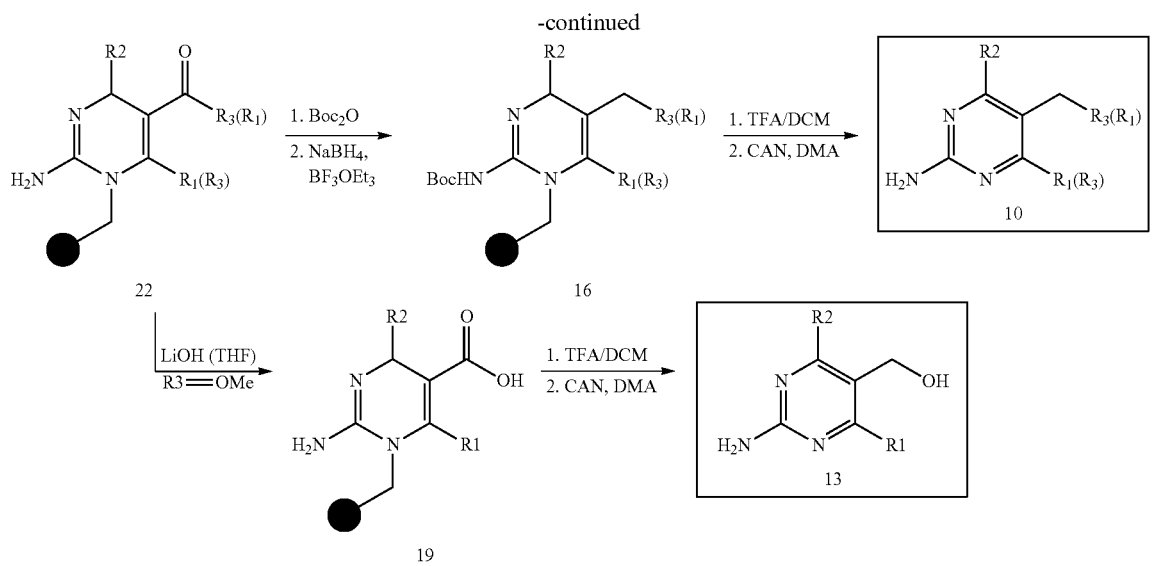

A core approach towards tetrasubstituted pyrimidines.

It was demonstrated[11] that dihydropyrimidine 5-carboxylic acid can be transformed into carboxylic azide which in turn undergoes Curtius rearrangement to give isocyanate. This reaction provide an excess of 5-amino dihydropyrimidines A.

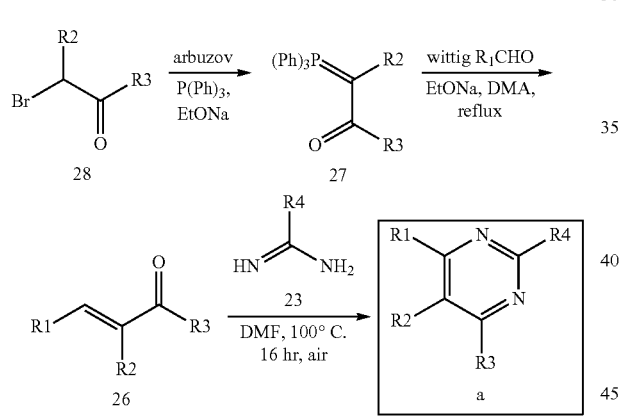

Pyrimidines can be prepared by cyclocondensation of amidines with α-β unsaturated ketone. Recently, the researchers have published the synthetic work[12], in which they describe the utilization of the Wittig reaction in formation of α,β-unsaturated ketones on SP for the synthesis of the various heterocycles. We propose the alternative three-step synthesis of pyrimidines a in solution, based on the formation of the α,β-unsaturated ketone building blocks 26 as a key step[12b-d] is described below:

α,β-unsaturated ketones 26 can be obtained in good yields and purity by Wittig reaction of the appropriate aldehyde and the corresponding triphenylphosphonium bromide 27 with NaOEt at reflux in DMA. The phosphorus yields 27 are readily available from a-bromo ketones 28 by the Arbuzov reaction, followed by treatment with a strong base, such as NaOEt. The reaction of ketones 26 with various amidines 23[12b-d] (FIG. 4) affords, the desired tetra-substituted pyrimidine sub library a.

Small sub-libraries b-g having one or more constant functional group on the six member aromatic ring, are characterized by better solubility.

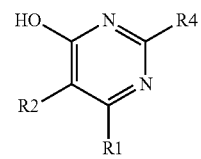
b

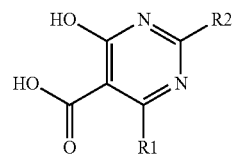
c

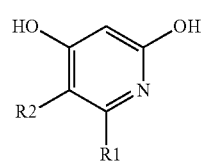
d

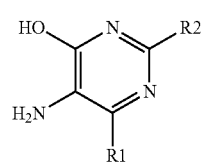
e

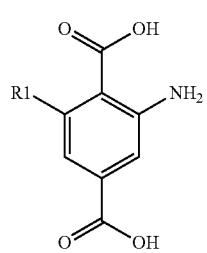
f

A series of 2,5,6-trisubstituted-4-oxo-dihydropyrimidines 29 can be prepared by SP using a cyclization-cleavage strategy[13] from readily available amidines 23 and resin attached α,β-unsaturated carboxylic acids 30[14] (see pathway below). Compound 30 is obtained via coupling of the polymer and acyl-chloride 31 (derivetized from commercially available α,β unsaturated carboxylic acids.

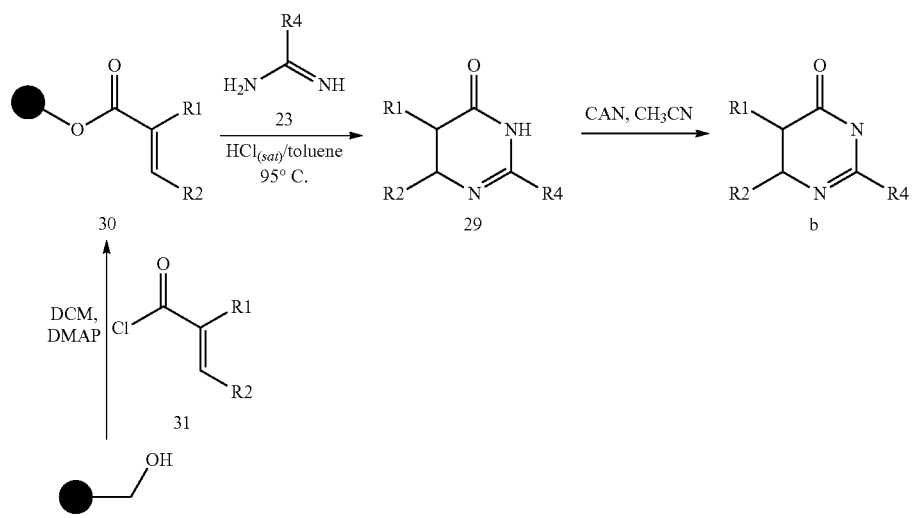

Compounds 29[13b] can be oxidized (CAN, CH$_3$CN) to corresponding pyrimidines b.

A solid phase method for the preparation of Knoevenagel condensation products from resin bound malonates and malonic acids has potential for the preparation of hetero- and carbocyclic compounds. (see pathway below)

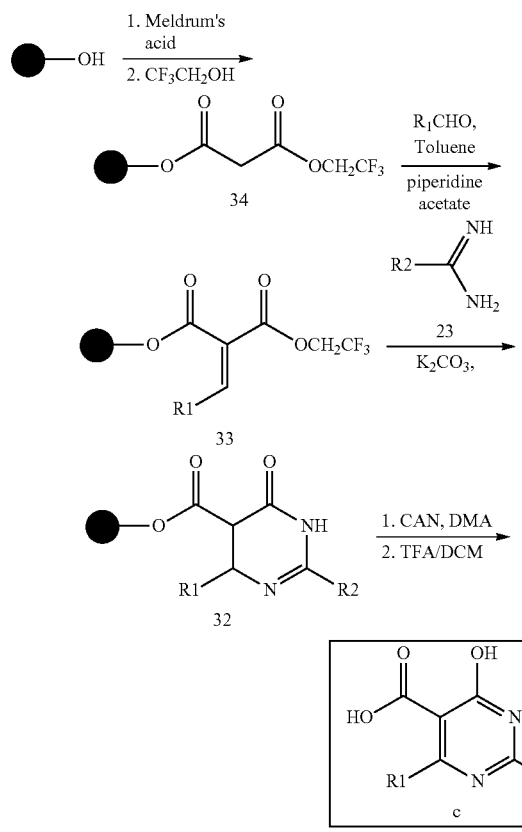

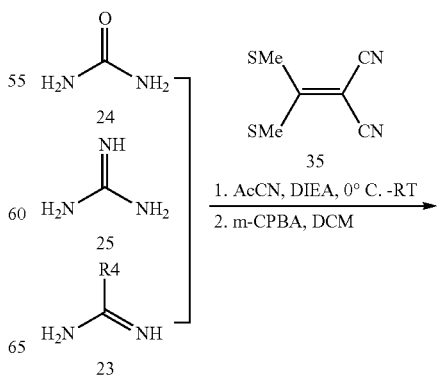

Malonic acid monoester (see pathway above) are prepared from macroporous Wang resin (AgroPore, Argonaut Technologies)[15] by treatment with Meldrum's acids.

Conversion of the unsymmetrical ester 34 was achieved by treatment with trifluoroethanol and DIC, followed by Knoevenagel condensation with the aldehyde in the presence of piperidine acetate to give substituted methylene malonate 33. For the bulk resin preparation of 33 (2-10 g of resin), the Knoevenagel condensations are carried out with Dean-Stark trap to eliminate water which gave consistently higher yields and faster reaction). Malonates 33 are treated with 10 equivalents of the amidine hydrochlorides 23 in dimethylacetamide (DMA) solution, with excess K$_2$CO$_3$ to neutralize the HCl amidine salt, at 70° C. for 4-8 h to give resin bound dihydropyrimidones 32. The reagent consumption progress can be monitored by FTIR observing the adsorptions of C=N and C=O groups. Oxidation of 32 with 0.2M ceric ammonium nitrate (CAN) in DMA[16] affords resin bound hydroxy-pyrimidines. Cleaving under acidic conditions (TFA/DCM, 1:1, RT, 1-2 h) gives secondary sub-library c (The sub-library c exists in its tautomeric form—4-pyrimidone).

The examples for tailor-made synthesis of miscellaneous tetrasubstituted 6-atom membered rings are described below.

The amidines 23-25 react in solution with commercially available [bis(methylthio)methylidene]malononitrile 35 (see pathway below) in the presence of DIEA[17] to give the corresponding methylthiopyrimidines. The latter are oxidized with 1.2 equiv. of m-CPBA in DCM or H$_2$O$_2$[18], to form the intermediate sulfinyl derivatives 36 which are subjected to amine substitution with NH$_3$[19] dioxane room temperature) leading, after nitrile hydrolysis (TFPA)[10], to the final aminopyrimidines 37. If LiOH is used instead of NH$_3$ the corresponding hydroxypyrimidines 38[21] after nitrile are obtained.

-continued

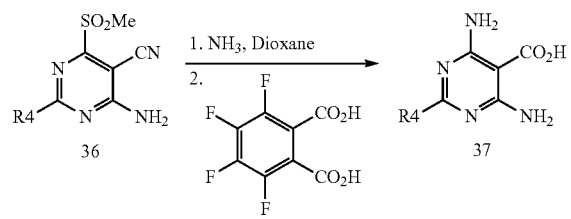

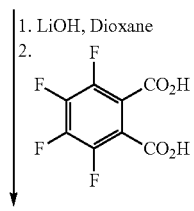

A series of various 3,4,5-trisubstituted phenols 39 can be synthesized in high yields using the "cyclization-cleavage" approach[22].

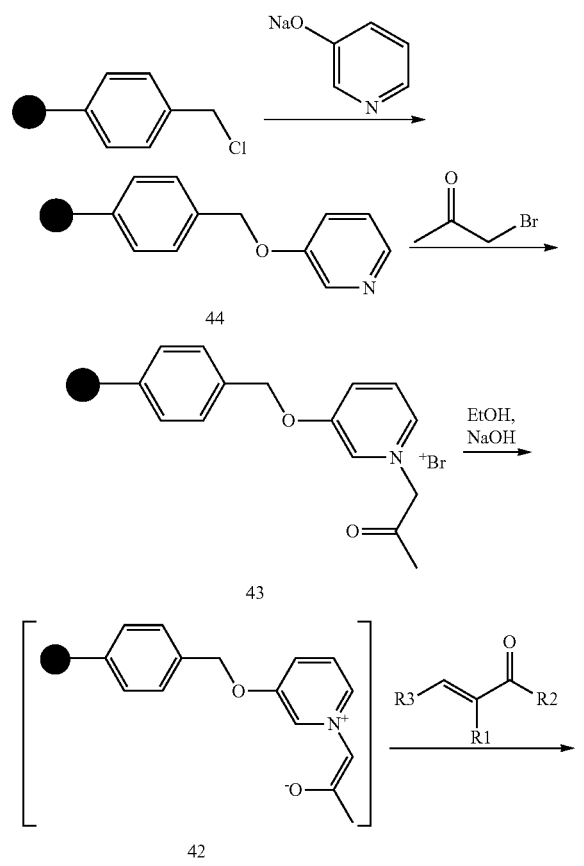

-continued

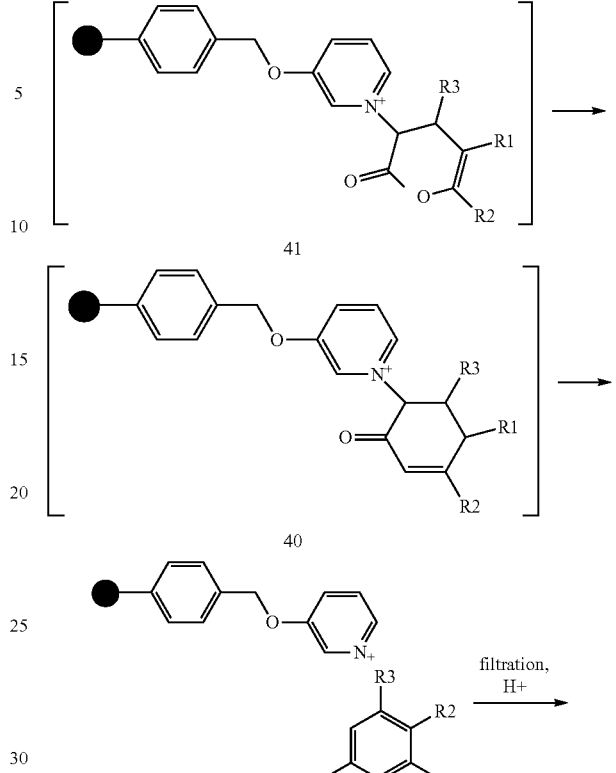

Base catalyzed reactions between α,β-unsaturated ketones and polymer bonded acetonyl groups 42 (see pathway above) result in a tandem Michael addition/annulation reaction with concomitant cleavage from the resin to obtain the desired phenols 39 The synthesis initiates using resin prepared from Merrifield resin by coupling with Sodium 3-hydroxypyridine, producing higher loading capacity resin 44, which was successfully quarternized by 1-bromopropane-2-one (or 2-bromo 1-phenyl propn-1-one; 2-bromo 1,2 diphenyl ethanone; 2-bromo-1-phenyl butane-1-one; 3-bromo butan-2-one) to afford poly-pyridinium salt 43. Reaction of 43 with α,β-unsaturated ketones was carried for 16 h, and after filtration of the resin the library 39 is obtained.

References

1. *Tet*, 32, 6937, (1993).
2. a. P. Wipf, *Tet. Lett.*, 36, 7819, (1995);
   b. K. Lewandowski, *J. Comb. Chem.* 1, 105, (1999).
3. D. Obrecht, *Helv. Chem. Acta*, 65, (1997).
4. Chenera, WO 95/16712, 1995.
5. Compounds 9 and 21 are stable in their carbonyl tautomer; *heterocyclic Chem.* 3. (1984).
6. *Pharmazie*, 5435, (1999)
7. *J. Heterocyclic Chem.* 24, 589, (1987)
8. *J. Heterocyclic Chem.* 23, 1821, (1986)
9. *Chem. Abst.* 90, 121631y, (1979).
10. *Montash Chem* 107 587 (1976).
11. *Tet*, 48, 5473, (1992).

12. a. A. Marzinzik, *J. Org. Chem.,* 63, 723, (1998)
    b. WO 9815532
    c. *Sib. Khim/Zh.* 87, (1991)
    d. *J. Heterocyclic Chem.* 24, 1141, (1987)
13. a. S. Kolodziej, *Tet. Lett.,* 37, 5277, (1996);
    b. *Synthesis,* 86, (1985).
14. a. D. Powers, *Tetrahedron,* 54, 4085, (1998);
    b. K. Ito, *J. Heterocyclic Chem.,* 29, 1037, (1992).
15. a. B. Hamper, *Tet. Lett.,* 40, 4973, (1999);
    b. C. Chiu, *J. Comb. Chem.* 1, 73, (1999).
16. a. M. Gordeev, *Tet. Lett.,* 37, 4643, (1996);
    b. S. Tadesse, *J. Comb. Chem.* 1, 184, (1999).
17. T. Masquelin, *Helv. Chem. Acta,* 646, (1998).
18. *J. Heterocyclic Chem.* 25, 959, (1988).
19. a. *Tet Lett.* 38, 211, (1997)
    b. *J. Med. Chem.* 39, 4156, (1996)
    c. *Synthesis,* 147, (1986)
20. *Tet. Lett.,* 6557, (1998).
21. Substitution of 4-sulfinyl derivative with OH will lead to 4-pyrimidone. *J. Heterocyclic Chem.* 22, 49, (1985).
22. Katrritzky A., Tet. Lett., 39, 8051, (1998).

16.2 Indolo[2,3-b]quinoline 6,6,5,6 Cyclic Scaffold

The indolo[2,3-b]quinolines 1a,b synthetic pathway is outlined in the pathway below. The key step in this synthesis is the decomposition of the corresponding triazoles 2a,b in polyphosphoric acid (PPA) at 110-160° C., which affords the desired 1a,b[1,2]. The isomers 2a and 2b can be separated during Purification. The starting triazoles 2a,b can be prepared by heating trisubstututed chloroquinolines 3 with benzotriazole building blocks 6a,b at 110-120° C. in presence of TEA.[1,3]. The benzotriazole building blocks 6a,b is prepared from monosubstituted nitro-anilines by reduction of $NO_2$ group ($SnCl_2$ or $H_2$/Pd) and subsequent diazotization of readily obtained diamines.[1,4].

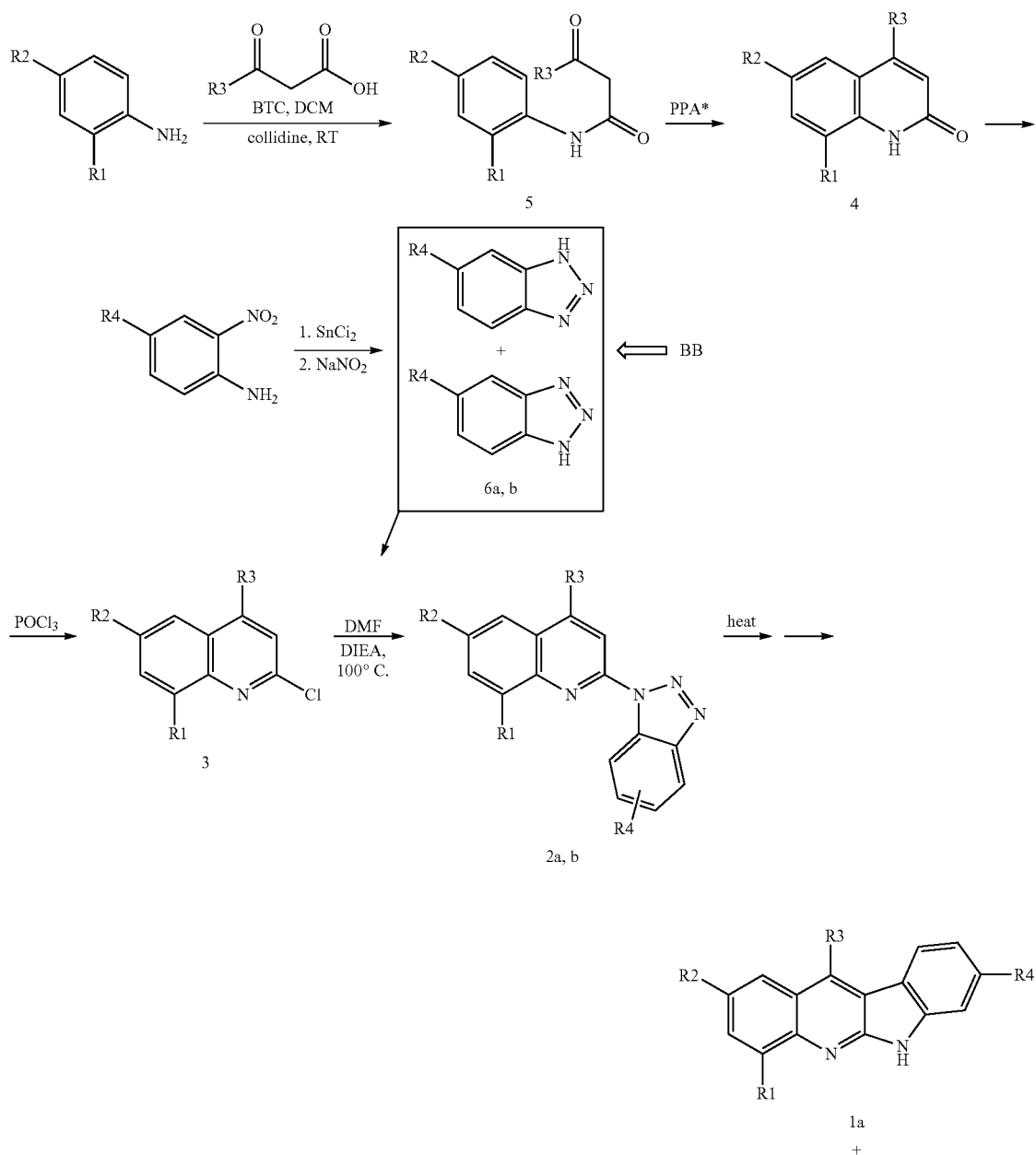

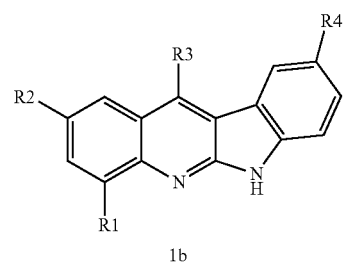

1b synthesis of Indolo[2,3-b]quinoline 2-chloro-quinolines 3 is prepared in three steps from disubstituted anilines first the anilide is formed either by reaction with preactivated (BTC, DMAP, collidine) β-keto-acids, or with the free acid at high temperature followed by intramolecular cyclization of 5 under acidic conditions. Finally the obtained quinolinone is chlorinated with freshly distilled $POCl_3$[5] to afford 3. Another approach, namely solid-phase synthesis of 1a,b, can be utilized using disubstituted anilines with solid support attachable functional groups ($CO_2H$, $NH_2$, OH).

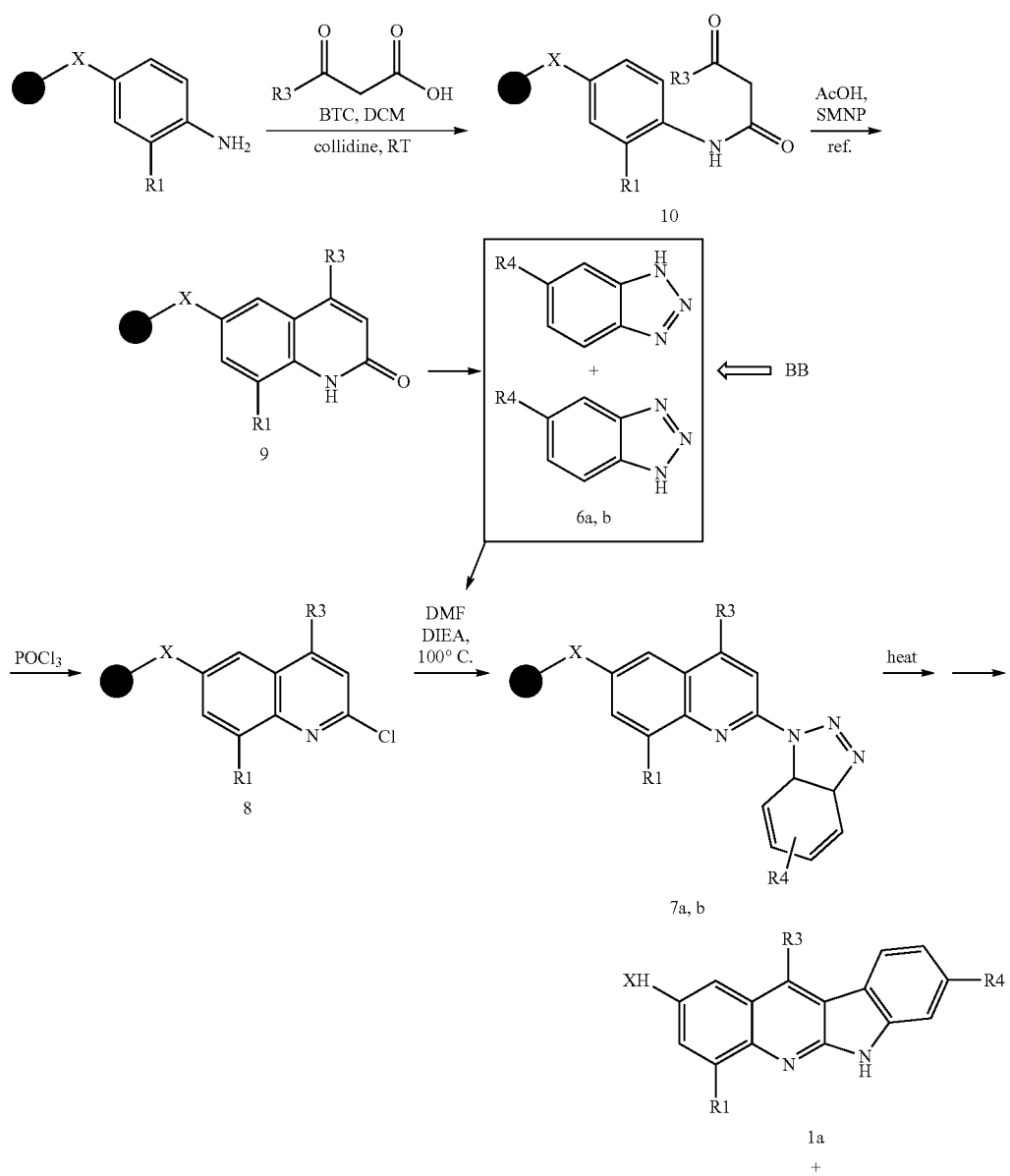

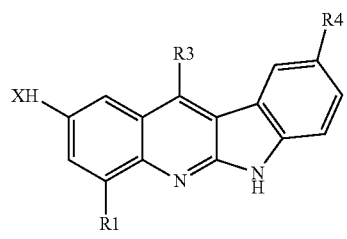

1b
solid phase synthesis of Indolo[2,3-b]quinoline

The starting anilines can be loaded on appropriate resin according to the type of the functional group to be attached. If the functional group is $CO_2H$, the resin will be phenolic (see quinoline chapter change formulation according with the format of the patent) and the loading is performed under esterification conditions (BTC, DMAP); if the functional group is OH, the loading can be performed by Mitsunobu reaction; and if the functional group is $NH_2$ the starting aniline will be loaded under sulfonation conditions on sulfonyl chloride resin or alternatively prepared by Curtius rearrangement from corresponding carboxyl derivatives.

References

1. *Bioorg. Med. Chem.*, 7, 2457, 1999
2. Arch Pharm 321 463, 1988
3. Tet Lett 39 1827 1998
4. Org Syn Col Vol 1 3 106
5. Org Syn Col Vol 3 194
6. for other synthetic method for the preparation of Indolo [2,3-b]quinoline see
   a. from acylbenzotriazole and acyl isocyante, J Org Chem 65 8069 2000
   b. coupling of 3-bromoquinoline with 2-amino boronate, Synlett 1067 1997
   c. via a modified Graebe Ulmann reaction, J. Med Chem 37 3503 1994

16.3 isoindoloindoles and isoindoloindolones 6,5,5,6 tetra Cyclic Scaffolds

Herein, is described the Pd catalyzed annulation[1] to form an isoindoloindole skeleton from readily prepared imines and internal aryl acetylenes.

Imines and disubstituted acetylenes undergo a multistep reaction in the presence of palladium catalyst to produce isoindoloindoles[2], which are obtained in good yields (see pathway below).

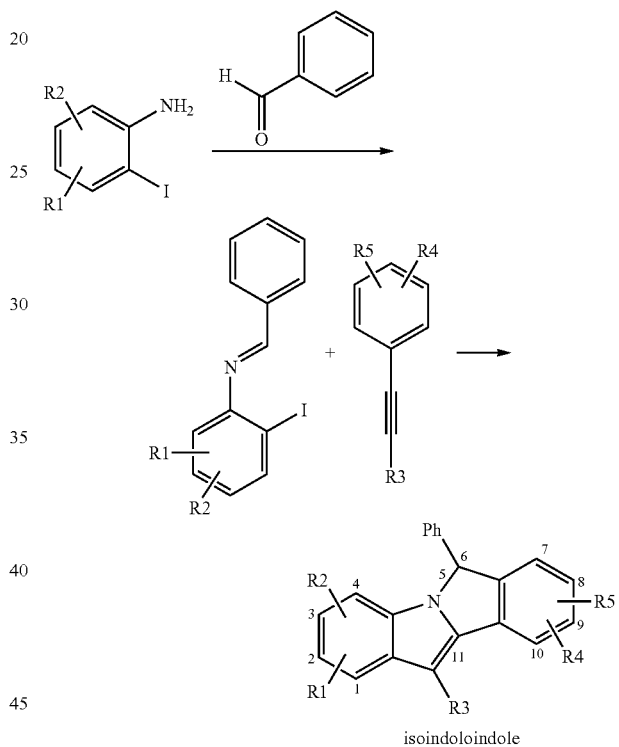

general scheme for the preparation of isoindoloindoles isoindoloindole

By using divers building blocks—either mono- or di-substituted iodo-anilines 7, and premade di- or trisubstituted phenyl acetylenes 5.

A large library of isoindoloindols1-4 can be obtained (see pathway below).

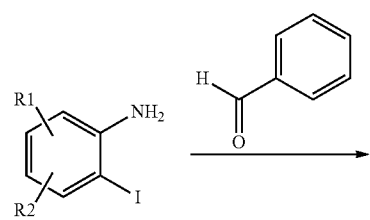

7

-continued

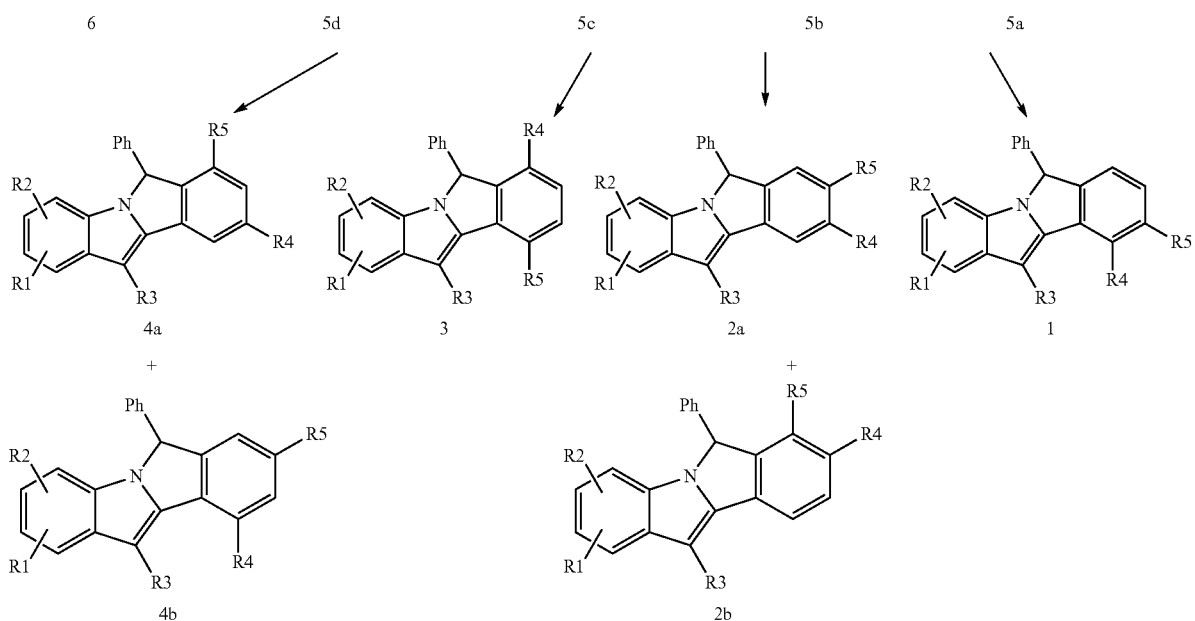

This annulation reaction comprise of two steps synthesis without isolation of intermediate iodoimines 6. The steps of the synthesis are as follows:
1. Imine 6 is formed in solution using drying reagents such as TMOF, molecular sieves or $Na_2SO_4$.
2. The acetylenes 5 are prepared by Heck reaction between commercially available or pre-formed di- and monosubstituted iodobenzenes and monosubstituted acetylenes using standard Pd catalysts[3-8] (see pathway below). Modified Heck reaction on solid phase can also be used[9-12]. When we use solution phase, the reaction mixture can be used for the next step as it, without recovering the catalyst, because the one is required for the next step.

3. The annulation of internal alkynes to isoindoloindoles using $Pd(OAc)_2$ in the presence of an amine LiCl or $Bu_4NCl$ in DMF.

When one of the substituents is at ortho-position, the ring closure will proceed in regioselective manner affording single tetra-substituted isondoloindoles 1,3.

When ortho-position on 5 is unoccupied, some substituents control regioselectivity of ring closure by chelating the palladium in the σ-palladium intermediate, which is formed during the reaction. Other cases the two isomers can be separated by chromatography.

For generation of 11-hydroxy isoindoloindoles: TMS protected hydroxyalkyne 11 can be utilized, generating after TMS removal (n-$Bu_4NF$) 11-hydroxy-isoindoloindole sublibrary 12 (see pathway below).

Heck reaction for the preparation of substituted phenyl acetylenes

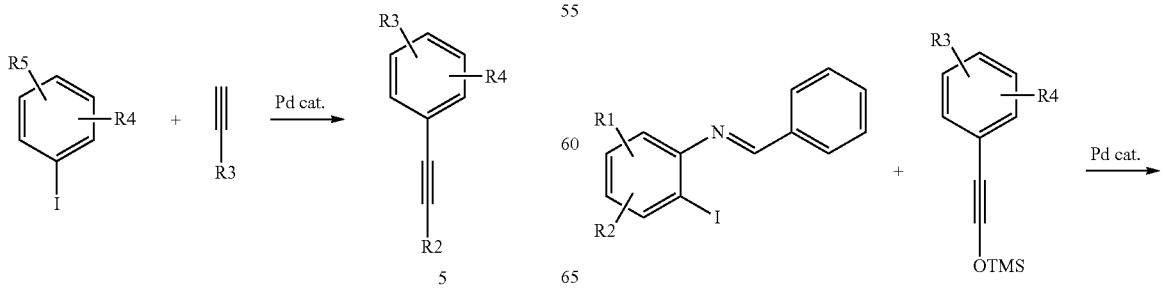

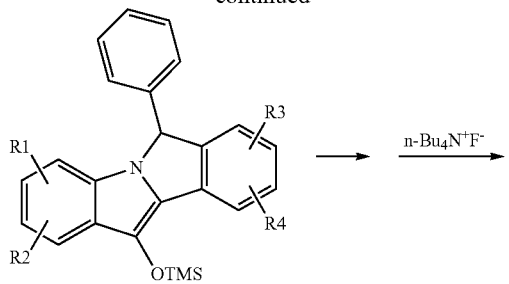

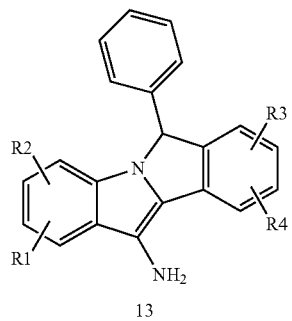

For generation of 11-amino-isoindoloindoles, carboxy-alkyne 5 can be used for preparation of 11-carboxy-isoindoloindoles 1-4. The last can be converted to corresponding azodocarbonyl 14(n-BuOCOCl, then NaN$_3$)[13-15] (see pathway below), which can undergo rearrangement through nitrene intermediate to provide desired 11-amino-isoindoloindole sub-library 13.

Constant polar functional group can be added such as guanidine. The most convenient location for this purpose is the para position on phenyl ring derived from imine 10 (see pathway below). The imine 10 bears Bpoc protected amine group, which can readily be deprotected, after annulation with appropriate alkyne, to give 9. Amino isoindoloindole 9 can react with bis-Boc thiourea[16](HgCl$_2$, TEA) to obtain, after subsequent deprotection (TFA/DCM), the final library 8.

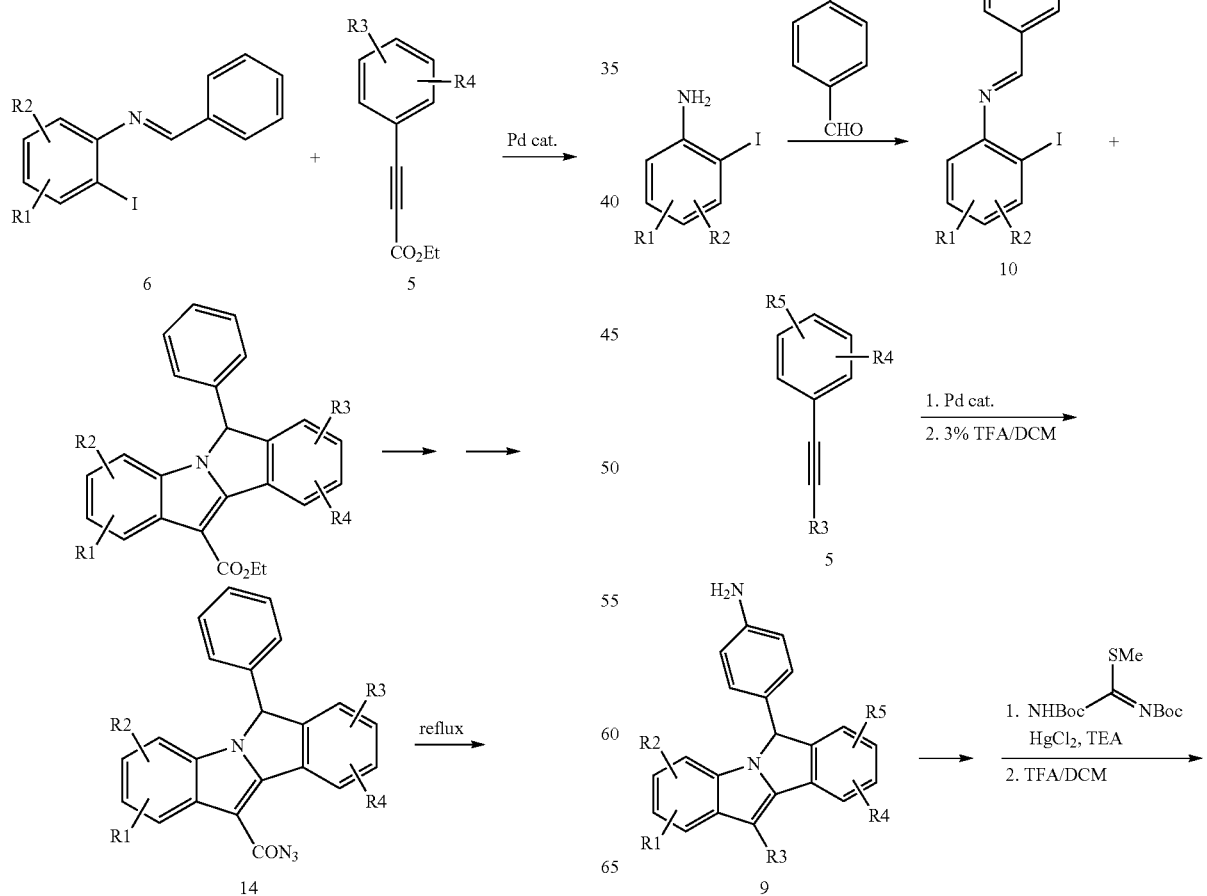

-continued

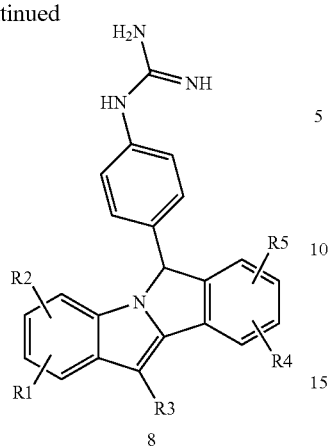

8

16.3.1 Isoindoloindolones

A slightly modified isoindoloindolone scaffold (see below) can be prepared by two systemic routes:

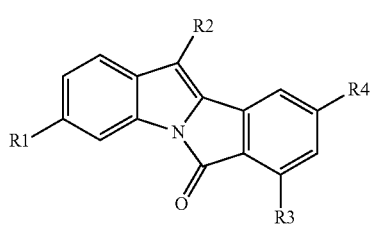

A schematic description is shown in the pathway below:

The approach presented above is divided to three major steps:

1. Formation of di- or tri-substituted indoles: via—Heck reaction between an acetylene and iodoaniline
2. Benzoylation of indole ring with ortho-iodo-benzoyl moiety. The coupling of disubstituted ortho-iodo benzoic acid BB to indole 18 can be carried out in to ways: 1. Regular coupling of BB to indole using DCC/DMAP[17]; 2. Using a pre formed acid chloride[18,19].

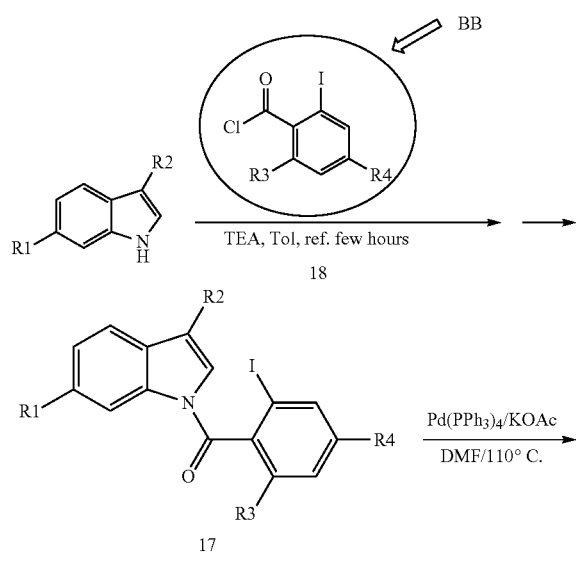

-continued

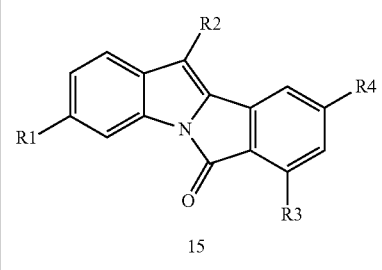

15

3. Cyclization using Pd catalyzed reaction (Heck annulation)[20,21]. The addition is very specific using iodo-benzoyl ring. In case the 7$^{th}$ position is not occupied it can add to 7 position of the indole instead of position 2. This addition gives us a new scaffold, which is another library (see pathway below).

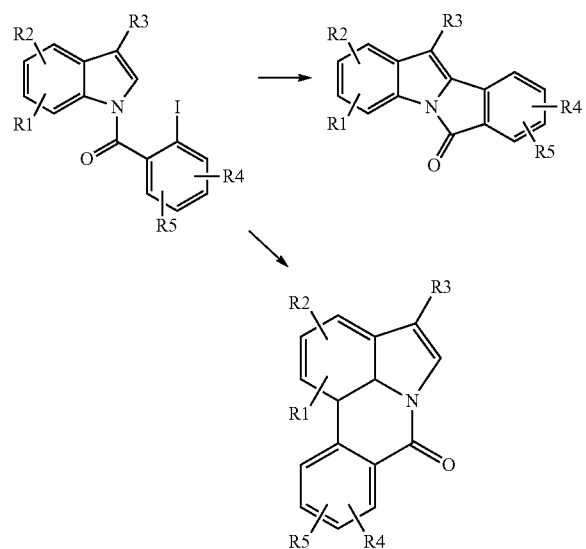

The indole 18 can be prepared by traceless solid phase indole synthesis using indole N—H as a resin attachment point[22], which could be cleaved to give the free indole 18. One of the most efficient solution phase methods of indole synthesis is the Pd(0)-mediated reaction of 2-iodo-anilines with acetylenes in the presence of base as developed by Larock[23,24].

Monosubstituted 2-Iodoaniline, after loading onto the THP resin through an animal linkage using PPTS can give 20 (see pathway below). Replacing the catalyst to Pd(PPh$_3$)$_2$Cl$_2$ and using the DCE soluble base TGM, were found to be beneficial in pushing the annulation reaction to completion, affording 19. Resin cleavage with 10% TFA then can give the free indole 18. It was found that TMS-substituted acetylenes readily went to completion at 80° C. with almost complete regiocelectivity.

The carboxylated 15 (R$_2$=CO$_2$H) can be converted to amine analog 16 through the corresponding azodocarbonyl, which can undergo rearrangement through nitrene intermediate to provide desired amino-isoindoloindolone sub-library.

preparation of isoindoloindolone

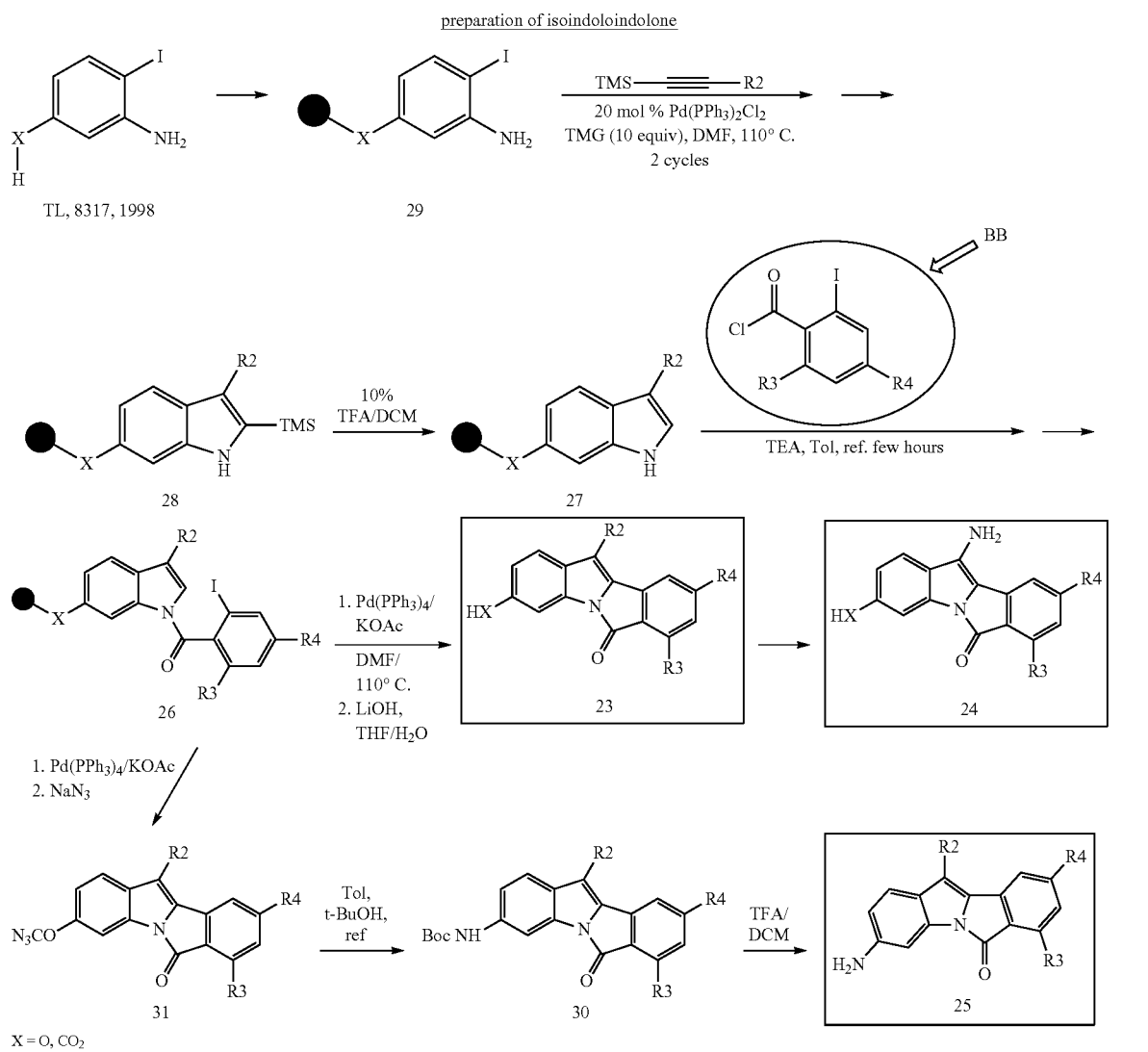

The hydroxy- and carboxy isoindolones 23 (X=O, CO$_2$) can be generated by SP synthesis (see pathway above) starting by loading the appropriate iodo-aniline on the resin[9] and effecting the annulation with TMS acetylenes.

The subsequent benzoylation and annulation of 27 followed by cleavage from the resin affords 25.

A second way of formation of isoindoloindolones presented in the following pathway[25]:

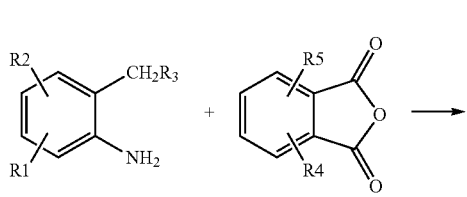

-continued

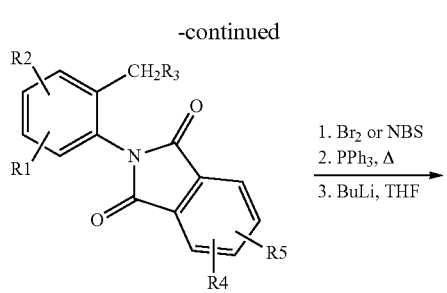

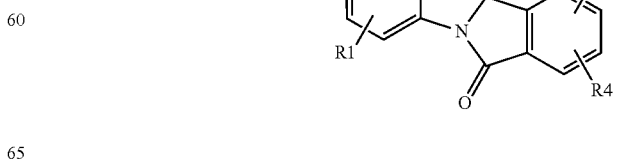

A key step is an intramolecular wittig reaction. Substituted ortho-alkyl anilines and phthalic anhydride derivatives react to form aryl phthalimides. These can be converted to phosphonium salts and can be closed to isoindoloindolone system.
References:
1. Larock R. *J. Am. Chem. Soc.* 121, 3238, (1999).
2. Roesch K. *Org. Lett.*, 1551, (1999).
3. Macdonald G. *Chem. Commun.* 2647, (1996).
4. Amatore C. *J. Org. Chem.* 60, 6829, (1995).
5. Amatore C. *J. Org. Chem.* 61, 8160, (1996).
6. Lavastre O., *Tetrahedron,* 53, 7595, (1997).
7. Cai M. *Synthetic Commun.* 27, 1935, (1997).
8. Watanabe T. *SynLett.* 207, (1992).
9. Collini M. *Tet. Lett.* 38, 7963, (1997).
10. *Tet. Lett.* 38, 2307, (1997).
11. *Tet. Len.* 38, 2439, (1997).
12. Amatore C. *J. Org. Chem.* 61, 5169, (1996).
13. Rawal V. *Tet. Lett.* 35, 4947, (1994).
14. Csuk R. *Tet. Len.* 36, 7193, (1995).
15. Paik S. *Tet. Lett.* 37, 5303, (1996).
16. Atigada V. *Bioorganic & Medicinal Chemistry,* 2487, (1999).
17. Kraus G. *Synthetic Commun.* 23, 55, (1993).
18. Kozikowski A. *Tet. Lett.* 32, 3317, (1991).
19. Black D. *Tetrahedron* 49, 151, (1993).
20. Shao H. *Tet. Lett.* 39, 7235, (1998).
21. Desarbre E. *Hetrocycles* 41, 1987, (1995).
22. Smith A. *Tet. Lett.* 39, 8317, (1998).
23. Larocke R. *J. Org. Chem.* 60, 3270, (1995).
24. Larocke R. *J. Org. Chem.* 63, 7652, (1998).
25. *J. Heterocycles Chem.* 21, 623, (1984).

16.4 The Single Atom Scaffold

The smallest scaffold used in this implementation is the single atom scaffold, namely one carbon scaffold, of the general structure a:

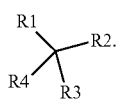
a

The library a consists of several sub-libraries b-e (see below) that represent compounds with one constant functional group and independent variety of substituents around the carbon:

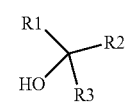
b

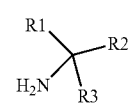
c

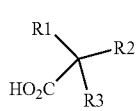
d

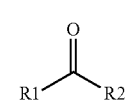
e

The secondary sub-libraries comprising two or three constant polar functionalities (see below) may be somewhat limited, because of the chemical instability of molecules bearing two or three geminal amines or hydroxyl atoms (compounds f-j):

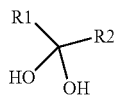
f

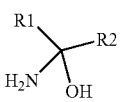
g

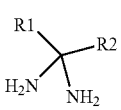
h

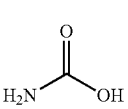
i

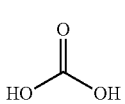
j

However, the synthesis of the α-amino acids k, α-hydroxy acids m and α-dicarboxylic 1 acids are known. For example they are described in: Synthesis of optically active α-amino acids by Robert M. Williams, Pergamon Press.

Some of the compounds based on the carbon scaffold are mostly commercially available. Those that are not commercially available can be synthesized, mostly in solution, by conventional methods.

The tetriary alcohols $b^1$ can be synthesized through the well known epoxidation of olefins 2 (as a key step, producing epoxides 1, which already possess the required substituents[2] (see pathway below)

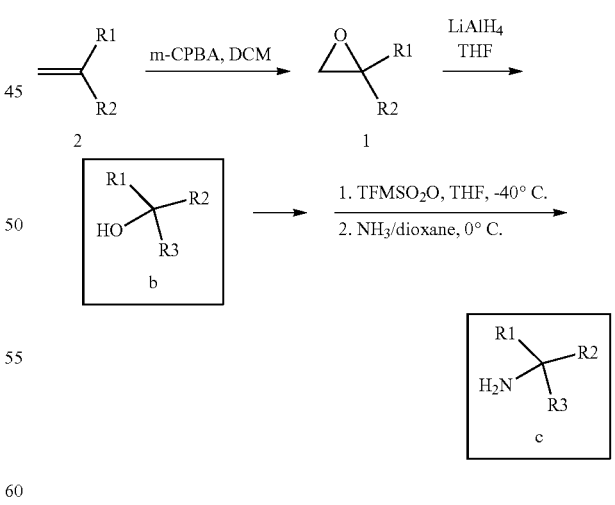

Electron-donating groups typically increase the rate. Conditions are mild and yields are high. The consequent reduction of epoxides is easily carried out. The most common reagent is $LiAlH_4$, which reacts through the inversion of configuration $2^3$. As expected from the SN2 mechanism, cleavage usually occurs so that the desired tertiary alcohol b is formed. Product b serves as the starting material for the tertiary amines c, which are obtained from b by substitution of corresponding trifluoromethylsulfonate with ammonia in dioxane.

The solid phase preparation of the tertiary alcohols b has been recently reported[4]. Actually, this new cleavage strategy involves addition of carbon nucleophiles to ester bound polymers 3.

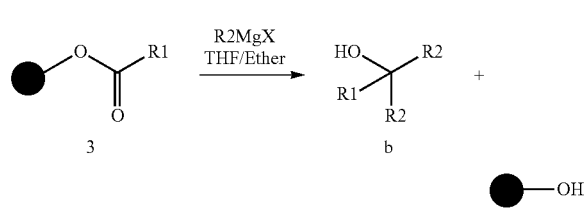

By this mode can be prepared only tetriary alcohols with two identical alkyl or phenyl substituents (R2), thus, limiting the diversity of the products, but still able to generate rapidly the secondary sub-library of the tetriary alcohols.

The α-hydroxy acids m can be obtained by straightforward one-pot procedure from the corresponding α-keto acids 4 (pathway below). α oxo acid 4 are commercially available and their treatment with Grigniard reagents (2 equiv., THF, −40° C.-RT) lead to the desired m products.

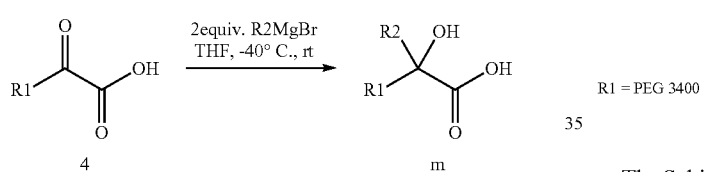

A Schiff base activated glycine supported on a soluble polymer (PEG) 6 can be readily alkylated with the wide variety of electrophiles in the presence of carbonate base ($Cs_2CO_3$) in acetonitrile[5] providing non-stereospecific amino acid esters.

Similarly, Schiff base activated amino acids t-Butyl esters 8 can be alkylated to α-C disubstituted analogs 7 (pathway below) using alkyl bromides and the LDA as a base (LDA, THF, −40° C.).

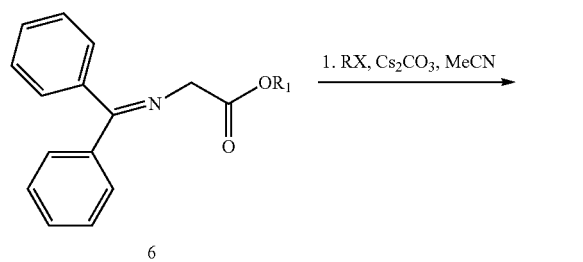

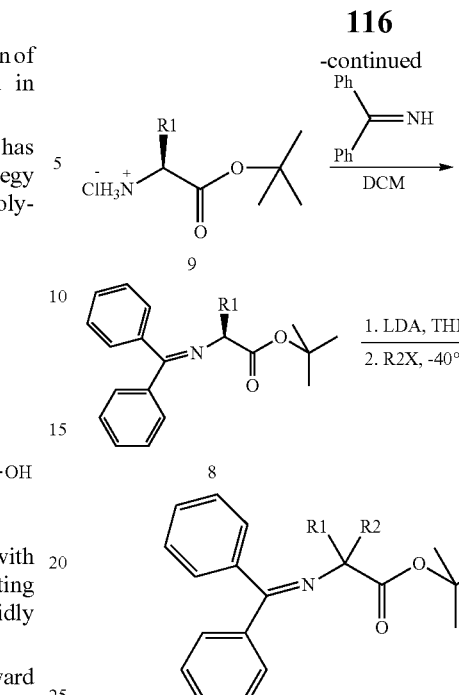

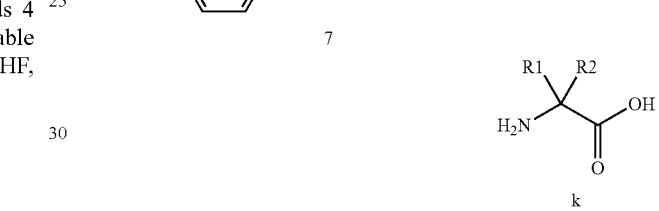

R1 = PEG 3400

The Schiff bases 8 can be prepared by transimination of the commercially available t-Bu ester of amino acids 9 with benzophenone imine. Finally, The alkylated product can be totally deprotected by TFA/DCM yielding the desired secondary sub-library k.

It should be mentioned that all products generated in this chapter are enantio-unselective and require separation of enantiomers on chiral column. The utilization of racemic mixtures could be also considered References:
1. *Tetrahedron*, 2855, (1976).
2. *Russ. Chem. Rew.*, 986, (1985).
3. *J. Org. Chem.*, 52, 14, (1981).
4. S. Chandrasekhar, *J. Comb. Chem.*, 2, 246, (2000).
5. a. B. Sauvagnat, *Tet. Lett.*, 39, 821, (1998);
   b. B. Sauvagnat, *J. Comb. Chem.*, 2, 134, (2000).

16.5 Benzodiazepines 6,7 bicyclic Scaffold

Benzodiazepines are therapeutic and anticonvulsant agents. As such the 1,4 benzodiazepines have been the target of several solid phase synthetic strategies.

The synthesis of 1,4-benzodiazepines, is based on the closure of a seven membered ring, via lactamization in high yield.[1-8]

A slightly modified solid phase approach, which is based on the ring closure, via an imine moiety is described in the pathway below.

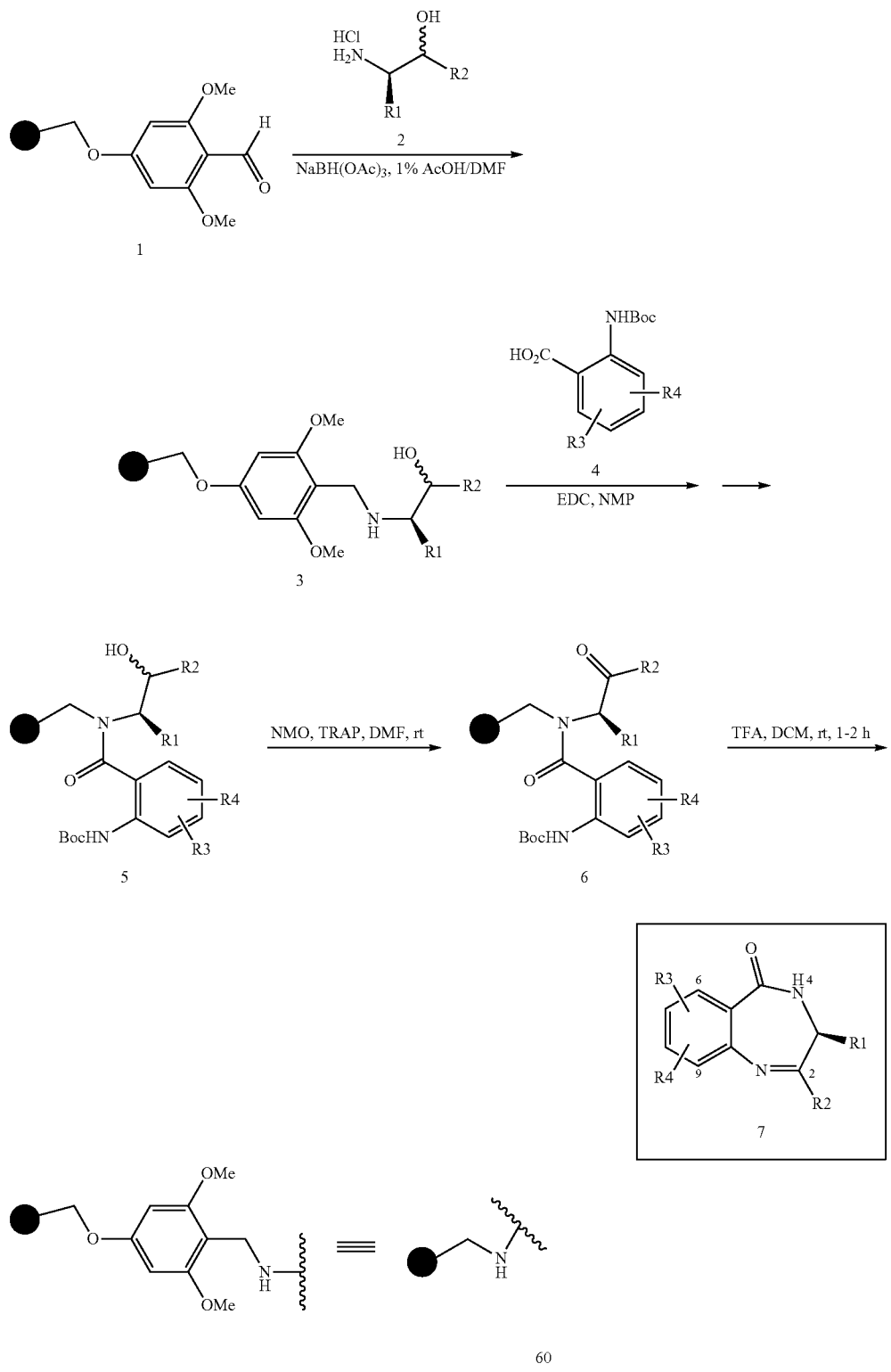

According to this strategy the aldehyde resin 1³ is coupled to β-amino-alcohol 2 via reductive alkylation (FIG. 1). β-aminoalcohol (2) can be prepared in two alternative routes (see pathway below):

(1) Coupling of N-methoxyhydroxamate (8) with Griniard reagents ($R_2MgBr$) to obtain the corresponding ketones, followed by reduction using $NaBH_4$ (MeOH, rt, few hours) to afford the Boc protected amino-alcohol derivative (9). Removal of the protecting group yield 2.

(2) Reducing N-methoxyhydroxamate (8) with $LiAlH_4$ to the aldehyde derivative followed by coupling with Grinard reagents ($R_2MgBr$) to form the Boc protected amino-alcohol derivative (9). Removal of the protecting group yield 2.

Synthesis of β-aminoalcohol

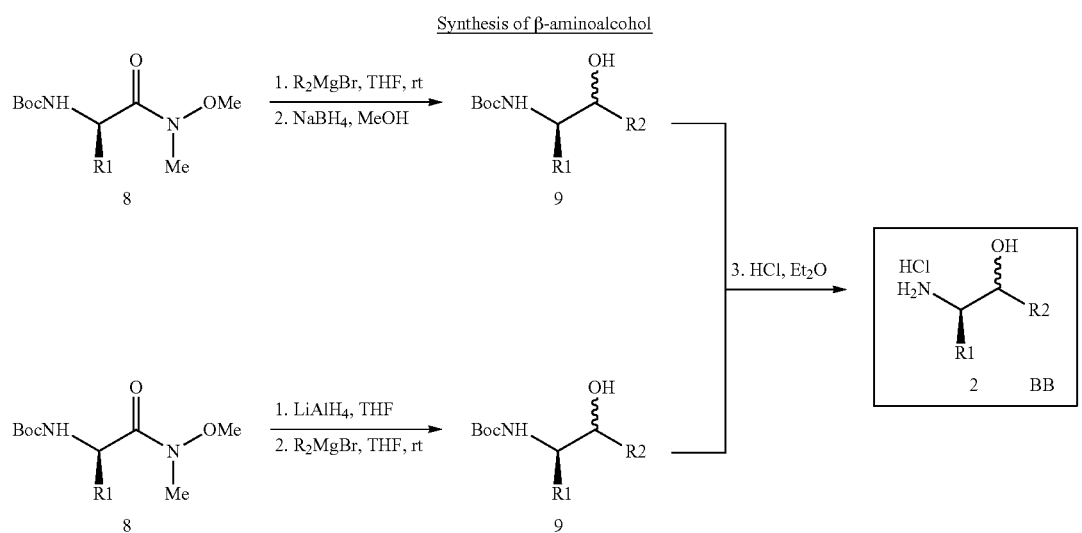

The coupling between the aldehyde resin (1) and the amino-alcohol hydrochloride salt (2) is done via reductive alkylation using NaBH(OAc)$_3$, 1% AcOH, DMF to give the resin immobilized β-amino-alcohols 3. To avoid racemization, it is desirable to obtain equilibrium between the resin bound aldehyde 1 and β-amino-alcohols 2 before addition of the reducing agent to the reaction mixture.

Coupling between the secondary amine 3 and Boc protected disubstituted anthranilic acids 4 leads to resin bound intermediate 5. Oxidation of the hydroxy group to affords 6. The oxidation on solid support can be carried out by Py.SO$_3$[9] complex in DMSO at room temperature, or by the alternative procedure using NMO[10] (N-methylmorpholine N-oxide) with TPAP (tetra-n-propylammoniumperruthenate) catalyst, in DMF at room temperature. Compound 6 is deprotected (TFA/DCM), and the free amine undergoes intramolecular cyclization under acidic conditions to obtain the desired benzodiazepine 7.

Introduction of amine or hydroxyl at position 3 of 1,4 benzodiazepines will result in decomposition of the material. At position 2, an OH group will isomerise to the keto form, while an NH$_2$ group can form tautomers with the imine group.

The synthesic route for the preparation of a benzodiazepine having an NH$_2$ substituent at position 2 is described in the two pathways below:

(1) Thioamino ester (10) is loaded onto aldehyde resin 1 by reductive alkylation (NaBH(OAc)$_3$, 1% AcOH in DMF) to obtain resin bound intermediate 11 (FIG. 3). The secondary amines (11) is coupled with disubstituted anthranilic acids (12) (EDC, NMP) to form amide 13, which can undergo the intramolecular cyclization using lithiated p-methoxy acetanilide (14)[1] to give thiobenzdiazepine 15. The cyclic resin bound thiointermediate 15 is submitted to methylation (MeI) followed by oxidation to generate preferable leaving group (namely methylsulfoxide) for nucleophylic substitution. Such substitution reactions can be operated with acid labile dimethoxy benzylamine under standard conditions (16) (DMF, DIEA) providing after acidic cleavage the desired 2-amine benzodiazepine sub-library 17.

(2) An alternative synthesis of 2-aminobenzodiazepine is as follows, Benzodiazepine 2,5 dione (20) is formed by coupling of substituted anthranilic acid with amino-acid followed by ring closure, which reacts with Lawesson reagent to form intermediate-2-thiobenzodiazepine-5 one (21). The amine 22 is obtained by reaction between the benzodiazepinethione 21 and ammonia.

synthesis of 2-aminobenzodiazepine

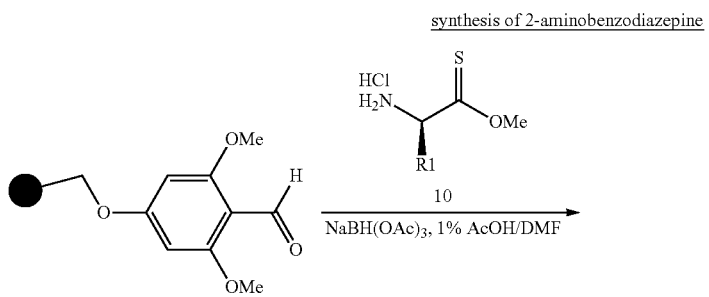

-continued
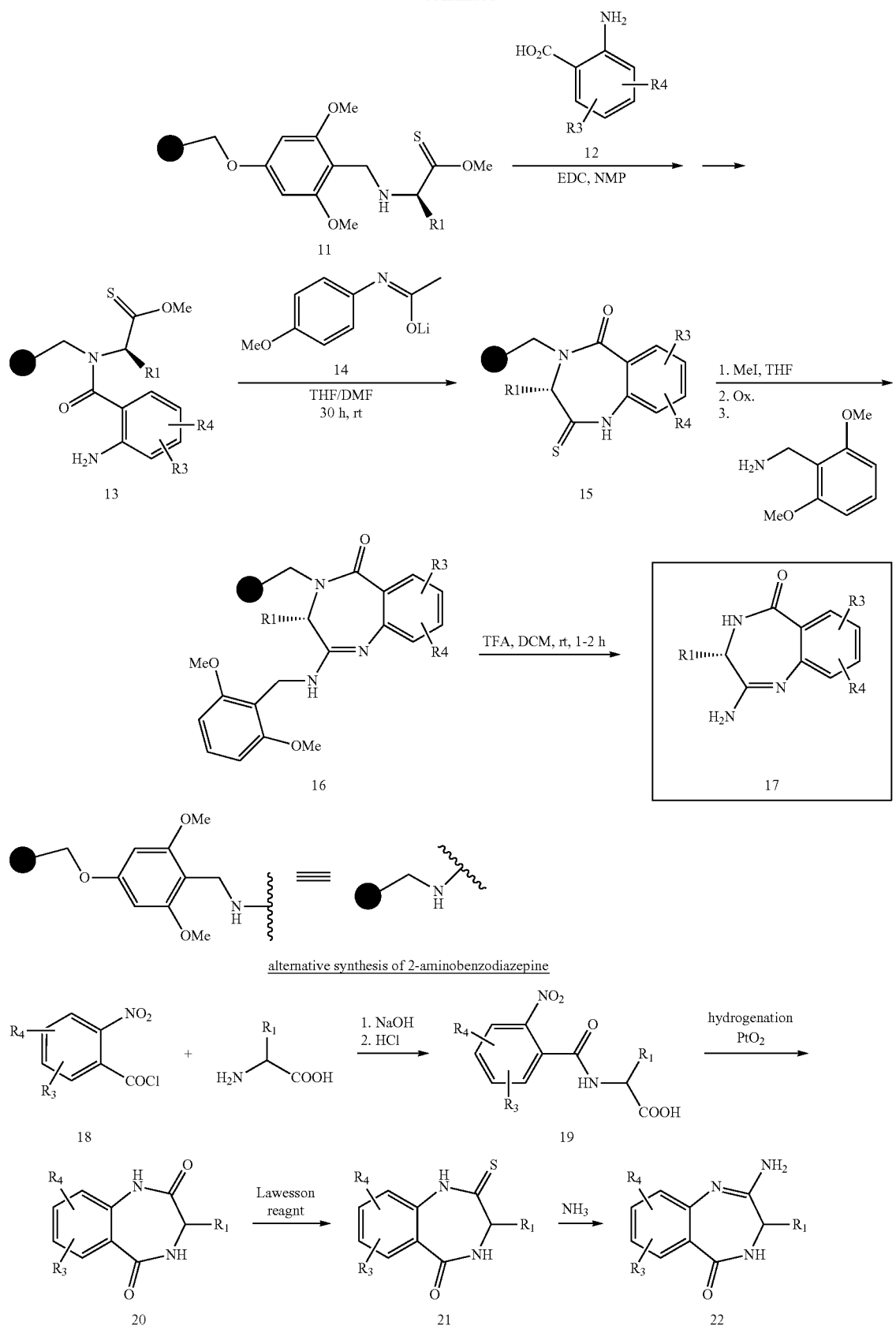
alternative synthesis of 2-aminobenzodiazepine

The synthesis of β-hydroxy α amino-acid, a building block used for the preparation of 2-carboxy benzodiazepine is described in the following pathway. Commercially available chiral Fmoc serine t-butyl ester 26, undergoes Sworn oxidation (($COCl)_2$, DMSO) to obtain the aldehyde 27. The aldehyde 27 is subjected to Gringard reaction R1MgX to form the Fmoc protected amino-alcohols, which after Fmoc removal (piperidine, MeOH) leads to desired building blocks 28. In case when both $R_1$ and $R_2$ are carboxyl groups, the starting material is di-t Butyl fumarate 23, which upon epoxidation (mCPBA, $NaHCO_3$, DCM) gives the epoxide 24, followed by ammonia in methanol to afford 25.

Preparation of b-hydroxy amino acid

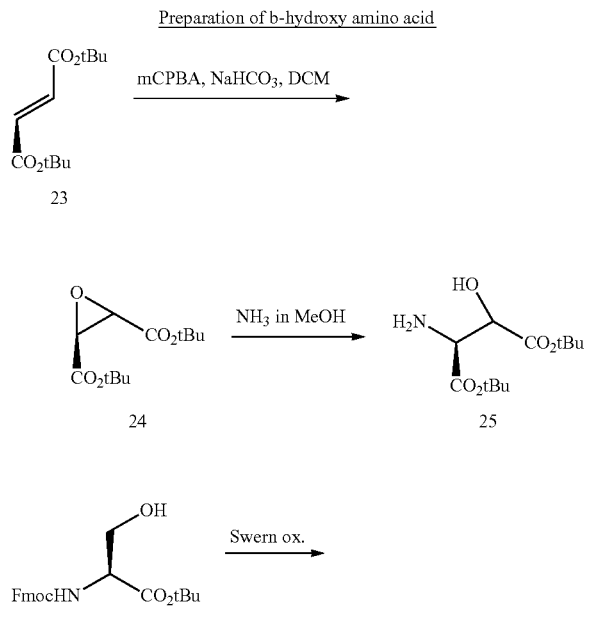

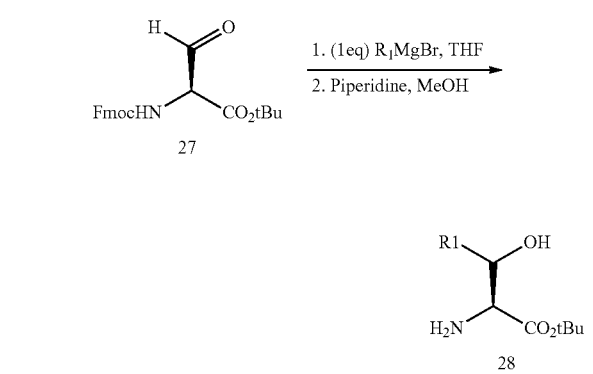

The synthesis of benzopyridodiazepine[11,12] 33 is described in the pathway below. 2-chloro-3-aminopyridines 29[12] is coupled with disubstituted azidobenzoyl chloride building block 30. Reduction of the azide 31 with $SnCl_2$ provides the 2-chlorooxazolidine intermediate 32, which upon treatment with acid rearranges to the desired pyridine-based tricyclic scaffold 33.

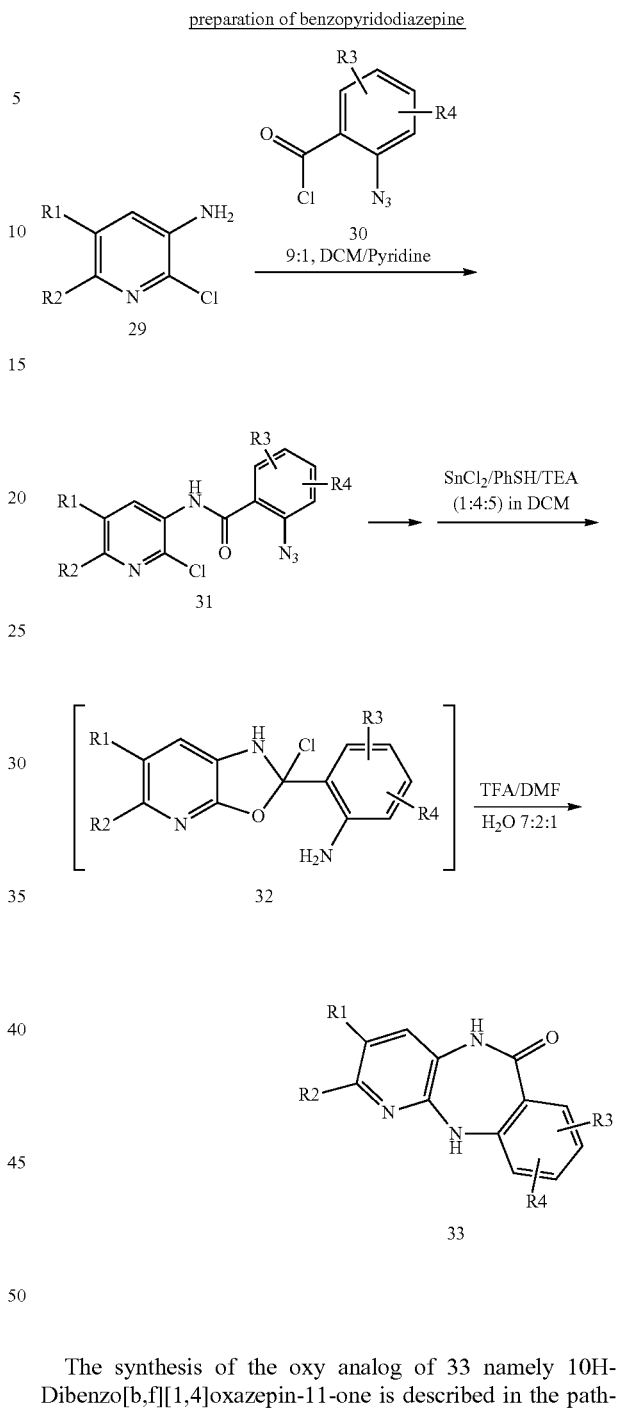

preparation of benzopyridodiazepine

The synthesis of the oxy analog of 33 namely 10H-Dibenzo[b,f][1,4]oxazepin-11-one is described in the pathway below. Disubstituted O-aminophenol building unit 35 is attached to the resin on the Acid sensitive MEthoxy BenzAldehyde (AMEBA) (34) via reductive amination, to form 36. Resin 36 was further modified with monosubstitued 2-fluoro-5-nitrobenzoic acid 37 using HOAt/DIC strategy to afford immobilized substrate 38, which was ready for the assembly of the nitro-10H dibenz[b,f][1,4]oxazepin-11-one analogs 39 (The key cyclization step ($S_NAr$) between the fluor and the phenolic oxygen was performed using a 5% DBU in $DMF^{23,24,25}$). The reduction of the nitro group in the resulting resin can be obtained with the 1.5 M solution of $SnCl_2$ $H_2O$ in DMF, and subsequent cleavage (TFA/DCM) from the resin 2-amino sub-library 39 is obtained.

Synthesis of dibenzo-oxazepinone

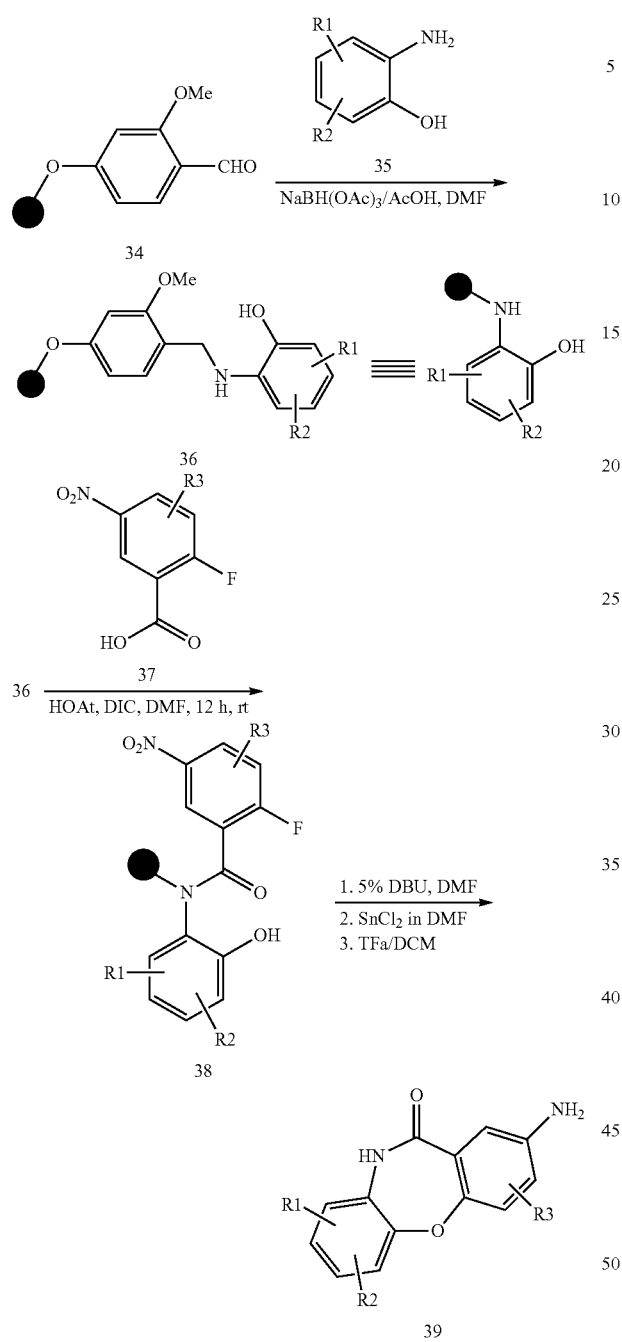

References
1. J. Org. Chem, 62,1240,1997,
2. JCC, 2, 513, 2000,
3. Synthetic Com., 21,167,1991
4. J. Org. Chem, 60,5742,1995,
5. Tet. Lett, 39, 7227,1998
6. J. Org. Chem, 63, 8021,1998,
7. Tet. Lett, 37, 8081,1996;
8. J. Org. Chem, 60, 5744,1995.
9. J. Am. Chem. Soc., 116, 2661,1994
10. J. Org. Chem, 61, 8765, 1996.
11. J. Het. Chem., 23,695,1986
12. J. Org. Chem, 62, 6102,1997.
13. Tet, 55, 2827,1999;
14. Tet, 55, 8295,1999;
15. Tet. Lett, 40, 5827,1999

16.6 Pyrazinoquinazolinone -6,6,6 tricyclic Scaffold

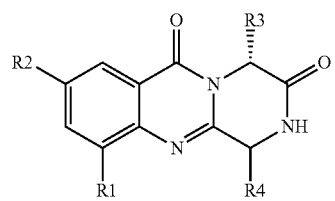

The pyrazino[2,1-b]quinazoline-3,6-dione system can be considered as a constrained peptidomometic and is present in several families of natural products. Some of these compounds exhibit very interesting biological activity (J. Antibiotics 46, 380, 1996, Annu Rev Biochem 62 385, 1993).

One currently known syntheses of this scaffold can be grouped as follows:

a: Transformation of 4-substituted 2,5-piperazinediones into the corresponding iminoethers followed by cyclocondensation with anthranilic acid or methyl anthranilate.[1-5]

iminoether anthranilic acid condensation to Pyrazinoquinazolinone

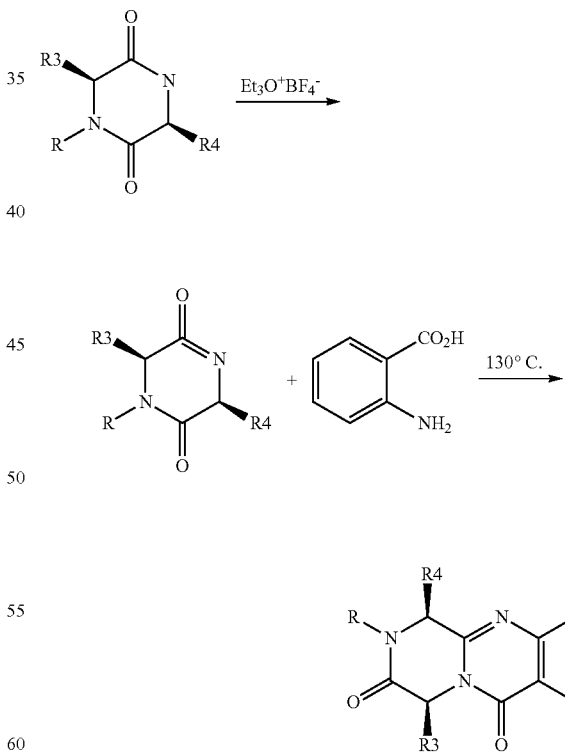

b: Acylation of 4-substituted 2,5-piperazinedione with o-azidobenzoyl chloride followed by Staudinger reaction with phosphine to yield the corresponding γ-phosphazene and subsequent intramolecular aza wittig cyclization of the latter intermediate.[6,7]

Pyrazinoquinazolinone via N-o-azidobenzoyl-diketopiperazine

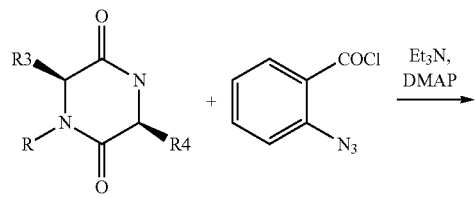

In a modified reaction sequence the N-o-azidobenzoyl-diketopiperazine is formed via an open chain tripeptide where the anthranilic acid unit is the N terminal unit bears an azido group as masked amino function[8]. Cyclization generates the quinazolinone ring.

c: Double cyclization of an open chain tripeptide via 4-imino-4-H-3,1-benzoxazine intermediate prepared through cyclodehydration of a suitable o-acylanthranilamide in the presence of iodine triphenyl phosphine.

This method was reported in solution[9-13] as well as on solid phase[14], which makes it a good mean for parallel array synthesis therefore suitable for our purpose.

Pyrazinoquinazolinone via benzoxazine intermediate.

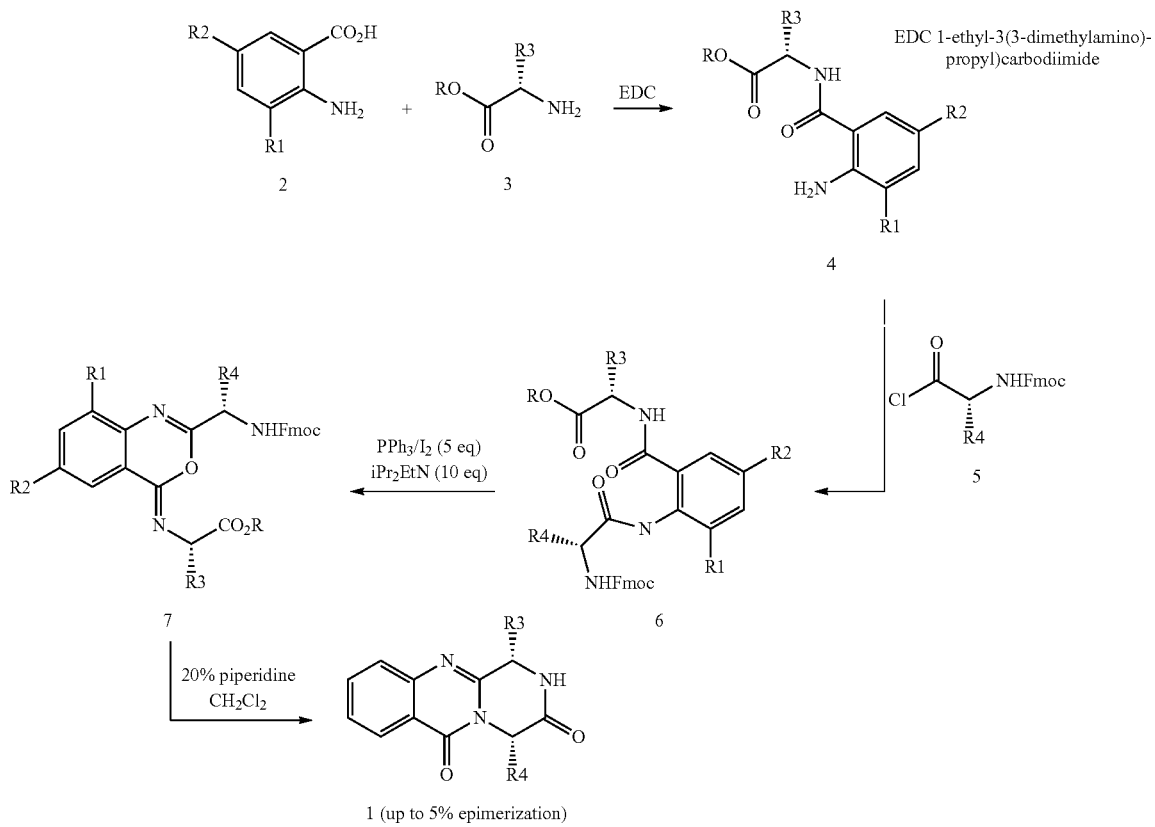

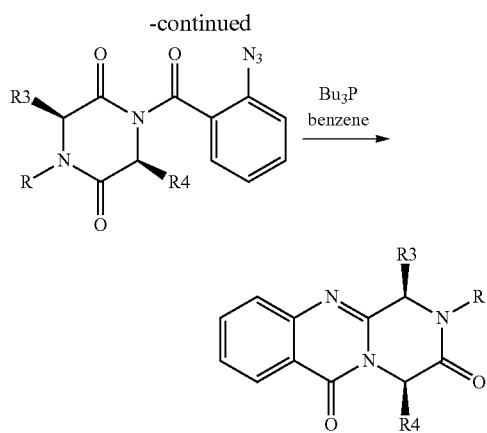

The tripeptide 6 is prepared by direct coupling of the amino acid esters (AA-OR) 3 with antranilic acid mediated by EDC. Condensation of 4 with the Fmoc amino acid chloride 5 under two phase Scotten-Bauman condition (CH2Cl2, aq Na2CO3) yields the tripeptide 6. amino acid chlorides 5 are prepared in situ by pre-activation of the corresponding Fmoc-AA-OH with BTC (triphosgene) and collidine in THF, DCM or Dioxane[15]. These conditions afford AA Clorides without racemization.

The transformation of the linear tri peptide to oxazine was accomplished using Wip's conditions (PPh$_3$/I$_2$/tertiary amine in large excess) Deprotection followed by rearrangement to quinazoline occurred upon treatment with 20% piperidine in methylene chloride. The cyclization to quinazoline is susceptible to steric hindrance and in case of R3,R4=bulky groups cyclization requires stronger condition (DMAP reflux CH$_3$CN). Some epimerization (5%) took place in case in some of the examples.

The application of the s synthesis in solution described above to combinatorical synthesis on solid phase initiates with loading of Wang resin with appropriate amino acid (AA) affording 7. For majority of AA the preloaded Wang resin is commercially available. 7 was deprotected (piperidine in DMF) and appropriate anthranilic acid along was coupled (EDC) to obtain 8 (pathway below).

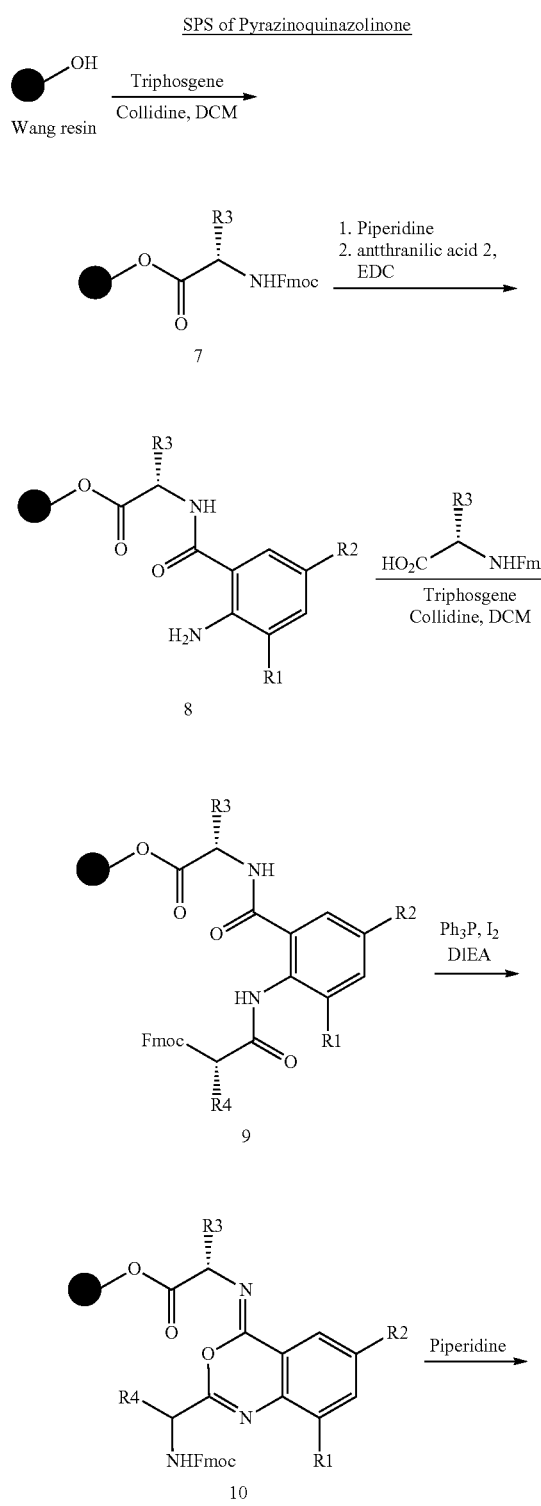

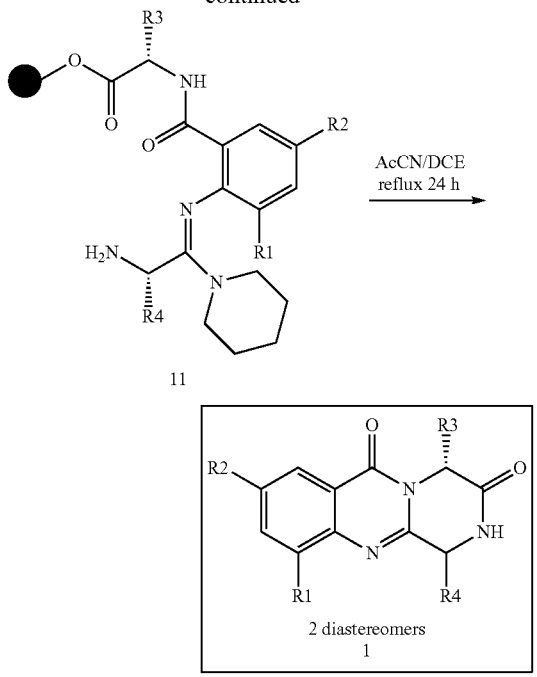

The next step is acylation of aniline 7, with Fmoc-AA-Cl to obtain linear tripeptide 9. The next step is the key dehydrative cyclization of linear tripeptide 9 to 10. To ensure complete conversion, 10 equivalents of $Ph_3P$ were used. The final reaction is piperidine mediated deprotection of Fmoc group and rearrangement of oxazine 10 to amidine carboamide 11. After washing, the resin was refluxed in acetonitrile to induce cyclative cleavage of 11 obtaining the desired pyrazinoquinozaline library 1. The yields and purity of crude compounds were claimed to be relatively high[14]. Final products 1 can be obtained in few cases as mixture of cis:trans diasteriosomers (usually the ratio is 5-8:1). the larger degree of epimerization on solid phase is probably due to the cyclizative cleavage, and HT purifier can separate the products. The above synthesis nicely illustrates the favorable features of the synthetic route. The first two steps involve peptide couplings—the reaction for which SPPS was developed and which proceeds in almost quantitative yield for a variety of amino acids. The dehydration of the liner tripeptide 9 requires large excess of $Ph_3P$, iodine and TEA—reagents which are readily removed by simple filtration on solid phase. The ester functionality undergoing cyclization in the final step was chosen as the position for solid-phase attachment, resulting in self-cleavage from the resin.

The synthesis of pyrazinoquinazoline scaffold requires 3 building blocks the 2 amino acids 3,5 and disubstituted anthranilic acid 2.

The amino acids and the Fmoc-amino acid are commercial available.

In order to introduce hetero functionalities ($NH_2$, OH) to Pyrazine ring (R3, R4) the synthesis of protected α-hydroxy-AA 14 and α-amino-AA and 12 should be performed. AA 12 is known in literature[16] and the synthesis is illustrated in the pathway below:

synthesis of protected α-amino-α-OH amino acids

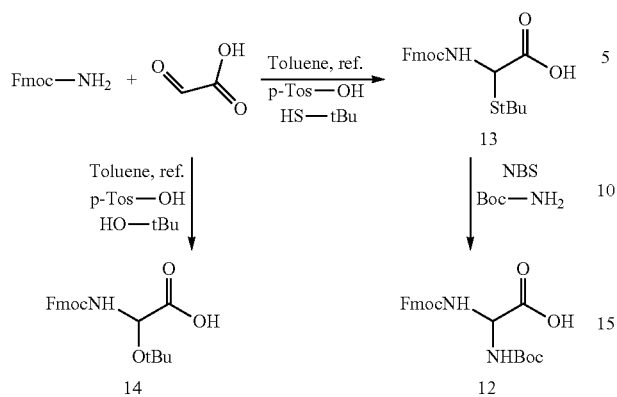

Another AA 14 can be prepared by the similar mode through the condensation between glyoxylic acid and FmocNH$_2$ in presence of t-BuOH in boiled toluene affording the desired 14.

Out of the third building block 3,5 dimethyl anthranilic acid is commercial the other substituted anthranilic acid should be prepared in a tailor-made synthesis.

3-methyl-5-phenyl-anthranilic acid 15 can be prepared by bromination of the commercial available 3-methyl-anthranilic acid 16[17]. Followed by Suzuki reaction[18].

Preparation of 3-methyl-5alkyl or phenyl anthranilic acid

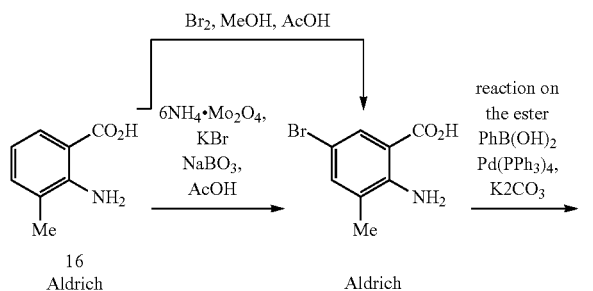

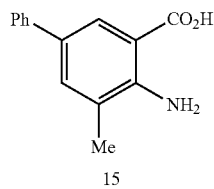

3,5-diphenyl-anthranilic 17 acid will be prepared from the corresponding dibromoanthranilic acid 18 (commercial) via Pd catalyzed cross coupling reaction with excess of phenyl boronic acid[19] (Aldrich).

Preparation of diphenyanthranilic acid

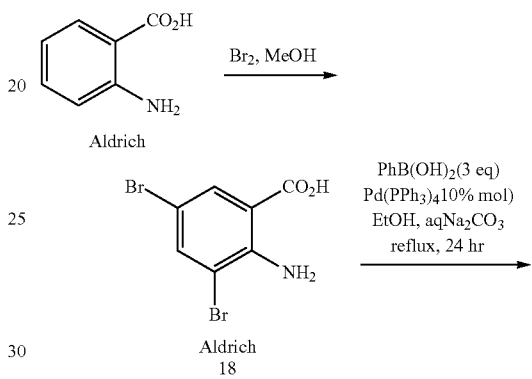

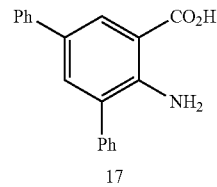

Substituted anthranilic acid can also be prepared from the corresponding substituted aniline 19 using a modified Sandmayer methodology. Reaction of the aniline with chloral and hydroxylamine affords the isonitrosoacetanilide followed by cyclization in sulphuric acid yields isatin20. Oxidation of the later with H$_2$O$_2$ affords anthranilic acid[20] 21. (see pathway below)

Preparation of anthranilic acids via isatin

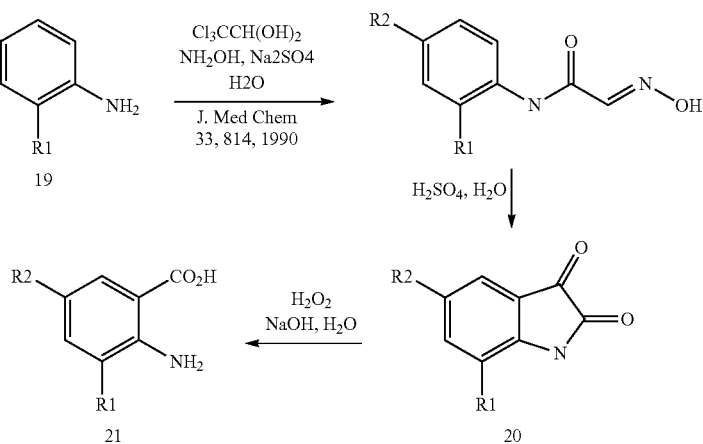

Anthralinic acids substituted in position 3 with an OH group 22 can be prepared following the reaction sequence described in the pathway below using 4-substituted anilines (Et, Pr, Me Aldrich) as starting materials. The aniline was first brominated (23) followed by selectively monomethoxylation in the presence of CuI. The 2-bromo-6-methoxy-4-alkylaniline 24 thus obtained was carbonylated using Pd complex as catalyst (CO, Pd(PPh$_3$)$_2$Cl$_2$) (=>25) and the final step is deprotection by hydrolysis in concentrated hydrobromic acid[21].

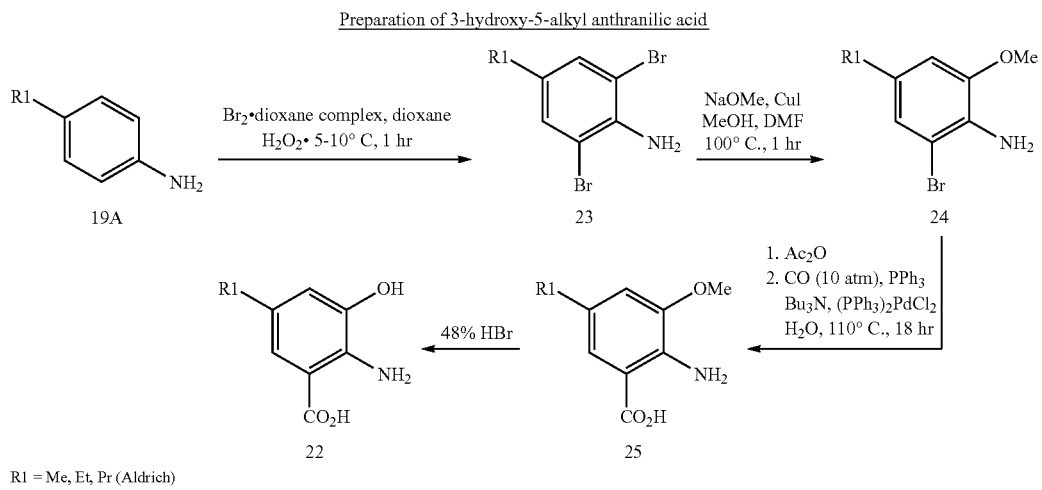

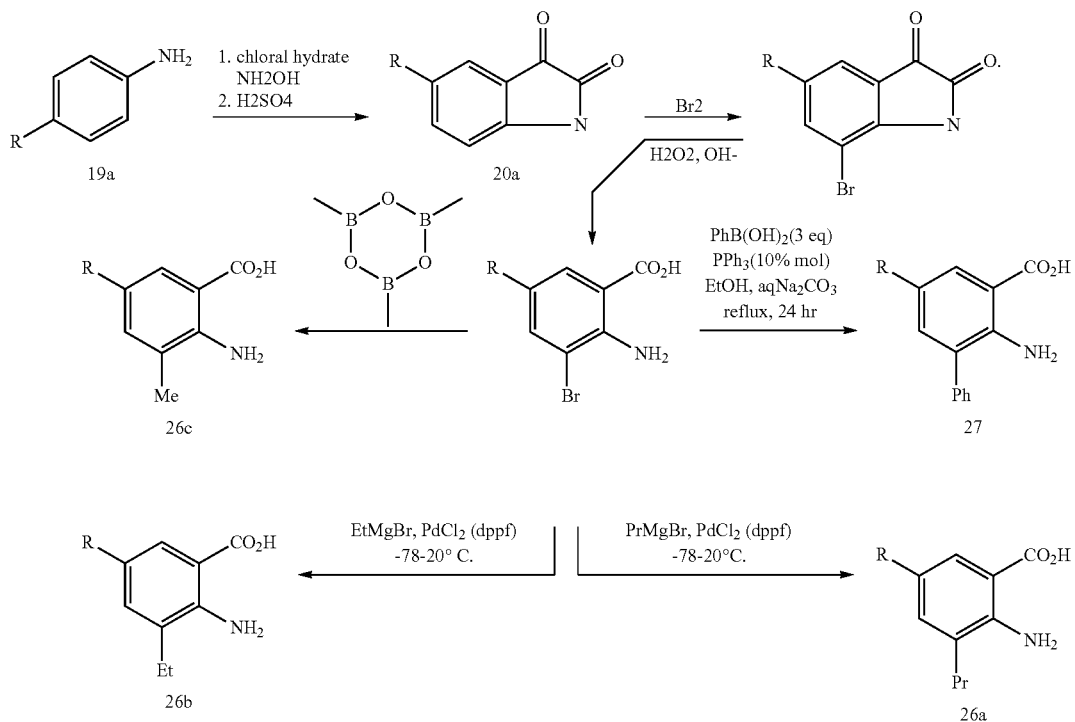

4-alkylaniline 19a can also serve as a starting material for the preparation of dialkyl anthranilic acid 26 and 5-alkyl 3-phenyl anthranilic acid 27 as described in the pathway below 3-alkyl-5-carboxylanthranilic acid 27 can be prepared starting from o-alkylaniline 19b that is converted to isatin 20a (1. chloral, NH2OH, 2. H2SO4), followed by bromination and oxidation to obtain the 5-bromo anthranilate 28 Substitution of the bromo with cyanide (29) and hydrolysis affords the 3-alkyl-5-carboxyl-anthranilic acid[22] 27.

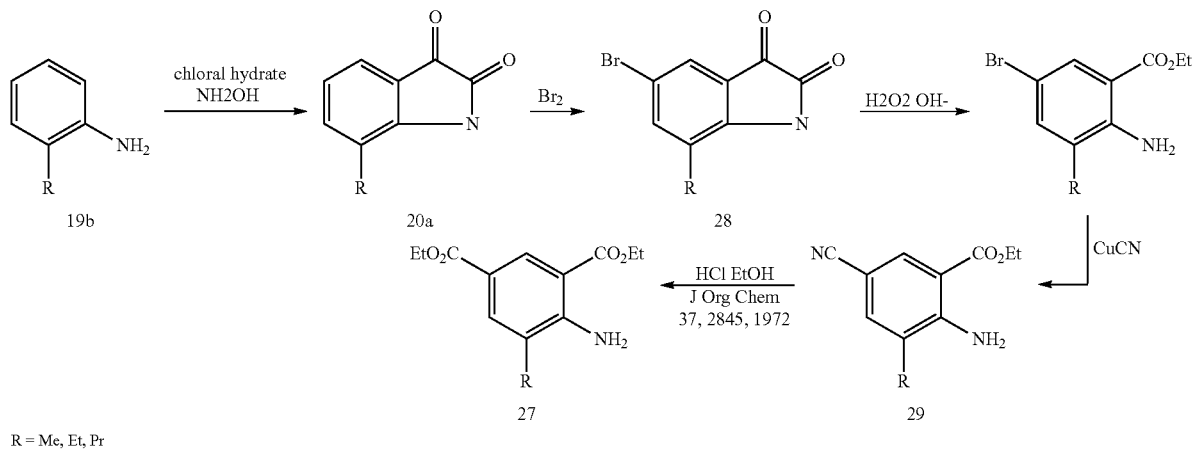

R = Me, Et, Pr

References

1. Tetrahedron Asym 9 3025 1998
2. Tetrahedron Asym 11, 3515, 2000
3. Tetrahedron 55 14185 1999
4. Tetrahedron 54, 969, 1998
5. Tetahedron Asym 113515, 2000
6. JACS 121 11953 1999
7. Tetrahedron 57 3301, 2001
8. JOC 65 1743 2000.
9. JOC 63 2432 1998
10. Tetrahedron Lett 40, 5429, 1999
11. Org Lett 2, 3103, 2000
12. JOC 65, 1022, 2000
13. *J. Org. Chem.*, 63, 2432, 1998
14. *J. Corn. Chem.*, 2, 186, 2000
15. a. *J. Peptide Res.*, 53, 507, 1999. b. Tet Let. 34 3861, 1993
16. *Proc. Natl. Acad. Sci. USA*, 93, 2031, 1996
17. *Tet Lett.* 41, 21083, 2000
18. *J. Am. Chem. Soc.* 112, 2707, 2000
19. *synthesis* 1410 1995
20. a. Synth. Commun 29, 3627, 1999 b., J. Org. Chem 59, 6823, 1994, c. J. Med. Chem. 34,1896, 1991, d. J. Indian. Chem. Soc. 66, 39, 1989, e. Tet Lett 29, 3709, 1988, f. J. Med. Chem 30, 1166, 1987
21. *J. Med Chem* 25 267 1990,
22. *Tetrahedron,* 50, 2543, 1994

16.7 Pyrrole-5 Membered Ring Scaffold

In this chapter is described the comprehensive synthesis of tetra-substituted pyrroles. The proposed synthetic methods are on Solid Phase (SPS) as well as in solution.

Overview of Pyrroles Library and Sub-Libraries

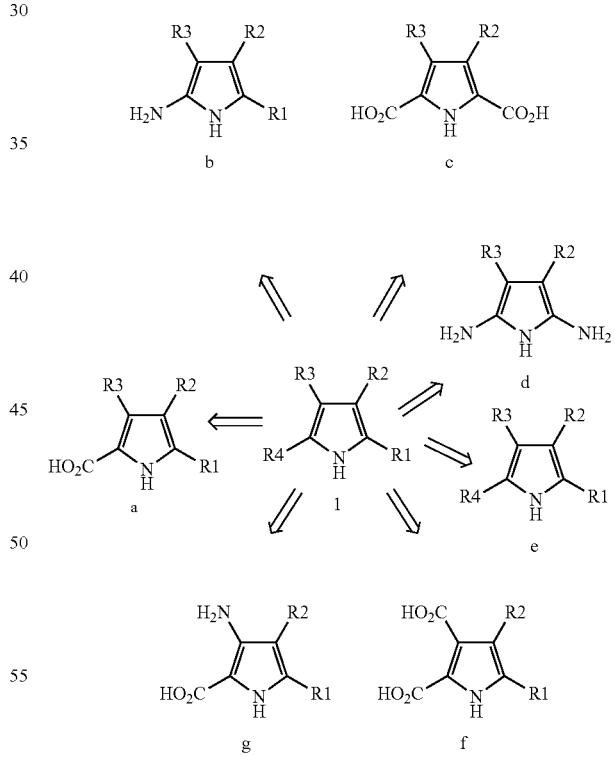

Sub-library a which has a carboxyl group at position 2 is prepared in solution. The synthesis starts from nitrosation of β-keto esters to obtain oximes 3, which by reductive condensation with 1,3-diketones lead to ethyl carboxyketopyrrols 5[1] (pathway below). Pyrroles 5 undergo reduction of the carbonyl group to methylene[1], following by hydrolysis of ethyl carboxylate to afford the sub-library a. Curtius rearrangement may convert the carboxyl into amine resulting in the conversion of sub-library a to sub library b most conveniently. (in case R1#R2 mixtures of two isomers are obtained and may be separated).

Synthesis of sub-libraries a, b.

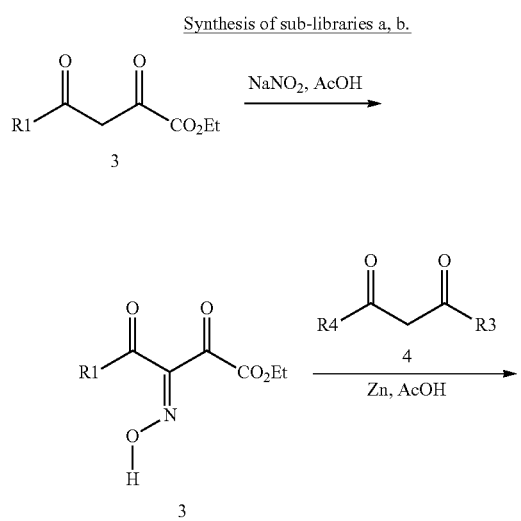

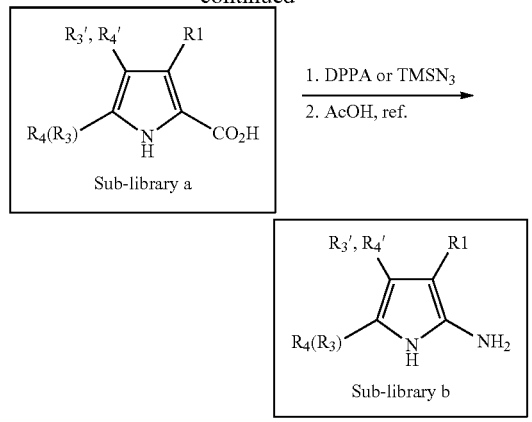

Two building blocks are required for the synthesis of sub library a, and b, β-ketoesters, 1,3 diketones which are mostly commercially available.

Compounds of sub-library c can be obtained by the synthetic method described in the pathway below. In contrast to the former method this approach involves solid phase synthesis (SPS). Namely: condensation of 1,2-diketones 7 with pre attached Boc imino diacetic acid mono ester 6 as follows:

Synthesis of additional ten compounds of category a by SPS.

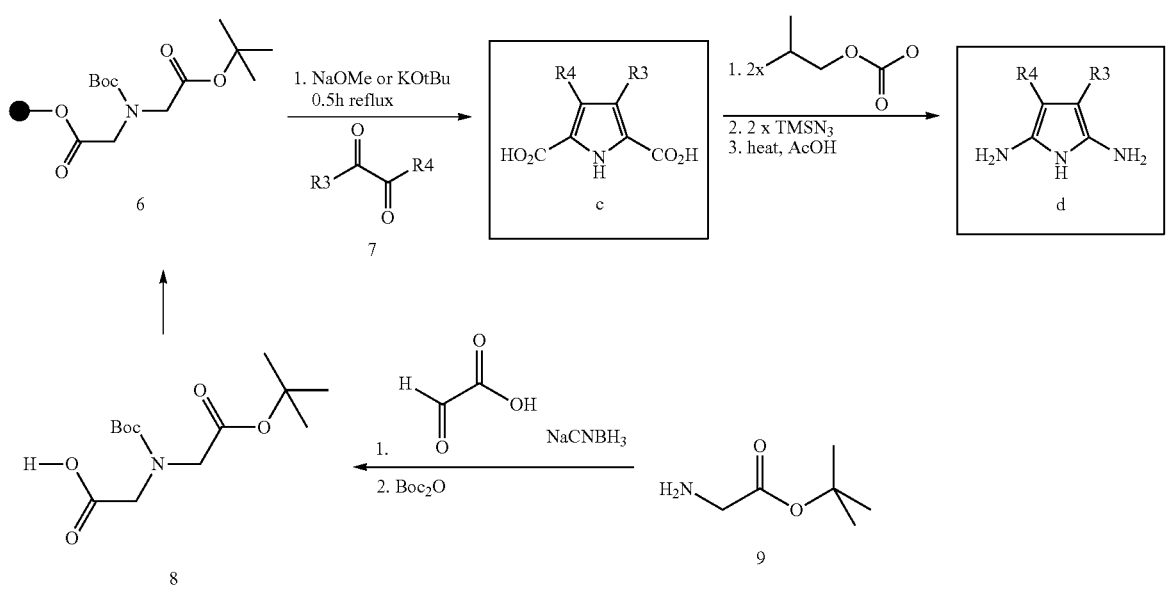

-continued

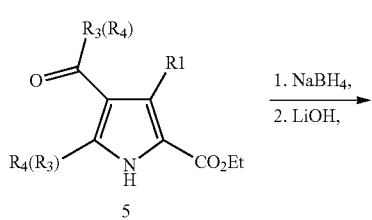

The reaction[2,3] is performed under basic conditions using NaOMe or KOtBu. Imino diacetic acid 6 can be easily prepared from t-Bu ester of Gly by reductive amination of Glyoxylic acid using Sodium cyanoborohydride as a reduction reagent and subsequent introduction of a Boc protecting group in multi-gram scale[4].

Sub-library e can be prepared using the method described in the pathway below. Position 3 in the resulting products has a fixed subtituent—an hydroxy group. Again, SPS is involved using pre-prepared building blocks as described above.

The process initiates from preparing five acyl Meldrum's acid building blocks (12)[5,6] in solution by reaction of acid chlorides 10 with Meldrum's acid 11 to give, in the presence of pyridine the corresponding compound 12 almost quantitatively[7,8].

Thus, heating 12 (5 equiv.) with the hydroxyl resin (the resin which generates carboxylic acid, for example the oxime resin[9]) in THF at reflux for a few hours[6] affords the polymer-bound β-ketoesters 13 with concomitant release of $CO_2$ and acetone, which helps to drive the reaction to completion. The reaction could be easily monitored by FT-IR on the resin (KBr pellets). The fuctionalization of the α-carbon of 13 is performed with excess of the alkylating reagent, avoiding O-alkylation as well as double alkylation.

Thus, haloalkanes (36 equiv.) in the presence of 1 M TBAF[8] in THF (26 equiv., 3 h) easily convert 13 to 14 at RT (FIG. 4). Typically it is important to exclude traces of water, which may decrease the yield. Addition of an excess of presynthesized amino ketones 15[10,11] (FIG. 5) (20 equiv., 3 h, RT), to the resin linked β-ketoesters 14 in THF/trimethylorthoformate (1/1) gives the Shiff bases 16, Cyclization of 16 under basic conditions with concomitant release of the product 17 into the solution followed by reduction of the ketone (R3=Me,Et). (NaBH4 BF3OEt2)[1] produces sub library e.

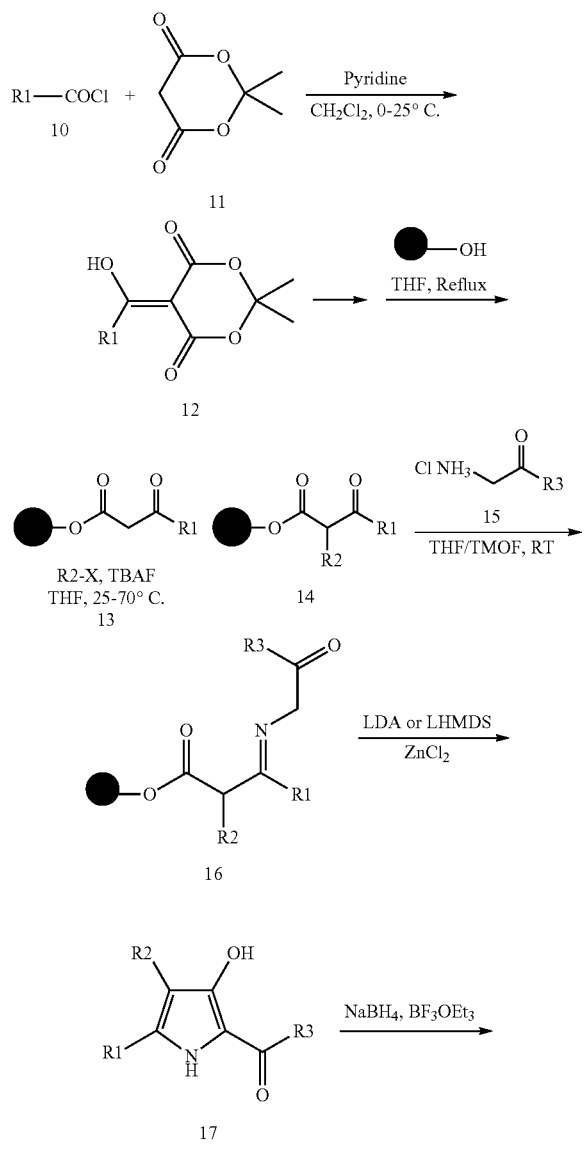

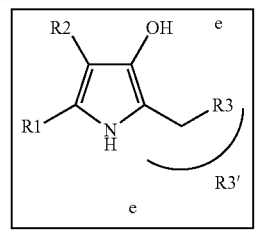

The reaction can also be performed in solution using α-substituted β-ketoesters following the same reaction sequence.

It should be noted that β-hydroxy pyrroles may exist to some extent in its keto tautomer[14] The required building blocks are β-keto esters which are commercial or the α-substituted-β-ketoesters.

The α-aminoketone building block can be prepared from the corresponding amino acid hydroxamate as described in the following pathway.

Synthesis of amino ketones from Gly Boc hydroxamates.

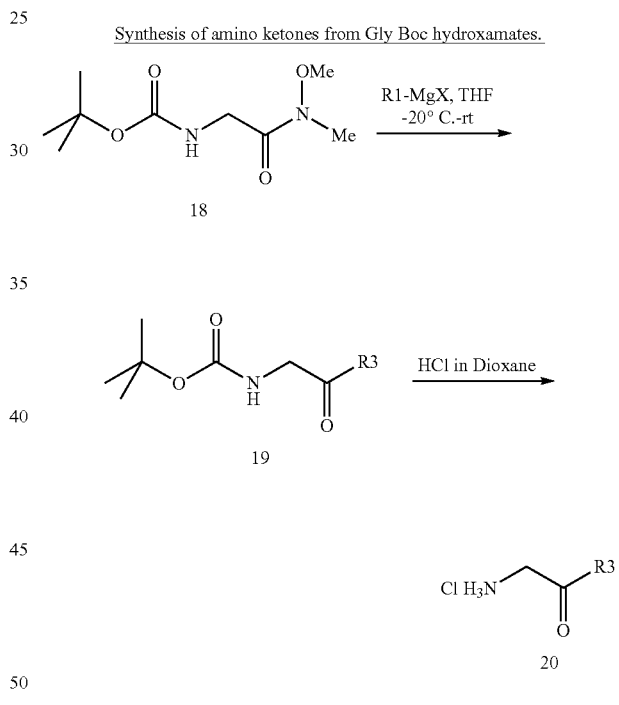

N-protected glycine recats with N—O-dimethyl hydroxyl amine to give hydroxamte 18 Reaction of the glycine hydroxamate with Gringard reagent (EtMgBr, MeMgBr) affords the ketone 19 no over adding is observed. Deprotection of 19 gives the amino ketone building blocks.

In case R3=OH, glycinate reacts with the substituted β-keto esters

Sixteen more products can be obtained by the method described in the pathway below. A key step for the preparation of sub library f is Michael addition of amino ketones 21 to DTAD (21)[12]. The obtained aminoolefine 23 undergoes cyclization in acidic conditions, to afford the sub-library f.

synthesis of 2-carboxy-3-amino-pyrroles

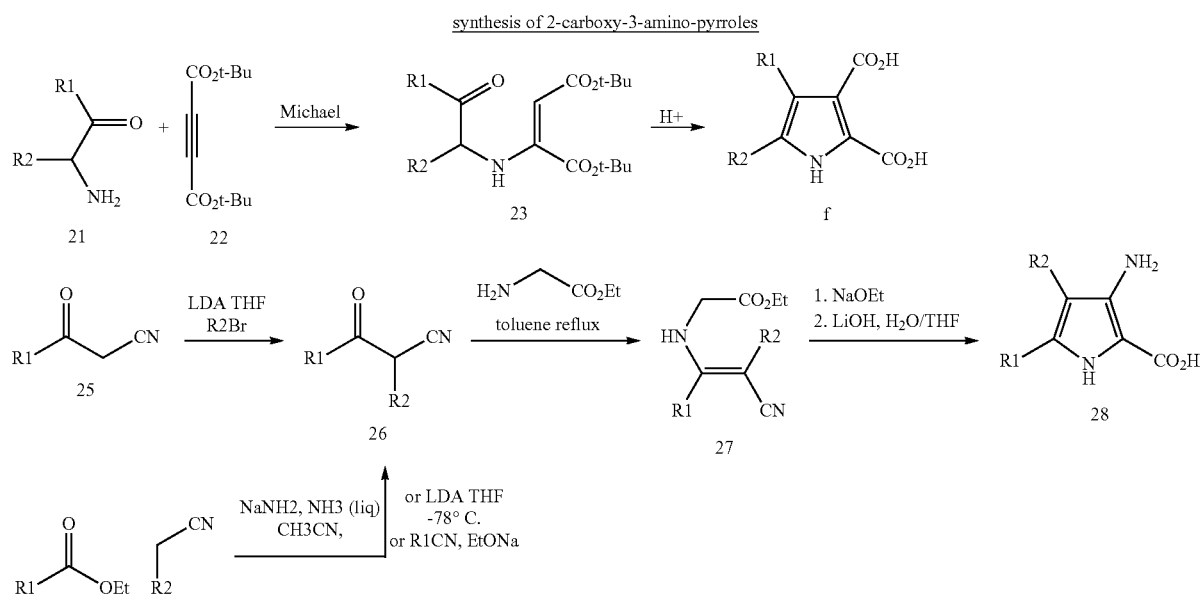

The synthesis of 2-carboxy, 3-amino pyrroles 28 is well known[12, 13] (see pathway above). It is performed through the enamine formation of 26 and subsequent intramolecular cyclization of 27 under basic conditions (NaOEt) to give 28. The β-keto nitriles 25. can be prepared by either alkylation of 25[15] or acylation of the corresponding nitrile.[16]

References

1) J. Paine III, *J. Org. Chem.*, 3857, (1976).
2) M. Friedman, *J. Org. Chem.*, 859, (1965).
3) K. Dimroth, *Ann. Chem.*, 639, 102, (1961).
4) G. Byk, *J. Org. Chem.*, 5687, (1992).
5) L. Tietze, *Bioorg. & Med Chem. Lett.*, 1303, (1997).
6) L. Tietze, *SYNLETT*, 667, (1996).
7) Y. Oikawa, *J. Org. Chem.*, 2087, (1978).
8) L. Weber, *SYNLETT*, 1156, (1998).
9) *The Combinatorial Index*, p. 15
10) S. Nahm, *Tet. Lett.*, 3815, (1981).
11) Eur. J. Org. Chem 2809, 2000
12) H. Ward, *Tet. Lett.*, 25, 527, (1969).
13) Mu-III Lim, *J. Org. Chem.*, 3826, (1979).
14) Aust J. Chem 20, 935, 1967.
15) J Org Chem 55 429 1990
16) a. Bull Chem Soc Jpn 62 3851 1989, b. Chem Pharm Bull 46 69 1998, c. J Med Chem 34 1741 1991

16.8 Thiophenes and Related Scaffolds

The chemistry of 2-aminothiophenes and related scaffolds has attracted special attention in the last 30 years because of their applications in pharmaceuticals, agriculture, pesticides and dyes.

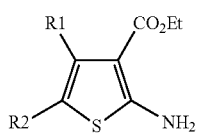

A

-continued

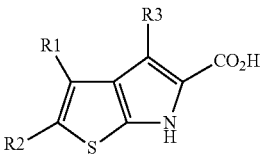

B

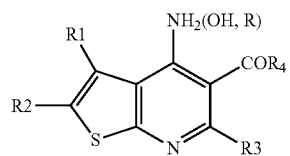

C

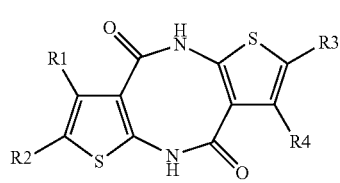

E

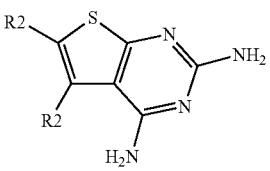

D

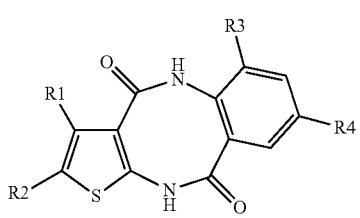

F

143
-continued
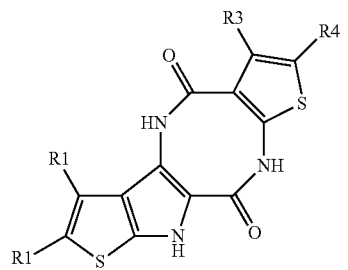
G
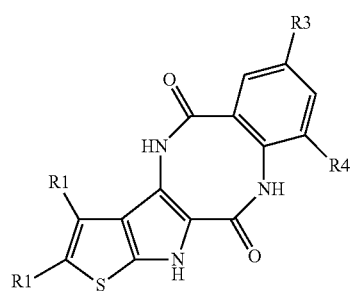
H
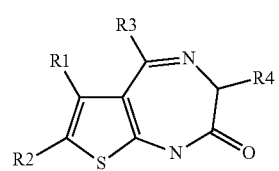
I
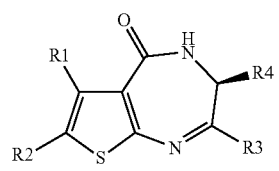
J
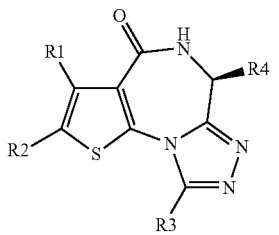
M
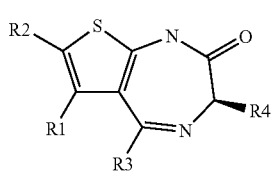
K
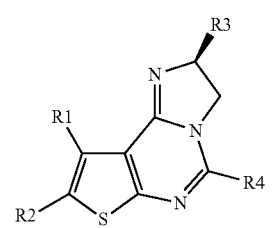
O
144
-continued
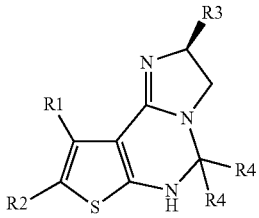
O1
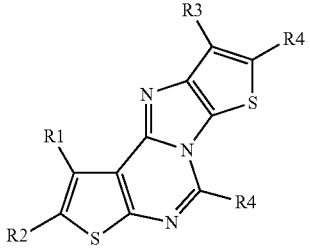
P
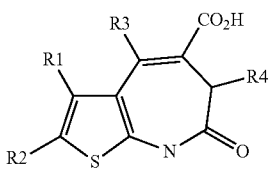
L
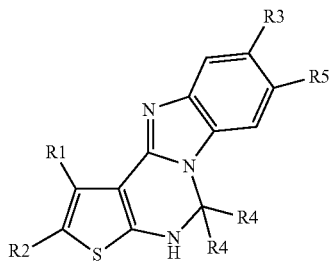
N1
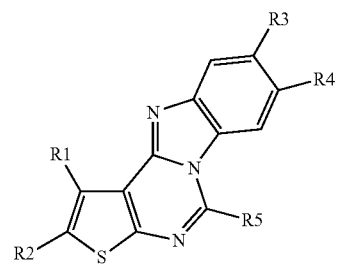
N
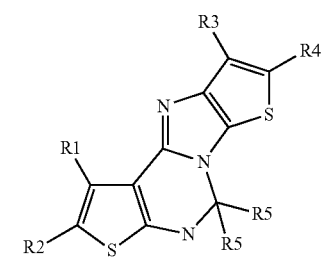
P1
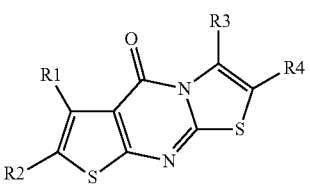
R -continued

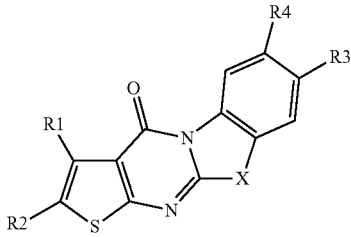

The chemistry of 2-aminothiophenes are conveniently available through the, synthetic method developed by Gewald[1a,b] who devised the most facile and promising synthetic route leading to 2-aminothiophenes A with electron withdrawing substituents such as cyano, carbethoxy etc. in the 3-positions and alkyl, aryl, cycloalkyl, and hetaryl groups in the 4- and 5-positions.

Gewald reaction

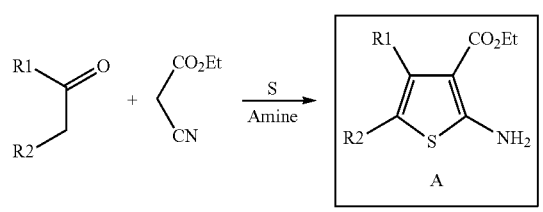

The simplest version of the Gewald reaction consists of a one-pot procedure, namely condensation of aldehydes, ketones or 1,3-dicarbonyl compounds with activated nitriles and sulfur in the presence of amine at room temperature. Ethanol, DMF, dioxane are preferred solvents and amines like diethylamine, morpholine, or triethylamine have been used[1-7]. This method offers considerable improvement over other methods by replacing an a-mercaptoaldehyde or an a-mercaptoketone by simpler starting materials. It is necessary to use 0.5-1 molar equivalents of amine based on the amount of nitrile to obtain high yield. In another synthesis version a two-step procedure is preferred. An a,b-unsaturated nitrile is first prepared by a Knoevenagle-Cope condensation and then treated with sulfur and an amine. This two-step version of the Gewald reaction gives higher yields. Alkyl aryl ketones do not give thiophenes in the one-pot modification, but gives acceptable yields in the two-step technique[2] (see pathway below).

Two step Gewald reaction

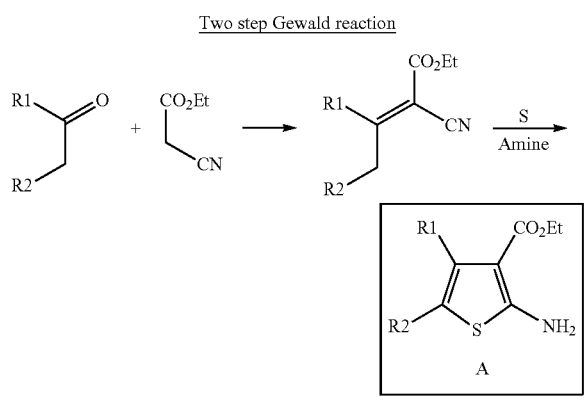

The use of t-butyl cyanoacetate instead of the ethyl ester enables to obtain free acid of 3-carboxy-2-aminothiophenes by convenient TFA/DCM hydrolysis[8]

The amino acid obtained as well as the protected acid can be used as building blocks for further transformation to more complex scaffolds as is exemplified below:

16.8.1 5, 5 bicyclic Scaffolds

Thienopyrrole synthesis

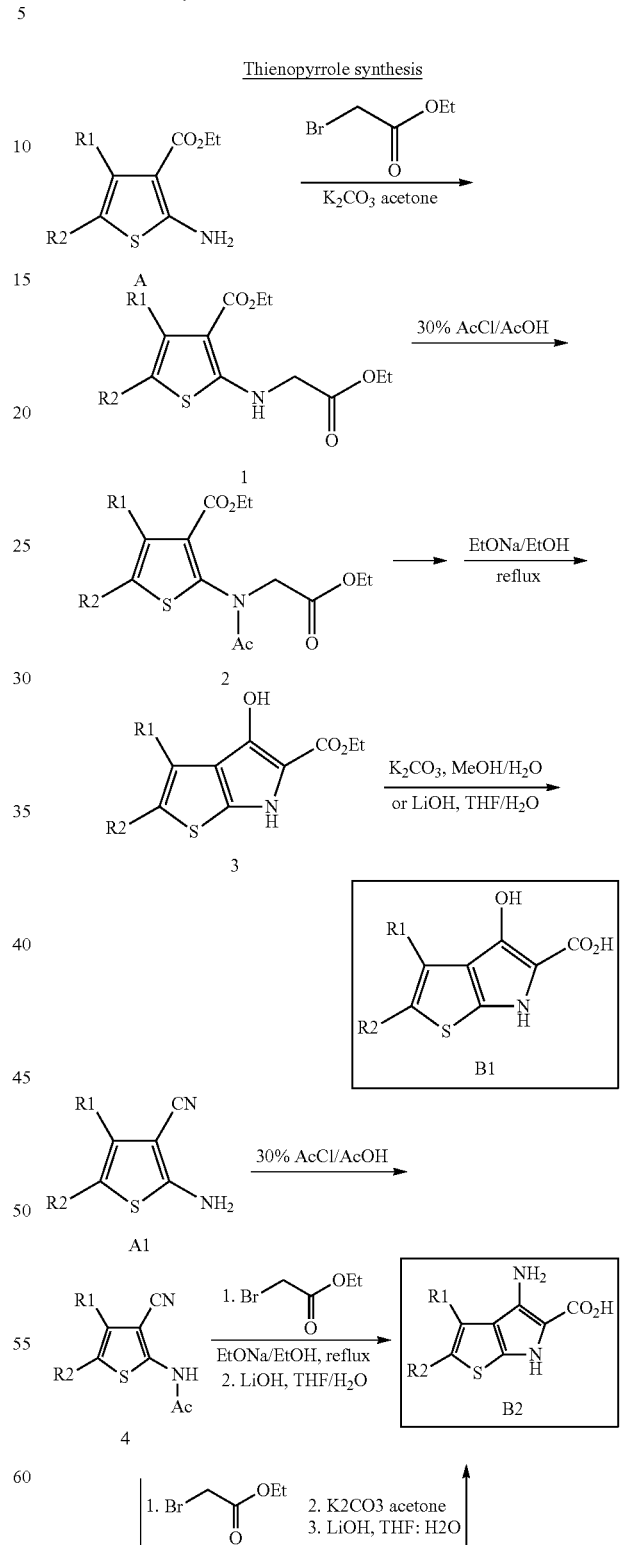

Thienopyrrole scaffold B[9] (pathway above) is prepared by the reaction of aminocarboxylate A with bromoacetate ($K_2CO_3$) to obtain diester intermediate 1, which after acetylation (compound 2) (30% AcCl in AcOH) undergoes Dieckmann condensation (EtONa, EtOH) to afford 3-hydroxy-2-carboxy thieno[2,3-b]pyrrole B1. The amino analog B2 requires starting with the 2-amino-3-cyano thiophene A1. Acetylation followed by alkylation with a-bromoacetate (K2CO3 acetone or NaH DMF) leads under similar reaction conditions to ring closure producing 3-amino-caboxy thienopyrrole B2. Acetylation of the amine at position 2 and LiOH are required to increase the nucleophilicity of the amine.

16.8.2 5,6-bicyclic Scaffolds

The thienopyridine scaffold C is prepared via modified Friedlander reaction, namely reaction of thiophene A, A1 and 5 with b-ketoesters, 1,3 diketones under basic condition to form thienopyridines as described in the pathway below

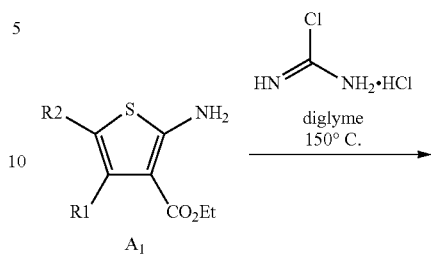

Thienopyridine synthesis

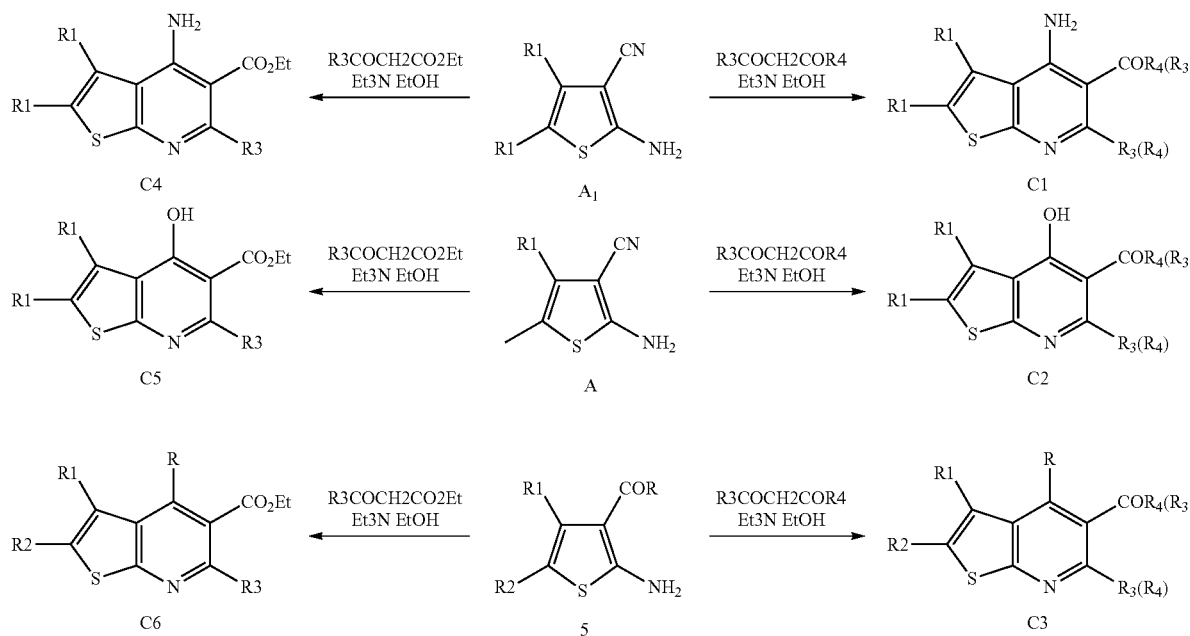

Another 5,6-bicyclic ring system—the thieno pyrimidine D is prepared by the reaction of thionhene A, A1 with chloro formamidine hydrochloride 4,11

Thienopyrimidine synthesis

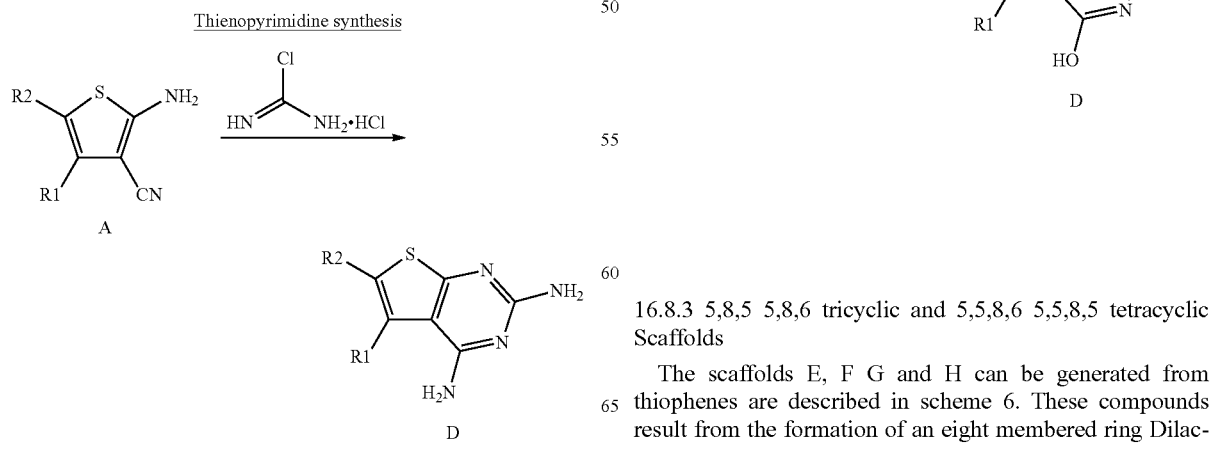

16.8.3 5,8,5 5,8,6 tricyclic and 5,5,8,6 5,5,8,5 tetracyclic Scaffolds

The scaffolds E, F G and H can be generated from thiophenes are described in scheme 6. These compounds result from the formation of an eight membered ring Dilactam.

preparation of 8 membered ring dilactam
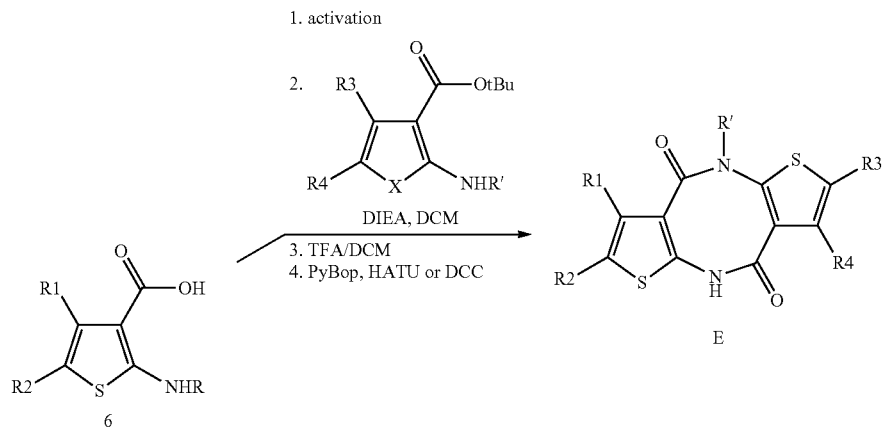
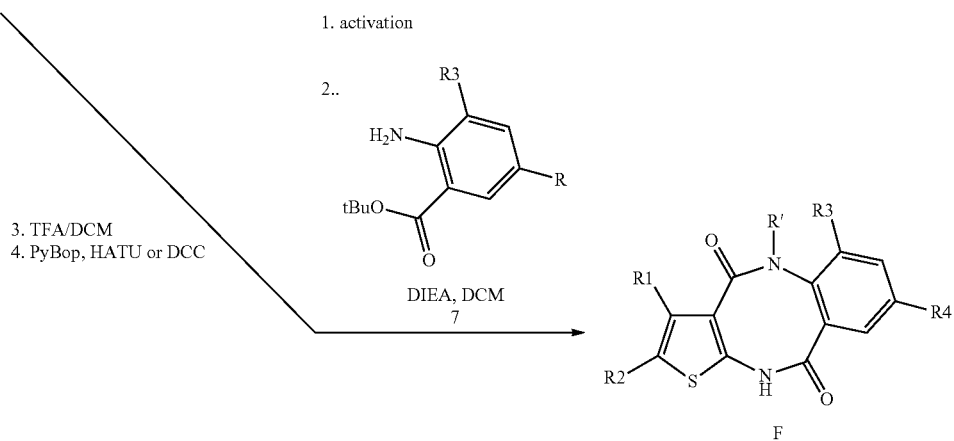
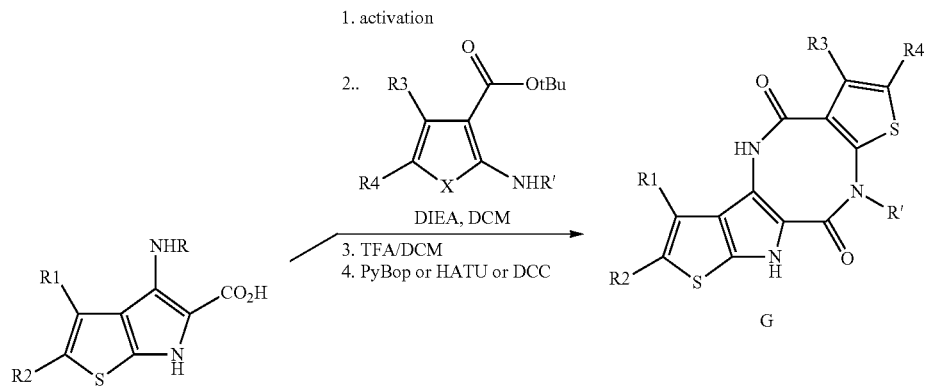

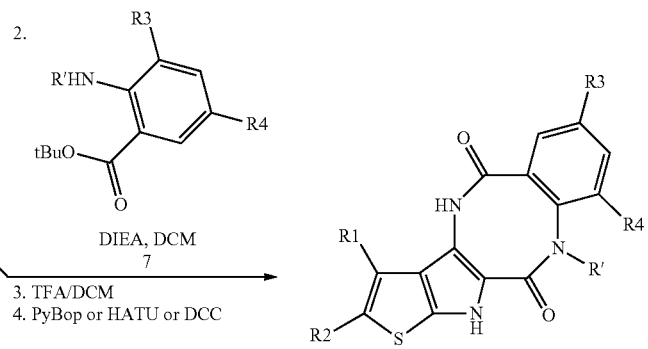

R = H Boc
R' = H Me, PhCH2

The formation of the eight membered ring includes several steps:

1. Activation of the β-amino acid using SOCl2[12a] or POCl3[12b] (in these cases the amine should be protected by Boc) or by DCC[12c] and methyl chloroformate[12d]
2. Coupling of the activated acid and another N-protected β-amino-t-butyl ester[13,]
3. Deprotection of the t-butyl ester and the N-Boc amine using TFA in DCM
4. Coupling by PyBop or any other analog in case R' is a benzyl group it can be removed at this stage by hydrogenation.

16.8.4 5,7 bicyclic Scaffold

The synthesis of I, J analogs of the benzodiazepines scaffold is illustrated in the following pathway. In both approaches chiral amino acid are introduced into the synthesis raising the diversity around the α carbon. Thieno diazepine I is prepared from 2-amino-3-acyl)-thiophenes 5. which reacts with pre formed Boc amino acid chloride (amino acid, BTC, collidine, THF or DCM). Deprotection of 8 (4N HCl) with concomitant ring closure leads to 2-oxothienodiazepine I. Thiophenodiazepine J can be prepared starting from 2-amino-3-carboxy-thiophenes A, which after pre activation to the thienooxzaine dione (BTC, collidine, THF or DCM)) reacts with amino ketone to obtain 9, ring closure afford 5-oxothienodiazepine. J[14]

synthesis of thienodiazepines

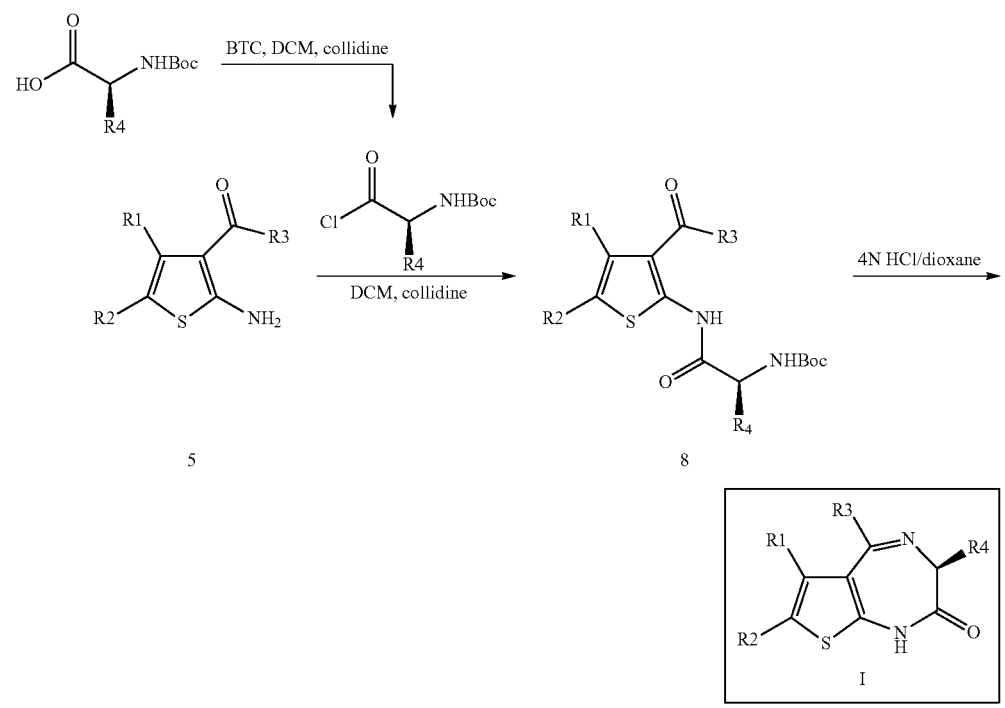

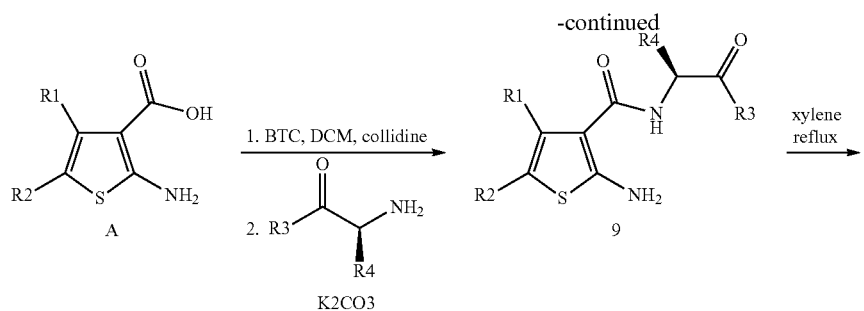
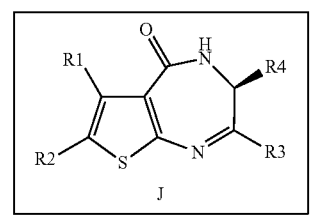

The synthesis of thienodiaepine K

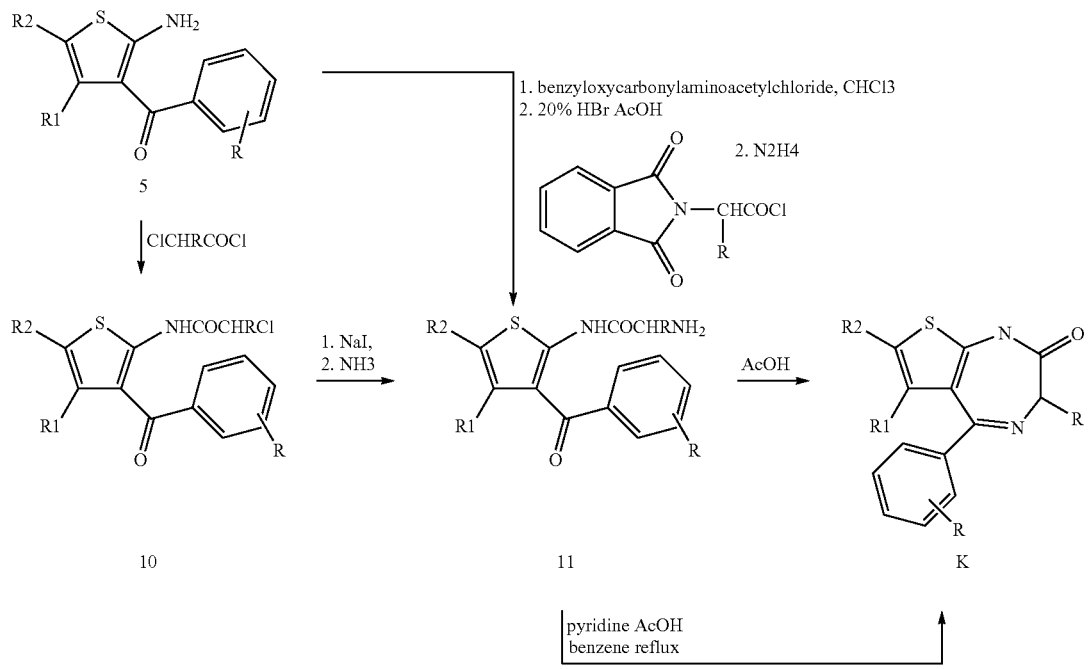

The synthesis of thienodiazepine K is described in the above pathway. 2-amino-3-acyl thiophene 5 is first acetylated with the appropriate α-haloacetyl chloride Nucleophilic substitution with NaI followed by ammonia to obtain the amino amide[15] 11. The latter undergoes ring closure to the thienodiazepine K under acidic conditions Another alternative is to react thiophene 5 with the phthalide protected amino acyl chloride, Deprotection with hydrazine (11) and ring closure to obtain thienodiazepine K[16]

The synthesis of thienozepine L is based on coupling of sucssinic anhydride or acid chloride monoester with thiophene 5 (see pathway below) The obtained amide 12 undergoes intramolecular condensation (NaH) to provide the targeted compounds[17].

preparation of thienozepine

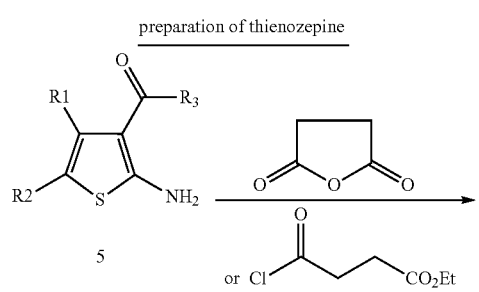

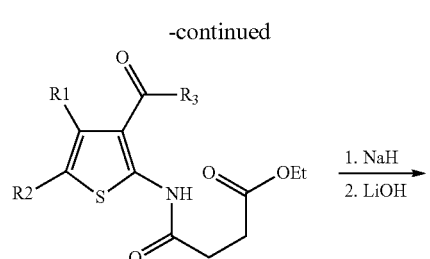

Scaffold M, having a thienodiazepinone skeleton may be prepared as described in the pathway below. The N-protected aminocarboxythiophene A is first preactivated (BTC, collidine, DCM) and submitted to reaction with α-amino acetonitriles 14 to afford amide 13.

The latter reacts under basic conditions (NaOMe) to provide through the intramolecular cyclization the disubstituted intermediate 2-aminothieno-1,4-diazepin-5-one 15[18.]. In the next step 2-aminothieno-1,4-diazepin-5-one 15 is heated with acetyl hydrazine leading to thienotriazolodiazepinone M

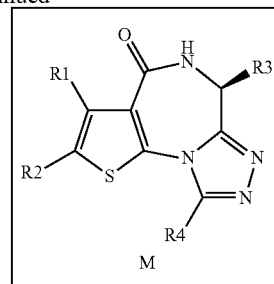

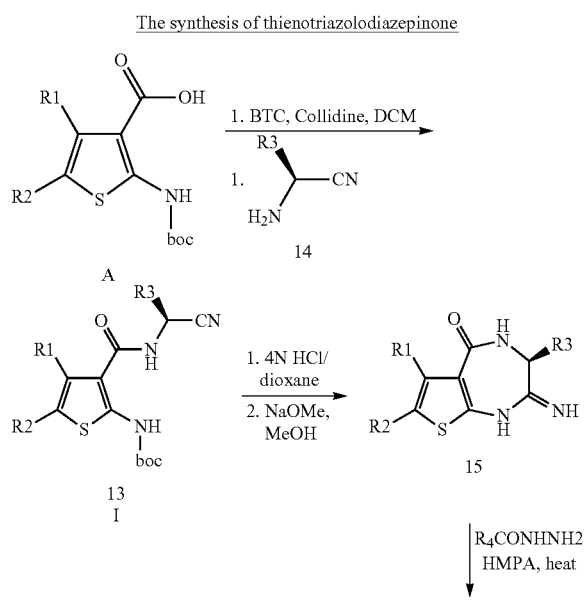

16.8.5 5,6,5,6 Tetracyclic and 5,6,5 tricyclic Scaffolds

The thiophene substituted in the 3 position with a benzimidazole namely benzimidazoloaminothiophene 16 can serve as a building block for the synthesis of thieno(2',3',4,5)pyrimidino(1,6)benzimidazole,N N1, The starting material 2-cyanomethylbenzimidazole 16, is prepared from substituted phenylene diamine 17 and malononitrile[19] Nitrile 18 is submitted to Gewald reaction using elemental sulfur powder and ketones[20] or cyanoacetamide[21] in dry DMF containing a catalytic amount of TEA under reflux to form thiophene 16 (see pathway below).

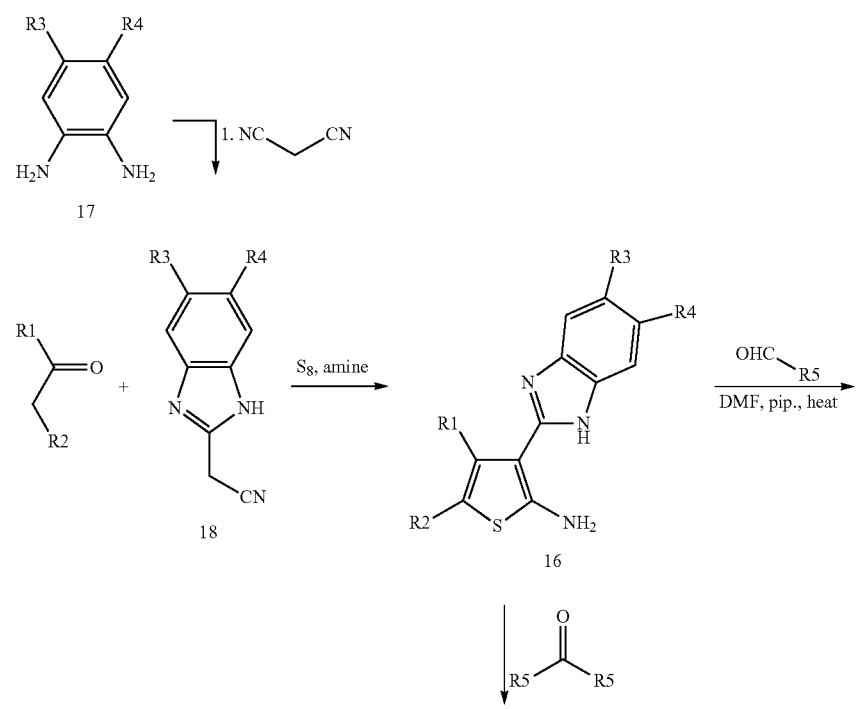

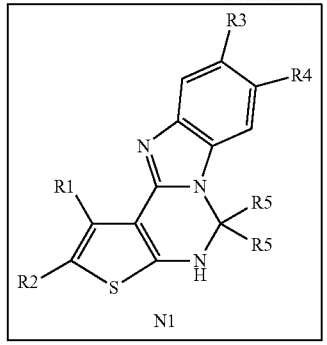

Condensation of 16 with aldehydes or ketones, afford N and N1 respectively[21, 22].

The synthesis of thienopyrimidinodihydroimidazole

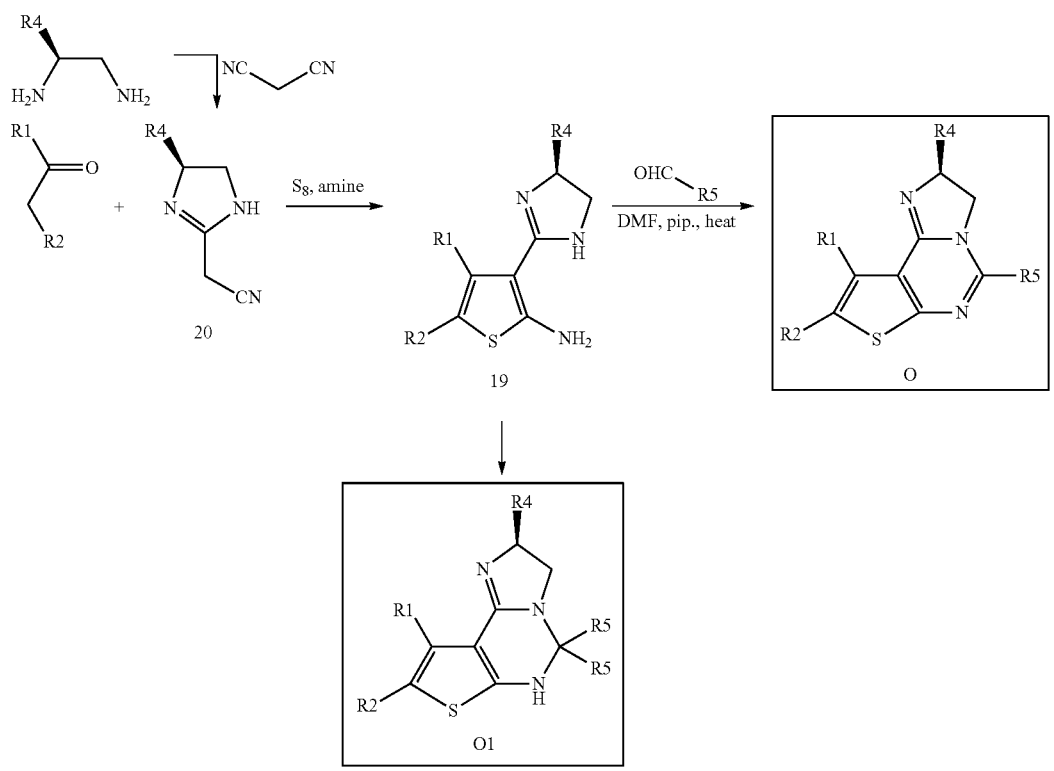

Using the same approach dihydroimidazoylacetonitrile 20[23] (see pathway above) and thienoimidazoyl-acetonitrile 21 (see pathway below) can be prepared from the corresponding diamines (ethylene diamine and thiophene2,3 diamine[24]) and malonolitrile The resulting nitriles react with ketones under Gewald conditions forming a O, O1 and P, P1.

The synthesis of scaffolds P and P1

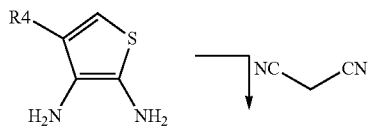

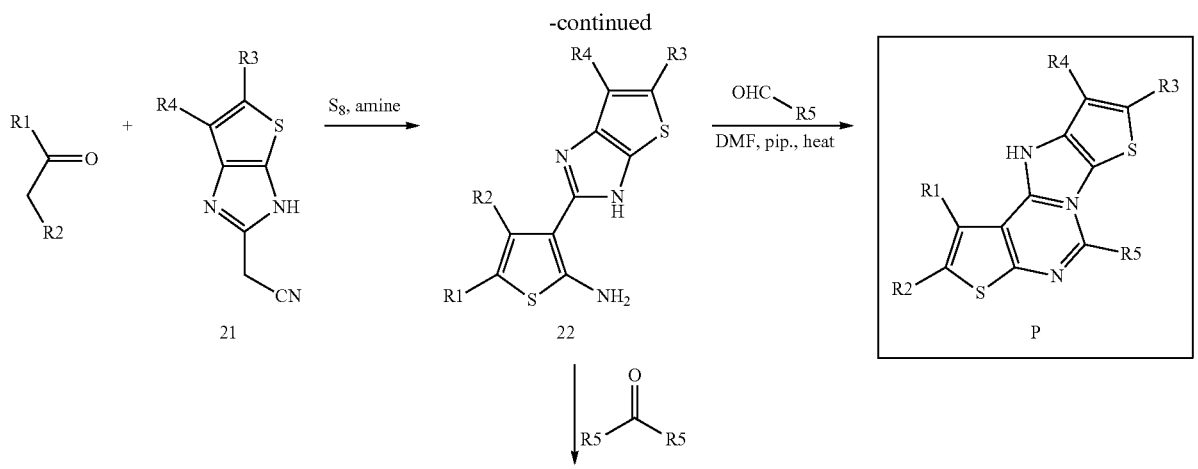

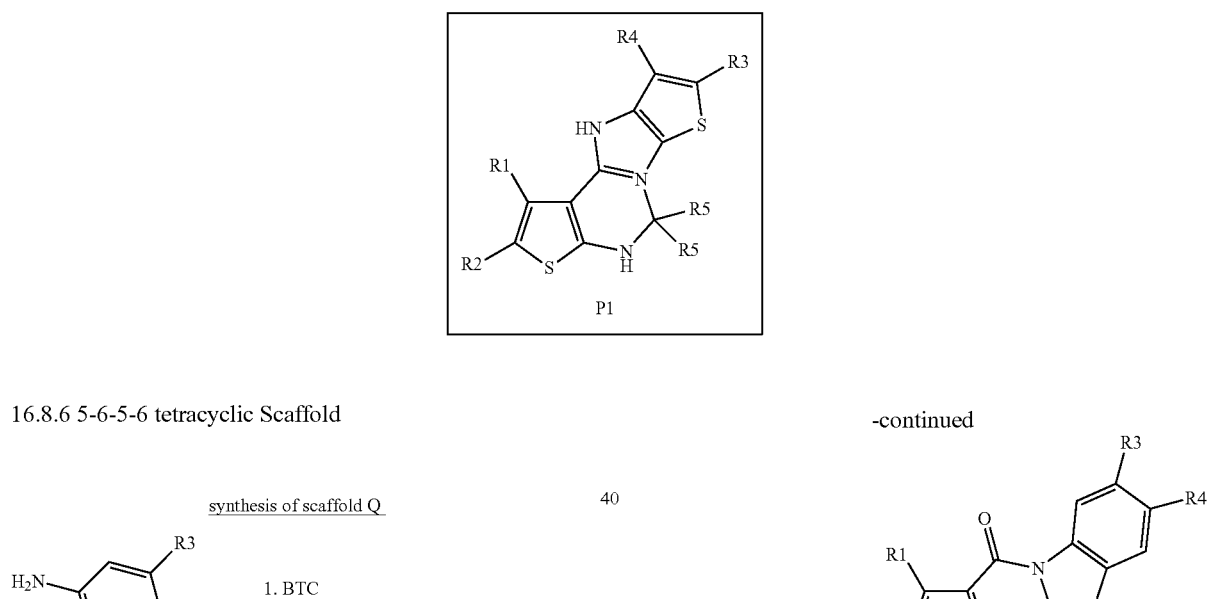

16.8.6 5-6-5-6 tetracyclic Scaffold

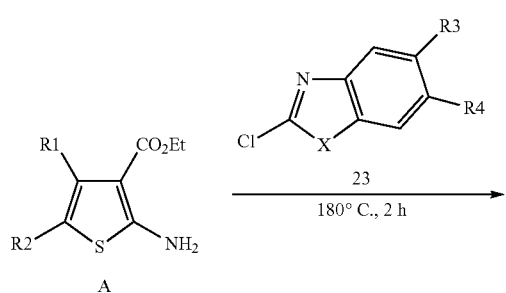

4H-thieno[2',3':4,5]pyrimido[2,1-b]benzothia—or—zoles Q can be prepared from amino thiophene A as outlined in the pathway above.[25] 2-Amino-3-carboxythiophene undergoes condensation at high temperature with chlorobenzimidazole[26]. chlorobenzthiazole 23 leading to the corresponding thienopyrimidinazoles Q.

16.8.7 5-6-5 tricyclic Scaffold

Thia-triaza-s-indacenone R (see pathway below), can be obtained according to literature procedures In this synthesis the aminothiophene A undergoes cyclization in boiling acetic acid with pre formed methylthio imidazoles 24 to give the desired system. R

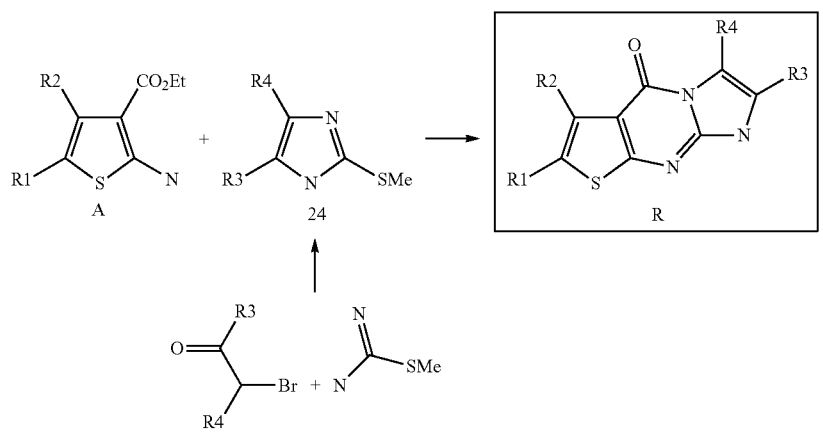

References
1. a. Chem Ber 99 94 1966, b. Pharmazia 51 833 1996
2. J Heterocycl Chem 36 333 1999
3. Bull Chem Soc Jp 64 3768
4. Bioorg Med Chem Lett 7 1629 1997
5. J Chem Tech Biotecnol 47n39 1990
6. Monatsch Chem 127 297 1996
7. Indian J Chem 1209 1971
8. a. J. Med Chem 41 1729 1998, b. Tet Lett 40 5471 1999 c. J Heerocycl Chem 32 1537 1995
9. Bull Soc Chim Fr 1786 1975
10. a. Chem Pharm Bull 47 993 1999, b. Phosphorus Sulfur Silicon and related elements 155 215 1999
11. a. J. Heterocycl Chem 9 775 1972, b J. Med Chem 16 191 1973
12. a. Heterocycles 27 105 1988 b. Org Prep roced. Int 29 711 1997 c. J. Chem Soc Perkin Trans 1 1649 1982 d. Dokl Akad Nauk USSR 41 1989
13. a. Acta Chim Acad Sci Hung 107 171 1981, b. Indian J Chem Sect B 16B 393 1978
14. J. Heterocycl Chem 16 793 1979
15. Eur J Med Chem 31 683 1996
16. a. J Med Chem 16 214 1973 b. Collect Cezch Chem Commun 49 621 1984
17. a. J. Med Chem, 18,192, 1975; b. J. Heterocycl Chem, 36,477, 1999; c. J. Heterocycl Chem, 33,271, 1996
18. a. Liebig Ann Chem, 328, 1979; b. J. Heterocycl Chem, 29,1477, 1992
19. J Am Chem Soc 65 1072 1943
20. Phosphorus Sulfur Silicon and related elements, 105, 51, 1995
21. Monatshefte Chem, 127,955, 1996
22. Phosphorus Sulfur Silicon and related elements 106, 193, 1995
23. Acta Chem Scand 50 432 1996
24. J Chem Research 296 1985
25. Eur J Med Chem, 29,569, 1994
26. a. Aust J Chem 35 775 1982, b. Farmaco 44 227 1989 c. Eur J Med Chem 24 623 1989
27. J Med Chem 30 1166 1987
28. J. Heterocycl. Chem., 38, 743, 2001

It will be appreciated that the above described methods of target measurement and drug discovery may be varied in many ways, including, changing the order of steps, which steps are performed on-line and which steps are performed off-line. In addition, various parallel and/or sequential configurations may be used to implement the above invention, optionally utilizing a variety of software tools and/or various hardware/software combinations. In addition, a multiplicity of various features, both of methods and of devices has been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. Also within the scope of the invention are computer readable media on which software, for performing part or all of an exemplary embodiment of the invention, are written. It should also be appreciated that many of the embodiments are described only as methods or only as apparatus. The scope of the invention also covers hardware and/or software adapted and/or designed and/or programmed to carry out the method type embodiments. In addition, the scope of the invention includes methods of using, constructing, calibrating and/or maintaining the apparatus described herein. Headers, where they appear, are provided for ease of browsing and should not be construed as necessarily limiting the contents of the section to that which is suggested by the heading. When used in the following claims, the terms "comprises", "comprising", "includes", "including", "having" or their conjugates mean "including but not limited to".

It will be appreciated by a person skilled in the art that the present invention is not limited by what has thus far been described. Rather, the scope of the present invention is limited only by the following claims.

The invention claimed is:
1. A method of obtaining information about a chemically active area of a target molecule, comprising:
providing a set of gauge molecules;
causing said target to singly interact with each of a plurality of gauges of said set of gauges, said plurality comprising at least 5,000 gauges;
assaying said interaction of said gauges with said target to assay binding of said gauges to said target, so as to obtain at least 5 gauges which bind to said target; and
analyzing a structure of said target bound to each of said at least 5 gauges; and
finding a set of binding points in said target which bind to the same chemical type of moiety in at least two of said at least 5 gauges; and
identifying binding points in set said of binding points in said target as binding points which bind to the same chemical type of moiety in at least two of said at least 5 gauges; and reconstructing a spatial map of identified binding points, said spatial map comprising at least 4 identified binding points in said target, each of said identified binding points being identified as binding to the same chemical type of moiety in at least two of said gauges, to thereby obtain information about said chemically active area, wherein said plurality of gauges is selected so as to comprise triangles of moieties capable of binding to the 3-point pharmacophores in at least 40% of a triangle space which defines all possible 3-point pharmacophores defined by a triplet of distances that form a triangle, each distance being in a range of 2-12 angstrom, and by a triplet of chemical binding point types for the triangle vertices, each chemical binding point type being selected from the group consisting of acid, base, hydrophobic, hydrogen-bond donor, hydrogen-bond acceptor, and aromatic.

2. The method of claim 1, wherein said analyzing comprises analyzing using a technique selected from the group consisting of NMR and X-ray crystallography.

3. The method of claim 1, wherein at least 60% of gauges of said plurality of gauges are substantially rigid.

4. The method of claim 1, comprising obtaining at least 25 gauges which bind to said target, and analyzing a structure of said target bound to each of said at least 25 gauges.

5. The method of claim 1, comprising virtually superimposing a plurality of structures obtained by said analyzing.

6. The method of claim 5, wherein said super-imposing uses said target as a reference frame.

7. The method of claim 1, wherein said identifying comprises identifying at least one 3-point pharmacophore in said target which bind to a triangular configuration of moieties in at least two of said at least 5 gauges.

8. The method of claim 1, wherein said plurality of gauges spans at least 40% of said triangle space with an overlap of 3.

9. The method of claim 1, wherein said binding points in said target bind to a compatible type of moiety of said at least two of said at least 5 gauges.

10. The method of claim 1, wherein said binding points in said target and said moieties of said gauges are characterized by a chemical type selected from the group consisting of acid, base, hydrophobic, hydrogen bond donor, hydrogen bond acceptor and aromatic.

11. The method of claim 1, wherein said finding a set of binding points comprises finding a set of binding points in said target which bind to the same type of moiety in at least three of said at least 5 gauges.

12. The method of claim 1, wherein said plurality of gauges comprises at least 10,000 gauges.

13. The method of claim 1, wherein said at least 5 gauges bind to said target at a concentration of 100 $\mu$M.

14. The method of claim 1, wherein said spatial map comprises at least 6 binding points of said target, each of said at least 6 binding points being identified as binding to the same chemical type of moiety in at least two of said at least 5 gauges.

15. The method of claim 14, further comprising selecting and/or constructing a drug candidate to match said spatial map identified binding points.

16. The method of claim 1, wherein said plurality of gauges comprises 3-methyl-5-phenyl-anthranilic acid.

17. The method of claim 1, comprising using a same set of gauge molecules for obtaining information about a different target molecule.

18. The method of claim 1, wherein said finding comprises identifying a set of three binding moieties and distances between the moieties.

19. The method of claim 1, wherein said assaying is at between 1 and 100 micro Molar.

20. The method of claim 1, wherein said reconstructing comprises reconstructing based on most of the successful binding assays.

21. The method of claim 14, wherein said spatial map comprises 10 binding points.

22. The method of claim 1, wherein said binding points of said spatial map comprise generic binding points with sufficient chemical freedom for a range of binding molecules.

23. The method of claim 1, wherein said binding points of said spatial map include at least one donor/acceptor binding point which is unidentified as a donor or acceptor.

24. The method of claim 1, wherein said binding points of said spatial map include at least one binding point allowing a variety of directional bindings thereto.

25. The method of claim 1, wherein said set of gauges is selected to cover a range of bond direction for a directional same bond, so as to be usable in a range of target molecules.

26. the method of claim 25, wherein said range is uniform.

27. The method of claim 1, wherein said set of gauges is selected so that said binding point types are generic for a range of target molecules.

28. The method of claim 1, wherein, at least 20% of gauges of said plurality of gauges are substantially rigid.

* * * * *